United States Patent [19]

Mezes et al.

[11] Patent Number: 5,993,813
[45] Date of Patent: Nov. 30, 1999

[54] FAMILY OF HIGH AFFINITY, MODIFIED ANTIBODIES FOR CANCER TREATMENT

[75] Inventors: Peter S. Mezes; Brian B. Gourlie; Mark W. Rixon, all of Midland, Mich.; Jeffrey Schlom, Potomac, Md.; Donald A. Kaplan, Cincinnati, Ohio; W. H. Kerr Anderson, Midland, Mich.

[73] Assignee: The Dow Chemical Company, Midland, Mich.

[21] Appl. No.: 08/822,028

[22] Filed: Mar. 24, 1997

Related U.S. Application Data

[60] Division of application No. 08/040,687, Mar. 31, 1993, which is a continuation-in-part of application No. 07/424,362, Oct. 19, 1989, abandoned, which is a continuation-in-part of application No. 07/261,942, Oct. 24, 1988, abandoned, which is a continuation-in-part of application No. 07/259,943, Oct. 19, 1988, abandoned.

[51] Int. Cl.$^6$ ............................................. A61K 39/395
[52] U.S. Cl. ................... 424/133.1; 424/130.1; 424/138.1; 530/387.3; 530/388.8; 530/391.3
[58] Field of Search ............................ 530/387.3, 388.8, 530/391.3; 424/130.1, 133.1, 138.1

[56] References Cited

U.S. PATENT DOCUMENTS

| | | |
|---|---|---|
| 4,522,918 | 6/1985 | Schlom et al. . |
| 4,612,282 | 9/1986 | Schlom et al. . |
| 4,642,334 | 2/1987 | Moore et al. . |
| 4,656,134 | 4/1987 | Ringold . |
| 4,800,159 | 1/1989 | Mullis et al. . |
| 5,091,513 | 2/1992 | Huston et al. ........................ 530/387 |

FOREIGN PATENT DOCUMENTS

| | | |
|---|---|---|
| 0 239 400 | 9/1987 | European Pat. Off. ........ C07K 15/06 |
| 8900692 | of 0000 | WIPO . |
| 9014424 | of 0000 | WIPO . |

OTHER PUBLICATIONS

Riechmann et al. Nature 332:323–327 (1988).
Muraro et al. Cancer REsearch 48:4588–4596 (1988).
Whittle, et al. (1987), Protein Engineering, 1(6):499–505.
Rice, et al., (1982), Proc. Natl. Acad. Sci., USA, 79:7862–7865.
Oi, et al. (1983), Proc. Natl. Acad. Sci., USA 80:825–829.
Boulianne et al. (1984), Nature, 312:643–64.
Cabilly et al. (1984), Proc. Natl. Aca. Sci., USA, 81:2955–2959.
Kenten et al. (1984), Proc. Natl. Aca. Sci., USA, 81:2955–2959.
Lui et al. (1984), Proc. Natl. Acad. Sci., USA, 81:5369–5373.
Morrison et al. (1984), Proc. Natl. Acad. Sci., USA, 6851–6855.
Nueberger et al. (1984), Nature, 312:604–608.
Potter et al. (1984), Proc. Natl. Acad. Sci., USA, 81:7161–7165.
Nueberger et al. (1984), Nature, 314:268–270.
Jones et al. (1986), Nature, 321:522–525.
Sahagan et al. (1986), The Journal of Immunology, 137(3):1066–1074.
Sun et al. (1986), Hybridoma,5(Suppl. 1):517–520.
Sun et al. (1987), Proc. Natl. Acad. Sci., USA, 84:214–218.
Liu et al (1987), The Journal of Immunology, 139(10):3521–3526.
Lui et al. (1987), Proc. Natl. Acad. Sci., USA, 84:3439–3443.
Shaw et al. (1987), The Journal of Immunology, 138(12):4534.
Brown et al. (1987), Cancer Research, 47:3577–3583.
Manser et al. (1984), Proc. Natl. Acad. Sci., USA, 81:2470–2474.
Short et al. (1988), Nucleic Acids Research, 16:7583–7600.

*Primary Examiner*—Thomas M. Cunningham
*Attorney, Agent, or Firm*—Karen L. Kimble; Mark S. Scott

[57] ABSTRACT

This invention concerns a family of chimeric antibodies with high affinities to a high molecular weight, tumor-associated sialylated glycoprotein antigen (TAG-72) of human origin. These antibodies have (1) high affinity animal $V_H$ and $V_L$ sequences which mediate TAG-72 binding and (2) human $C_H$ and $C_L$ regions. They are thought to produce significantly fewer side-effects when administered to human patients by virtue of their human $C_H$ and $C_L$ antibody domains. The nucleotide and amino acid sequences of $V_H \alpha TAG\ V_H$, CC46 $V_H$, CC49$_H$, CC83 $V_H$, and CC92 $V_H$, and CC49$_L$, CC83 $V_L$, and CC92 $V_L$ idiotype sequences are disclosed, as well as in vivo methods of treatment and diagnostic assay using these chimeric antibodies.

13 Claims, 62 Drawing Sheets

FIG. 2A

```
V_H αTAG  TCTCTTCCTC  CACCACCAAA  TCCACCATTT  GTAAATCAAC  CCT
CC49      ..........  ..........  ..........  ..........  ...
CC83      ..........  ..........  ..........  ..........  ...

V_H αTAG  ATGTTAACAT  ATCACAGAGT  GGAGCAACAG  AATCAGGGCA
CC49      ..........  ..........  ..........  ..........
CC83      ..........  ..........  ..........  ..........

V_H αTAG  AAAATATGCT  GAGAGATTTA  TCCCTGTCGT  TACAACCAAA
CC49      ..........  ...T......  ..........  ..........
CC83      ..........  ..........  ..........  ..........

V_H αTAG  GCATCTGTCT  AGAATTCATA  AAAACTTTAT  GGGATACATT
CC49      ..........  ..........  ..........  ..........
CC83      ..........  ..........  ..........  ..........

V_H αTAG  TCCTCAGAGA  GGAATAGGAT  TTGGACCTGA  CGATCCTGCT
CC49      ..........  ..........  ..........  ..........
CC83      ..........  ..........  ..........  ..........
```

FIG. 2B

```
         GCCCGAGCCA  TGTGATGACA  GTTCTTCTCC  AGTTGAACTA
VHαTAG   ..........  ..........  ..........  ..........
CC49     ..........  ..........  ..........  ..........
CC83     ..........  ..........  ..........  ..........

GGTCCTTATC  TAAGAAATGC  ACTGCTCATG  AATATGCAAA
VHαTAG   ..........  ..........  ..........  ..........
CC49     ..........  ..........  ..........  ..........
CC83     ..........  ..........  ..........  ..........

TCACCCGAGT  CTATGGCAGT  AAATACAGAG  ATGTTCATAC
VHαTAG   ..........  ..........  ..........  ..........
CC49     ..........  ..........  ..........  ..........
CC83     ..........  ..........  ..........  ..........

CATAAAAACA  ATATATGATC  AGTGTCTTCT  CCGCTATCCC
VHαTAG   ..........  ..........  ..........  ..........
CC46     ..........  ..........  ..........  ..........
CC49     ..........  ....G.....  ..........  ..........
CC83     ..........  ..........  ..........  ..........
CC92     ..........  ..........  ..........  ..........
```

FIG. 2C

```
         TGGACACACT  GACTCTAACC  ATG  GAA  TGG  AGC  TGG
VHαTAG   ..........  ..........  ...  ...  ...  ...  ...
CC46     ..........  ..........  ...  ...  ...  ...  ...
CC49     ..........  ..........  ...  ...  ...  ...  ...
CC83     ..........  ..........  ...  ...  ...  ...  ...
CC92     ..........  ..........  ...  ...  ...  ...  ...

GTC  TTT  CTC  TTC  TTC  CTG  TCA  GTA  ACT  ACA   G
VHαTAG   ...  ...  ...  ...  ...  ...  ...  ...  ...  ...  .
CC46     ...  ...  ...  ...  ...  ...  ...  ...  ...  ...  .
CC49     ...  ...  ...  ...  ...  ...  ...  ...  ...  ...  .
CC83     ...  ...  ...  ...  ...  ...  ...  ...  ...  ...  .
CC92     ...  ...  ...  ...  ...  ...  ...  ...  ...  ...  .

GTAAGGGGCT  CACCATTTCC  AAATCTAAAG  TGGAGTCAGG
VHαTAG   ..........  ..........  ..........  ..........
CC46     ..........  ..........  ..........  ..........
CC49     ..........  ..........  ..........  ..........
CC83     ..........  ..........  ..........  ..........
CC92     ..........  ..........  ..........  ..........
```

FIG. 2D

```
           GCCTGAGGTG   ACAAAGATAT   CACCTTTGGC   TTTCCACAG
VHαTAG
CC46       ..........   ..........   ..........   ........
CC49       ..........   .......G..   ..........   .G......
CC83       ..........   ..........   ..........   ........
CC92       ..........   ..........   ..........   ........

GT  GTC CAC  TCC CAG GTT  CAG CTG CAG  TCT
VHαTAG
CC46       ..  ... ...  ... ..A T..  ... ..A ...  ...
CC49       ..  ... ...  ... ... ...  ..A T.. ...  ...
CC83       ..  ... ...  ... ... ...  ... T.. ...  ...
CC92       ..  ... ...  ... ... ...  ... ... ...  ...

GAC GCT GAG  TTG GTG AAA  CCT GGG GCT  TCA GTG
VHαTAG
CC46       ... ... ...  ... ... ...  ... ... ...  ... ...
CC49       ... ... ...  ... ... .G.  ... ... ...  ... ...
CC83       ... ... ...  ... ... ...  ... ... ...  ... ...
CC92       ... ... ...  ... ... ...  ... ... ...  ... ...
```

FIG. 2E

```
          AAG  ATA  TCC  TGC  AAG  TCT  GCT  AAG  TAC  GGC  ACC  TTC
VHαTAG    
CC46      ...  .T.  ...  ...  ...  ...  ...  ...  ...  ...  ...  ...
CC49      ...  .T.  ...  ...  ...  ...  ...  ...  ...  ...  ...  ...
CC83      ...  .T.  ...  ...  ...  ...  ...  ...  ...  ...  ...  ...
CC92      ...  ...  ...  ...  ...  ...  ...  ...  ...  ...  ...  ...

|←———————— CDR1 ————————→|
          ACT  GAC  CAT  GCT  ATT  CAC  TGG  GTG  AAG  CAG  AAG  AAG
VHαTAG    
CC46      ...  ...  ...  ..A  ...  ...  ...  ...  ...  ...  .A.  ..C
CC49      ...  ...  ...  ...  ...  ...  ...  ...  ...  ...  ...  ...
CC83      ...  ...  ...  ...  ...  ...  ...  ...  ...  ...  ...  ...
CC92      ...  ...  ...  ...  ...  ...  ...  ...  ...  ...  ...  ..A

|←———————— CDR2
          CCT  GAA  CAG  GGC  CTG  GAA  TGG  ATT  GGA  TAT  ATT
VHαTAG    
CC46      ...  ...  ...  ...  ...  ...  ...  ...  ...  ...  T..
CC49      ...  ...  ...  ...  ...  ...  ...  ...  ...  ...  T..
CC83      ...  ...  ...  ...  ...  ...  ...  ...  ...  ...  ...
CC92      ...  ...  ...  ...  ...  ...  ...  ...  ...  ...  ...

———————— CDR2 ——————————→|
          TCT  CCC  AAT  GGT  GAT  ATT  AAG  TAC  AAT  GAG
VHαTAG    
CC46      ...  ...  ...  .A.  ...  T..  .A.  ...  ...  ...
CC49      ...  ...  ...  .A.  ...  ...  ...  ...  ...  ...
CC83      ...  ...  ...  .A.  ...  ...  ...  ...  ...  ...
CC92      ...  ...  ...  ...  ...  ...  ...  ...  ...  ...
```

FIG. 2F

|  | | | | CDR2 → | | | | | | | | | | | |
|---|---|---|---|---|---|---|---|---|---|---|---|---|---|---|---|
| V$_H$αTAG | AAG | TTC | AAG | GGC | AAG | GCC | ACA | CTG | ACT | GCA | GAC |
| CC46 | . . G . | . . . . | . . . . | . . . . | . . . . | . . . . | . . . . | . . . . | . . . . | . . . . | . . . . |
| CC49 | . . . . | . . . . | . . . . | . . . . | . . . . | . . . . | . . . . | . . . . | . . . . | . . . . | . . . . |
| CC83 | . . . . | . . . . | . . . . | . . . . | . . . . | . . . . | . . . . | . . . . | . . . . | . . . . | . . . . |
| CC92 | . . . . | . . . . | . . . . | . . . T | . . . . | . . . . | . . . . | . . . . | . . . . | . . . . | . . . . |

| V$_H$αTAG | AAA | TCC | TCC | AGC | ACT | GCC | TAC | ATG | CAG | CTC | AAC |
| CC46 | . . . . | . . . . | . . . . | . . . T | . . . . | . . . . | . . . . | . . . . | . . . . | . . . . | . . . . |
| CC49 | . . . . | . . . . | . . . . | . . A . | . . . . | . . . . | . . . . | . G . . | . . . . | T . . . | . . . . |
| CC83 | . . . . | C . . . | . . . . | . . . . | . . . . | . . . T | . . . . | . . . . | . . A . | . . . . | . . . . |
| CC92 | . . . . | . . . . | . . . . | . . . . | . . . . | . . . . | . . . . | . . . . | . . . . | . . . . | . . . . |

| V$_H$αTAG | AGC | CTG | ACA | TCT | GAG | GAT | TCT | GCA | GTG | TAT | TTC |
| CC46 | . . . . | . . . . | . . . . | . . . . | . . . . | . . C . | . . . . | . . . . | . . . . | . . . . | . . . . |
| CC49 | . . . . | . . . . | . . . . | . . . . | . . . . | . . . . | . . . . | . . . . | . . . . | . . . . | . . . . |
| CC83 | . . . . | . . . . | . . . . | . . . . | . . . . | . . . . | . . . . | . . . . | . . . . | . . . . | . . . . |
| CC92 | . . . . | . . . . | . . . C | . . . . | . . . . | . . . . | . . . . | . . . . | . . . . | . . . . | . . . . |

FIG.2G

```
         TGT AAA AGA CACAGTGTTG TAACCACATC CTGAGTGTGT
VHαTAG
CC46     ... .CG G.C GGC TAC GGG GTT GCT TTC TGG GGC
CC49     ... ... .C. TCC CTG AAT ATG GCC TAC TGG GGT
CC83     ... ... .G. TCC TTC TAC GGC AAC --- TGG GGC
CC92     ... ... .C. TCT CTA TCC GGG AAC TCC TGG GGC
                                       |———CDR3———|

CAGAAATCCT GGGGGAGCAG AAAGATACAC TGGGACTGAG
VHαTAG
CC46     CAA GGG ACT CTG GTC ACT GTC TCT GCA G
CC49     CAA GGA ACC TCA GTC ACC GTC TCC TCA G
CC83     CAA GGC ACC ACC CTC ACA GTC TCC TCA G
CC92     CAG GGC ACC ACT CTC ACA GTC TCC TCA G

VHαTAG   AAGACAGAAA AATTAATCCT TAGACTTGCT CAGAAATCGT

VHαTAG   AATTTGAAT  GCCTATTTAT TTCATCTTGC TCACACACCT

VHαTAG   ATATTGCTTT TGTAAGCTT
```

FIG.3A

← 19 ———————————— LEADER PEPTIDE ———————————— 10 →

| | | | | | | | | | | |
|---|---|---|---|---|---|---|---|---|---|---|
| V$_H$αTAG | Met | Glu | Trp | Ser | Trp | Val | Phe | Leu | Phe | |
| CC46 | . | . | . | . | . | . | . | . | . | |
| CC49 | . | . | . | . | . | . | . | . | . | |
| CC83 | . | . | . | . | . | . | . | . | . | |
| CC92 | . | . | . | . | . | . | . | . | . | |

| | | | | | | | | | | |
|---|---|---|---|---|---|---|---|---|---|---|
| V$_H$αTAG | Leu | Ser | Val | Thr | Thr | Gly | Val | His | Ser | Gln |
| CC46 | . | . | . | . | . | . | . | . | . | . |
| CC49 | . | . | . | . | . | . | . | . | . | . |
| CC83 | . | . | . | . | . | . | . | . | . | . |
| CC92 | . | . | . | . | . | . | . | . | . | . |

10

| | | | | | | | | | | |
|---|---|---|---|---|---|---|---|---|---|---|
| V$_H$αTAG | Val | Gln | Leu | Gln | Gln | Ser | Asp | Ala | Glu | Leu |
| CC46 | Phe | . | . | . | . | . | . | . | . | . |
| CC49 | . | . | . | . | . | . | . | . | . | . |
| CC83 | . | . | . | . | . | . | . | . | . | . |
| CC92 | . | . | . | . | . | . | . | . | . | . |

FIG. 3B

|  | | | | | | | | | 20 | |
|---|---|---|---|---|---|---|---|---|---|---|
| V_H αTAG | Val | Lys | Pro | Gly | Ala | Ser | Val | Lys | Ile | Ser |
| CC46 | . | Arg | . | . | . | . | . | . | . | . |
| CC49 | . | . | . | . | . | . | . | . | . | . |
| CC83 | . | . | . | . | . | . | . | . | . | . |
| CC92 | . | . | . | . | . | . | . | . | . | . |

|  | | | | | | | | | 30 | ↓Asp |
|---|---|---|---|---|---|---|---|---|---|---|
| V_H αTAG | Cys | Lys | Ala | Ser | Gly | Tyr | Thr | Phe | Thr | Asp |
| CC46 | . | . | . | . | . | . | . | . | . | . |
| CC49 | . | . | . | . | . | . | . | . | . | . |
| CC83 | . | . | . | . | . | . | . | . | . | . |
| CC92 | . | . | . | . | . | . | . | . | . | . |

|  | | |←CDR1 | | | | | | 40 | |
|---|---|---|---|---|---|---|---|---|---|---|
| V_H αTAG | His | Ala | Ile | His | Trp | Val | Lys | Gln | Lys | Pro |
| CC46 | . | . | . | . | . | . | . | . | . | . |
| CC49 | . | . | . | . | . | . | . | . | . | . |
| CC83 | . | . | . | . | . | . | . | Asn | . | . |
| CC92 | . | . | . | . | . | . | . | . | . | . |

|  | | | | | | | | | ↓50 | |
|---|---|---|---|---|---|---|---|---|---|---|
| V_H αTAG | Glu | Gln | Gly | Leu | Glu | Trp | Ile | Gly | Tyr | Ile |
| CC46 | . | . | . | . | . | . | . | . | . | Phe |
| CC49 | . | . | . | . | . | . | . | . | . | Phe |
| CC83 | . | . | . | . | . | . | . | . | . | . |
| CC92 | . | . | . | . | . | . | . | . | . | . |

FIG. 3C

CDR2
                                              60
| | | | | | | | | | Ash |
|---|---|---|---|---|---|---|---|---|---|
| V_H αTAG | Ser | Pro | Gly | Asn | Gly | Asp | Ile | Lys | Tyr | Asn |
| CC46 | . | . | . | . | . | . | . | . | . | . |
| CC49 | . | . | . | . | Asp | . | Phe | . | . | . |
| CC83 | . | . | . | . | Asp | . | . | . | . | . |
| CC92 | . | . | . | . | Asp | . | . | . | . | . |

70
| | | | | | | | | | Thr |
|---|---|---|---|---|---|---|---|---|---|
| V_H αTAG | Glu | Lys | Phe | Lys | Gly | Lys | Ala | Thr | Leu | Thr |
| CC46 | . | . | . | . | . | . | . | . | . | . |
| CC49 | . | Arg | . | . | . | . | . | . | . | . |
| CC83 | . | . | . | . | . | . | . | . | . | . |
| CC92 | . | . | . | . | . | . | . | . | . | . |

80
| | | | | | | | | | Met |
|---|---|---|---|---|---|---|---|---|---|
| V_H αTAG | Ala | Asp | Lys | Ser | Ser | Ser | Thr | Ala | Tyr | Met |
| CC46 | . | . | . | . | . | . | . | . | . | . |
| CC49 | . | . | . | . | . | . | . | . | . | . |
| CC83 | . | . | . | Pro | . | Asn | . | . | . | Val |
| CC92 | . | . | . | . | . | . | . | Val | . | . |

FIG.3D

|  | | | | | | | | | | |
|---|---|---|---|---|---|---|---|---|---|---|
| V_H αTAG | Gln | Leu | Asn | Ser | Leu | Thr | Ser | Glu | Asp | Ser |
| CC46 | . | Phe | . | . | . | . | . | . | . | . |
| CC49 | . | . | . | . | . | . | . | . | . | . |
| CC83 | . | . | . | . | . | . | . | . | . | . |
| CC92 | . | . | . | . | . | . | . | . | . | . |

|  | | | 90 | | | | |
|---|---|---|---|---|---|---|---|
| V_H αTAG | Ala | Val | Tyr | Phe | Cys | | |
| CC46 | . | . | . | . | . | Lys | Arg |
| CC49 | . | . | . | . | . | Thr | Gly |
| CC83 | . | . | . | . | . | Arg | . |
| CC92 | . | . | . | . | . | Thr | . |

CDR3 (starting 105):

|  | | | | | | | 105 | | |
|---|---|---|---|---|---|---|---|---|---|
| CC46 | Gly | Tyr | Gly | Phe | Ala | Phe | Trp | Gly | Gln |
| CC49 | Ser | Leu | Asn | Met | Ala | Tyr | Trp | Gly | Gln |
| CC83 | Ser | Phe | Tyr | Gly | Asn | - | Trp | Gly | Gln |
| CC92 | Ser | Leu | Ser | Gly | Asn | Ser | Trp | Gly | Gln |

FIG. 3E

|  |  |  |  |  | 110 |  |  |  |
|---|---|---|---|---|---|---|---|---|
| CC46 | Gly | Thr | Leu | Val | Thr | Val | Ser | Ala |
| CC49 | Gly | Thr | Ser | Val | Thr | Val | Ser | Ser |
| CC83 | Gly | Thr | Thr | Leu | Thr | Val | Ser | Ser |
| CC92 | Gly | Thr | Thr | Leu | Thr | Val | Ser | Ser |

FIG.4A

| | | | | | | | | | | | | | | | |
|---|---|---|---|---|---|---|---|---|---|---|---|---|---|---|---|
| 1 | | | CC | CAC | TCT | CAC | ACA | CAC | GGC | ATT | TGC | TTT | TGT | ATT | 47 |
| 48 | TGG | ATC | CTG | CTT | TGC | ATA | GAC | CCC | CTA | ACC | CAG | CTG | CTC | AGA | 95 |
| 96 | TAT | AAA | CCA | GTA | TGA | ACT | GAG | CAT | GGC | ACA | GGC | AGG | GGA | AGC | 143 |
| 144 | ATG | GAT | TCA | CAG | GCC | CAG | GTT | ATT | ATG | CTG | TTA | CTA | TGG | GTA | 191 |
| 192 | GGT | GAG | AAA | TTT | AAA | AGT | ATT | ATC | TCA | GAG | TTA | CAC | CTT | TTT | 239 |
| 240 | TAA | GAA | ATT | TAT | ACT | TTG | AAG | ATT | GTA | ATA | TTA | CTT | CCA | TAA | 287 |
| 288 | CTC | TGA | CAA | CAA | GAC | TGC | ACA | GAC | CAT | GAC | AAA | TTT | CAA | CTG | 335 |
| 336 | TAA | TAA | TCT | ATT | TGT | ATT | GTA | TGT | CAT | TCA | TTT | CTA | CTT | ATT | 383 |
| 384 | GGT | ACC | TGT | GGG | GAC | GAG | AAG | ATG | ACT | TGG | CCA | TCC | AGT | CTA | 431 |
| 432 | GTG | TCA | GTT | TAT | AGT | AAT | GGT | GTT | CAG | ACT | AAG | GCC | TGG | CAG | 479 |
| 480 | CTT | TTA | TAT | GGG | TCT | CCT | GGT | CAA | ATT | AAG | TTG | TGG | GCA | CAG | 527 |
| 528 | AAA | CCA | CAG | GTC | CCT | GAT | AAA | AAA | CTG | TAC | ATT | TAC | TCC | GCT | 575 |
| 576 | GAA | TCT | GTC | TCC | ATC | AGC | CGC | AGT | GGC | ACA | CTG | GGA | TCC | ACA | 623 |
| 624 | TTC | ACT | TCC | CAG | TAT | AGC | AGT | GAA | TAT | ACA | TCT | GAC | TTC | GAT | 671 |
| 672 | TAC | TGT | CAG | CAG | TAT | AGC | AAG | CCC | CTC | ACG | TTC | GGT | GCT | TAT | 719 |
| 720 | AAG | CTG | GTG | AAA | CGT | AAG | GTT | CTC | ACT | CTC | TTT | TTT | GGG | ACC | 767 |
| 768 | TAA | GAC | ACA | GGT | TTT | CAT | GTT | TAT | | T | | | | | |

FIG. 4B

| VAL | SER |  | MET | ASP | SER | GLN | ALA | GLN | VAL | LEU | MET | LEU | LEU | LEU | LEU | TRP |
|---|---|---|---|---|---|---|---|---|---|---|---|---|---|---|---|---|
| PRO | VAL | GLY | THR | CYS | GLY//ASP | ILE | VAL | MET | SER | GLN | SER | PRO | SER | LEU | LEU | LEU |
| LEU | SER | SER | VAL | GLY | LYS | VAL | MET | LEU | SER | CYS | LYS | SER | SER | GLN | SER | SER |
| PRO | LEU | TYR | SER | GLY | ASN | LYS | THR | LEU | SER | ALA | TRP | TYR | SER | GLN | GLN | LYS |
| GLY | TYR | GLN | SER | PRO | GLN | LEU | ASN | TYR | TRP | ALA | SER | ALA | TYR | ARG | GLN | SER |
| SER | VAL | PRO | ASP | ARG | PHE | THR | ILE | TYR | SER | GLY | THR | ASP | ASP | PHE | GLU | LEU |
| ILE | PRO | ASP | SER | VAL | LYS | GLU | SER | GLY | ALA | VAL | TYR | TYR | CYS | PHE | THR | GLN |
| TYR | SER | SER | TYR | PRO/LEU | LEU | THR | THR | GLY | ALA | GLY | THR | LYS | LEU | VAL | LEU | LYS |

FIG. 5A

| | | | | | | | | | | | | | | | |
|---|---|---|---|---|---|---|---|---|---|---|---|---|---|---|---|
| 1 | CCT | AGA | GGC | CAG | CAC | AGC | TGC | CCA | TGA | TTT | ATA | AAC | CAG | GTC | TTT | GCA | 48 |
| 49 | GTG | AGA | TCT | CAA | ATA | CAT | CAG | ACC | AGC | ATG | GGC | ATC | AAG | ATG | GAG | ACA | 96 |
| 97 | CAT | TCT | CAG | GTC | TTT | GTA | TAC | ATG | TTG | CTG | TGG | TCT | TGT | GAG | A | 142 |
| 143 | CAT | TTA | AAA | GTA | TAA | AAT | CTT | AAA | AGT | AAT | TTG | CTA | TTT | GGT | TAG | CTT | 190 |
| 191 | TTT | CCT | ATA | GGA | AGC | CAA | TAT | CTT | TAG | AGT | GAC | CAA | ATT | AGA | TAA | GAC | 238 |
| 239 | ATT | TTG | GAT | TCT | AAC | ATT | TGT | ATC | AAG | GGT | TTA | TCT | TAT | GTG | TGA | GTT | 286 |
| 287 | TAT | ACA | CAT | TAT | CTG | TTT | CTG | TTT | CAA | GCA | GAA | GTT | GGA | GAC | ATT | GTG | 334 |
| 335 | ATG | ACC | CAG | TCT | CAC | AAA | TTC | ATG | TCC | TTT | TCA | GTG | GCA | GAC | AGG | GTC | 382 |
| 383 | AAC | ATC | ACC | TGC | AAG | GCC | AGT | CAG | TAT | CCT | AGC | GTG | ACT | GCT | GTA | GCC | 430 |
| 431 | TTT | CAG | CAT | AAA | CCA | GGT | CAG | TCT | CCT | GAT | AAA | CTA | CTG | ATT | TAC | GGG | 478 |
| 479 | TCC | ACC | CGG | CAC | ACT | GGA | GTC | AGT | GAT | CGC | AAT | AGC | GGT | TTC | AGG | GGA | 526 |
| 527 | GGG | ACA | GAT | TTC | ACT | CTC | ATC | CCT | AGC | AAT | GGC | GTG | CAG | GAG | GAC | TTG | 574 |
| 575 | GCA | GAT | TAT | TTG | TGT | CAG | CAT | TAT | AGC | TAT | CCA | TTC | TTT | TAC | GGC | GCA | 622 |
| 623 | TCG | ACA | ACA | AAG | TTG | GAA | ATA | AAA | CGT | AAG | AGT | ACG | CAT | TTC | TTG | GGC | 670 |
| 671 | CTT | GTG | ACG | TTT | TGG | TGG | TAG | AAA | AAG | GCT | CAT | TCT | TTT | ACT | GCT | TTA | |

FIG. 5B

| | | | | | | | |
|---|---|---|---|---|---|---|---|
| MET | GLY | ILE | LYS | MET | GLU | THR | HIS |
| TRP | LEU | SER | GLY | VAL | GLU | GLY // | ASP |
| MET | SER | ALA | SER | VAL | GLY | ASP | ARG |
| TYR | VAL | ALA | THR | ALA | VAL | ALA | TRP |
| LYS | LEU | LEU | ILE | TYR | GLY | ALA | SER |
| PHE | THR | GLY | SER | GLY | SER | GLY | THR |
| GLN | SER | GLU | ASP | LEU | ALA | ASP | TYR |
| PHE | THR | PHE | GLY | SER | GLY | THR | LYS |

| | | | | | | |
|---|---|---|---|---|---|---|
| SER | GLN | VAL | PHE | VAL | TYR | MET | LEU | LEU |
| ILE | VAL | MET | THR | GLN | SER | HIS | LYS | PHE |
| VAL | ASN | ILE | THR | CYS | LYS | ALA | SER | GLN |
| PHE | GLN | HIS | LYS | PRO | GLY | GLN | SER | PRO |
| THR | ARG | HIS | THR | GLY | VAL | PRO | ASP | ARG |
| ASP | PHE | THR | LEU | ILE | ILE | SER | ASN | VAL |
| LEU | CYS | GLN | HIS | TYR | SER | GLY | TYR | PRO / |
| LEU | GLU | ILE | LYS | | | | | |

FIG.6A

CC-92 Light Chain Variable Region Sequence

GAGTCACAGATCCAGGTCCTTTGTATTCGTGTTTCTGGTTGTCTGGTGTTGACGGAGACATTGTGATGACCCAGTCTCACAAATTCATGTCCACATCAGTAGGAGACAGGGTCAGCAT

CACCTGCAAGGCCAGTCAGGATGTGAGTAGTGCTGTAGGGTGGTTTCAACAGAAACCAGG

ACAATCTCCTAAATTACTGATTTATTCGGCATCCTACCGGTATACTGGAGTCCCTGATCGCTTCACTGGCAGTGGATCTCGGACGGATTTCACTTTCACCATCACCAGTGCAGGCTGAAGACCTGGCAGTTTATTACTGTCAGCAACATTATAGTAGTCCCGCTCACGTTCGGTGCTGGGACCAAGCTGGAGCTGAAAC

FIG.6B

```
Ser His Arg Ser Arg Ser Phe Val Phe Leu Trp Leu Ser Gly Val Asp Gly
Asp Ile Val Met Thr Gln Ser His Lys Ser Thr Ser Val Gly Asp Arg Val
Ser Ile Thr Cys Lys Ala Ser Gln Asp Ser Ser Val Gly Trp Phe Gln Gln
Lys Pro Gly Gln Ser Pro Lys Leu Ile Ser Ala Ser Tyr Arg Phe Thr Gly
Val Pro Asp Arg Phe Thr Gly Ser Gly Tyr Thr Tyr Thr Arg Tyr Ile Thr
Ser Val Gln Ala Glu Asp Leu Ala Asp Tyr Cys Phe His Phe Tyr Ser Pro
Leu Thr Phe Gly Ala Gly Thr Lys Leu Gln Tyr
```

```
AAGCTTTCGCCTACCCACTGCTCTGTTCCTCTTCAGTGAGGAGGGTTTTTGTACAGCCAG
ACAGTGGAGTACTACCACTGTGGTGGACGTTCGGTGGAGGCACCAAGCTGGAAATCAA
AC
GTAAGTAGAATCCAAAGTCTCTTTCTTCCGTTGTCTATGTCTGTGGCTTCTATGTCTAAA
AATGATGTATAAATCTTACTCTGAAACCAGATTCTGGCACTCTCCAAGGCAAAGATAC
A
GAGTAACTCCGTAAGCAAAGCTGGGAATAGGCTAGACATGTTCTCTGGAGAATGAATG
CC
AGTGTAATAATTAACACAAGTGATAGTTTCAGAAATGCTCAAAGAAGCAGGGTAGCCT
GC
CCTAGACAAACCTTTACTCGGTGCTCAGACCATGCTCAGTTTTTGTATGGGGGTTGAGTG
AAGGGACACCAGTGTGTGTACACGTTCGGAGGGGGGACCAAGCTGGAAATAAAACGT
AAG
TAGTCTTCTCAACTCTTGTTCACTAAGTCTAACCTTGTTAAGTTGTTCTTTGTTGTGTGT
TTTTCTTAAGGAGATTTCAGGGATTTAGCAAATTCCATTCTCAGATCAGGTGTTAAGGAG
GGAAAACTGTCCCACAAGAGGTTGGAATGATTTTCAGGCTAAATTTTAGGCTTTCTAAA
C
CAAAGTAACTAAACTAGGGGAAGAGGGATAATTGTCTACCTAGGGAGGGTTTTGTGGA
GG
TAAAGTTAAAATAAATCACTGTAAATCACATTCAGTGATGGGACCAGACTGGAAATAA
AA
CCTAAGTACATTTTTGCTCAACTGCTTGTGAAGTTTTGGTCCCATTGTGTCCTTTGTATG
AGTTTGTGGTGTACATTAGATAAATGAACTATTCCTTGTAACCCAAAACTTAAATAGAA
G
AGAACCAAAAATCTAGCTACTGTACAAGCTGAGCAAACAGACTGACCTCATGTCAGATT
T
GTGGGAGAAATGAGAAAGGAACAGTTTTTCTCTGAACTTAGCCTATCTAACTGGATCGC
C
TCAGGCAGGTTTTTGTAAGGGGGGCGCAGTGATATGAATCACTGTGATTCACGTTCGG
C
TCGGGGACAAAGTTGGAAATAAAACGTAAGTAGACTTTTGCTCATTTACTTGTGACGTT
T
TGGTTCTGTTTGGGTAACTTGTGTGAATTTGTGACATTTTGGCTAAATGAGCCATTCCTG
GCAACCTGTGCATCAATAGAAGATCCCCCAGAAAAGAGTCAGTGTGAAAGCTGAGCGA
AA
AACTCGTCTTAGGCTTCTGAGACCAGTTTTGTAAGGGGAATGTAGAAGAAAGAGCTGG
GC
TTTTCCTCTGAATTTGGCCCATCTAGTTGGACTGGCTTCACAGGCAGGTTTTTGTAGAGA
GGGGCATGTCATAGTCCTCACTGTGGCTCACGTTCGGTGCTGGGACCAAGCTGGAGCTG
A
AACGTAAGTACACTTTTCTCATCTTTTTTTATGTGTAAGACACAGGTTTTCATGTTAGGA
GTTAAAGTCAGTTCAGAAAATCTTGAGAAAATGGAGAGGGCTCATTATCAGTTGACGT
GG
CATACAGTGTCAGATTTTCTGTTTATCAAGCTAGTGAGATTAGGGGCAAAAAGAGGCTT
T
AGTTGAGAGGAAAGTAATTAATACTATGGTCACCATCCAAGAGATTGGATCGGAGAAT
AA
GCATGAGTAGTTATTGAGATCTGGGTCTGACTGCAG*
```

FIG. 7

FROM pNP9

```
5' - GGATCCTGGC    CAGCATTGCC    GCTAGGTCCC
     TCTCTTCTAT    GCTTTCTTTG    TCCCTCACTG
     GCCTCCATCT    GAGATAATCC    TGGAGCCCTA
     GCCAAGGATC    ATTTATTGTC    AGGGGTCTAA
     TCATTGTTGT    CACAATGTGC    CTGGTTTGCT
     TACTGGGGCC    AAGGGACTCT    GGTCACTGTC
     TCTGCAGGTG    AGTCCTAACT    TCTCCCATTC
     TAAATGCATG    TTGGGGGGAT    TCTGAGCCTT
     CAGGACCAAG    ATTCTCTGCA    AACGGGAATC
     AAGATTCAAC    CCCTTTGTCC    CAAAGTTGAG
     ACATGGGTCT    GGGTCAGGGA    CTCTCTGCCT
     GCTGGTCTGT    GGTGACATTA    GAACTGAAGT
     ATGATGAAGG    ATCTGCCAGA    ACTGAAGCTT
     GAAGTCTGAG    GCAGAATCTT    GTCCAGGGTC
     TATCGGACTC    TTGTGAGAAT    TAGGGGCTGA
     CAGTTGATGG    TGACAATTTC    AGGGTCAGTG
     ACTGTCAGGT    TTCTCTGAGG    TGAGGCTGGA
     ATATAGGTCA    CCTTGAAGAC    TAAAGAGGGG
     TCCAGGGGCT    TTTCTGCACA    GGCAGGGAAC
     AGAATGTGGA    ACAATGACTT    GAATGGTTGA
     TTCTTGTGTG    ACACCAAGAA    TTGGCATAAT
     GTCTGAGTTG    CCCAAGGGTG    ATCTTAGCTA
     AAAACCCACT    ATTGTGATTA    CTATGCTATG
     GACTACTGGG    GTCAAGGAAC    CTCAGTCACC
     GTCTCCTCAG    GTAAGAATGG    CCTCTCCAGG
     TCTTTATTTT    TAACCTTTGT    TATGGAGTTT
     TCTGAGCATT    GCAGACTAAT    CTTGGATATT
     TGCCCTGAGG    GAGCCGGCTG    AGAGAAGTTG
     GGAAATAAAT    CTGTCTAGGG    ATCTCAGAGC
     CTTTAGGACA    GATTATCTCC    ACATCTTTGA
     AAAACTAAGA    ATCTGTGTGA    TGGTGTTGGT
     GGAGTCCCTG    GATGATGGGA    TAGGGACTTT
```

FIG. 13A

```
GGAGGCTCAT    TTGAGGGAGA    TGCTAAAACA
ATCCTATGGC    TGGAGGGATA    GTTGGGGCTG
TAGTTGGAGA    TTTTCAGTTT    TTAGAATGAA
GTATTAGCTG    CAATACTTCA    AGGACCACCT
CTGTGACAAC    CATTTTATAC    AGTATCCAGG
CATAGGGACA    AAAAGTGGAG    TGGGCACTT
TCTTTAGATT    TGTGAGGAAT    GTTCCACACT
AGATTGTTTA    AAACTTCATT    TGTTGGAAGG
AGCTGTCTTA    GTGATTGAGT    CAAGGGAGAA
AGGCATCTAG    CCTCGGTCTC    AAAAGGGTAG
TTGCTGTCTA    GAGAGGTCTG    GTGGAGCCTG
CAAAAGTCCA    GCTTTCAAAG    GAACACAGAA
GTATGTGTAT    GGAATATTAG    AAGATGTTGC
TTTTACTCTT    AAGTTGGTTC    CTAGGAAAAA
TAGTTAAATA    CTGTGACTTT    AAAATGTGAG
AGGGTTTTCA    AGTACTCATT    TTTTTAAATG
TCCAAAATTT    TTGTCAATCA    ATTTGAGGTC
TTGTTTGTGT    AGAACTGACA    TTACTTAAAG
TTTAACCGAG    GAATGGGAGT    GAGGCTCTCT
CATACCCTAT    TCAGAACTGA    CTTTTAACAA
TAATAAATTA    AGTTTAAAAT    ATTTTTAAAT
GAATTGAGCA    ATGTTGAGTT    GAGTCAAGAT
GGCCGATCAG    AACCGGAACA    CCTGCAGCAG
CTGGCAGGAA    GCAGGTCATG    TGGCAAGGCT
ATTTGGGGAA    GGGAAAATAA    AACCACTAGG
TAAACTTGTA    GCTGTGGTTT    GAAGAAGTGG
TTTTGAAACA    CTCTGTCCAG    CCCCACCAAA
CCGAAAGTCC    AGGCTGAGCA    AAACACCACC
TGGGTAATTT    GCATTTCTAA    AATAAGTTGA
GGATTCAGCC    GAAACTGGAG    AGGTCCTCTT
TTAACTTATT    GAGTTCAACC    TTTTAATTTT
AGCTTGAGTA    GTTCTAGTTT    CCCCAAACTT
AAGTTTATCG    ACTTCTAAAA    TGTATTTAGA
ATTC-3'
```

| 239 | TTA | ACA | TAT | CAC | AGA | GTG | GAG | CAA | AAT | CAG | GGC | AAA | AAT | ATG | CTG | 286 |
|---|---|---|---|---|---|---|---|---|---|---|---|---|---|---|---|---|
| 287 | AGA | GAT | TTT | TCC | CTG | TCG | TTA | CAA | AAG | CAT | CTG | TCT | AGA | ATT | CAT | 334 |
| 335 | AAA | AAC | TTT | ATG | GGA | TAC | ATT | TCC | GAG | AGG | AAT | ATT | TGG | ACC | 382 |
| 383 | TGA | GCA | TCC | TGC | ATC | CCG | AGC | CAT | ATG | CAC | CTT | CTC | GCA | CAG | TTG | 430 |
| 431 | AAC | TAG | GTC | CTT | TAA | GAA | ATG | TGA | ACA | TCA | TGA | TAT | AAA | AAC | CAC | 478 |
| 479 | CCG | AGT | CTA | TGG | CAG | TAA | ATA | CAG | AGA | TCA | TAC | CAT | ACT | CTA | AAT | 526 |
| 527 | ATG | TGA | TCA | GTG | TCT | CCG | CAG | TCC | CTG | ACA | CTG | ACT | ACA | ACC | 574 |
| 575 | ATG | GAA | AGC | CCA | TGG | CTC | TTT | CTC | TTT | CTC | AGT | GTA | GGC | ACT | GGTA | 623 |
| 624 | AGG | GGC | TGG | TCA | TGG | CCA | AAT | CTA | TCC | AAG | TGG | GTC | CAG | CAG | TGA | 671 |
| 672 | CAA | AGA | TCA | TGT | CTT | CCA | CTG | GAG | TTG | ACA | GGT | CCT | TTC | CAC | CAG | 719 |
| 720 | TTG | CAG | CAG | TCT | GAC | GCT | GAG | GGC | TAC | GTG | AAA | TTC | ACT | GCA | ATT | 767 |
| 768 | ATT | TCC | TGC | AAG | TGC | TCT | GGC | TAC | ACC | TTC | GCA | ATT | TAT | CAC | 815 |
| 816 | TGG | GTG | AAA | CAG | AAC | CCT | GAA | CAG | GGC | CTG | GAA | TGG | ATT | GGA | TTG | 863 |
| 864 | <u>TCT</u> | <u>CCC</u> | <u>GGA</u> | <u>GAT</u> | <u>TTT</u> | <u>AAA</u> | <u>TAC</u> | <u>AAT</u> | <u>GAG</u> | <u>TTC</u> | <u>AAG</u> | <u>GGC</u> | <u>AAG</u> | 911 |
| 912 | <u>GCC</u> | <u>ACA</u> | <u>CTG</u> | <u>GAC</u> | <u>AAA</u> | <u>TCC</u> | <u>TCC</u> | <u>AGC</u> | <u>ACT</u> | <u>GCC</u> | <u>TAC</u> | <u>GTG</u> | <u>CAG</u> | <u>CTC</u> | 959 |
| 960 | <u>AAC</u> | <u>AGC</u> | <u>CTG</u> | <u>ACA</u> | <u>TCT</u> | <u>GAG</u> | <u>GAT</u> | <u>TCT</u> | <u>GCA</u> | <u>GTG</u> | <u>TAT</u> | <u>AGA</u> | <u>TCC</u> | 1007 |
| 1008 | <u>CTG</u> | <u>AAT</u> | <u>ATG</u> | <u>GCC</u> | <u>TAC</u> | <u>TGG</u> | <u>GGT</u> | <u>CAA</u> | <u>GGA</u> | <u>ACC</u> | <u>GTC</u> | <u>ACC</u> | <u>GTC</u> | <u>TCAG</u> | 1056 |

FIG. 17

| | | | | | | | | | | | |
|---|---|---|---|---|---|---|---|---|---|---|---|
| 478 | TTA | ACA | TAT | CAC | AGA | GTG | GAG | CAA | CAG | GGC | AAA | AAT | ATG | CTG | 525 |
| 526 | AGA | GAT | TTA | TCC | CTG | TCG | TTA | CAA | CCA | CTG | TCT | AGA | ATT | CAT | 573 |
| 574 | AAA | AAC | TTT | ATG | GGA | TAC | ATT | TCC | TCA | AAT | AGG | ATT | TGG | ACC | 621 |
| 622 | TGA | GCA | TCC | TGC | TGC | CCG | AGC | CAT | GTG | ACA | CTT | CTC | CAG | TTG | 669 |
| 670 | AAC | TAG | TCC | CTT | ATC | TAA | GAA | ATG | CAC | TAT | GCA | AAT | CAC | 717 |
| 718 | CCG | AGT | CTA | TGG | CAG | TAA | ATA | CAG | AGA | TCA | CAT | AAA | AAC | AAT | 765 |
| 766 | ATA | TGA | TCA | GTG | TCT | TCT | TAA | CTA | TCC | GAC | TCA | ACT | CTA | ACC | 813 |
| 814 | ATG | GAA | TGG | AGC | TGG | GTC | CCG | TTT | CTC | CTG | CTG | ACA | ACT | GGTA | 862 |
| 863 | AGG | GGC | TCA | CCA | AGC | TCT | AAT | CTA | TCC | AGT | GGC | CAG | CTG | TGA | 910 |
| 911 | CAA | AGA | TAT | CCA | TCT | TGG | CTT | TCC | ACA | CCT | TCC | GGC | AGT | CAG | 958 |
| 959 | TTG | CAG | CAG | TCT | GCT | GAG | GGC | TTG | GTG | GTG | GGG | TCC | TCA | AAG | 1006 |
| 1007 | ATT | TCC | TGC | AAG | CTT | TCT | TAC | ACC | GAC | GCT | CAT | GCT | ATT | CAC | 1054 |
| 1055 | TGG | GTG | AAG | CAG | CCT | GAA | GGC | CAG | GAA | TGG | ATT | GGA | TAT | ATT | 1102 |
| 1103 | TCT | CCC | GGA | AAT | GAT | GAC | ATT | AAA | TAC | AAT | GAG | AAG | TTC | GGC | AAA | AAG | 1150 |
| 1151 | GCC | ACA | CTG | ACT | GCA | GAC | AAA | TCC | TCC | AGT | ACT | TAC | ATG | AGA | CTC | 1198 |
| 1199 | AAC | AGC | CTG | ACA | TCT | GAG | GAT | TCT | GCA | TAT | TTT | TGT | AGA | CTC | 1246 |
| 1247 | TTC | TAC | GGC | AAC | TGG | CAA | GGC | ACC | CAA | CTC | ACA | TCC | TCA | G | |

FIG. 18

| MET | GLU | TRP | SER | TRP | VAL | PHE | LEU | PHE | LEU | SER | VAL | THR | THR |
|-----|-----|-----|-----|-----|-----|-----|-----|-----|-----|-----|-----|-----|-----|
| GLY | VAL | HIS | SER/GLN | VAL | VAL | LEU | LEU | GLN | SER | ASP | ALA | GLU | LEU |
| VAL | LYS | PRO | GLY | SER | VAL | LYS | LYS | GLN | CYS | LYS | ALA | SER | GLY |
| TYR | THR | PHE | THR | HIS | ALA | ILE | ILE | SER | VAL | LYS | ALA | ASN | PRO |
| GLU | GLN | GLY | LEU | TRP | ILE | GLY | HIS | TRP | PHE | PRO | GLN | ASN | ASP |
| ASP | PHE | LYS | TYR | ASN | ARG | PHE | TYR | PHE | SER | ALA | GLY | GLY | ASP |
| ASP | PHE | LYS | TYR | GLU | ARG | PHE | GLY | PHE | SER | ALA | GLY | ASN | ASP |
| ASP | PHE | LYS | TYR | ASN | ARG | PHE | TYR | PHE | SER | ALA | GLY | GLY | ASP |
| ALA | ASP | LYS | SER | SER | THR | ALA | ALA | GLY | LYS | LEU | THR | LEU | THR |
| ALA | GLU | LYS | ASP | SER | ALA | VAL | TYR | TYR | VAL | ARG | ASN | SER | LEU |
| THR | SER | GLU | ASP | ALA | ALA | TYR | THR | SER | CYS | ARG | SER | LEU | ASN |
| MET | ALA | TYR | TRP | GLN | GLY | THR | GLY | VAL | THR | VAL | SER | SER |     |

FIG. 19

| | | | | | | | | |
|---|---|---|---|---|---|---|---|---|
| MET | GLY | VAL | TYR | GLU | ASP | ALA | THR | TYR |
| GLU | VAL | LYS | THR | GLN | ILE | ASP | SER | GLY |
| TRP | HIS | PRO | PHE | GLY | LYS | LYS | GLU | ASN |
| SER | SER | GLY | THR | LEU | TYR | SER | ASP | TRP |
| TRP | //GLN | ALA | ASP | GLU | ASN | SER | SER | GLY |
| VAL | VAL | SER | HIS | TRP | GLU | SER | ALA | GLN |
| PHE | GLN | VAL | ALA | ILE | LYS | THR | VAL | GLY |
| LEU | LEU | LYS | ILE | GLY | PHE | ALA | TYR | THR |
| PHE | GLN | ILE | HIS | TYR | LYS | TYR | PHE | THR |
| PHE | GLN | SER | TRP | ILE | GLY | MET | CYS | LEU |
| LEU | SER | CYS | VAL | SER | LYS | GLN | ARG | THR |
| SER | ASP | LYS | LYS | PRO | ALA | LEU | ARG | VAL |
| VAL | ALA | ALA | GLN | GLY | THR | ASN | SER | SER |
| THR | GLU | SER | LYS | ASN | LEU | SER | PHE | SER |
| THR | LEU | GLY | PRO | ASP | THR | LEU | | | gamma-1

7.8 kb gamma-2

4.0 kb gamma-3

8.0 kb gamma-4

|  | | | | | | | | CDR 1 | | | | | | | |
|---|---|---|---|---|---|---|---|---|---|---|---|---|---|---|---|
|  | AAG | GCT | TCT | GGC | TAC | ACC | TTC | ACT | GAC | CAT | GCT | ATT | CAC | TGG | GTG | AAG |
| V$_H$αTAG | | | | | | | | | | | | | | | | |
| AHC46 | ... | ... | ..N | ... | ... | ... | ... | ... | ... | ... | ... | ... | ... | ... | ... | ... |
| AHC121 | ... | ... | .N. | ... | .N. | ... | ... | .N. | ... | .T. | ... | ... | ... | ... | ... | ... |
| AHC139 | ... | ... | ... | ... | ... | ... | ... | ... | ... | ... | ... | ... | ... | ... | ... | ... |
| AHC160 | ... | ... | ... | ... | ... | ... | ... | ... | ... | ... | ... | ... | ... | ... | ... | ... |

|  | CAG | AAG | CCT | GAA | CAG | GGC | CTG | GAA | TGG | ATT | GGA | TAT | ATT | TCT | CCC | GGA |
|---|---|---|---|---|---|---|---|---|---|---|---|---|---|---|---|---|
| V$_H$αTAG | | | | | | | | | | | | | | | | |
| AHC46 | . | | | | | | | | | | | | | | | |
| AHC121 | ... | ... | ... | ... | ... | ... | ... | ... | ... | ... | ... | ... | ... | ... | ... | ... |
| AHC139 | ... | | | | | | | | | | | | | | | |
| AHC160 | ... | | | | | | | | | | | | | | | |

FIG. 42C

|  |  |  |  | CDR 2 |  |  |  |  |  |  |  |  |  |
|---|---|---|---|---|---|---|---|---|---|---|---|---|---|
| V$_H$αTAG | AAT | GGT | GAT | ATT | AAG | TAC | AAT | GAG | AAG | TTC | AAG | GGC | AAG | GCC | ACA | CTG |
| AHC46 | ... | ... | ... | ... | ... | ... | ... | T.. | ... | ... | T.. | ... | N.. | ... | ... | ... |
| AHC139 | ... | ... | ... | ... | ... | ... | ... | ... | ... | ... | ... | ... | ... | ... | ... | ... |
| AHC160 | ... | ... | ... | ... | ... | ... | ... | ... | ... | ... | ... | ... | ... | ... | ... | ... |

| V$_H$αTAG | ACT | GCA | GAC | AAA | TCC | TCC | AGC | ACT | GCC | TAC | ATG | CAG | CTC | AAC | AGC | CTG |
|---|---|---|---|---|---|---|---|---|---|---|---|---|---|---|---|---|
| AHC46 | ... | ... | ... | .G. | ... | ... | ... | ... | ... | .N. | N.. | ... | ... | ... | ... | ... |
| AHC139 | ... | ... | ... | ... | ... | ... | ... | ... | ... | ... | ... | ... | ... | ... | ... | ... |
| AHC160 | ... | ... | ... | ... | ... | ... | ... | ... | ... | ..T | ... | ..A | ... | .G. | ... | ... |

|  |  |  |  |  |  |  |  |  |  |  |  | CDR 3 |  |  |
|---|---|---|---|---|---|---|---|---|---|---|---|---|---|---|
| V$_H$αTAG | ACA | TCT | GAG | GAT | TCT | GCA | GTG | TAT | TTC | TGT | AAA | AGA | TCG | GTC | AAT | GCT |
| AHC46 | ... | ... | ... | ... | ... | ... | ... | ... | ... | ... | ... | ... | TCC | CTG | GGA | CGT |
| AHC139 | ... | ... | ... | ... | ... | ... | ... | ... | ... | ... | ... | GCC | TCC | TAC | TAT | GGT |
| AHC160 | ... | ... | ... | ... | ... | ... | ... | ... | ... | ... | ... | ... | TCC | TAC | TAT | GGT |

| AHC46 | TTT | GAC | TAC | TGG | GGC | CAA | GGC | ACC | NCT | CTC | NNN | GTC | TCC | TCA |
|---|---|---|---|---|---|---|---|---|---|---|---|---|---|---|
| AHC139 | TTT | GAC | TAC | TGG | GGC | CAA | GGC | ACC | ACT | CTC | ACA | GTC | TCC | TCA |
| AHC160 | AAC | * | * | TGG | GGC | CAA | GGC | ACN | ACT | CTC | ACA | GTC | TCC | TCA |

FIG. 44

5' - AGCTTTCTGGGGCAGGCCAGGCCTGACCTTGGCTTTGGGCAGGGAGGGGCTAAGGTGA
GGCAGGTGGCGCCAGCAGGTGCACACCCAGGGCCTCTGCGCCTGGGCCCAGCTCTGTCCCACACC
CCTCGCGGACACAGTTAAGAACCCAGGGGCCTCTGCGCCTGGGCCCAGCTCTGTCCCACACC
GCGGTCACATGGCACCACCTCTCTTGCAGCCTCCACCAAGGGCCCATCGTCTTCCCCCT
GGCACCCCTCCTCCCGAAGAGCACCTCTGGGGCACAGCGGCCCTGGGCTGCCTGGTCAAGGA
CTACTTCCCCGAACCGGTGACGGTGTCGTGGAACTCTCAGGCGCCCTGACCAGCGGCGTGCA
CACCTTCCCGGCTGTCCTACAGTCCTCAGGACTCTACTCCCTCAGCGTGGTGACCGT
GCCCTCCCAGCAGCTTGGGCACCCAGAGACCTACATCTGCAACGTGAATCACAAGCCCAGCAA
CACCAAGGTGGACAAGAAAGTTGGTGAGACGCAGGCCAGCACAGAGGGGTGTCTGTGG
AAGCAGGCTCAGCGCTCCGTCTGCCTCTTCACCCGGAGCCTCTGGGCACAGCTAGGTGCCCCTAACC
CAAGCAGGCCCCGTCTGCCTTTTCCCAGGCTCTGGGCAGGCACAGCTAGGTGCCCCTAACC
GAGAGGGTCTTTCTGCACACAAGGGCCAGGTGCTCAGAGCCAAACTCTTCCACTCCCTCAGG
CAGGCCCTGCCCCTGACCTAAGCCACCCCAAAGGGCCAAAGCCCAAACTCTCCACTCCCTCAGCTCG
AGGACCCCTGCCCCTGACCCTCCCCAGATTCCAGTACCTCCCAGTAACTCTCCACTCCCTCAGCTCG
GACACCTTCTCTCCTCCCCAGATTCCACACATGGTGCCCAGTAGCCTGCATCCAGGACCAGCCCCAGCCG
CTTGTGACAAAACTCACACATGGTGCCCCATTCTCCTCAGCACCTGAACTCCTGGGGGACCGTCA
CCAGCTCAAGGCGGGACAGGTCCACCTCCATTCTCCTCAGCACCCTGATGATCTCCCGAGCCCTGAGTC
GGTGCTGACACGTCCACCTCCCCAAAACCCAAGGACACCCTCATGATCTCCCGAGCCCTGAGTC
GTCTTCCCTCTTCCCCCCAAAACCCAAGGACACCCTCATGATCTCCCGAGCCCTGAGTC
ACATGCGTGGTGGTGGACGTGAGCGTGCATAATGCCAAGACCCTGAGGTCAAGTTCAACTGGTACGTG
GACGGCGTGGAGGTGCATAATGCCAAGACCCTGAGGTCAAGTTCAACTGGTACGTG
TACCGGGTGGTCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCATCTCCAAAGCC
AAA - 3'

SEQUENCE 1

FIG.45

```
5' - AGCTTTCTGGGGCAGGCCAGGCCCTGACCCTTGGCTTTGGGCAGGGAGGGGCTAAGGTGA
     GGCAGGTGGCGCCAGCAGGTGCACAGCCCAGAGAGCCCAGACACTGGACGCTGAA
     CCTCGCGGACACAGTTAAGAACCCAGGGGGCCTCTGCGCCTCCAGCTCTGTCCCACACC
     GCGGTCACATGGCACCACCTCTCTTGCAGCCTCCACCAAGGCCCATGGTCTTCCCCT
     GGCACCCCTCCTCCAAGAGCACCCTGGGGGCACAGCCCCTGGGCTGCCTGGTCAAGGA
     CTACTTCCCCGAACCGGTGACGGTGTCGTGGAACTCTCAGGCGCCCTGACCAGCGCGTGCA
     CACCTTCCCGGCTGTCCTACAGTCCTCACCCAGAACGTGAATCACAAGCCCAGCAA
     GCCCTCCAGCTGTGGGCACCCAGGACCTACATCTGCAACGTGAATCACAAGCCCAGCAA
     CACCAAGGTGGACAAGAAAGTTGGTGAGAGGCCAGCATCCCGGCCTATGCAGCCCAGGCAG
     AAGCAGGCTCAGCGCTCCCTGCCCTCTTCACCCAGGCCTCCGCCCCAGTCCATGCTCAGG
     CAAGGCAGGCCCCGTCTGCTTTGCTTCCCAGGGCAGTGCAGACCTGGGCTAGGTGCCCTAACC
     GAGAGGGTCTCTGGCTTTGCTTCCCAGGGCAGTGCAGACCTGGGCTAGGTGCCCCTAACC
     CAGGCCCCTGCACACAAAGGGGCAGTGCCCACCCCCAAAGGCCAAGAGACCTCCACTCCGGG
     AGGACCCCTGCCCTCCCTGACCCCTAAGGCCCCAGATTCCAGTAACTCCCATTCTTCCCACCACTCCCCT
     GACACCTTCTCTCCTCCCTGCACACAAACTCACACACGCCCACCGTGCCCA - 3'
```

SEQUENCE 2

FIG. 46

5' - AGCTTTCTGGGGCAGGCCTGACTTTGGCTGGGGCAGGGAGGGGCTAAGGTGAC
GCAGGTGGCGCCAGCGCCAGGCGCCACACCCAATGCCCGTGAGCCCAGACACTGGACCCTGCC
TGGACCCTCGTGGATAGACAAGAACCGAGGGGCCTCTGCGCCCTGGCGCCCAGCTCTGTCC
CACACCGCAGTCACATGGCGCCATCTCTCTTGCAGCTTCCACCAAGGCCCATCGGTCTT
CCCCCTGGCGCCCTGCTCCAGGAGCACCCTCTGGGGCACAGCAGCCCTGGGCTGCCTGGT
CAAGGACTACTTCCCCGAACCGGTGACGGTGTCGTGGAACTCAGGCGCCCTGACCAGCGG
CGTGCACACCTTCCCGGCTGTCCTACAGTCCTCAGGACTCTACTCCCTCAGCAGCGTGGT
GACCGTGCCCTCCAGCAGCTTGGGCACCCAGACCTACACCTGCAACGTGAATCACAAGCC
CAGCAACACCAAGGTGGACAAGAGAGTT - 3'

SEQUENCE 3 phumCk

FAMILY OF HIGH AFFINITY, MODIFIED ANTIBODIES FOR CANCER TREATMENT

CROSS REFERENCE

The present application is divisional application from application U.S. Ser. No. 08/040,687, filed Mar. 31, 1993, which is a continuation-in-part of U.S. Ser. No. 07/424,362, filed Oct. 19, 1989 (now abandoned), which is a continuation-in-part of U.S. Ser. No. 07/261,942, filed Oct. 24, 1988 (now abandoned), which is a continuation of U.S. Ser. No. 07/259,943, filed Oct. 19, 1988 (now abandoned).

FIELD OF THE INVENTION

This invention relates to the field of immunoglobulin production and modifications to naturally occurring antibody amino acid sequences. Specifically, the invention relates to using recombinant DNA techniques to produce chimeric genes and to take advantage of these gene modification techniques to construct chimeric antibodies.

BACKGROUND OF THE INVENTION

Antibodies are specific immunoglobulin (Ig) polypeptides produced by the vertebrate immune system in response to challenges by foreign proteins, glycoproteins, cells, or other antigenic foreign substances. The sequence of events which permits the organism to overcome invasion by foreign cells or to rid the system of foreign substances is at least partially understood. An important part of this process is the manufacture of antibodies which bind specifically to a particular foreign substance. The binding specificity of such polypeptides to a particular antigen is highly refined, and the multitude of specificities capable of being generated by the individual vertebrate is remarkable in its complexity and variability. Millions of antigens are capable of eliciting antibody responses, each antibody almost exclusively directed to the particular antigen which elicited it.

Two major sources of vertebrate antibodies are presently utilized—generation in situ by the mammalian B lymphocytes, and generation in cell culture by B-cell hybrids. Antibodies are generated in situ as a result of the differentiation of immature B lymphocytes into plasma cells, which occurs in response to stimulation by specific antigens. In the undifferentiated B cells, the portions of DNA coding for the various regions on the immunoglobulin chains are separated in the genomic DNA. The sequences are assembled sequentially prior to expression. A review of this process has been given by Gough, *Trends in Biochem Sci,* 6:203 (1981).

The resulting rearranged gene is capable of expression in the mature B lymphocyte to produce the desired antibody. However, even when a particular mammal is exposed to only a single antigen a uniform population of antibodies does not result. The in situ immune response to any particular antigen is defined by the mosaic of responses to the various determinants which are present on the antigen. Each subset of homologous antibodies is contributed by a single population of B cells—hence in situ generation of antibodies is "polyclonal".

This limited but inherent heterogeneity has been overcome in numerous particular cases by use of hybridoma technology to create "monoclonal" antibodies in cell cultures by B cell hybridomas [See Kohler and Milstein, *Nature* 256:495–497 (1975)].

In this process, the relatively short-lived, or mortal, splenocytes or lymphocytes from a mammal which has been injected with antigen are fused with an immortal tumor cell line, thus producing hybrid cells or "hybridomas" which are both immortal and capable of producing the genetically coded antibody of the B cell.

The hybrids thus formed are segregated into single genetic strains by selection, dilution, and regrowth, and each strain thus represents a single genetic line. They therefore, produce antibodies which are assured to be homogeneous against a desired antigen. These antibodies, referencing their pure genetic parentage, are called "monoclonal".

Monoclonal antibodies with mono-specificity have greatly influenced immunology, and their usefulness has already been demonstrated in such sciences as biology, pharmacology, chemistry and others. Such monoclonal antibodies have found widespread use not only as diagnostics reagents [see, for example, *Immunology for the 80's,* Eds. Voller et al., MTP Press, Lancaster, (1981), but also therapy (see, for example, Ritz and Schlossman, *Blood,* 59:1–11, (1982)].

Monoclonal antibodies produced by hybridomas, while theoretically effective as discussed above and clearly preferable to polyclonal antibodies because of their specificity, suffer from an important disadvantage. In many applications, the use of monoclonal antibodies produced in non-human animals is severely restricted where the monoclonal antibodies are to be used in humans. Repeated injections of a "foreign" antibody in humans, such as a mouse antibody, may lead to harmful hypersensitivity reactions. Such a non-human derived monoclonal antibody, when injected into humans, causes a anti-nonhuman antibody (ANHA) response. For a discussion of a specific ANHA response caused by using murine-derived antibodies, human anti-mouse antibody (HAMA) response, see Shawler et al., *Journal of Immunology,* 135:1530–1535 (1985).

It is believed that animal immunoglobulins having human constant regions will generate less of an ANHA response when injected into humans than animal immunoglobulins having nonhuman constant regions. As such, monoclonal antibodies having good binding affinities for selected antigens and having human constant regions are thought to possess great potential utility for immunological diagnosis and therapy of human patients with cancer.

Various attempts have so far been made to manufacture human-derived monoclonal antibodies by using human hybridomas. For example, human-human hybridomas [Olsson et al., *Proc. Natl. Acad. Sci. (USA),* 77:5429 (1980)]; human-murine hybridomas [(Schlom et al., *Proc. Natl. Acad. Sci. (USA),* 77:6841 (1980)] and several other xenogenic hybrid combinations have been prepared. Human monoclonal antibodies have also been produced by transformation of lymphocytes using Epstein-Barr virus. However, such hybridomas may potentially harbor pathogenic human viruses. Alternatively, primary, antibody producing B cells have been immortalized in vitro by transformation with viral DNA. Unfortunately, yields of monoclonal antibodies from human hybridoma cell lines are relatively low (1 μg/mL in human compared to 100 μg/mL in mouse hybridomas), and production costs are high.

While human immunoglobulins are highly desirable in immunological diagnosis and therapy of human cancer patients, human hybridoma techniques have not yet reached the stage where human monoclonal antibodies with required antigenic specificities can be easily obtained. In addition, for obvious ethical reasons, researchers can not immunize human subjects with selected toxic or otherwise deleterious antigens to generate antibodies against the specific antigen.

This imposes great restrictions on immunological diagnosis and therapy of human patients.

No human antibody has been isolated which relatively strongly binds to TAG-72. Consequently, suitable antibodies must be engineered. The production of human-derived monoclonal antibodies is certainly possible, but is still inefficient in view of its low reproducibility and the other problems noted above. Consequently, most monoclonal antibodies are derived from non-human animals.

A monoclonal antibody which reacts with high binding affinity to human tumor antigens, but which is not recognized as a foreign substance by humans is highly desirable. A method to overcome this difficulty is to artificially create an antibody which is very similar to a human antibody and is not recognized as a foreign substance within the human body, i.e., a chimeric, or "humanized" antibody.

Typically in chimeric antibodies, the variable region of both light and heavy chains mimics the variable regions of antibodies derived from one species of mammals, while the constant portions are homologous to the sequences in antibodies derived from humans. One clear advantage to such chimeric forms is that, for example. the variable regions can conveniently be derived from presently known sources using readily available hybridomas of B cells from non-human host organisms in combination with constant regions derived from, for example, human cell preparations. While the specificity of the variable region is not affected by its source, the constant region being human, is less likely to elicit an immune response from a human subject when the antibodies are injected than would the constant region from a non-human source.

One known human tumor antigen is tumor-associated glycoprotein (TAG-72). TAG-72 is associated with the surface of certain tumor cells of human origin, specifically the LS174T tumor cell line. LS174T [American Type Culture Collection (herein ATCC) No. CL 188] is a variant of the LS180 (ATCC No. CL 187) colon adenocarcinoma line.

The karyotype of LS174T is similar to that of LS180 with a missing X chromosome in a majority of the cells. Data has been presented as described in Johnson et al., *Cancer Res.*, 46:850–857 (1986), to characterize the TAG-72 molecule as a mucin. This conclusion is based on the following observations: (a) TAG-72 has a high molecular weight ($>1\times10^6$) as shown by its exclusion from a Sepharose CL-4B column; (b) the density of TAG-72 determined by equilibrium centrifugation in CsCl was 1.45 gm/mL, indicating a heavily glycosylated glycoprotein; (c) TAG-72 demonstrates a change in migration after neuraminidase digestion, indicating that it is a heavily sialylated molecule with an abundance of O-glycosidically linked oligosaccharides characteristic of mucins; (d) blood group antigens commonly found on mucins are found on affinity-purified TAG-72; and (e) Chondroitinase ABC digestion had no effect on TAG-72, thus demonstrating that the TAG-72 epitope is not expressed on a chondroitin sulfate proteoglycan.

Numerous murine monoclonal antibodies have been developed which have binding specificity for TAG-72. One of these monoclonal antibodies, designated B72.3, is a murine IgG1 produced by hybridoma B72.3 (ATCC No. HB-8108). B72.3 is a first generation monoclonal antibody developed using a human breast carcinoma extract as the immunogen (see Colcher et al., *Proc. Natl. Acad. Sci. (USA)*, 78:3199–3203 (1981); and U.S. Pat. Nos. 4,522,918 and 4,612,282). As used herein, the expression "first generation monoclonal antibody" means a monoclonal antibody produced using, as the immunogen, a crude cell extract.

Other monoclonal antibodies directed against TAG-72 are designated "CC" (colon cancer). CC monoclonal antibodies are a family of second generation murine monoclonal antibodies. As used herein, the expression "second generation monoclonal antibody" means a monoclonal antibody produced using, as the immunogen, an antigen purified with a first generation monoclonal antibody. CC monoclonal antibodies were prepared using TAG-72 purified with B72.3. A discussion of the method for producing the CC antibodies is set forth in U.S. patent application 7-073,685 (U.S. patent application 7-073,685); the application was filed by Schlom et al. on Jul. 15, 1987 and is available to the public from the National Technical Information Service. Because of their relatively good binding affinities to TAG-72, the following CC antibodies have been deposited at the ATCC, with restricted access having been requested: CC49 (ATCC No. HB 9459); CC 83 (ATCC No. HB 9453); CC46 (ATCC No. HB 9458); CC92 (ATCC No. HB 9454); CC30 (ATCC No. HB 9457); CC11 (ATCC No. 9455); and CC15 (ATCC No. HB 9460).

U.S. patent application 7-073,685 teaches that the CC antibodies may be altered into their chimeric form by substituting, e.g., human constant regions (Fc) domains for mouse constant regions by recombinant DNA techniques known in the art. It is believed that the proposals set out in U.S. patent application 7-073,685 did not lead to an actual attempt to express any chimeric Ig polypeptide chains, nor to produce Ig activity, nor to secrete and assemble Ig chains into the desired chimeric Igs.

It is known that the function of an Ig molecule is dependent on its three dimensional structure, which in turn is dependent on its primary amino acid sequence. Thus, changing the amino acid sequence of an Ig may adversely affect its activity. Moreover, a change in the DNA sequence coding for the Ig may affect the ability of the cell containing the DNA sequence to express, secrete or assemble Ig.

Numerous articles confirm the fact that an antibody has a very complicated, a delicate three-dimensional structure. Dr. Kameyma Koh-Zoh commented, in an article in *Saibo Kogaku*, 4(12):1025–1035 (1985), in attempting to prepare a chimeric antibody to a melanoma antigen:

"Using a chimeric antibody purified by means of HPLC, its bindability to a purified melanoma antigen was measured, but regretfully, for the time being there could not be obtained results showing its binding activity. As causes, first, there is a possibility that the C region affected the steric structure of the V region caused by the changing the mouse IgM antibody to human IgG antibody."

Idiotypes are antigenic determinants that involve variable regions of heavy and light chains of immunoglobulin molecules. Isotypes and/or allotypes are antigenic determinants that are restricted to the constant regions of heavy chains. Attention is further directed to Morahan et al., *Nature*, 301:720–722 ((1983), which teach:

"The TI5 idiotype", defined by sera raised in A strain mice, or in rabbits, is considered identical to that expressed by the majority of BALB/c anti-PC antibodies. To define the idiotypic determinants (idiotopes) of which the TI5 idiotype is comprised, monoclonal anti-TI5 antibodies were used here to examine both serum and monoclonal anti-PC antibodies. The latter were found to differ from TI5 with respect to the idiotope defined by the monoclonal anti-idiotope antibody, 21A5, in that the '21A5 idiotope' was absent from anti-PC sera; of the monoclonal anti-PC antibodies examined, only those which were both TI5+ and of the IgA isotype seemed to express this idiotype fully. This result suggests that not only the V region, but also the constant region, of the immunoglobulin molecule can contribute to the formation of an idiotypic determinant. (emphasis added)

Nishinarita et al., *The Journal of Immunology*, 134(4): 2544–2549_ ((1985) teach:

Recently, Morahan et al. (12) described an anti-TI5 hybridoma antibody, 21A5, that identified an idiotypic determinant associated with TI5 Id and the IgA CH region . . . we have shown that NL24 binding to C3 is inhibited by not only PC-binding IgA and TI5 Id+MP, but also by numerous PC-binding hybridoma proteins (HP) and the IgA fraction of normal anti-PC antibodies of BALB/c mice and presumably other strains . . . The high frequency of C3–24 Id expression in IgA PC-binding MP and HP and in the IgA fraction if normal antibody of BALB/c mice suggest that isotype-restricted Id may not be an unusual occurrence. (emphasis added)

Clearly, based upon the teachings in the art, the influence of a homologous constant region to the three-dimensional conformation of a particular variable region is not predictable. In other words, the teachings of the prior art suggest that the binding ability of a particular antibody may be dependent upon the unique constant region associated therewith.

It is, therefore, not at all clear from the prior art that known recombinant DNA techniques will routinely produce a chimeric animal-human antibody from selected DNA sources that generate functional chimeric antibodies which bind specifically to selected human carcinomas and which reduce the initiation of ANHA side-effects when injected into humans.

Consequently, it is an object of the present invention to fuse genes coding for at least a part of an animal Ig which binds to human carcinomas expressing TAG-72 and genes coding for at least part of a human Ig. It is a further object of the invention to achieve expression of protein which can be secreted and assembled to give a functional chimeric antibody.

It is a still further object to provide an expression vector containing a DNA sequence which encodes antibodies and portions thereof which are directed against TAG-72.

It is also an object of the invention to provide cells transformed with expression vectors containing a DNA sequence which encodes antibodies and portions thereof which are directed against TAG-72.

Finally, it is an object of the present invention to provide novel antibodies for use in in vivo diagnostic assays; in vivo therapy; and radioimmunoguided surgery.

SUMMARY OF THE INVENTION

Surprisingly, the present invention is able to meet many of these above mentioned needs and provides a method for supplying the desired antibodies.

This invention concerns an antibody or antibody fragment comprising a variable region having a heavy chain ($V_H$), said $V_H$ being encoded by a DNA sequence effectively homologous to the $V_H\alpha$TAG germline gene ($V_H\alpha$TAG), wherein the variable region binds to TAG-72 at least 25 percent greater than the variable region of B72.3 binds to TAG-72, with the binding affinities of the antibody and B72.3 being measured by the same technique.

This invention also concerns a DNA sequence encoding at least a portion of an antibody heavy chain, said sequence comprising a DNA sequence segment being effectively homologous to the $V_H\alpha$TAG germline gene ($V_H\alpha$TAG), wherein the DNA sequence segment encodes at least a portion of a heavy chain variable region ($V_H$).

The invention includes the aforementioned antibody alone or conjugated to an imaging marker or therapeutic agent. The invention also includes a composition comprising the aforementioned antibody in unconjugated or conjugated form in a pharmaceutically acceptable, non-toxic, sterile carrier.

The invention is directed to a method for in vivo diagnosis of cancer which comprises administering to an animal a pharmaceutically effective amount of the aforementioned composition for the in situ detection of carcinoma lesions.

The invention is also directed to a method for intraoperative therapy which comprises (a) administering to an animal a pharmaceutically effective amount of the aforementioned composition, whereby the tumors are localized, and (b) excision of the localized tumors.

In other aspects, the invention is directed to expression vectors or plasmids capable of effecting the production of such aforementioned antibodies in suitable host cells. It also includes the host cells and cell cultures which result from transformation with these vectors.

BRIEF DESCRIPTION OF THE DRAWINGS

FIG. 2, i.e. FIGS. 2A–2G, illustrates the nucleotide sequences of $V_H\alpha$TAG $V_H$, CC46 $V_H$, CC49 $V_H$, CC83 $V_H$ and CC92 $V_H$.

FIG. 3, i.e. FIGS. 3A–3E, illustrates the amino acid sequences of $V_H\alpha$TAG $V_H$, CC46 $V_H$, CC49 $V_H$, CC83 $V_H$ and CC92 $V_H$.

FIG. 4A illustrates the nucleotide sequence and FIG. 4B illustrates the corresponding amino acid sequence of the CC49 $V_L$.

FIG. 5A illustrates the nucleotide sequence and FIG. 5B illustrates the corresponding amino acid sequence of the CC83 $V_L$.

FIG. 6A illustrates the nucleotide sequence and FIG. 6B illustrates the corresponding amino acid sequence of the CC92 $V_L$.

FIG. 7 illustrates the nucleotide sequence of the Hind III-Pst I fragment isolated from the plasmid pGD1.

FIG. 13 including FIGS. 13A–13B illustrates the nucleotide sequence of the Eco RI-Bam HI fragment isolated from the plasmid pNP9.

FIG. 16 shows the nucleotide sequence of CC49 $V_H$, with the underlined segments showing the sequences derived using oligonucleotide primers on mRNA.

FIG. 17 shows the nucleotide sequence of CC83 $V_H$, with the underlined segments show the sequences derived using oligonucleotide primers on mRNA.

FIG. 18 shows the amino acid sequence of CC49 $V_H$, with the underlined segments show the sequences determined by protein sequencing.

FIG. 19 shows the amino acid sequence of CC83 $V_H$, with the underlined segments show the sequences determined by protein sequencing.

FIG. 21, i.e.

FIG. 42, i.e. FIGS. 42A–42B illustrates the partial nucleotide sequences of heavy chain variable regions of several antibodies derived from $V_H\alpha TAG$: AHC46, AHC121, AHC139, AHC160.

FIG. 44 illustrates the heavy chain constant region sequence of Ch44-CH3-: a constant region of the human γ1 heavy chain with removed CH3 domain.

FIG. 45 illustrates the heavy chain constant region sequence of Ch44-F(ab')2: a constant region of he human γ1 heavy chain with removed CH2 and CH3 domains.

FIG. 46 illustrates the heavy chain constant region sequence of Ch44-Fab: a constant region of the human γ3 heavy chain with a removed hinge region and CH2 and CH3 domains.

DETAILED DESCRIPTION

The immunoglobulins of this invention have been developed to address the problems of murine monoclonal antibodies disclosed in the prior art. Each is characterized by having a chimeric structure composed of a heavy chain variable region encoded by DNA derived from the $V_H\alpha TAG$.

Definitions

As used herein, "immunoglobulin" refers to a tetramer or aggregate thereof whether or not specific immunoreactive activity is a property. "Antibodies" refers to such assemblies which have significant known specific immunoreactive activity to an antigen, comprising light and heavy chains, with or without covalent linkage between them; "Non-specific immunoglobulin" ("NSI") means those immunoglobulins which do not possess known specificity to an antigen.

Figure 1:
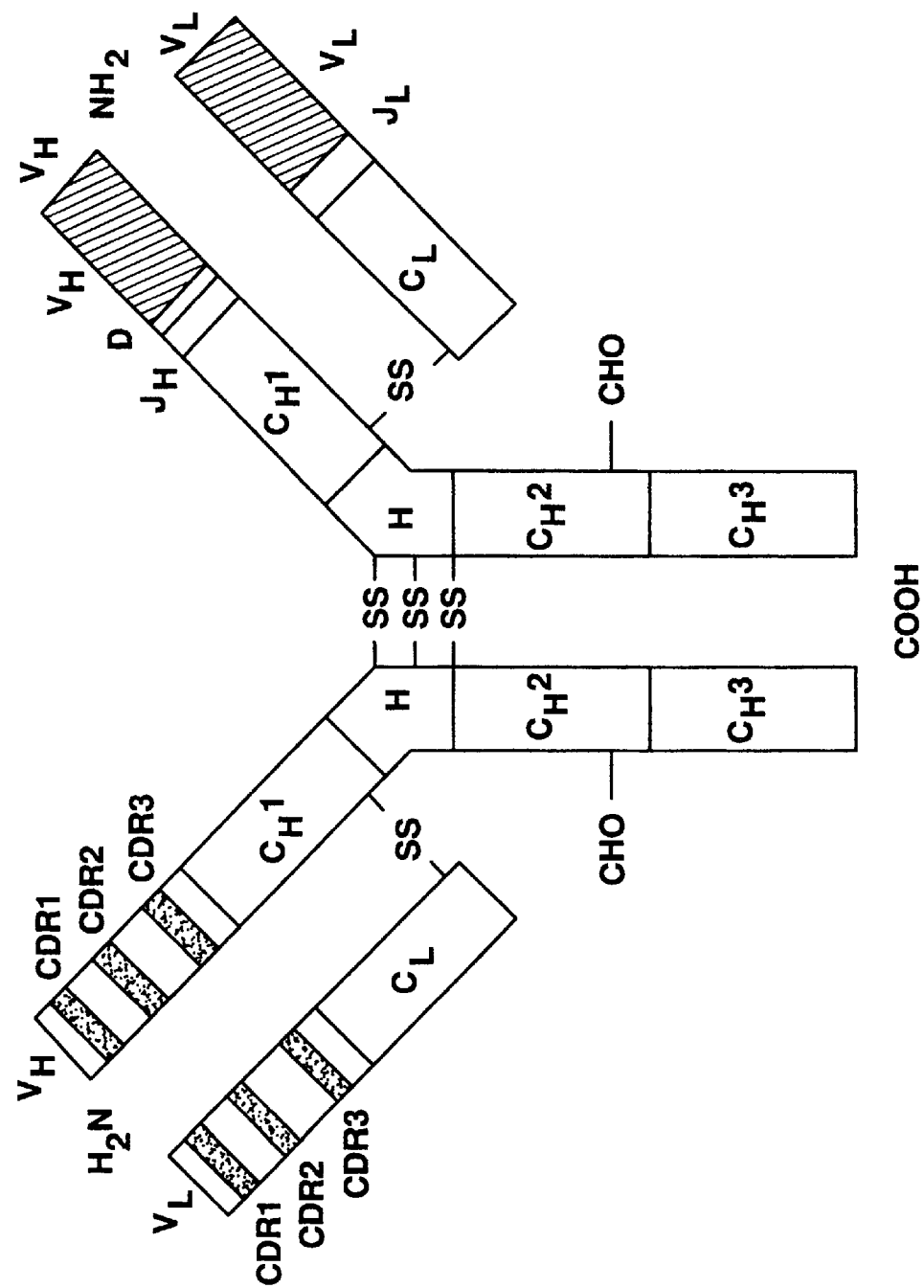
FIG. 1 illustrates a basic immunoglobulin structure, with the enzymatic cleavage sites being indicated.

The basic immunoglobulin structural unit in vertebrate systems is relatively well understood (Edelman, *Ann. N.Y. Acad. Sci.*, 190:5 (1971)). As seen in FIG. 1, the units are composed of two identical light polypeptide chains of molecular weight approximately 23,000 daltons, and two identical heavy chains of molecular weight 53,000–70,000. The four chains are joined by disulfide bonds in a "Y" configuration wherein the light chains bracket the heavy chains starting at the mouth of the "Y" and continuing through the diversity region.

Heavy chains are classified as gamma, mu, alpha, delta, or epsilon, with some subclasses among, them. The nature of this chain, as it has a long constant region, determines the "class" of the antibody as IgA, IgD, IgE IgG, or IgM.

Light chains are classified as either kappa (κ) or lambda (λ). Each heavy chain class may be bound with either a kappa or lambda light chain. In general, the light and heavy chains are covalently bonded to each other, and the "tail" portions of the two heavy chains are bonded to each other by covalent disulfide linkages when the immunoglobulins are generated either by hybridomas or by B cells. However, if non-covalent association of the chains can be effected in the correct geometry, the aggregate of non-disulfide-linked chains will still be capable of reaction with antigen.

The amino acid sequences run from an N-terminus at the forked edges of the Y to the C-terminus at the bottom of each chain. At the N-terminus is a variable region and at the C-terminus is a constant region.

The terms "constant" and "variable" are used functionally. The variable regions of both the light ($V_L$) and heavy ($V_H$) chains determine binding recognition and specificity to the antigen. The constant region domains of the light ($C_L$) and heavy ($C_H$) chains confer important biological properties such as antibody chain association, secretion, transplacental mobility, complement binding, and the like.

The variable region is linked in each chain to the constant region by a linkage linking the V gene sequence and the C gene sequence. The linkage occurs at the genomic level, combining nucleotide sequences via recombination sites. The linking sequence is known as a "J" sequence in the light chain gene, which encodes about 12 amino acids, and as a combination of a "D" sequence and a "J" sequence in the heavy chain gene, which together encode approximately 25 amino acids.

"Chimeric antibody" for purposes of this invention refers to an antibody having in the heavy chain a variable region amino acid sequence encoded by a nucleotide sequence derived from a murine germline gene and a constant region amino acid sequence encoded by a nucleotide sequence derived from a human gene.

However, the present invention is not intended to be narrowly limited to merely substituting human C gene sequences encoding immunoglobulin constant regions for murine C gene sequences encoding immunoglobulin constant regions. Thus, the present invention is not limited to whether or not the fusion point is at the variable/constant boundary.

Through various techniques, it is now possible to produce altered chimeric antibodies, composite chimeric antibodies, and fragmented chimeric antibodies encoded by nucleotide sequences disclosed herein.

"Composite" immunoglobulins comprise polypeptide variable regions not hitherto found associated with each other in nature. It is not critical whether any of the above are covalently or non-covalently aggregated, so long as the aggregation is capable of selectively reacting with a particular antigen or antigen family.

"Altered antibodies" means antibodies wherein the amino acid sequences, particularly in the variable region, has been varied. Because of the relevance of recombinant DNA techniques to this invention, one need not be confined to the amino acid sequences of antibodies selected from natural sources; amino acid sequences of the antibodies can be redesigned to obtain desired characteristics. The possible variations are many and range from the changing of just one or a few amino acids to the complete redesign of an antibody variable and/or constant region.

Changes in the variable region will be made in order to improve the antigen binding characteristics. Changes in the constant region will, in general, be made in order to improve the cellular process characteristics, such as complement fixation, interaction with membranes, and other effector functions. Alterations, can be made by standard recombinant techniques and also by oligonucleotide-directed mutagenesis techniques [Dalbadie-McFarland, et al. *Proc. Natl. Acad. Sci (USA)* 79:6409 (1982)].

"Fragments" of immunoglobulins include segments of proteolytically-cleaved or recombinantly-prepared portions of an antibody molecule that are capable of selectively reacting with a particular antigen or antigen family. Non-limiting examples of such proteolytic and/or recombinant fragments include "Fab", "F(ab')$_2$,", and "Fab'", with their proteolytic cleavage sites being shown in FIG. 1; as well as "Fv" fragment. Recombinant techniques for producing Fv fragments are set forth in WO 88/01649, WO 88/–06630, WO 88/07085, WO 88/07086, and WO 88/09344. By a "$V_H$" fragment is meant that the variable region has at least a portion of a heavy chain variable region capable of being used as an antigen binding functionality. The preparation and use of a light chain variable region ($V_L$) as an antigen binding functionality is set forth in an article entitled "Development of Biologically Active Peptides Based on Antibody Structure" by Williams et al. is set forth in *Proc. Natl. Acad. Sci. (USA)* 86:5537–5541 (1989).

In this invention, "animals" is meant to include primates, bovines, porcine, and rodents, etc.

"Expression vector" is given a functional definition, and any DNA sequence which is capable of effecting expression of a specified DNA code in a suitable host is included in this term. As at present, such vectors are frequently in the form of plasmids, thus "plasmid" and "expression vector" are often used interchangeably. However, the invention is intended to include such other forms of expression vectors which serve equivalent functions and which may, from time to time, become known in the art.

"Transformation" refers to the introduction of DNA into a recipient host cell that changes the genotype and consequently results in a change in the recipient cell.

"Host cells" refers to cells which have been recombinantly transformed with vectors constructed using recombinant DNA techniques. As defined herein, the antibody or modification thereof produced by a host cell is by virtue of this transformation.

In descriptions of processes for isolation of antibodies from recombinant hosts, the terms "cell" and "cell culture" are used interchangeably to denote the source of antibody unless it is clearly specified otherwise. In other words, recovery of antibody from the "cells" may mean either from spun down whole cells, or from the cell culture containing both the medium and the suspended cells.

Abbreviations

Nucleic acids, amino acids, peptides, protective groups, active groups and so on, when abbreviated, are abbreviated according to the IUPACIUB (Commission on Biological Nomenclature) or the practice in the fields concerned. The following are examples.

Reagents

EDTA: Ethylenediaminetetraacetic acid

SDS: Sodium dodecylsulfate

Nucleic Acids

RNA: Ribonucleic acid DNA: Deoxyribonucleic acid

| Nitrogenous Bases | |
| --- | --- |
| Purines | Pyrimidines |
| A: Adenine | T: Thymine |
| G: Guanine | C: Cytosine |
|  | U: Uracil |

Both DNA and RNA contain long chains of phosphoric acid, a sugar, and nitrogenous bases. DNA is a double stranded helix, wherein the sugar is 2-deoxyribose, whereas RNA is single stranded, wherein the sugar is D-ribose. The four nitrogenous bases which characterize DNA nucleotides are linked in complementary pairs by hydrogen bonds to form the double helix of DNA: adenine is linked to thymine and guanine is linked to cytosine. In RNA, uracil is substituted for thymine in the listed DNA pairs.

| Amino Acids | |
| --- | --- |
| Gly: glycine | Phe: phenylalanine |
| Ala: alanine | Tyr: tyrosine |
| Val: valine | Thr: threonine |
| Leu: leucine | Cys: cysteine |
| Ile: isoleucine | Met: methionine |
| Ser: serine | Glu: glutamic acid |
| Asp: aspartic acid | Trp: tryptophan |
| Lys: lysine | Pro: proline |
| Arg: arginine | Asn: asparagine |
| His: histidine | Gln: glutamine |

Variable Region

The DNA encoding the heavy chain consists of a $V_H$ gene sequence, a $D_H$ gene sequence, and a $J_H$ gene sequence. The DNA encoding the light chain consists of a $V_L$ gene sequence, and a $J_L$ gene sequence.

$V_H$ Gene Sequence

The present invention is directed to selected chimeric antibodies having the $V_H$ region encoded by a DNA sequence derived from a germline gene that is specifically reactive against TAG-72 ($V_H \alpha$TAG), the sequence of which is set forth in FIG. 2 (SEQ ID NO: 1). The chimeric antibodies are selected on the basis of their ability to bind TAG-72, namely wherein the variable region binds to TAG-72 at least 25 percent greater than the variable region of B72.3 binds to TAG-72. Generally, the binding affinities of the chimeric antibody and B72.3 are measured by the same technique. Exemplary techniques for measuring antibody binding affinity are set forth in the following references: Scatchard, *Annals of the N.Y. Acad. of Sciences* 51:660 (1949); Steward and Petty, *Immunology,* 23:881 (1972); Muraro et al., *Cancer Research,* 48:4588 (1988); and Heyman, *J. of Immunol. Methods,* 68:193–204 (1984).

A skilled artisan will appreciate that, as a result of the inventors' discovery, namely the nucleotide sequence of (and amino acid sequences encoded by) the $V_H \alpha$TAG, the present invention is intended to include effectively homologous nucleotide sequences and corresponding amino acid sequences. "Effectively homologous" refers to identity or near identity of nucleotide or amino acid sequences. Thus, in this disclosure it will be understood that minor sequence variation can exist within homologous sequences and that any sequences exhibiting at least 80 percent homology are deemed equivalent.

Homology is expressed at the fraction or percentage of matching bases (or amino acids) after two sequences (possibly of unequal length) have been aligned. The term alignment is used in the sense defined by Sankoff and Kruskal in Chapter One of their book, *The Time Warps, String Edits, and Macromolecules: The Theory and Practice of Sequence Comparison,* Addison-Wesley, Reading, Mass., USA, (1983). Roughly, two sequences are aligned by maximizing the number of matching bases (or amino acids) between the two sequences with the insertion of a minimal number of "blank" or "null" bases into either sequence to bring about the maximum overlap.

As is understood in the art, nucleotide mismatches can occur at the third or wobble base in the codon without causing amino acid substitutions in the final polypeptide sequence. Also, minor nucleotide modifications (e.g., substitutions, insertions or deletions) in certain regions of the gene sequence can be tolerated and considered insignificant whenever such modifications result in changes in amino acid sequence that do not alter functionality of the final product. It has been shown that chemically synthesized copies of whole, or parts of, gene sequences can replace the corresponding regions in the natural gene without loss of gene function.

Homologs of specific DNA sequences may be identified by those skilled in the art using the test of cross-hybridization of nucleic acids under conditions of stringency as is well understood in the art [as described in *Nucleic Acid Hybridization,* Hames and Higgens (eds.), IRL Press, Oxford, UK (1985)]. Given two sequences, algorithms are available for computing their homology: e.g. Needleham and Wunsch, *J. Mol. Biol.,* 48:443–453 (1970); and Sankoff and Kruskal (183), supra. Also, commercial services are available for performing such comparisons, e.g. Intelligenetics, Inc. (Palo Alto, Calif., USA).

$D_H$ and $J_H$ Gene Sequences

The $D_H$ and $J_H$ gene segments exist in various types, although the type of D or J gene segment selected is not critical to the invention. That is the $D_H$ and $J_H$ may be derived from any animal. Preferred animals include mice and humans. Obviously, human $D_H$ and/or $J_H$ gene segments are particularly preferred, but the invention is not so limited if a D or J gene segment from another animal species provides an important property, i.e., increased binding to TAG-72.

Exemplary murine $D_H$ and $J_H$ sequences are set forth in Kurosawa and Tonegawa, *J. Exp. Med.,* 155:201 (1982); and Gough and Bernard, *Proc. Natl. Acad. Sci.* (*USA*), 78:509 (1981).

Exemplary human $D_H$ and $J_H$ sequences are set forth in Siebenlist et al., *Nature,* 294:631 (1981); and exemplary human $J_H$ sequences are set forth in Ravetch et al., *Cell,* 27:583 (1981).

$V_L$ and $J_L$ Gene Sequences

Generally, any $V_L$ and $J_L$ gene sequences may be employed that encodes a portion of a $V_L$ which is complementary to the $V_H$ encoded by a nucleotide sequence effectively homologous to $V_H \alpha$TAG. By "complementary" means a $V_L$ that binds to the $V_H$ and which yields an antibody variable region having a binding affinity of at least 25 percent more than B72.3, as measured by any standard technique for measuring binding affinity constants.

The type of $V_L$ and $J_L$ gene segment selected is not critical to the invention. That is the $V_L$ and $J_L$ may be derived from any animal. Preferred animals include mice and humans. Obviously, human $V_L$ and/or $J_L$ gene segments are particularly preferred, but the invention is not so limited if a $J_L$ gene segment from another species provides an important property, i.e., increased binding to TAG-72.

Murine $J_L$ sequences are set forth in Max et al., *J. Biol. Chem.,* 256:5116–5120 (1981). Human $J_L$ sequences are set forth in Heiter et al., *The Journal of Biological Chemistry,* 357(2):1516–1522 (1982).

Derivation of Variable Regions

Given the above teachings, it now becomes possible to derive numerous specific embodiments of antibody variable regions within the scope of the present invention, i.e., having effectively homologous $V_H$ sequences to $V_H \alpha$TAG and binding to TAG-72 at least 25 percent greater than the variable region of B72.3 binds to TAG-72, with the binding affinities of the antibody and B72.3 being measured by the same technique. Several nonlimiting techniques are set forth below.

Naturally-Produced Variable Regions

In response to an immunogen, TAG-72, an immunized animal will expand selected antibody-producing B cells. The variable region of antibodies produced by the B cells will be encoded by rearranged germline heavy and light chain DNA. For example, the rearranged germline heavy chain will include the V, D, and J gene segments including the leader sequence, as well as any introns which may be subsequently removed. The light chain coding DNA will include the V and J gene segments including the leader sequence, as well as any introns which may be subsequently removed.

Variability may result from somatic mutations occurring in a B cell during productive rearrangement of the $V_H \alpha$TAG. These somatic mutations are nucleotide changes that may or may not result in an amino acid change that alters the activity toward TAG-72 of the productively rearranged $V_H$.

Screening Techniques

Monoclonal or polyclonal antibodies may be screened to determine which of said antibodies selectively bind to TAG-72. Such screening may be accomplished by any of a number of well-known procedures, such as solid-phase radioimmunoassay, enzyme-linked immunosorbent assays, rosetting assays, blocking assays, and the like. The above-described procedures are well-known in the art.

The nucleotide sequences encoding variable regions of antibodies produced from the productive rearrangement of the $V_H\alpha TAG$ have now been obtained. In addition to the nucleotide sequence of $V_H\alpha TAG$, FIGS. 2A–2G also show the nucleotide sequences encoding the heavy chain variable regions of CC46, CC49, CC83 and CC92 antibodies (SEQ ID NO: 7, SEQ ID NO: 3, SEQ ID NO: 5, and SEQ ID NO: 9, respectively). FIGS. 3A–3B (SEQ ID NO: 2, SEQ ID NO: 8, SEQ ID NO: 4, SEQ ID NO: 6 and SEQ ID NO: 10, respectively) show the amino acid sequences of $V_H\alpha TAG$ $V_H$, CC46 $V_H$, CC49 $V_H$, CC83 $V_H$, and CC92 $V_H$, corresponding to the nucleotide sequences set forth in FIGS. 2A–2G.

The relative similarity of the DNA encoding the CC46 $V_H$, CC49$_H$, CC83 $V_H$, and CC92 $V_H$ regions, particularly in the 5' flanking segment, proves that those DNA sequences are derived from $V_H\alpha TAG$. Somatic mutations occurring during productive rearrangement of the $V_H$ region gene to be expressed in a B cell give rise to some nucleotide changes that may or may not result in a homologous amino acid change between two productively rearranged $V_H\alpha TAG$ producing hybridomas.

The nucleotide sequences and corresponding amino acid sequences of CC49 $V_L$ are shown in FIGS. 4A and 4B (SEQ ID NO: 11 and SEQ ID NO: 12, respectively). The nucleotide sequences and corresponding amino acid sequences of CC83 $V_L$ are shown in FIGS. 5A and 5B, respectively (SEQ ID NO: 13 and SEQ ID NO: 14, respectively. The nucleotide sequences and corresponding amino acid sequences of CC92 $V_L$ are shown in FIGS. 6A and 6B, respectively.

Probe Techniques

Other antibodies encoded by DNA derived from $V_H\alpha TAG$ may be derived by using $V_H\alpha TAG$ as a hybridization probe. Generally, a probe made from the DNA or RNA of the $V_H\alpha TAG$ or rearranged genes containing the recombined $V_H\alpha TAG$ could be used to find homologous genes in unknown hybridomas to those skilled in the art. This essentially provides a prototype sequence for a starting point in discovering antibody variable region genes derived from the same germline gene, i.e., a "subset". Such homologous antibodies will have a DNA sequence whose mRNA hybridizes with the probe of all or a part of the $V_H\alpha TAG$ germline gene and its flanking regions. By "flanking regions" is meant to include those DNA sequences from the 5' end of the $V_H\alpha TAG$ to the 3' end of the upstream gene, and from 3' end of the $V_H\alpha TAG$ to the 5' end of the downstream gene.

The subject method may be used for the detection of specific sequences of nucleic acids from a wide variety of sources. The target sequence can be any whole or portion of genomic material, or nucleic acid gene product such as messenger RNA. Any source of nucleic acid, in purified or nonpurified form, can be utilized provided it contains or is suspected of containing the 5' nontranslated region of interest.

The probes may comprise a probe region, that is a nucleotide sequence which is complementary to a target sequence; and a non-probe region, that is, a nucleotide sequence which is not complementary to the target sequence. The probe need not be a single continuous polynucleotide segment, but may be comprised of two or more individual segments. Moreover, a single probe sequence may be interrupted by noncomplementary sequences. It will be understood that the probe may refer to more than one polynucleotide, particularly in the case where there is some ambiguity in the information regarding the 5' nontranslated region. Probes may be single stranded or double stranded DNA or RNA.

There are a number of ways in which a probe sequence can be selected. It is only necessary that a number of bases in the 5' nontranslated region be known in sufficient detail that a probe can be produced so as to identify such a unique sequence, i.e., the effective sequence to distinguish subset members. The greater the knowledge of the bases of the 5' nontranslated region of the sequence, the greater can be the specificity of the probe for the target nucleic acid sequence, and thus the greater the efficiency of the process.

The probe sequences complementary to the target can be large or small, so long as sufficiently stable double stranded hybrids form between the probe and the target sequence. The polynucleotide probe will have enough bases to provide specificity for the target sequence. Generally, the polynucleotide probe will have at least about 15 bases, more usually at least about 20 to about 50 bases, and may have up to about 10,000 bases or more.

The target sequence is likely to be found in the presence of a vast abundance of polynucleotides of different sequence. It is therefore necessary that its method of detection be highly specific. Further, since little DNA of the characteristic sequence may be available for analysis, a method of high sensitivity is also desirable. Consequently, the probe is preferably selected to be capable of hybridizing with as long a piece of the target sequence as possible. Moreover, the greater percentage of bases in the target sequence for which the probe is specific, the greater will be the specificity of the probe for members of a given subset.

The probe sequence need not reflect the exact sequence of the 5' nontranslated region since hybridization may occur in the presence of mismatched pairs. In fact, there may be unhybridized regions of the target (without complementary regions present on the probe) extending from the hybrid or within the hybridized regions of the two molecules. Such unhybridized regions of DNA may affect (generally reduce) the efficiency of the process.

The complementary probe sequence can be composed of RNA or DNA regardless of whether the sample sequence of interest is composed of either DNA or RNA. Thus, hybrids resulting from hybridization between the probe and the sample sequence may be DNA:RNA, DNA:DNA, or RNA:RNA duplexes.

The nucleic acids for use as a probe may be obtained from a variety of sources known to those of ordinary skill in the art. Polynucleotides used in preparing the probe of the invention can be prepared by known techniques. These include biological and synthetic techniques. The probe may be obtained from the "isolation" of a polynucleotide sequence from natural sources or from the chemical manufacture of a polynucleotide sequence.

It is necessary for the probes to be detectable after hybridization with the target sequence. This may be achieved by any known labeling technique. A skilled person will be aware of the techniques required for the introduction of these and other known labels and for the detection of such labels.

Generally, the specimens screened will be animal (e.g., human and mouse) tissues or body fluids. More preferably the specimens will be tissue expected to have a relatively high concentration of lymphocytes sensitized to an antigen of interest (e.g., primary and secondary lymph organs, white blood cells in the peripheral blood, neoplastic tissue, and hybridomas).

In one aspect of this embodiment, the probe may be used to merely screen target sequences isolated from selected tissues. A preferred tissue is hybridoma cells, because individual cells may be easily isolated by limiting dilution techniques. In some instances, it may however be possible to isolate and stimulate spleen or peripheral blood cells in vitro to generate an antibody (see, for example, U.S. Pat. No. 4,444,887).

The screening is accomplished by contacting the sample with an amount of a reagent sufficient to lyse the cells and to expose and separate the strands of the nucleic acid(s). The probe is contacted with the lysed cells under suitable conditions to permit hybridization of only substantially complementary molecules to remain hybridized and causing imperfectly hybridized molecules to separate. Conditions that influence the formation of polynucleotide hybrids are well known and described in detail in Sambrook et al. (1989), Molecular Cloning: A Laboratory Manual, (2nd ed.), supra; and Crosa et al., *J. Bact.*, 115:904–911 (1973), the teachings of which are hereby incorporated by reference.

The probe itself can be detected by a variety of techniques including spectroscopic, photochemical, immunochemical, radiochemical, biochemical or chemical means. These protocols may include, for example, radioimmunoassay (RIA), immunoradiometric assay (IRMA), sandwich IRMA, fluoroimmunoassay (FIA), chemiluminescent assays, bioluminescent assays and enzyme linked immunosorbent assays (ELISA).

In another embodiment, it may be possible to probe polynucleotides from a limited number of cells expressing a desired antibody following polymerase chain reaction (PCR) amplification of target sequences. PCR in essence involves exponentially amplifying DNA in vitro using sequence specified oligonucleotides. As a consequence, the fusion step in B cell hybridoma production may be omitted entirely, since PCR will increase the target pool by alleviating the problem of low fusion frequencies often observed in hybridoma fusions. PCR is described in Mullis and Faloona, *Meth. Enz.*, 155:335–350 (1987).

Rationally Synthesized Variable Regions

Yet a further approach is the rational synthesis of altered variable regions of the antibodies disclosed herein, as well as antibodies discovered via probing. Such an approach has several potential advantages. Namely, a researcher would not have to screen immunized host animals attempting first to cull those antibodies which bind to TAG and next to cull those antibodies which specifically have $V_H$ regions encoded by DNA derived from $V_H\alpha$TAG.

Mutagenic Techniques

The $V_H$ and/or $V_L$ gene segments may be altered by mutagenesis. Exemplary techniques include the addition, deletion, or nonconservative substitution of a limited number of various nucleotides or the conservative substitution of many nucleotides, provided that the proper reading frame is maintained.

Substitutions, deletions, insertions or any subcombination may be combined to arrive at a final construct. Since there are 64 possible codon sequences but only twenty known amino acids, the genetic code is degenerate in the sense that different codons may yield the same amino acid. However, the code is precise for each amino acid; thus there is at least one codon for each amino acid, i.e., each codon yields a single amino acid and no other. It will be apparent that during translation, the proper reading frame must be maintained in order to obtain the proper amino acid sequence in the polypeptide ultimately produced.

Techniques for additions at predetermined amino acid sites having a known sequence are well known. Exemplary techniques include oligonucleotide-mediated, site-directed mutagenesis and polymerase chain reaction.

Techniques for deletions at predetermined amino acid sites having a known sequence are well known. Exemplary techniques include oligonucleotide-mediated site-directed mutagenesis and the polymerase chain reaction.

Techniques for substitutions at predetermined amino acid sites having a known sequence are well known. Exemplary techniques include site-directed mutagenesis, and the polymerase chain reaction technique.

Oligonucleotide site-directed mutagenesis in essence involves hybridizing an oligonucleotide coding for a desired mutation with a single strand of DNA containing the region to be mutated and using the single strand as a template for extension of the oligonucleotide to produce a strand containing the mutation. This technique, in various forms, is described by Zoller and Smith, *Nuc. Acids Res.*, 10:6487–6500 (1982); Norris et al., *Nuc. Acids Res.*, 11:5103–5112 (1983); Zoller and Smith *DNA*, 3:479–488 (1984); Kramer et al., *Nuc. Acids Res.*, 10:6475–6485 (1982).

PCR may be employed to use sequence specified oligonucleotides to incorporate sequence alterations, if desired. Examples of mutagenesis using PCR are described in Higuchi et al., *Nucl. Acids Res.*, 16:7351–7367 (988); Ho et al., *Gene*, 77:51–59 (1989), and Horton et al., *Gene*, 77:61 (1989).

Recombinant Techniques

The antibodies may be constructed by recombinant techniques. In other words, because the inventors have provided the nucleotide sequences of various $V_H$- and $V_L$-encoding regions, a skilled artisan could in vitro produce a complete gene coding for the heavy and light chain variable regions.

The constructed gene may be engineered in which selected $D_H$ and $J_H$ gene segments are in functional combination with a selected $V_H$ gene segment, i.e., the $V_H\alpha$TAG segment, or the $V_H$ gene segment of CC49 or CC83.

For example, the constructed heavy chain coding DNA will include $D_H$ and $J_H$ gene sequences which are contiguous with the 3' end of the germline $V_H\alpha$TAG gene segment, thereby completing the CDR3 and framework (FR4) of the $V_H$ domain. A leader sequence may be present but may be subsequently removed.

Depending upon the light chain employed, it may also be necessary to provide a constructed light chain coding DNA. Such a DNA gene will comprise a $V_L$ gene segment in functional combination, e.g., contiguous with a $J_L$ gene segment, including the leader sequence which may be subsequently removed. The $J_L$ gene segment will vary depending upon whether the light chain is of the lambda or kappa system. The J region sequence is contiguous with the end of the $V_L$ exon to complete FR 4 of the $V_L$ domain. Such a construction may be carried out by the techniques used to construct the $V_H$ gene.

The constructed gene may be engineered by conventional recombinant techniques, for example, to provide a gene insert in a plasmid capable of expression. Thereafter, the plasmids may be expressed in host cells. Exemplary recombinant biological techniques are set forth below.

In providing a fragment encoding either the light chain or heavy chain variable region, it will usually be desirable to include all or a portion of the intron downstream from the J region, particularly where the variable region is derived from the host in which the fused gene is to be expressed. Where the intron is retained, it will be necessary that there be functional splice acceptor and donor sequences at the intron termini. The intron between the J and the constant region of the fused gene may be primarily the intron sequence associated with (1) the constant region, (2) the J domain, or (3) portions of each. The last may be a matter of convenience where there is a convenient restriction site in the introns from the two sources. It may be necessary to provide adapters to join the intron to the constant region. In some instances, all or a portion of the intron may be modified by deletion, nucleotide substitution(s) or insertion, to enhance ease of manipulation, expression, or the like. Preferably, a sufficient amount of the intron should be present to contain an enhancer that is functionally active with the naturally-occurring promoter.

Alternatively, it may be desirable to have the fused gene free of the intron between the J gene and C gene. Thus, the 3' terminus of the J gene will be adjacent to the 5' terminus of the C gene. One can use an exonuclease and, by employing varying periods of digestion, one can provide for varying 3'-termini, which can then be used for linking to the constant region and selection made for a functional product in a variety of ways; or by splicing with overlap extension using polymerase chain reaction technology, see Horton et al. (1989), supra. In this case, an artificial promoter, which does not need to be functionally active with an enhancer, will be generally be utilized.

In one preferred embodiment, the genes encoding the $V_H$ and $V_L$ regions may be altered by replacing at least parts of the complementarity determining regions (CDRs) in the light or heavy chain variable domains of the antibody with analogous parts of CDRs from an antibody of different specificity. An exemplary technique for replacing the CDRs is taught in European Published Patent Application 0 239 400, by Gregory Winter; and in PCT Application WO 88/09344.

The inventors have disclosed the nucleotide sequences corresponding to the $V_H$ amino acid sequences of the $V_H\alpha$TAG, CC46, CC49, CC83 and CC92, as well as of the CC49, CC83 and CC92 $V_L$ gene segments. Consequently, it is envisaged that the CDRs from the antibodies of the present invention can be grafted onto the framework regions of a human antibody.

Generally, the CDR regions from a human $V_H$ or $V_L$ domain may be replaced by CDRs from the $V_H$ or $V_L$ regions of antibodies of the present invention. Exemplary human antibodies from which the framework portions may be used include human plasmacytoma NEWM, [Jones et al., Nature, 321:522–525 (1986)], publicly available from Dr. Greg Winter; and various other human $V_H$ and $V_L$ genes available from Dr. Terrence Rabbitts; both researchers being from the Medical Research Council, 20 Park Crescent, London, W1N 4AL.

The determination as to what constitutes a CDR and what constitutes a framework region may be made on the basis of the amino-acid sequences of a selected Ig as indicated in Kabat et al., *Sequences of Proteins of Immunological Interest*, Fourth Edition (1987), U.S. Dept. of Health and Human Services, NIH.

The four framework regions largely adopt a β-sheet conformation and the CDRs form loops connecting, and in some cases forming part of, the β-sheet structure. Moreover, not all of the amino-acid residues in the loop regions are solvent accessible and in one case, amino-acid residues in the framework regions are involved in antigen binding (see Amit et al., *Science*, 233:747–753, (1986)). It is also known that the variable regions of the two parts of an antigen binding site are held in the correct orientation by inter-chain, non-covalent interactions.

Thus, in order to transfer the antigen binding capacity of one variable domain to another, it may not be necessary to replace all of the CDRs with the complete CDRs from the donor variable region. It may be necessary only to transfer those residues which are necessary for the antigen binding site, and this may involve transferring framework region residues as well as CDR residues. Given the explanations set forth in European Published Patent Application 0 239 400, it will be well within the competence of those skilled in the art, either by carrying out routine experimentation or by trial and error testing to obtain a functional altered antibody.

Preferably, the variable domains in both the heavy and light chains are altered by at least partial CDR replacement and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species.

Composite Variable Regions

Generally, the V gene encoding the $V_L$ is the same V gene which encodes the $V_L$ naturally combined with the $V_H$ of choice. For example, the V gene which encodes the $V_L$ regions of CC49 and CC83 are beneficially used when employing the V gene which encodes the $V_H$ of CC49 and CC83, respectively.

Surprisingly, because the $V_H$ regions of the antibodies of the present invention are encoded by $V_H$ genes derived from $V_H\alpha$TAG, composite antibodies may be beneficially formed. In other words, the $V_H$ region of one antibody of the present invention may suitably be combined with the $V_L$ region of another antibody of the present invention. Although the amino acid sequences of the CC49 and CC83 heavy chains are superficially close, it would be expected that a change of a few or even one amino acid may drastically affect the binding function of the antibody, i.e., the resultant antibodies are generally presumed to be a non-specific immunoglobulin (NSI), i.e.—lacking in antibody character, (see European Published Patent Application 0 125 023).

Quite surprisingly, it has now been found that an antibody having the requisite $V_H$ of this invention, need not be recombined only with a $V_L$ from the same naturally occurring animal antibody. For instance, as set forth in the examples, it is possible to produce a chimeric antibody having a heavy chain with a $V_H$ from CC83 and a light chain with a $V_L$ from CC49, wherein the composite antibody thus formed has a binding specificity 25 percent greater than the binding affinity of B72.3 to TAG-72.

Constant Regions

Heavy Chain ($C_H$) Domain

The $C_H$ domains may be of various human isotypes, i.e., IgG (e.g., $IgG_1$, $IgG_2$, $IgG_3$, and $IgG_4$), IgA, IgD, IgM, as well as the various subtypes of the individual groups.

For a discussion of the human γ1, see Ellison et al., *Nucl. Acid Res*, 10:4071–4079 (1982); Takahashi et al., *Cell*, 29:671–679 (1982). For a discussion of the human gamma 2 (γ2), see Krawinkel et al., *EMBO J.*, 1:403–407 (1982); Ellison et al., *Proc. Nat. Acad. Sci. (USA)*, 79:1984–1988 (1982); Takahashi et al. (1982), supra. For a discussion of human gamma 3 (γ3), see Krawinkel et al., (1982), supra, and Takahashi et al. (1982), supra. For a discussion of human gamma 4 (γ4), see Ellison et al. (1982), *DNA*, 1:11–18 (1982), Krawinkel et al. (1982), supra, and Takahashi et al. (1982), supra.

For a discussion of the human mu, see Rabbitts et al., *Nucl.. Acid Res.* 9:4509–45024 (1981).

For a discussion of the human alpha, see Flanagan et al., *Cell*, 36:681–688 (1984).

For a discussion of the human delta, see White et al., *Science*, 228:733–737 (1985).

For a discussion of the human epsilon, see Max et al., *Cell*, 29:691–699 (1982).

Light Chain ($C_L$) Domain

The $C_L$ domain may be human kappa (κ) or human lambda (λ).

For a discussion of the human κ, see Heiter et al., *Cell*, 22:197–207 (1980).

For a discussion of the human λ, see Hollis et al., *Nature*, 296:321–325 (1982).

The $C_H$ and/or $C_L$ gene segments may be "altered" by mutagenesis. Exemplary techniques include the addition, deletion, or nonconservative substitution of a limited number of various nucleotides or the conservative substitution of many nucleotides, provided that the proper reading frame is maintained. In addition, entire domains of the protein can be altered, for example, by substituting $C_H2$ for $C_H3$. This substitution is made at the DNA level by inserting, deleting or substituting entire exons of sequence.

Construction of Antibodies

Immunizations

The first technique for producing antibodies, whether monoclonal or polyclonal, having $V_H$ regions encoded by DNA derived from $V_H\alpha$TAG is to immunize a host animal with purified TAG-72. Exemplary protocols for immunizing a host animal with TAG-72 are set forth in U.S. Pat. Nos. 4,522,918 and 4,612,282, using a human breast carcinoma extract as the immunogen; and U.S. patent application 7-073,685 (which is available to the public), using TAG-72 purified with B72.3 as the immunogen.

Thereafter, monoclonal or polyclonal antibodies produced from the immunization protocol are screened to determine which of said antibodies selectively bind to TAG-72. Such screening may be accomplished by any of a number of well-known procedures, such as solid-phase radioimmunoassay, enzyme-linked immunosorbent assays, resetting assays, blocking assays, and the like. The above-described procedures are well known in the art.

Synthesis of Amino Acid Sequences

Immunoglobulins of the present invention can be synthesized from their constituent amino acids. Suitable techniques are the Merrifield solid phase method, as described in *J. Amer. Chem. Soc.*, 85:2149–2154 (1963). This solid phase method for synthesizing sequences of amino acids is also described on pages 1–4 of a book by Stewart and Young, *Solid Phase Peptide Synthesis* (W. H. Freemen and Co., San Francisco, 1969).

Construction of DNA

DNA Encoding the $V_H$ and $V_L$

The DNA encoding the antibody heavy and light chains may be obtained from a variety of sources known to those of ordinary skill in the art, for example, genomic DNA, cDNA, synthetic DNA, or a combination thereof.

Cells coding for the desired sequence may be isolated, and genomic DNA fragmented by one or more restriction enzymes. The genomic DNA may or may not include naturally-occurring introns. The resulting fragments may then be cloned and screened using a heavy chain J region ($J_H$) probe for the presence of the DNA sequence coding for the polypeptide sequence of interest. DNA fragments isolated by preparative agarose gel electrophoresis are ligated. Recombinant plaques of the libraries are screened with a mouse $J_H$ probe.

The DNA may also be obtained from a cDNA library. Messenger RNA coding for heavy or light chain is isolated from a suitable source, either mature B cells or a hybridoma culture, employing standard techniques of RNA isolation, and the use of oligo-dT cellulose chromatography to segregate the poly-A mRNA. The poly-A mRNA may, further, be fractionated to obtain sequences of sufficient size to code for the amino acid sequences in the light or heavy chain of the desired antibody as necessary.

A cDNA library is then prepared from the mixture of mRNA using a suitable primer, preferably a nucleic acid sequence which is characteristic of the desired cDNA. Such a primer may be synthesized based on the amino acid sequence of the antibody. In the alternative cDNA from unfractionated poly-A mRNA from a cell line producing the desired antibody or poly-dT may also be used. The resulting cDNA is optionally size fractionated on polyacrylamide gel and then extended with, for example, dC residues for annealing with pBR322 or other suitable cloning vector which has been cleaved by a suitable restriction enzyme, such as Pst I, and extended with dG residues. Alternative means of forming cloning vectors containing the cDNA using other tails and other cloning vector remainder may, of course, also be used but the foregoing is a standard and preferable choice. A suitable host cell strain, typically *Escherichia coli* (*E. coli*), is transformed with the annealed cloning vectors, and the successful transformants identified by means of, for example, ampicillin or tetracycline resistance or other phenotypic characteristics residing on the cloning vector plasmid.

Successful transformants are picked and transferred to microtiter dishes or other support for further growth and preservation. Nitrocellulose filter imprints of these growing cultures are then probed with suitable nucleotide sequences containing bases known to be complementary to desired sequences in the cDNA. Several types of probe may be used, preferably synthetic single stranded DNA sequences labeled by kinasing with $\gamma$-$^{32}$P ATP. The cells fixed to the nitrocellulose filter are lysed, the DNA denatured, and then fixed before reaction with kinased probe. Clones which successfully hybridize are detected by contact with a photoplate, then plasmids from the growing colonies isolated and sequenced by means known in the art to verify that the desired portions of the gene are present.

The desired gene fragments are excised and tailored to assure appropriate reading frame with the control segments when inserted into suitable expression vectors. Typically, nucleotides are added to the 5' end to include a start signal and a suitably positioned restriction endonuclease site.

The DNA also may be synthetically synthesized, for example, using an Applied Biosystems™ Model 380A DNA Synthesizer, and constructed by standard techniques.

Finally, an exemplary technique for utilizing combination of the above techniques is by splicing with overlap extension using polymerase chain reaction technology, see Horton et al. (1989), supra. Generally, a synthetically synthesized primer, having a so-called "wagging tail", may be inserted with a selected sequence, for example genomic DNA. Thereafter, the sequences are amplified and spliced together.

DNA Encoding the $C_H$ and $C_L$

The DNA fragment encoding the amino acid sequence of the human constant region may be obtained by screening the chromosomal DNA of cells producing human immunoglobulin.

Vectors

The desired DNA fragment may be positioned in a biologically functional expression vehicle which may contain appropriate control sequences not present in the selected DNA fragment. By "biologically functional" is meant that the expression vehicle provides for replication and/or expression in an appropriate host, either by maintenance as an extra chromosomal element or by integration into the host genome. A large number of vectors are available or can be readily prepared, and are well known to skilled artisans.

A number of plasmids, such as those described in European Published Patent Applications 0036776, 0048970 and 0051873, have been described which already contain a promoter in reading frame with the gene and compatible with the proposed host cell.

The vectors and methods disclosed herein are suitable for use over a wide range of microorganisms, either prokaryotic and eukaryotic, which are susceptible to transformation. The plasmid will be capable of replicating in the microorganism, particularly a bacterium.

In general, plasmid vectors containing the appropriate promoters, which can be used by the microbial organism for expression of its own protein, also contain control sequences, ribosome binding sites, and transcription termination sites. Generally, the replicon and control sequences which are derived from species compatible with the host cell are used in connection with these hosts.

Smaller or larger SV40 fragments may also be used, provided there is included the approximately 250 base pair (bp) sequence extending from the Hind III site toward the Pvu II site located in the viral origin of replication. Further, it is also possible, and often desirable, to utilize promoter or control sequences normally associated with the desired gene sequence, provided such control sequences are compatible with the host cell systems.

Finally, the plasmid should desirably have a gene, a marker gene, that is capable of providing a phenotypical property which allows for selection of host cells containing the expression vector. Particularly useful is a gene that provides for survival selection. Survival selection can be achieved by providing resistance to a growth inhibiting substance or providing a growth factor capability to a bacterium deficient in such capability.

In general, prokaryotes are preferred. For example, pBR322 a plasmid derived from an *E. coli* species [Bolivar et al., *Gene*, 2:95 (1977)] is particularly useful. pBR322 contains genes for ampicillin and tetracycline resistance and thus provides an easy means for identifying transformed cells.

While these prokaryotes are the most commonly used, other microbial strains which may be used include *E. coli* strains such as *E. coli* B, *E. coli* K12 strain 294 (ATCC No. 31446) and *E. coli* X1776 (ATCC No. 31537), *E. coli* W3110 (F⁻, γ⁻, prototrophic, ATCC No. 27325), bacilli such as *Bacillus subtilus*, and other enterobacteriaceae such as *Salmonella typhimurium* or *Serratia marcesans*, and various Pseudomonas species may be used. These examples are intended to be illustrative only.

In addition to prokaryates, eukaryotic microbes may also be used. *Saccharomyces cerevisiae*, or common baker's yeast, is the most commonly used among eukaryotic microorganisms although a number of other strains are commonly available.

For expression in Saccharomyces, the plasmid YRp7, for example, (Stinchcomb et al., *Nature*, 282:39 (1979); Kingsman et al., *Gene*, 7:141 (1979); Tschemper et al., *Gene*, 10:157 (1980)) is commonly used. This plasmid already contains the trpl gene which provides a selection marker for a mutant strain of yeast lacking the ability to grow in tryptophan, for example ATCC No. 44076 or PEP4-1 (Jones, *Genetics*, 85:12 (1977)). The presence of the trpl lesion as a characteristic of the yeast host cell genome then provides an effective environment for detecting transformation by growth in the absence of tryptophan.

Any plasmid vector containing a yeast-compatible promoter, origin of replication and termination sequence is suitable for use in yeast. Suitable promoting sequences in yeast vectors include the promoters for 3-phosphoglycerate kinase [Hitzeman et al., *J. Biol. Chem.* 255:2073 (1980)] or other glycolytic enzymes [Hess et al., *J. Adv. Enzyme Reg.*, 7:149 (1968); Holland et al., *Biochemistry*, 17:4900 (1978)].

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication [see Fiers et al., *Nature*, 273:113 (1978)].

For example, pSV2neo contains a gene for ampicillin resistance neomycin resistance, which is under the control of an SV40 promoter. Thus, pSV2neo provides easy means for identifying cells transformed with genes for both the animal variable region and human constant region.

Preparation of Chimeric DNA

The genes coding for the heavy chain or the light chain will be constructed by joining the 5'-end of a DNA fragment which encodes the constant region to the 3' end of a DNA fragment which encodes the variable region. The DNA sequence coding for the antibody amino acid sequence may be obtained in association with the promoter and replication site from genomic DNA. To the extent that the host cells recognize the transcriptional regulatory and translational initiation signals associated with the heterologous genes, then the region 5' and 3' of the variable region coding sequence may be retained with the variable region coding sequence and employed for transcriptional and translational initiation regulation. The non-coding region 3' to the constant region may be retained for its transcriptional termination regulatory sequences, such as termination and polyadenylation. In referring to 5' or 3' for a double strand, it is intended to mean the direction of transcription, with 5' being upstream from 3'.

The intron sequence between the variable region for each respective chain may be joined to the corresponding human constant DNA fragment at any convenient restriction site. In providing a fragment encoding the variable region, it will usually be desirable to include a portion of the intron downstream from the J region. Where the intron is retained, it will be necessary that there be functional splice acceptor and donor sequences at the intron termini. The contiguous non-coding region 5' to the variable region will normally include those sequences involved with initiation of transcription and translation, such as the TATA box, capping sequence, CAAT sequence, and the like. Usually, the 5'-non-coding sequence does not exceed about 1–2 kilo bases (kb).

An enhancer sequence should exist between the J region and the constant region. The enhancer employed may be the enhancer of either (1) the animal V region or the (2) the human constant region.

By retaining the 3'-region naturally contiguous to the DNA sequence coding for the constant region, the transcriptional termination signals may be provided for the gene. Where the transcriptional termination signals are not satisfactorily functional in the expression host cell, then a 3' region functional in the host cell may be substituted. Conveniently, the non-coding 3' region may be obtained from a non-coding contiguous 3' region of a constant region from the expression host. The 3'-non-coding region may be joined to the constant region by any of the means described previously for manipulation and ligation of DNA fragments.

This region could then be used as a building block in preparing the gene.

Preparation of Expression Vehicles

Construction of suitable expression vehicles containing the desired coding and control sequences may be produced as follows. The termini of the vectors and DNA fragments may then be relegated to form the desired expression vehicles. The methods employed are not dependent on the DNA source, or intended host.

DNA fragments coding for the light chain and heavy chain may be inserted into separate expression vehicle, or into the same vector. Preferably, the fused genes encoding the light and heavy chimeric chains are assembled in two different expression vectors which can be used to cotransform a recipient cell, either concurrently or sequentially.

The means for insertion of the DNA fragments containing the chimeric genes into expression vectors includes using restriction endonucleases. "Restriction endonucleases" (or "restriction enzymes") are hydrolytic enzymes capable of catalyzing site-specific cleavage of DNA molecules. The locus of restriction endonuclease action is determined by the existence of a specific nucleotide sequence. Such a sequence is termed the recognition site for the restriction endonuclease. Many restriction endonucleases from a variety of bacterial species have been isolated and characterized in terms of the nucleotide sequence of their recognition sites. Some restriction endonucleases hydrolyze the phosphodiester bonds on both strands at the same point, producing blunt ends. Others catalyze hydrolysis of bonds separated by a few nucleotides from each other, producing free single stranded regions at each end of the cleaved molecule. Such single stranded ends are self-complementary, hence cohesive, and may be used to rejoin the hydrolyzed DNA. Exemplary restriction enzymes include Aat II, Bam HI, Eco RI, Hind III, Nde I, Spe I, Xba I, Sac I, Bgl II, Pst I, Sal I and Pvu II.

Additionally, the expression vector may have a polylinker inserted therein which has a a plurality of unique restriction sites. By digestion of the expression vector with the appropriate restriction enzymes, the polylinker will be cleaved so that at least one DNA fragment containing the gene can be inserted. Where the polylinker allows for distinguishable termini, the DNA fragment can be inserted in a single orientation; where the termini are the same, insertion of the DNA fragment will result in plasmids having two different orientations.

Cleavage is performed by treating the plasmid with a restriction enzyme(s). In general, about 10 $\mu$g plasmid or DNA fragments is used with about 10 unit of enzyme in about 100 $\mu$l of buffer solution. Endonuclease digestion will normally be carried out at temperatures ranging from about 37° to 65° C., at a pH of about 7 to about 9. (Appropriate buffers and substrate amounts for particular restriction enzymes are specified by the manufacturers.) Time for the reaction will be from about 1 to about 18 hours.

It may be useful to prevent religation of the cleaved vector by pretreatment with alkaline phosphatase. Specific conditions are prescribed by the manufacturer.

After the restriction enzyme digest is complete, protein is removed by extraction with phenol and chloroform. The nucleic acid is recovered from the aqueous fraction (containing about 0.3 K sodium acetate) by precipitation with about 2.5 volumes of ethanol.

Descriptions of methods of cleavage with restriction enzymes may be found in the following articles: Greene et al., *Methods in Molecular Biology*, Vol. 9, ed. Wickner, R. B., Marcel Dekker, Inc., New York; Mertz and Davis, *Proc. Nat. Acad. Sci., (USA)*, 69:3370 (1972).

Size separation of the cleaved fragments by agarose gel electrophoresis is readily performed to follow the course of the reaction. Once the digestion has gone to the desired degree, the endonuclease may be inactivated by heating above 65° C. for about 10 minutes or organic extraction.

The desired fragment is then purified from the digest. Suitable purification techniques include gel electrophoresis or sucrose gradient centrifugation.

The plasmid vehicle and foreign DNA fragments are then ligated with DNA ligase to recircularize. This process is referred to as annealing and DNA ligation.

An appropriately buffered medium containing the DNA fragments, DNA ligase, and appropriate cofactors is employed. The temperature employed will be between about 25° to about 4° C. When DNA segments hydrogen bond, the DNA ligase will be able to introduce a covalent bond between the two segments. The time employed for the annealing will vary with the temperature employed, the nature of the salt solution, as well as the nature of the sticky ends or cohesive termini. Generally, the time for ligation may be from 5 to 18 hours. See Maniatis, *Molecular Cloning*, Cold Spring Harbor (1982), supra.

Host Cells

Thereafter, the expression vehicle constructs may be used to transform an appropriate host cell. Suitable host cells include cells derived from unicellular as well as multicellular organisms.

The chimeric immunoglobulin genes can be expressed in nonlymphoid cells such as bacteria or yeast.

Various unicellular microorganisms can be transformed, such as bacteria. That is, those unicellular organisms which are capable of being grown in cultures or fermentation. Since bacteria are generally the most convenient organisms to work with, bacteria will be hereinafter referred to as exemplary of the other unicellular organisms. Bacteria, which are susceptible to transformation, include members of the Enterobacteriaceae, such as strains of *Escherichia coli*; Salmonella; Bacillaceae, such as *Bacillus subtilis*; Pneumococcus; Streptococcus, and *Haemophilus influenzae*.

When expressed in bacteria, the immunoglobulin heavy chains and light chains become part of inclusion bodies. The chains then must be isolated, purified and then assembled into functional immunoglobulin molecules.

In addition to prokaryates, eukaryotic microbes, such as yeast cultures may also be used. *Saccharomyces cerevisae*, or common baker's yeast is the most commonly used among eukaryotic microorganisms, although a number of other strains are commonly available. The presence of the trpl lesion as a characteristic of the yeast host cell genome provides an effective environment for detecting transformation by growth in the absence of tryptophan.

In addition to microorganisms, cultures of cells derived from multicellular organisms may also be used as hosts. In principle, any such cell culture is workable, whether from vertebrate or invertebrate culture, provided that the cell line is one that at least originally produced antibodies. Propagation of vertebrate cells in culture has become a routine procedure in recent years (*Tissue Culture*, Academic Press, Kruse and Patterson, editors (1973)). Examples of such useful host cell lines are Sp2/0, VERO and HeLa cells, Chinese hamster ovary (CHO) cell lines, and W138, BHK, COS-7 and MDCK cell lines.

The preferred recipient cell line is a plasmacytoma cell such as B lymphocytes or hybridoma cells. Plasmacytoma cells can synthesize, assemble and secrete immunoglobulins encoded by transformed immunoglobulin genes. Further, they possess the mechanism for glycosylation of the immunoglobulin. Sp2/0 is a preferred recipient cell because it is an immunoglobulin-nonproducing plasmacytoma cell. The cell produces only immunoglobulin encoded by the transformed immunoglobulin genes. Plasmacytoma cells can be grown in culture or in the peritoneum of mice where secreted immunoglobulin can be obtained from ascites fluid.

Transformation of Host Cells

Transformation of host cells is accomplished as follows. The expression vehicle is linearized and the DNA is inserted into host cells for production of the antibody. Exemplary methods for inserting the DNA into host cells include electroportion, protoplast fusion, calcium phosphate-precipitation, or other conventional techniques, which use dextran sulfate and PEG.

If cells without formidable cell wall barriers are used as host cells, transformation may be carried out by the calcium phosphate precipitation method as described by Graham and Van der Eb, *Virology,* 52:546 (1978).

If prokaryotic cells or cells which contain substantial cell wall constructions are used, the preferred method of transformation is calcium treatment using calcium chloride as described by Cohen et al, *Proc. Natl. Acad. Sci. (USA),* 69:2110 (1972).

The host cells may be transformed via either cotransformation or targeted transformation.

For cotransformation, the genes coding for the light chain and heavy chain may be used to transform separate cell cultures, either of the same or of differing species; separate plasmids for light and heavy chain may be used to co-transform a single cell culture; or finally, a single expression plasmid containing both genes and capable of expressing the genes for both light and heavy chain may be transformed into a single cell culture.

In the targeted transformation technique, the host cells are transformed with genes encoding for the light chain, and the cells containing the light chain marker are selected. The light chain is found using cytostaining or possibly by detection of the light chain in the supernatant if it has been secreted. Cells selected to have the light chain are transformed with the heavy chain construct, and resultant cells additionally containing the heavy chain marker selected.

It is known that some immortalized lymphoid cell lines, such as plasmacytoma cell lines, in their normal state secrete isolated Ig light or heavy chains. Consequently, if such a cell line is transformed with the vector containing the chimeric heavy or light chain of the present invention, it will not be necessary to transform the cell line or another cell line with the other Ig chain, provided that the normally secreted chain is complementary to the variable domain of the Ig chain encoded by the vector initially used to transform the cell line.

Selection and Expression of Transformed Host Cells

Generally, after transformation of the host cells, the cells may be grown for about 48 hours to allow for expression of marker genes. The cells are then placed in a selective medium, where untransformed cells are killed, leaving only cells transformed with the DNA constructions.

Heavy and light chains or portions thereof, may be produced in isolation from each other and antibodies and fragments thereof may be obtained. Such preparations require the use of techniques to reassemble isolated chains.

The ability of the method of the invention to produce heavy and light chains or portions thereof, in isolation from each other offers the opportunity to obtain unique assemblies of immunoglobulins, Fab regions, and univalent antibodies. It is possible to recombine the heavy and light chains in vitro, disrupted by cleavage of only the interchain disulfides, and to regain antibody activity even without restoration of the inter-chain disulfides [see Edelman et al., *Proc. Natl. Acad. Sci. (USA),* 50:753 (1963)].

The transformed cells are grown under conditions appropriate to the production of the light chains and/or heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

The binding affinity of monoclonal antibodies for TAG-72 is determined by means well known in the art (see Heyman et al., *J. Immunol. Methods,* 68:193–204 (1984) and as described in detail in the Examples provided hereinafter).

Selected positive cultures are subcloned in order to isolate pure transformed colonies. A suitable technique for obtaining subclones is via the limited dilution method taught by McKeara in *Monoclonal Antibodies,* Plenum Press, N.Y. (1980).

Hybridomas that produce such chimeric antibodies may be grown using known procedures. The transformed cells can secrete large quantities of the light chains and/or heavy chains by culture in vitro, such as by hollow fiber systems, spinner culture, static culture, or in vivo such as ascites production.

The chimeric antibodies may be produced in large quantities by injecting a hybridoma into the peritoneal cavity of pristane-primed mice, and after an appropriate time (about 1–2 weeks), harvesting ascites fluid from the mice, which yields a very high titer of homogeneous monoclonal antibody, and isolating the monoclonal antibodies therefrom by methods well known in the art (see Stramignoni et al., *Intl. J. Cancer,* 31:543–552 (1983)). The hybridomas are grown up in vivo, as tumors in animals, the serum or ascites fluid of which can provide up to about 50 mg/mL of monoclonal antibodies. Usually, injection (preferably intraperitoneal) of about $10^6$ to $10^7$ histocompatible hybridoma cells into mice or rats will result in tumor formation after a few weeks. The antibodies can then be collected and processed by well-known methods. See generally, *Immunological Methods,* Vols. I & II, Eds. Lefkovits and Pernis, (1979 & 1981) Academic Press, New York, N.Y.; and *Handbook of Experimental Immunology,* ed. Weir, (1978) Blackwell Scientific Publications, St. Louis, Miss., USA.

The antibodies can then be stored in various buffer solutions such as phosphate buffered saline (PBS), which gives a generally stable antibody solution for further use.

The chimeric antibodies of the present invention may be fragmented using known protease enzymes, for example papain and pepsin, to obtain highly immunoreactive F(ab')2, F(ab') and Fab fragments. In addition, active fragments of Ig formed by proteolysis (approximately 50,000 MW) can be split into their fully reduced heavy chain and light chain components and fairly efficiently reconstructed to give an active antibody [Haber, *Proc. Natl. Acad. Sci. (USA),* 52:1099 (1964); and Whitney et al., *Proc. Natl. Acad. Sci. (USA),* 53:524 (1965)]. The reactivity of the resulting F(ab') 2, F(ab') and Fab fragments are determined by methods as described above for the complete monoclonal antibody molecule.

Uses of the Antibodies

The antibodies of the present invention as well as immunoreactive fragments or recombinants thereof, provide unique benefits for use in a variety of cancer treatments. In addition to the ability to bind specifically to malignant cells and to localize tumors, the antibodies have constant variable regions which do not bind detectably to normal cells such as fibroblasts, endothelial cells, or epithelial cells in the major organs.

Specifically, the antibodies, immunoreactive fragments or recombinants thereof are useful for, but not limited to, the following types of cancer treatment: (1) in vivo diagnostic assays conjugated to an imaging marker, for the in situ detection of carcinoma lesions, as further described below; (2) in vivo therapy, using the antibodies of the present invention alone or conjugated to a therapeutic agent such as a radionuclide, toxin, effector cells, other antibodies or via a complement mechanism, as described below; and (3) radioimmunoguided surgery, as described below.

Moreover, a pharmaceutical composition comprising the antibodies of the present invention in a pharmaceutically acceptable, non-toxic, sterile carrier such as physiological saline, non-toxic buffers and the like, is also now possible.

Injectable compositions of the present invention may be either in suspension or solution form. In solution form the complex (or when desired the separate components) is dissolved in a pharmaceutically acceptable carrier. Such carriers comprise a suitable solvent, preservatives such as benzyl alcohol, if needed, and buffers. Useful solvents include, for example, water, aqueous alcohols, glycols, and phosphonate or carbonate esters. Such aqueous solutions contain no more than 50 percent of the organic solvent by volume.

Injectable suspensions as compositions of the present invention require a liquid suspending medium, with or without adjuvants, as a carrier. The suspending medium can be, for example, aqueous polyvinylpyrrolidone, inert oils such as vegetable oils or highly refined mineral oils, or aqueous carboxymethylcellulose. Suitable physiologically acceptable adjuvants, if necessary to keep the complex in suspension, may be chosen from among thickeners such as carboxymethylcellulose, polyvinylpyrrolidone, gelatin, and the alginates. Many surfactants are also useful as suspending agents, for example, lecithin, alkylphenol, polyethylene oxide adducts, naphthalenesulfonates, alkylbenzenesulfonates, and the polyoxyethylene sorbitan esters. Many substances which effect the hydrophibicity, density, and surface tension of the liquid suspension medium can assist in making injectable suspensions in individual cases. For example, silicone antifoams, sorbitol, and sugars are all useful suspending agents.

Cancer cells are heterogeneous and consequently, a single monospecific chimeric antibody may not be able to recognize all cells expressing different epitopes of a tumor.

Thus, it may be desirable to administer several different chimeric antibodies of the present invention. The sequential use of these various antibodies should substantially reduce the anti-idiotypic responses in human patients when compared to repeated use of a single antibody. For example, CH92, CH88, and CH44 could be sequentially administered to a patient. Since these antibodies have different light chains and, in fact different CDR3 regions anti-idiotypic responses should be minimized.

In Vivo Diagnostic Assays

In vivo diagnostic assays of human tumors or metastasis thereof using the antibodies, immunoreactive fragments or recombinants thereof are conjugated to a marker, administered to a patient, and then the presence of the imaging marker in the patient is detected by exposing the patient to an appropriate detection means.

Administration and detection of the antibody-imaging marker conjugate as well as methods of conjugation of the antibody to the imaging marker are accomplished by methods readily known or readily determined, as described, for example, in Goldenberg et al., *New England J. Med.*, 298:1384–1388 (1978); Goldenberg et al., *J. Amer. Med. Assoc.*, 280:630–635 (1983); Goldenberg et al., *Gastroenterol.* 84:524–532 (1983); Siccardi et al., *Cancer Res.*, 46:4817–4822 (1986); Epenetos et al., *Cancer,* 55:984–987 (1985); Philben et al., *Cancer,* 57:571–576 (1986); Chiou et al., *Cancer Inst.* 76:849–855 (1986); Colcher et al., *Cancer Res.,* 43:736–742 (1983); Colcher et al., *Laboratory Research Methods in Biology and Medicine Immunodiagnostics*, New York, Alan R. Liss, pp. 215–258 (1983); Keenan et al., *J. Nucl. Med.* 25:1197–1203 (1984); Colcher et al., *Cancer Res.,* 47:1185–1189 (1987); Estaban et al., *Intl. J. Cancer,* 39:50–59 (1987); Martin et al., *Curr. Surg.,* 41:193–194 (1984); Martin et al., *Hybridoma,* 5:S97-S108 (1986); Martin et al., *Am. J. Surg.,* 150:672–675 (1985); Meares et al.,*Anal. Biochem.* 142:68–78 (1984); and Krejcarek et al., *Biochem. and Biophys. Res. Comm.,* 77:581–585 (1977).

The dosage will vary depending upon the age and weight of the patient. Generally, the dosage should be effective to visualize or detect tumor sites, distinct from normal tissues. Preferably, a one-time dosage will be between about 0.1 to about 200 mg of an antibody-marker conjugate per patient.

Examples of imaging markers which can be conjugated to the antibody are well known to those skilled in the art and include substances which can be detected by diagnostic imaging using a gamma scanner or hand held gamma probe or positron emission tomography or the like, as described in the references cited above, and substances which can be detected by nuclear magnetic resonance imaging using a nuclear magnetic resonance spectrometer or the like, as described in the references cited above.

Suitable but not limiting examples of substances which can be detected using a gamma scanner or the like include $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$, $^{188}Re$ and $^{99m}Tc$ are preferred due to their low energy and suitability for long range detection.

An example of a substance which can be detected using a nuclear magnetic resonance spectrometer or the like is gadolinium (Gd).

In Vivo Cancer Treatment

In this method, the antibody-therapeutic agent conjugate can be delivered to the carcinoma site thereby directly exposing the carcinoma tissue to the therapeutic agent.

The antibodies of the present invention, immunoreactive fragments or recombinants thereof may be administered in a pharmaceutically effective amount for the in vivo treatment of human carcinomas or metastasis thereof. A "pharmaceutically effective amount" of the antibody, immunoreactive fragment or recombinant thereof, conjugated or unconjugated to a therapeutic agent, means the amount of said antibodies in the pharmaceutical composition should be sufficient to achieve effective binding with the antigens against which said antibodies have specific affinity. The pharmaceutical composition may be administered in a single or multiple dosage.

Methods of preparing and administering conjugates of the antibody, immunoreactive fragments or recombinants thereof, and a therapeutic agent are well known to or readily determined by those skilled in the art. Moreover, suitable dosages will depend on the age and weight of the patient and the therapeutic agent employed and are well known to or readily determined by those skilled in the art. Representative protocols are described in the references cited below.

Examples of the antibody-therapeutic agent conjugates which can be used in therapy include the following: (1) antibodies coupled to radionuclides, such as $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$ and $^{188}Re$, and as described, for example, in Goldenberg et al., Cancer Res., 41:4354–4360 (1981); Carrasquillo et al., Cancer Treat. Rep., 68:317–328 (1984); Zalcberg et al., J. Natl. Cancer Inst., 72:697–704 (1984); Jones et al., Int. J. Cancer, 35:715–720 (1985); Lange et al., Surgery, 98:143–150 (1985); Kaltovich et al., J. Nucl. Med., 27:897 (1986); Order et al., Int. J. Radiother. Oncol. Biol. Phys., 8:259–261 (1982); Courtenay-Luck et al., Lancet, 1:1441–1443 (1984) and Ettinger et al., Cancer Treat. Rep., 66:289–297 (1982); (2) antibodies coupled to drugs or biological response modifiers such as methotrexate, adriamycin, and lymphokines such as interferon as described, for example, in Chabner et al., Cancer, Principles and Practice of Oncology, Philadelphia, Pa., J. B. Lippincott Co. Vol. 1, pp. 290–328 (1985); Oldham et al., Cancer, Principles and Practice of Oncology, Philadelphia, Pa., J. B. Lippincott Co., Vol. 2, pp. 2223–2245 (1985); Deguchi et al., Cancer Res., 46:3751–3755 (1986); Deguchi et al., Fed. Proc., 44:1684 (1985); Embleton et al., Br. J. Cancer, 49:559–565 (1984) and Pimm et al., Cancer Immunol. Immunother., 12:125–134 (1982); (3) antibodies coupled to toxins, as described, for example, in Uhr et al., Monoclonal Antibodies and Cancer, Academic Press, Inc., pp. 85–98 (1983); Vitetta et al., Biotechnology and Bio. Frontiers, Ed. P. H. Abelson, pp. 73–85 (1984) and Vitetta et al., Sci., 219:644–650 (1983); (4) heterofunctional antibodies, for example, antibodies coupled or combined with another antibody so that the complex binds both to the carcinoma and effector cells, e.g., killer cells such as T cells, as described, for example, in Perez et al., J. Exper. Med., 163:166–178 (1986); and Lau et al. Proc. Natl. Acad. Sci. (USA), 82:8648–8652 (1985); and (5) native, i.e., non-conjugated or non-complexed, antibodies, as described in, for example, in Herlyn et al., Proc. Natl. Acad. Sci., (USA), 79:4761–4765 (1982); Schulz et al., Proc. Natl. Acad. Sci., (USA), 80:5407–5411 (1983); Capone et al., Proc. Natl. Acad. Sci., (USA), 80:7328–7332 (1983); Sears et al., Cancer Res., 45:5910–5913 (1985); Nepom et al., Proc. Natl. Acad. Sci., (USA) 81:2864–2867 (1984); Koprowski et al., Proc., Natl. Acad. Sci. (USA), 81:216–219 (1984); and Houghton et al., Proc. Natl. Acad. Sci. (USA), 82:1242–1246 (1985).

The methods for combining the antibody or antibody fragment to a desired therapeutic agent as described above are conventional and well known in the art. For example, the methods given in the references above.

RadioImmunoguided Surgery

Antibodies, immunoreactive fragments or recombinants thereof, are important for radioimmunoguided surgery (RIGS). In RIGS, an intraoperative therapy, tumors are localized and excised. An antibody labeled with an imaging marker is injected into the patient, and bound antibody localized by a hand-held gamma detecting probe (GDP) and excised. An exemplary GDP is NEOPROBE™ gamma detecting probe, commercially available from Neoprobe Corporation, Columbus, Ohio, USA. See Martin et al.,Amer. J. Surg., 156:386–392 (1988); Martin et al., Hybridoma, 5:S97-S108 (1986).

Administration and detection of the antibody-imaging marker conjugate as well as methods of conjugation of the antibody to the imaging marker are accomplished by methods readily known to or readily determined, as described, for example, above.

The dosage will vary depending upon the age and weight of the patient, but generally a one time dosage of about 0.1 to 200 mg of antibody-marker conjugate per patient is sufficient.

EXAMPLES

The following nonlimiting examples are merely for illustration of the construction and expression of chimeric DNA sequences encoding the antibodies of this invention. All temperatures not otherwise indicated are Centigrade. All percents not otherwise indicated are by weight.

Replacement of Mouse Constant Regions

CC antibodies were derived from mice, and are significantly less capable of carrying out the effector functions possessed by the human constant regions.

Consequently, in the following examples, selected antibodies are "humanized" by genetically removing the constant regions of the heavy and light chains and replacing them with their human equivalents.

The mouse light chain constant region genes were replaced with the human kappa (k) gene, and the mouse heavy chain genes were replaced with each of the four human gamma isotypes ($\gamma 1$, $\gamma 2$, $\gamma 3$, and $\gamma 4$). Each of these four gamma isotypes possess unique biological properties. For a general review, see Hamilton, (1989) Doc. No. CB0051-289, Calbiochem Corporation.

Preparation of Heavy and Light Chain Variable Region

Isolation of CC49 light chain

CC49 hybridoma cells secrete an antibody having an $IgG_1$ isotype heavy chain and a kappa light chain.

Total DNA from CC49 hybridoma cells, BALB/C mouse kidney cells and NSI plasmacytoma cells was isolated according to the procedures taught by Maki et al. and set forth in Cell, 24:353–356 (1981).

Generally, about 10–20 µg of the extracted DNA from each cell line was digested to completion with 80 units of Bam HI, Eco RI, Hind III, Spe I, Xba I, Sac I, Bgl II, and Pst I in 50–100 µL of a reaction mixture containing the appropriate reaction buffer at 37° C. overnight.

Next, the total extracted DNA from each cell line was subjected to the Southern hybridization technique, developed by E. M. Southern (Southern, J. Mol. Biol., 98:503–517 (1975)). The DNA fragments were fractionated on the basis of their size by means of electrophoresis on a 0.8 percent agarose gel. The double-stranded DNA fragments were modified into single-stranded DNA fragments in an alkali solution; and then a nitrocellulose filter was placed into close contact with the gel to transfer the modified DNA segments onto the filter in the presence of a high salt concentration solution.

Hybridization was carried out using, as the probe, a random primed <32P>-labeled L chain.

More specifically, the probe was a 1.71 kilo base pair (kbp) Hind III-Pst I fragment containing the coding exons for the murine $J_L$ regions (J1-J5) and was isolated from the plasmid pGD1. A nucleotide sequence of the probe fragment is provided in FIG. 7 (SEQ ID NO: 15). This plasmid is described in Agostaro et al., Can. J. Biochem. Cell Biol., 63:969–976 (1985). The plasmid was provided by Nobumichi Hozumi and John Roder, Mt. Sinai Research Institute, Toronto, Ontario, Canada.

To radiolabel the probe, alpha<32P> dCTP was obtained from Amersham, Arlington Heights, Ill., and the random priming kit was obtained from Pharmacia, Piscataway, N.J., USA.

The signals in Southern transfers were visualized by autoradiography using Kodak X-OMAT™ AR film. No obviously rearranged band was observed. Thus, relative to the standards, no unique band was detected on the autoradiogram for the CC49 DNA digested with Hind III. It could not be ruled out from the Southern data, however, that the rearranged band for the L chain was masked by a band migrating in the CC49 Hind III digested DNA parallel to the band resulting from a Hind III digest of mouse kidney cell DNA (representing the germline DNA). This actually turned out to be the case.

Preparation of Plasmid Containing Mouse $V_L$ Genes

LAMBDA-ZAP™ vector, a lambda-based insertion cloning vector capable of self excision, was purchased from Stratagene Company, La Jolla, Calif., USA. LAMBDA-ZAP vector is described on pages 20–21 of the 1987 Stratagene catalog. The cohesive (cos) ends of LAMBDA-ZAP vector were ligated overnight by following the manufacturer's protocol.

Twenty micrograms of the ligated LAMBDA-ZAP vector were digested with 5 µL (15 units) of Spe I, purchased from New England Biolabs, Inc. The total volume of the digest was 100 µL. After 55 minutes of digestion, another 6 units of Spe I were added. After 70 minutes, the reaction was stopped by phenol extraction and ethanol precipitation carried out as per Stratagene's protocol.

Digestion with Spe I restriction enzyme results in production of "sticky ends" at both termini. These sticky ends were modified with T4 DNA polymerase to create half filled-in Spe I sticky ends, e.g., 5'ACT/3'TCATG. To accomplish the half fill-in reaction, the DNA pellet obtained in the ethanol precipitation above was dissolved in 8 µL of water. To this was added 2 µL of 10 mM dTTP, 2 µL of 10 mM dCTP, 2 µL of Stratagene's 10x ligase buffer, 4 µL of reionized, distilled water, and 2 µL of a Klenow fragment from Bethesda Research Laboratories (BRL). The reaction was carried out at ambient temperatures for 30 minutes. The reaction was stopped by inactivating the DNA polymerase at 65° C. for 10 minutes.

One hundred sixty micrograms of total CC49 hybridoma DNA (containing the mouse light chain promoter and the L and VJ exons) were digested to completion with Hind III. Fragments between about 1 kb to about 20 kb were cut out of 0.8 percent agarose gels. The DNA was purified using GENECLEAN™, which is commercially available from BIO 101 (La Jolla, Calif., USA).

The total CC49 hybridoma DNA Hind III digested fragments were half-filled similarly to the Spe I fragments of the LAMBDA-ZAP vector with the exception that dATP and dGTP were employed. The half-filled Hind III digested fragments produced 5'AGCTT/3'GAA sticky ends, which are compatible with the Spe I half-filled LAMBDA-ZAP vector fragment above.

After phenol extraction and ethanol precipitation, according to the teachings of Maniatis, the total CC49 hybridoma Hind III modified- and LAMBDA-ZAP vector Spe I modified-DNA fragments were ligated by means of T4 DNA ligase. The ligation reaction was set using a 6.1 µL ligation mixture containing the following: About 0.2 µg of the total CC49 hybridoma Hind III modified-DNA in a 3 µL solution, about 1 µg of LAMBDA-ZAP vector Spe I modified DNA in a 1 µL solution, 0.6 µL of Stratagene's 10x ligase buffer, 0.5 µL 10 millimolar ATP, and 1 µL of Stratagene ligase. This was incubated overnight in a water bath and the temperature lowered incrementally from about 18° C. to about 4° C. This ligation eliminated both the Hind III and the Spe I sites.

A genomic library of ligated mix was made according to Stratagene's protocol. Briefly, 2 µL of the ligation mix produced above was used in Stratagene's Gigapack Gold™ packaging system, following the directions of the manufacturer. Fifteen 150 mm plates having a density of 50,000 plaques per plate were screened, as per manufacturer's directions, for positive clones by hybridization to nitrocellulose filters, obtained from Schleicher-Schuell, Keene, N.H., USA. The <32P> random-labeled probe derived from pGD1, which was described above, was used for hybridization. Two positive clones were obtained.

Figure 8:
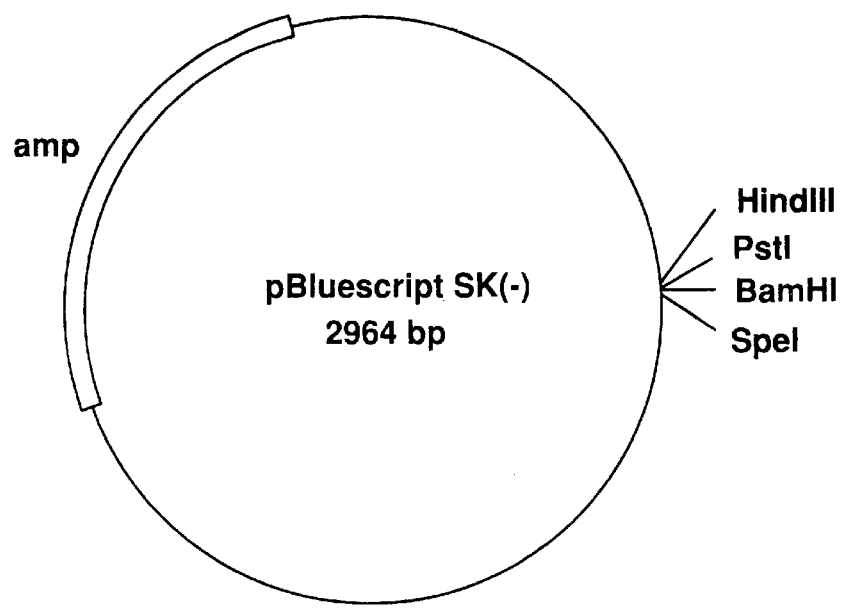
FIG. 8 illustrates the plasmid map of the pBLUESCRIPT SK(-).

Each clone was plaque purified and recombinant plasmids (phagemids) of LAMBDA-ZAP vector containing the CC49 L chain variable region were obtained by using Stratagene's automatic excision protocol. The vector portion of the resulting recombined plasmid is called pBLUESCRIPT SK(-) and consists of 2964 bp as described in the 1987 Stratagene catalog. A plasmid map of pBLUESCRIPT SK(-) is shown in FIG. 8.

The DNA from the two positive clones was partially sequenced and both were identical. One of the clones, which was named pRL101, was used for further studies.

Figure 9:
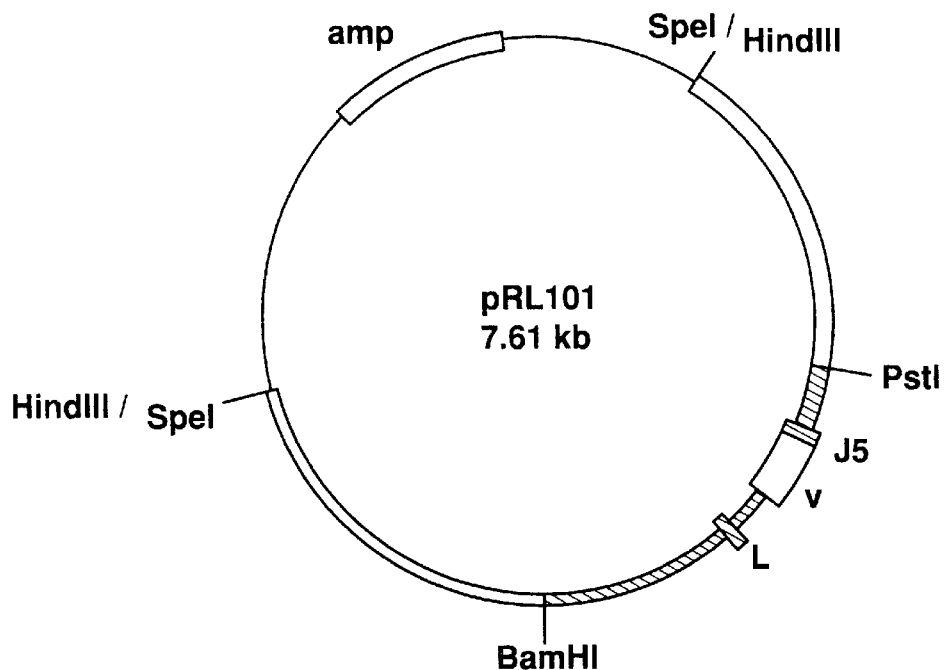
FIG. 9 illustrates the plasmid map of the pRL101.
Figure 10:
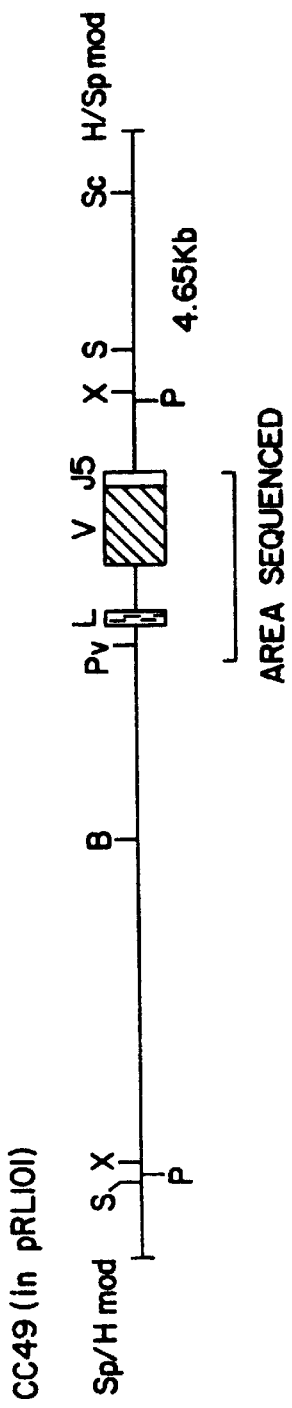
FIG. 10 illustrates a restriction enzyme map of the CC49 L chain genomic DNA insert in pRL101.

Restriction Mapping of CC49 Light Chain pRL101 was 7.61 kb, and the size of the DNA insert was determined by restriction enzyme mapping to be 4.65 kb. A plasmid map of pRL101 is shown in FIG. 9. A restriction enzyme map of the CC49 L chain genomic DNA insert in pRL101 is shown in FIG. 10.

Isolation of CC83 Light Chain Variable Region

The procedures used to isolate the CC83 light chain were essentially those used to isolate the CC49 light chain, with the following exception.

A genomic library containing $7 \times 10^5$ plaques was screened using as the probe the <32P> random-labeled 1.71 Hind III-Pst I fragment derived from pGD1, as described above. One positive clone was obtained. The positive clone was named pRL200.

Figure 11:
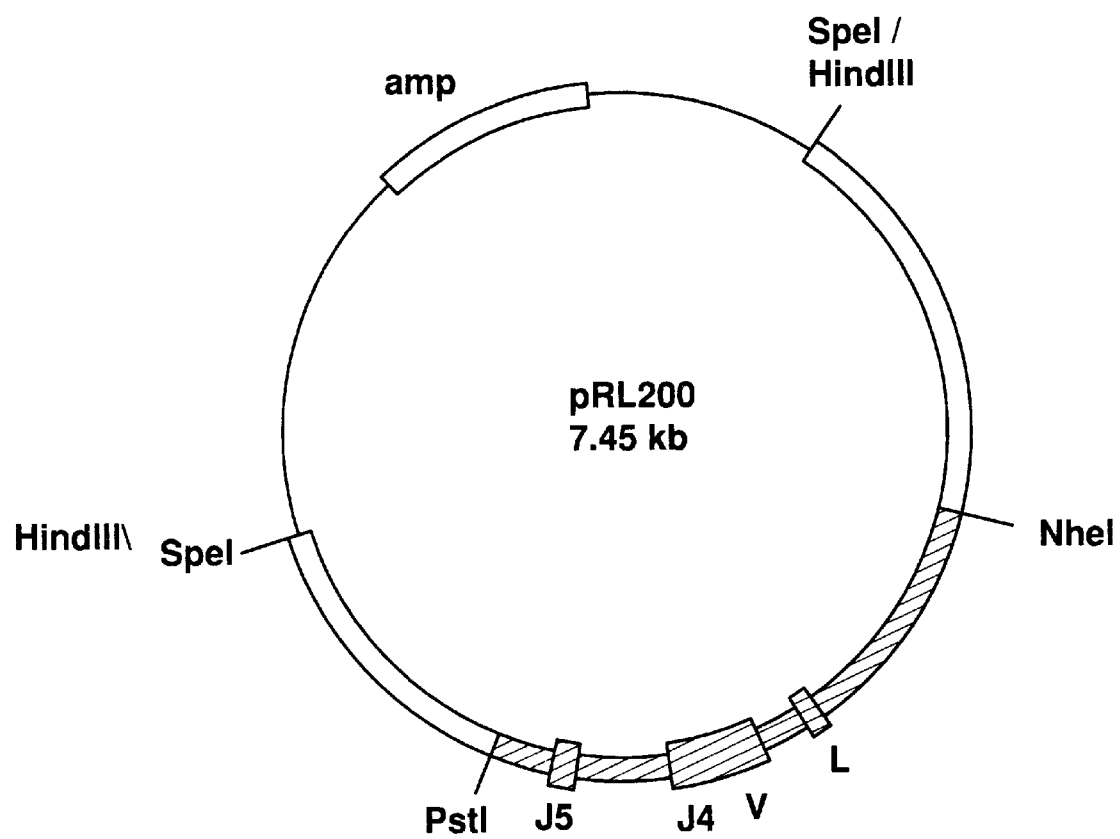
FIG. 11 illustrates the plasmid map of the pRL200.
Figure 12:
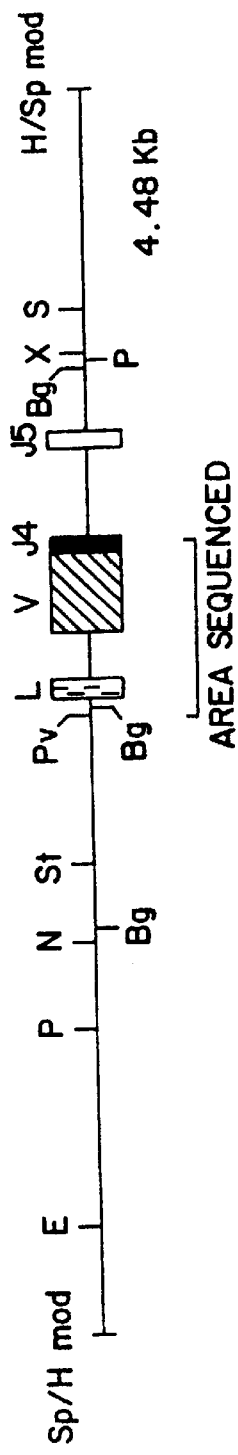
FIG. 12 illustrates a restriction enzyme map of the CC83 L chain genomic DNA insert in pRL200.

Restriction Mapping of CC83 Light Chain pRL200 was 7.44 kb, and the size of the DNA insert was determined by restriction enzyme mapping to be 4.48 kb. A plasmid map of pRL200 is shown in FIG. 11. A restriction enzyme map of the CC83 L chain genomic DNA insert in pRL200 is shown in FIG. 12.

Isolation of CC49 Heavy Chain Variable Region

The procedures used to isolate the CC49 heavy chain were essentially those used to isolate CC49 light chain, including the screening of the same CC49 Hind III modified DNA.

The hybridization probe used to screen the library was generated from pNP9, which contains a 1.98 kbp Eco RI-Bam HI fragment containing the coding exons for $J_H3$ and $J_H4$ of the CC49 immunoglobulin heavy chain. The nucleotide sequence of the probe fragment is provided in FIGS. 13A–13B (SEQ ID NO: 16).

A genomic library containing $9.5 \times 10^5$ plaques was screened, from which one positive clone was obtained. The positive clone was named pHH49.

Figure 14:
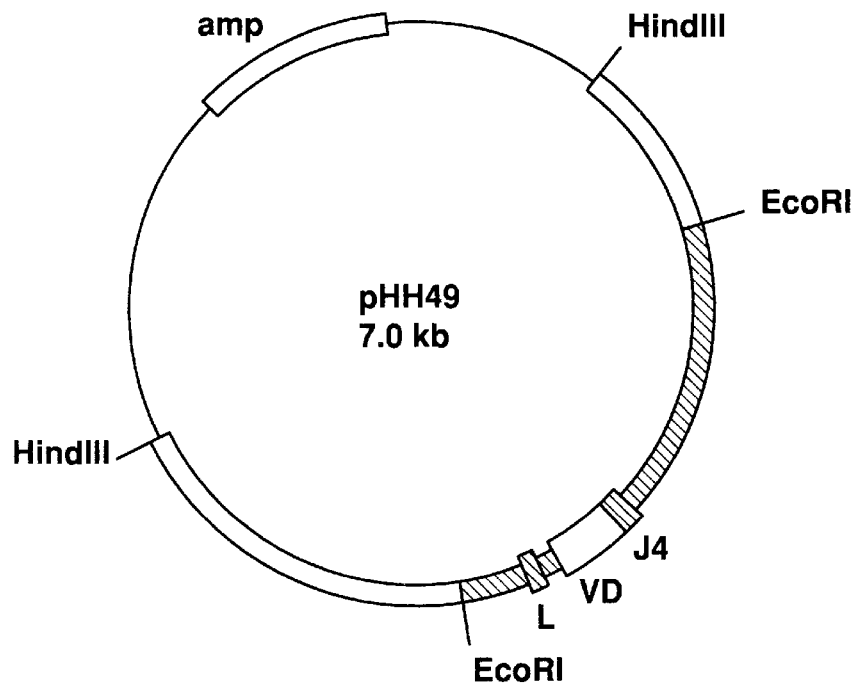
FIG. 14 illustrates the plasmid map of the pHH49.

Restriction Mapping of CC49 Heavy Chain pHH49 was about 7.0 kb, and the size of the DNA insert was determined by restriction enzyme mapping to be about 4.0 kb. A plasmid map of pHH49 is shown in FIG. 14.

Isolation of CC83 Heavy Chain Variable Region

The procedures used to isolate the CC83 heavy chain were essentially those used to isolated CC49 heavy chain, with the following exceptions.

About 13 g of ligated LAMBDA-ZAP vector DNA were digested with 12 units of Spe I, purchased from New England Biolabs, Inc., in a total of 100 µL of an appropriate buffer. The LAMBDA-ZAP vector was digested at 37° C. for one hour. The reaction mixture was phenol extracted and ethanol precipitated as per Stratagene's protocol. The Spe I-digested LAMBDA-ZAP vector was dephosphorylated according to procedures set forth in Maniatis except that 40 fold excess of calf intestinal alkaline phosphatase (Boehringer Mannheim, Indianapolis, Ind., USA) was used.

DNA from CC83 was digested to completion with Spe I. Fragments between about 3 kb to about 40 kb were isolated from a 0.8 percent agarose gel slice by electroelution as described by Maniatis, and ligated with the dephosphorylated Spe I-cut LAMBDA-ZAP vector.

A genomic library containing $5 \times 10^5$ plaques was screened using the probe generated from pNP9, the sequence of which is provided in FIGS. 13A–13B. One positive clone was obtained. The positive clone was named pHS83.

Figure 15:
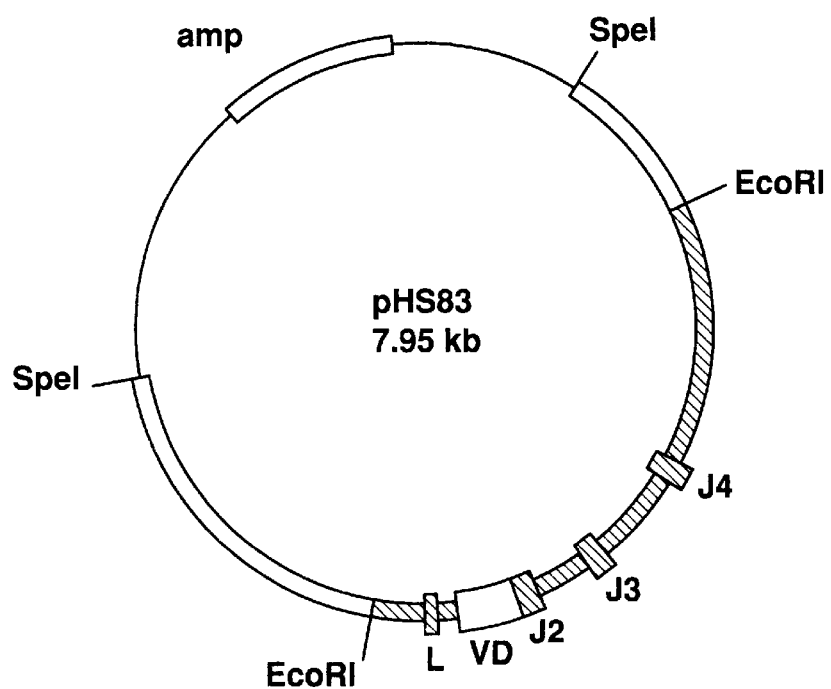
FIG. 15 illustrates the plasmid map of the pHS83.

Restriction Mapping of CC83 Heavy Chain pHS83 was 7.95 kb, and the size of the DNA insert was determined by restriction enzyme mapping to be about 5 kb. A plasmid map of pHS83 is shown in FIG. 15.

Sequencing of CC46, CC49, CC83 and CC92 mRNA

Total RNA from about $1 \times 10^7$ CC49 cells frozen at $-70°$ C. was extracted essentially as reported by Maniatis, with the following exceptions. Four molar guanidinium isothiocyanate and 2.5 molar sodium citrate, pH 7.0, and a SW40Ti rotor centrifuged at 31,000 rpm were used.

A total of 2.7 mg of CC49 RNA was isolated. After centrifugation, poly A+ mRNA was purified from about 1.68 mg of RNA by oligo(dT)-cellulose chromatography using Type 3 oligo(dT)-cellulose obtained from Collaborative Research, Inc., Bedford, Mass., USA. The procedure was as described by Aviv and Leder, *Proc. Natl. Acad. Sci.* (*USA*), 69:1408 (1972). A total of 50.24 µg of poly A+ mRNA was obtained from 1.68 milligrams of mRNA.

A total of 3.82 mg of CC83 RNA was isolated from approximately $1 \times 10^7$ cells. A total of 54.6 µg of poly A+ mRNA was isolated from 1.91 µg of total RNA.

A total of 0.814 mg of CC92 RNA was isolated from approximately $2.6 \times 10^8$ cells. A total of 41.88 µg of poly A+ RNA was isolated from 0.814 mg of total RNA.

A total of 1.7 mg of CC46 RNA was isolated from approximately $2.89 \times 10^8$ cells. A total of 68.88 µg of poly A+ RNA was isolated from 1.7 mg of total RNA.

Synthetic oligonucleotide primers were synthesized using an Applied Biosystems' (Applied Biosystems (ABI), Foster City. Calif.) Model 380A DNA synthesizer, by phosphoramadite-based chemistry as specified by ABI. The oligonucleotides were purified, as specified by the manufacturer, after electrophoresis on a 20 percent polyacrylamide gel containing 7 M urea. Oligonucleotide concentrations were determined spectrophotometrically at an optical density of 260 nm, where 1 OD 260 nm unit is equal to 33 µg/mL of single-stranded DNA.

The following oligonucleotide primers were made for mRNA sequencing: (1) For the CC49, CC83 and CC92 light chains, $K_L(-)$, a 22-mer (SEQ ID NO: 17):

5'-GGAAGATGGATACAGTTGGTGC-3' complimentary to the coding sequence of the 5' end of the constant region for mouse immunoglobulin kappa chains, is used to determine the 3' most mRNA sequence of the light chain variable region.

Additionally, for CC49 light chain, 49FR1(−), a 17-mer (SEQ ID NO: 18):

5'-GGAAGATGGATACAGTTGGTGC-3' was used to determine the remaining sequence.

Additionally, for CC83 light chain, J4(−), a 24-mer ( SEQ ID NO: 19):

5'-CCAACTTTGTCCCCGAGCCGAACG-3' and also 83L CDR2(−), a 17-mer: 5'-CAGGGACTCCAGTGTGC-3' was used to determine the remaining sequence.

Additionally, for CC92 light chain, J5(−) (SEQ ID NO: 20):

5'-CGTTTCAGCTCCAGCTTGGTCCC-3' was used to determine the remaining sequence.

For the CC46, CC49, CC83, and CC92 γ1 heavy chains, CH1(−), a 24-mer (SEQ ID NO: 21):

5'-ATGGAGTTAGTTTGGGCAGCAGAT-3' complimentary to the coding sequence of the 5' end of the murine γ1 heavy chain constant region. The CH1 (−) 24-mer is used to determine the 3'-most mRNA sequence of heavy chain variable regions.

Additionally, for the CC49 heavy chain, JH4(−)-20 mer (SEQ ID NO: 22):

5'-GGTGACTGAGGTTCCTTGAC-3' was used to determine the remaining sequence.

Additionally, for the CC83 heavy chain, JH2(−)-16 mer (SEQ ID NO: 23):

5'-CTGAGGAGACTGTGAG-3' was used to determine the remaining sequence.

Additionally, for the CC92 heavy chain and the B72.3 heavy chain, B72.3/CC92 HC-20 mer (SEQ ID NO: 24):

5'-CCTTGAACTTCTCATTGTAC-3' was used to determine the remaining sequence.

The following procedures were carried out as outlined in Gelliebter, *BRL FOCUS*, 9:1 (1987).

The oligonucleotide primers were end-labeled as follows: 100 ng of oligonucleotide were combined in 50 mM Tris HCl (pH 8), 10 mM MgCl$_2$, 5 mM dithiothreitol, and 1 mM spermidine, 100 µCi (γ-$^{32}$P) ATP (Amersham, 5000 Ci/mMole) and 7 units of T4 polynucleotide kinase in a volume of 13 µl. The reaction was allowed to proceed at 37° C. for 30 minutes, then heated for 5 minutes at 65° C. to inactivate the kinase, and then 7 µl of water was added to make the concentration 5 ng/µl. The labeled primers were stored at −20° C. until needed.

Separate samples, each containing about 13 µg of poly (A)$^+$ mRNA of CC49, CC83, CC92, or CC46, respectively, were resuspended in 10 µl of annealing buffer (10 mM Tris HCl (pH 8.3), and 250 mM KCl).

A 5 ng sample of end-labeled oligonucleotide primer was added to each mRNA sample, heated to 80° C. for 3 minutes, and annealed for 45 minutes at 61° C. for the $K_L(-)$ oligonucleotide and 65° C. for the CH1(−) oligonucleotide. AMV reverse transcriptase (Boehringer Mannheim) was used at a level of 6 units for each mRNA sequencing reaction. The remainder of the sequencing was carried out as set forth in Gelliebter (1987), supra.

Initial sequence data showed that the heavy and light chains were rearranged as follows: CC49 kappa light chain used a J5, CC49 γ1 heavy chain used a $J_H4$. The CC83 light chain used a J4; the CC83 gamma 1 used a $J_H2$. The CC46 kappa light chain used a J2, and the CC46 heavy chain used a $J_H3$. The CC92 light chain used a J5, and the CC92 gamma 1 used a $J_H^2$.

FIG. 16 (SEQ ID NO: 25) shows the nucleotide sequence of CC49 $V_H$, with the underlined segments showing the sequences derived using oligonucleotide primers on mRNA.

FIG. 17 (SEQ ID NO: 26) shows the nucleotide sequence of CC83 $V_H$, with the underlined segments show the sequences derived using oligonucleotide primers on mRNA.

The entire nucleotide sequences of CC46 $V_H$ and CC92 $V_H$, shown in FIGS. 2A–2G, were derived using oligonucleotide primers on mRNA.

FIG. 4A shows the nucleotide sequence of CC49 $V_L$, with the underlined segments show the sequences derived using oligonucleotide primers on mRNA.

FIG. 5A shows the nucleotide sequence of CC83 $V_L$, with the underlined segments show the sequences derived using oligonucleotide primers on mRNA.

The entire nucleotide sequence of CC92 $V_L$, shown in FIG. 6 (SEQ ID NO: 27), was derived using oligonucleotide primers on mRNA. The amino acid sequence of CC92 VL is given in SEQ ID NO: 28.

Protein Sequence

Purified murine CC49 and CC83 immunoglobulin molecules analyzed for $NH_2$-terminal amino acid sequence using the Edman degradation method, as modified by Tarr, (1986) in "Manual Edman Sequencing System", *Microcharacterization of Polypeptides: A Practical Manual* (John E. Shively, ed., Humana Press, Inc., Clifton, N.J., pp 155–194). The immunoglobulin molecules were reduced and alkylated. The light and heavy chains of the immunoglobulin molecules were separated by reverse phase HPLC.

FIG. 4B shows the amino acid sequence for CC49 $V_L$, with the results of the amino acid sequence determination for the first 24 amino acids of the mature CC49 $V_L$ being underlined. FIG. 5B shows the amino acid sequence for CC83 $V_L$, with the results of the amino acid sequence determination for the first 51 amino acids of the mature CC83 $V_L$ being underlined. ASN-20 could not be determined in the CC83 light chain, because of the presence of N-linked carbohydrate residues at this position, which is shown in the PNGase F experiment below. The sequence Asn-Ile-Thr corresponds to the consensus sequence Asn-X-Thr/Ser for carbohydrate attachment to Asn.

Since the heavy chains of immunoglobulins CC49 and CC83 are blocked at the N-terminus and unavailable for amino acid sequence determination, the native glycopeptide was treated with cyanogen bromide (CNBr) to cleave at the methionine residues. The cleavage resulted in fragments, which were purified by reverse phase HPLC. N-terminal amino acid sequencing was performed on the CNBr fragments.

The results of the amino acid determination of one of the CC49 $V_H$ CNBr peptide fragments are indicated as underlined residues in FIG. 18 (SEQ ID NO: 29). The results of the amino acid determination of one of the CC83 $V_H$ CNBr peptide fragments are indicated as underlined residues in FIG. 19 (SEQ ID NO: 30). As with CC49, all other peptide sequences correspond to CNBr fragments derived from the constant region of mouse γ1.

Determination of N-Linked Carbohydrate on CC83 L Chain

This experiment was done to verify that there is an N-linked carbohydrate attached to the CC83 light chain, presumably at ASN-20 (see FIG. 5B). The enzyme glycopeptidase F (PNGase F), which is isolated from the culture filtrate of *Flavobacterium meningosepticum* (Tarentino et al., *Biochemistry*, 24:4665–4671 (1985)), will cleave high mannose and/or biantennary complex sugars N-linked to ASN to generate a free carbohydrate structure and an ASP residue from the ASN to which it was attached. The difference in molecular weight between the glycosylated and unglycosylated form of the same peptide can be determined by SDS-PAGE.

Figure 20:
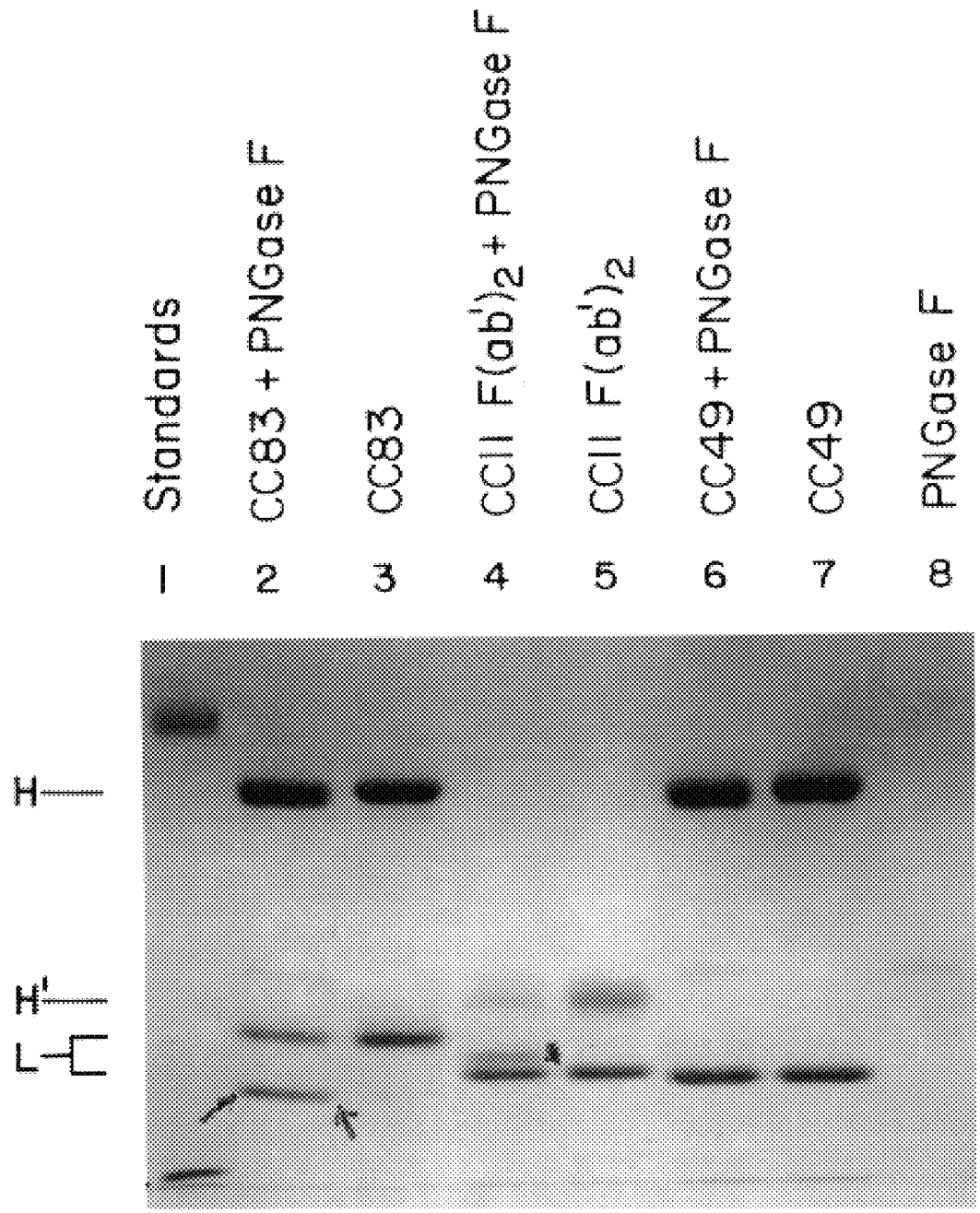
FIG. 20 shows the results of a SDS polyacrylamide gel, with the results of PNGase F treatment of CC83 antibody.
Figure 21A:
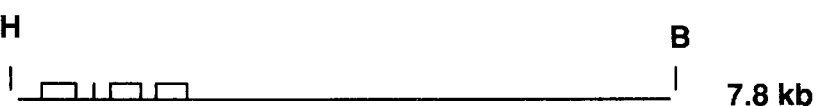
FIGS. 21A–21D, illustrates the restriction enzyme maps of human gamma 1, (21A) gamma 2, (21B) gamma 3, (21C) and gamma 4 (21D).
Figure 21B:
Figure 21C:
Figure 21D:

Twelve microgram reactions with and without PNGase F (Boehringer Mannheim, Indianapolis, Ind., USA) for the purified murine antibodies CC49, CC83 and CC11 F(ab')$_2$ (a positive control) were carried out in a final aqueous reaction volume of 40 μL. Four microliters of 10×buffer (1 M potassium phosphate, 0.1 M disodium EDTA pH 7.4) were added to each reaction mix. To those tubes designated "with PNGase F", 7.5 μL of PNGase F were also added and all tubes were incubated at 37° C. for 1 hour. To the reaction tubes was added 40 μL of Laemmli 2× sample dilution buffer containing β-mercaptoethanol. A 10 percent SDS polyacrylamide gel was electrophoresed, the gel stained with Coomassie Brilliant Blue R-250 and destained. FIG. 20 shows the results. As shown in lane 2, a new band (*) appears in the PNGase F treated CC83 sample but not in the untreated CC83 sample (lane 3). The new band is approximately 2,000–3,000 molecular weight smaller than the native light chain band, which represents the removal of an N-linked carbohydrate moiety. The only consensus glycosylation site for the CC83 light chain is at ASN 20, so by inference it is assumed that this is the actual site of glycosylation. The CC49 light chain does not change mobility when treated with PNGase F (lane 6), but a new band is observed for the heavy chain fragment of CC11 F(ab')$_2$ (lane 4*) which serves as a positive control. mRNA sequence data of CC11 heavy chain indicates a consensus glycosylation site in the V domain (data not shown). The standards (lane 1) are bovine serum albumin (BSA), MW 68,000 and soybean trypsin inhibitor (STI), MW 21,500.

DNA Sequence

Plasmid DNA was sequenced directly using the Sequenase™ DNA sequencing kit, obtained from United States Biochemical (USB), Cleveland, Ohio, USA. USB's protocol was followed to sequence double stranded DNA. The DNA of each variable region was sequenced using the $J_H$ or $J_L$ oligo determined from the mRNA sequence information to be specific for each productively rearranged heavy chain or light chain gene, respectively.

After the initial sequences were determined, the sequence was extended further by using additional primers. The additional primers were synthesized using information gathered from the sequences previously generated.

Using the above technique, the DNA sequences of the entire heavy chain variable region exons and light chain variable region exons of CC49 and CC83 were obtained. The DNA sequence was compiled and analyzed using a DNASIS™ DNA sequence analysis software program (Hitachi).

The following oligonucleotide primers were made for DNA sequencing:

(1) For both light chains, $C_K$ K intron(−) (SEQ ID NO: 31):

5'-GAAAACCTGTGTCTTACAC 3'.

(2) For the CC49 light chain, CC49 FRI(+) (SEQ ID NO: 32):

5'-GTACCTGTGGGGACATTG 3', and JK5(−)-23 mer (SEQ ID NO: 33)

5'CGTTTCAGCTCCAGCTTGGTCCC-3'.

(3) For the CC83 light chain, CC83 CDR2(−) (SEQ ID NO: 34):

5'-CAGGGACTCCAGTGTGC 3',
CC83 L intron (−) (SEQ ID NO: 35):
5'GACTTCAAGATACAAATGTTAG-3', and JK4(−)-20 mer (SEQ ID NO: 36):

5'-CCAACTTTGTCCCCGAGCCGAACG.

The complete nucleotide sequences for CC49 $V_L$ and CC83 $V_L$ are shown in FIGS. 4A and 5A, respectively.

For the CC49 heavy chain, $J_H4$ (−)-20 mer (SEQ ID NO: 37):
  5'GGTGACTGAGGTTCCTTGAC-3' and $J_H4$ Intron (−) (SEQ ID NO: 38):
  5'-GCAATGCTCAGAAAACTCC.

For the CC83 heavy chain, JH2(−)-16 mer (SEQ ID NO: 39):
  5'CTGAGGAGACTGTGAG-3' and $J_H2$ Intron(−) (SEQ ID NO: 40):
  5'-GCAGTAAAATCTATCTAAGCTG.

Thereafter, the sequencing of each heavy chain was extended with the following sequences: CC49/83 HC/5'(+) (SEQ ID NO: 41)
  5'-GCACTGCTCATGATATGCAAATC-3'; CC49/83 HC/5'(−) (SEQ ID NO: 42)
  5'-GATTTGCATATCATGAGCAGTGC-3'; and CC49/83 H chain FRI(−) (SEQ ID NO: 43)
  5'-CTCAGCGTCAGACTGCTG-3'.

The complete nucleotide sequences for CC49 $V_H$ and CC83 $V_H$ are shown in FIGS. 2A–2G.

Comparisons were made between the characterized mRNA sequence and the characterized DNA sequence, and between the characterized amino acid sequence with the amino acid sequence predicted from the DNA sequence. Based on these comparisons, the plasmid clones were identified to contain the correct DNA sequence to code for the CC49 and CC83 heavy and light chain variable regions.

The predicted amino acid sequences from the nucleotide sequences of the heavy chain variable regions of CC49 and CC83, as shown in FIGS. 2A–2G, show extensive sequence similarity throughout the framework regions and hypervariable regions 1 and 2. Hypervariable region 3 is quite different between the two due to the recombination of the $V_H$ region with different D and $J_H$ sequences, namely that the CC49 γ1 heavy chain used a $J_H4$, and the CC83 gamma 1 used a $J_H2$.

The extensive DNA sequence homology 5' to the coding regions in the CC49 and CC83 heavy chain variable region genes shows the two heavy chain variable region genes were derived from the same germline exons.

Isolation of $V_H\alpha$TAG, Germline Precursor Gene to the Heavy Chain of CC46, CC49, CC83, and CC92.

The procedures used to isolate the germline precursor gene to the heavy chain variable regions of CC46, CC49, CC83, and CC92 were essentially those used to isolate the CC49 heavy chain variable region except that the DNA used to generate the LAMBDA-ZAP vector library came from an irrelevant hybridoma cell line (i.e., a cell line which produces antibodies that do not appreciably bind to TAG-72). A genomic library containing approximately 900,000 plaques was screened from which one positive clone was isolated. The positive clone was named p$V_H\alpha$TAG. p$V_H\alpha$TAG was about 5.2 kb, and the size of the DNA insert was determined by restriction enzyme mapping to be about 2.2 kb.

DNA sequence of $V_H\alpha$TAG

The following oligonucleotide primers were used for determining the DNA sequence of $V_H\alpha$TAG:
  B72.3/CC92 HC-20 mer (SEQ ID NO: 44): 5'-CCTTGAACTTCTCATTGTAC-3';
  CC49/CC83 HC 5'(+) (SEQ ID NO: 45): 5'-GCACTGCTCATGATATGCAAATC-3';
  CC49/CC83 HC 5'(−) (SEQ ID NO: 46): 5'-GATTTGCATATCATGAGCAGTGC-3';
  $V_H\alpha$TAG IVS (+) (SEQ ID NO: 47): 5'-CTAAAGTGGAGTCAGGGCCTG-3';
  $V_H\alpha$TAG IVS (−) (SEQ ID NO: 48): 5'-CAGGCCCTGACTCCACTTTAG-3';
  $V_H\alpha$TAG CDR2 (+) (SEQ ID NO: 49): 5'-GAATGGATTGGATATATTTCTC-3'.

The complete nucleotide sequence of $V_H\alpha$TAG is shown in FIGS. 2A–2G.

Isolation of Human Heavy Constant Genes

Plasmid constructs containing the various heavy chain human constant regions (pγ1, pγ2, pγ3, and pγ4) were provided by Dr. Ilan R. Kirsch of the National Cancer Institute, Bethesda, Md., USA.

Restriction enzyme mapping was performed on these genes to confirm their identity. Restriction maps for the human constant regions are enclosed in FIGS. 21A–21D.

Chimeric Light Chain

Murine CC49 V Region

The Hind III site of the CC49 light chain genomic DNA located in the murine intron region between J5 and $C_k$ (see Max et al., *J. Biol. Chem.*, 256:5116 (1981) was lost in the cloning procedure where half-filled in Hind III sites were ligated to half-filled in Spe I sites in the LAMBDA-ZAP vector. The plasmid pRL101 (FIG. 9) carried this modification. The intron Hind III site was regenerated as outlined in the steps below in order to enable a Hind III-Bam HI human germline kappa light chain DNA fragment (see Hieter et al., *J. Biol. Chem.*, 257:1516 (1982)) to be ligated to the murine variable region directly. All steps were performed using standard molecular biology techniques familiar to artisans and can be found in a manual such as Manatis.

A 1.69 kb Bam HI-Pst I fragment was isolated from pRL101, described supra. A 2.96 kb Bam HI-Pst I fragment was isolated from pBluescript SK(−) (purchased from Stratagene), supra. The two fragments were then ligated and pRL103, (FIG. 47), was isolated.

Plasmid pGD1, (described supra), was digested with Pst I and Hind III restriction enzymes to yield the necessary 1.03 kb intron-containing fragment, and pRL103 was also digested with Pst I and Hind III restriction enzymes to remove the small fragment of DNA in the polylinker.

Figure 47:
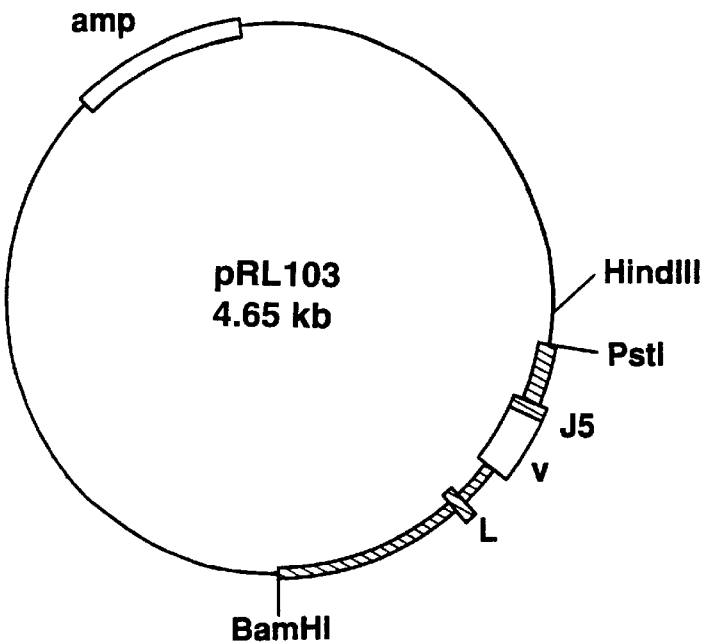
FIG. 47 illustrates the plasmid map of pRL103.
Figure 48:
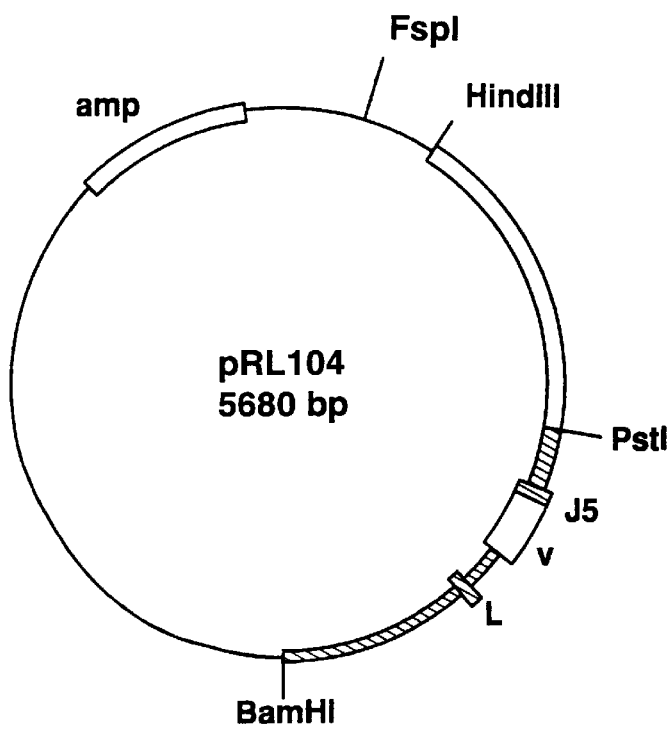
FIG. 48 illustrates the plasmid map of pRL104.
Figure 49:
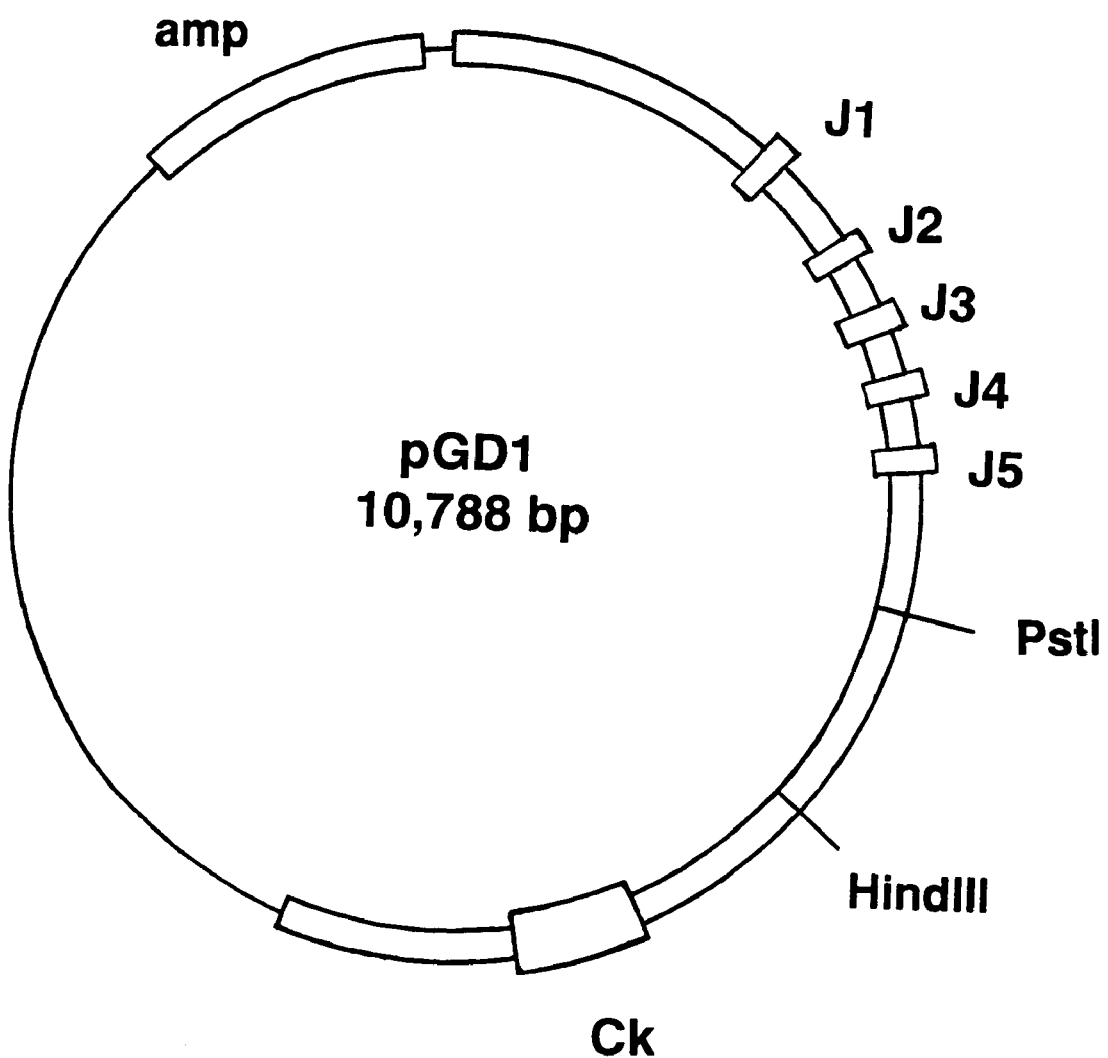
FIG. 49 illustrates the plasmid map of pGD1.

The resulting fragments were ligated with T4 DNA ligase to produce a 5.68 kb plasmid, called pRL104. A partial restriction map of pGD1 and pRL104 is shown in FIGS. 47 and 48.

Human $C_K$ Region

Figure 50:
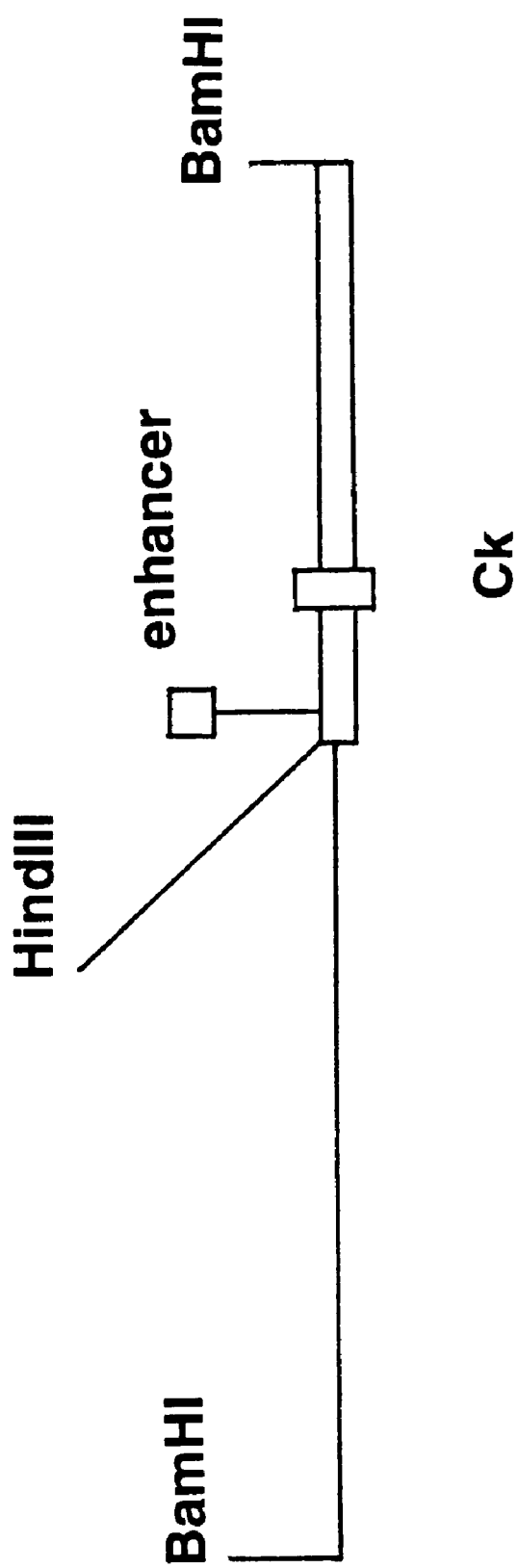
FIG. 50 illustrates the restriction map of the Bam HI fragment of phumCk.

Plasmid phum $C_K$ was obtained from Dr. John Roder, Mt Sinai Research Institute, Toronto, Ontario, Canada. The plasmid is derived from pBR322, with a 12 kb Bam HI fragment containing the human $C_K$ exon inserted therein. pBR322 is described on page 171 of the 1987 Stratagene catalog. The 12 kb Bam HI fragment restriction map is shown in FIG. 50 (from Heiter et al. *J. Biol. Chem,* 257:1516 (1982)).

The plasmid phum $C_k$ was digested with Hind III and Bam HI restriction enzymes to yield a 5.0 kb fragment, containing the human $C_k$ exon. pRL104 was digested with Fsp I and Hind III restriction enzymes to yield a 4.2 kb fragment, containing the mouse light chain variable exons of CC49.

The two resulting fragments were joined with T4 DNA ligase to produce a 9.2 kb fragment among the mixture of resulting fragments. This mixture was digested with Bam HI to yield a 7.7 kb Bam HI CC49 L chain chimeric construct with Bam HI sticky ends, which contains both the mouse variable region exons and the human constant region (kappa) exon. These constructions utilize the human enhancer sequences and the murine promoter sequences.

The chimeric Bam HI fragment containing both the murine light chain variable region exons (L and VJ) and the human constant region kappa (k) exon was ligated into the Bam HI site with the plasmid pSV2neo (5.6 kb), a pBR322-derived plasmid containing the selectable marker gene neo (obtained from ATCC). The presence of the active neo gene renders a cell resistant to growth inhibition by GENETI-CIN™ aminoglycoside, a neomycin-like drug also called G418.

Figure 51:
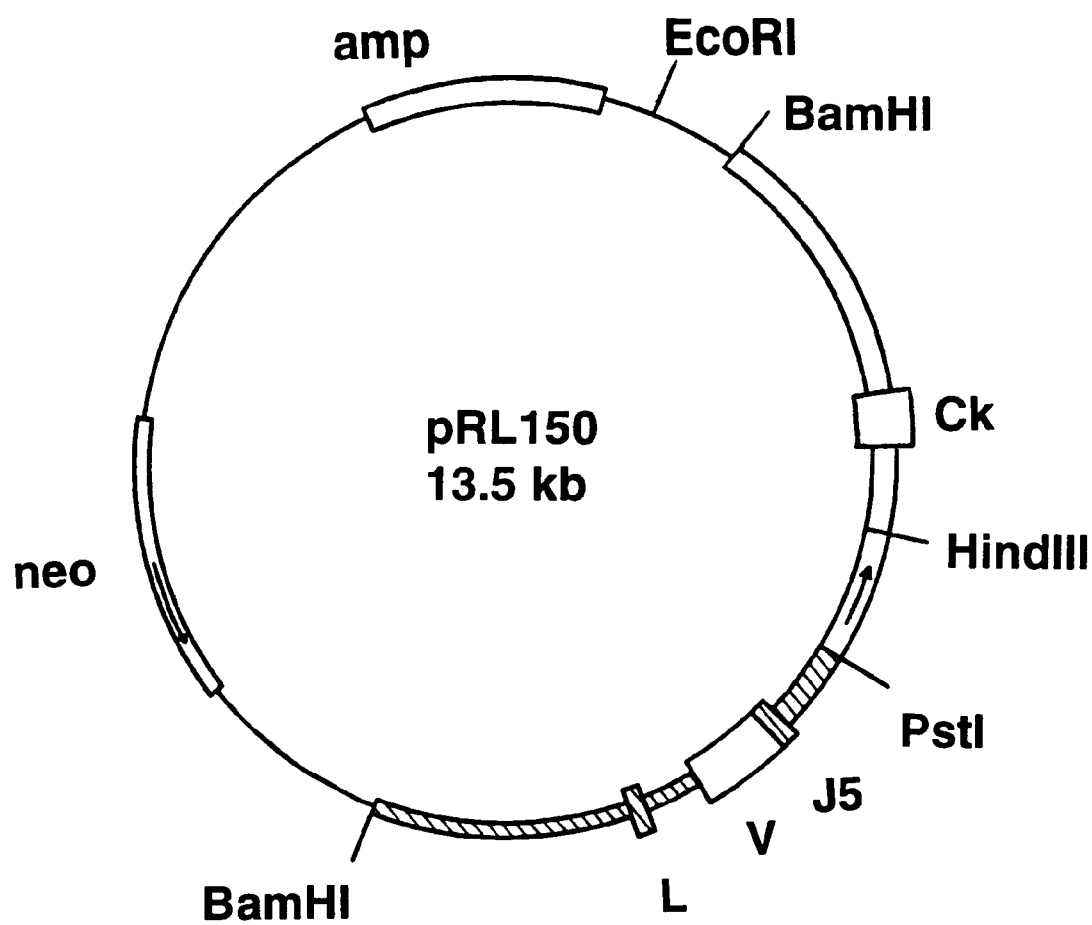
FIG. 51 illustrates the plasmid map of pRL150.
Figure 52:
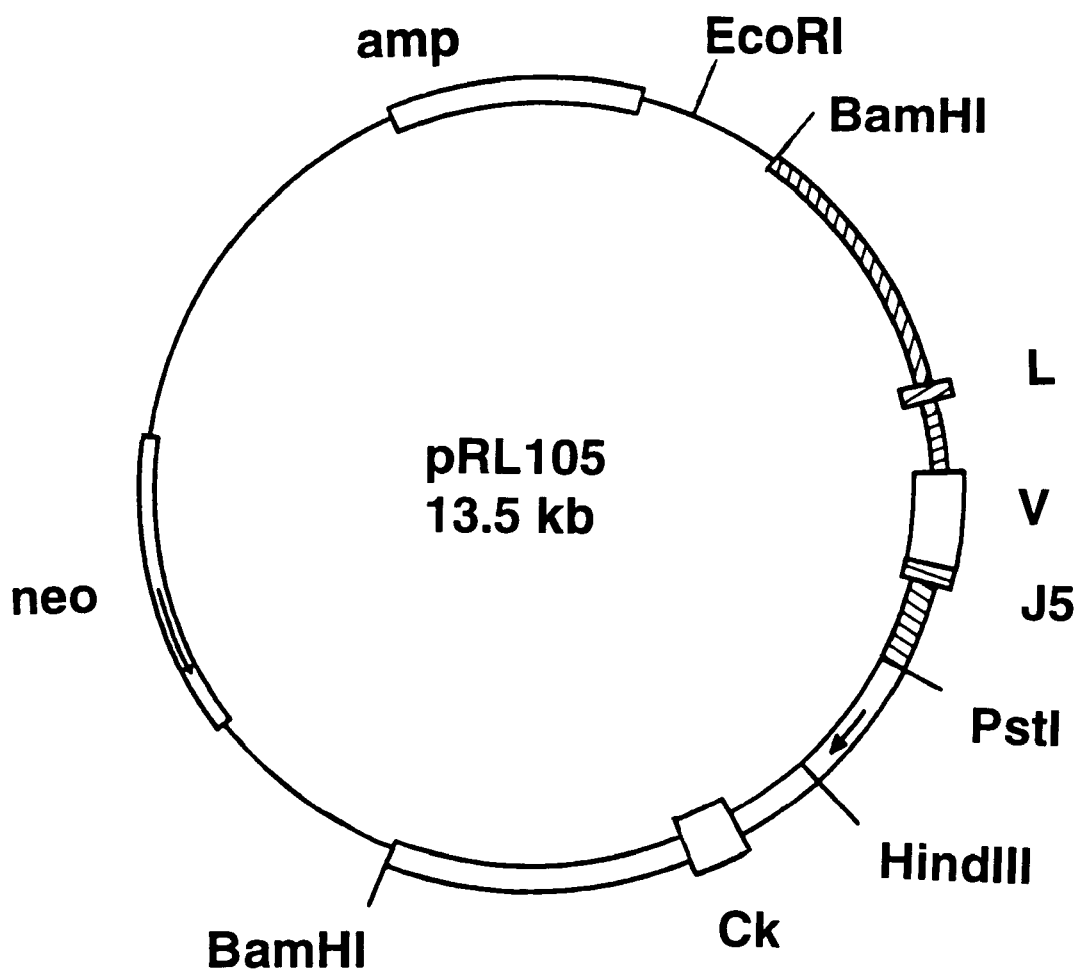
FIG. 52 illustrates the plasmid map of pRL105.

The chimeric Bam HI fragment was inserted into pSV2neo in both orientations as shown in FIGS. 51 and 52. Both transcriptional orientations of the chimeric light chain gene, relative to the neo gene, were constructed. Plasmid pSV2neo was linearized at the Bam HI site, dephosphorylated (according to procedures set forth in Maniatis) using calf intestinal alkaline phosphatase (to prevent self-ligation) and ligated with chimeric CC49 L chain Bam HI fragments from above to form pRL150 and pRL105.

The transcriptional orientations of the neo gene and the CC49 chimeric light chain are indicated by arrows in pRL150 and pRL105. The portions derived from pSV2neo are indicated. These plasmids were purified on a large scale from preparative scale (1.0 L) fermentation of *E. coli* clones replicating each of the plasmids. The purified plasmids were used to introduce the chimeric CC49 light chain into SP2/0 plasmacytoma cells as discussed below.

Murine CC83 $V_L$ Region and Human $C_K$ Region

The Hind III site in pRL200 which was lost in the cloning process of the CC83 light chain was regenerated for the same reason as for the CC49 light chain chimeric construction. The regeneration was accomplished as follows. The plasmid pRL200 was linearized at a unique Nhe I site, and both of its sticky ends were converted to blunt ends by filling in with dNTPs and DNA polymerase I. A Bam HI phosphorylated linker (purchased from New EnglandBiolabs) was ligated to the filled-in site. The new plasmid is called pRL201.

Figure 53:
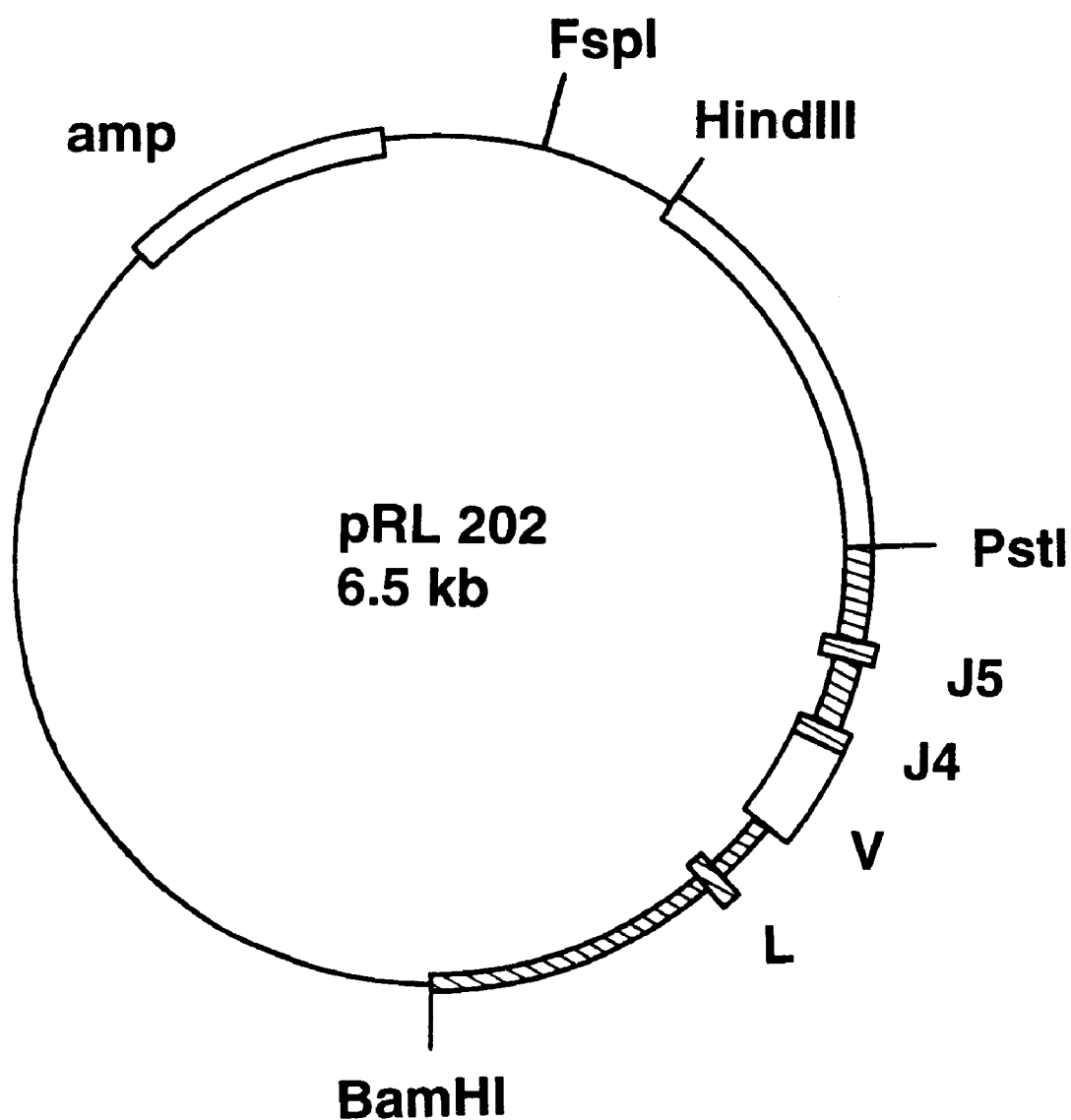
FIG. 53 illustrates the plasmid map of pRL202.

The 2.5 kb Bam HI-Pst I fragment from pRL201 containing the CC83 light chain variable region genomic DNA was conveniently ligated to the 4 kb Bam HI-Pst I vector fragment from pRL104 which was described earlier in the CC49 light chain constructions and which already had the Hind III-bearing intron fragment. The new plasmid is called pRL202 and is shown in FIG. 53.

Figure 54:
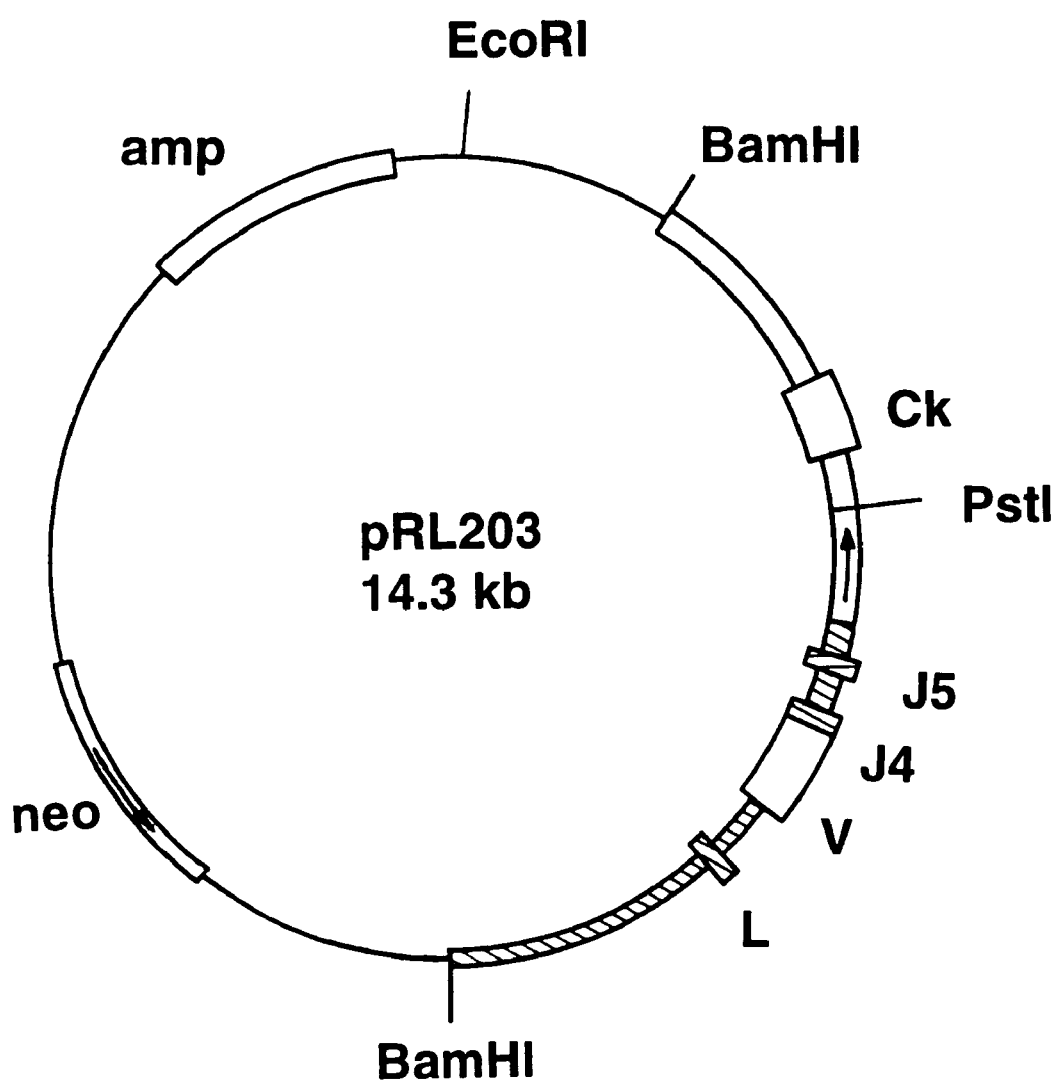
FIG. 54 illustrates the plasmid map of pRL203.
Figure 55:
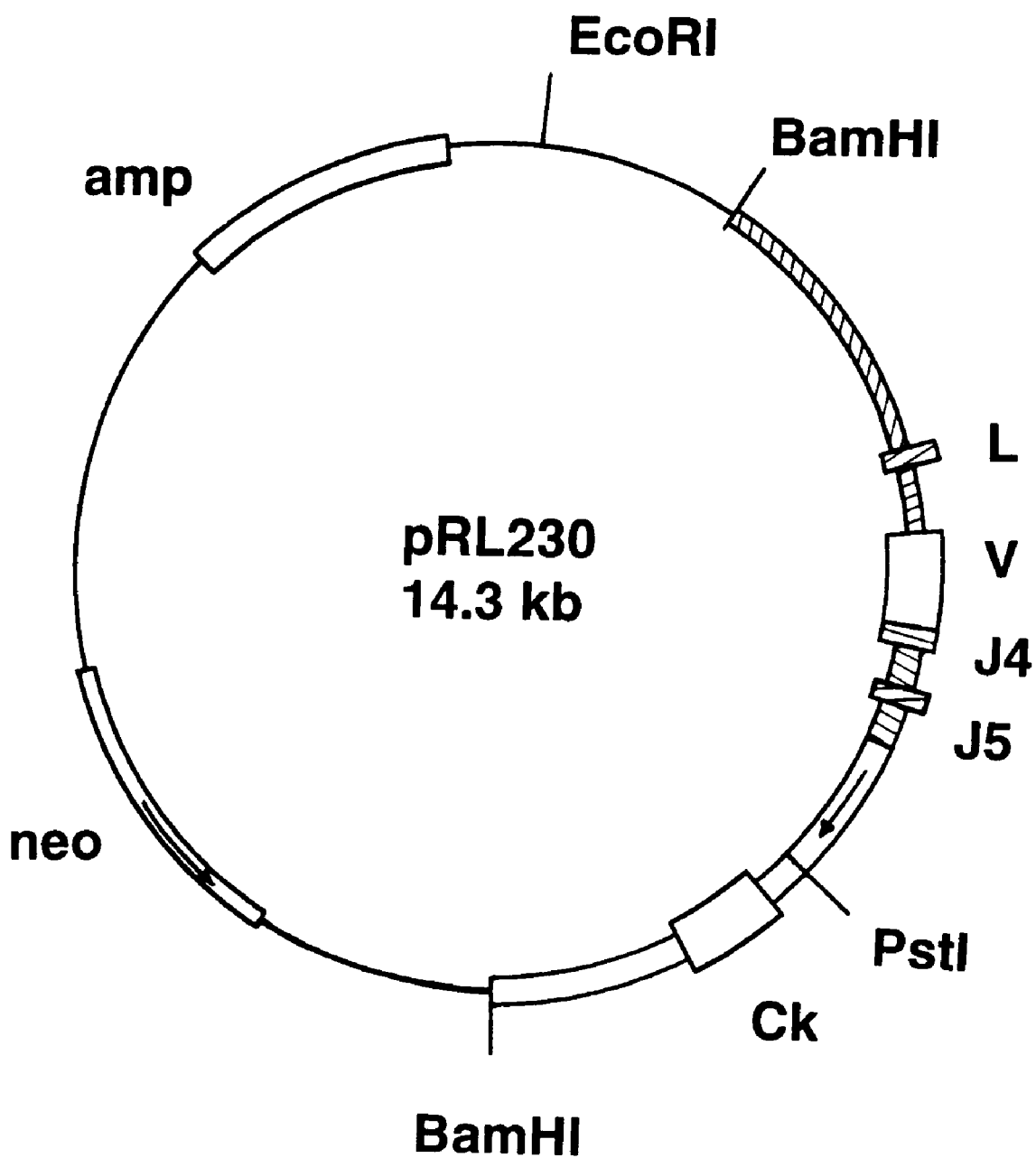
FIG. 55 illustrates the plasmid map of pRL230.

The approximately 5.05 kb Fsp I-Hind III fragment from pRL202 was isolated and ligated with the human $C_k$-containing 5.0 kb Hind III-Bam HI fragment already described for the CC49 light chain chimeric construction. The generation of the CC83 light chain vector was accomplished from this point in an identical fashion as carried out for the CC49 light chain. The resulting 8.5 kb Bam HI CC83 light chain chimeric construct was also ligated to pSV2neo-Bam HI (phosphatased) and plasmids with both possible orientations of the insert were obtained as diagramed in FIGS. 54 and 55.

The transcriptional orientations of the neo gene and the CC83 chimeric light chain are indicated by arrows in pRL203 and pRL230. These plasmids were purified on a large scale from a preparative scale of about 1 Liter (1.0 L) fermentation in a commercial incubator of *E. coli* clones replicating each of the plasmids. The purified plasmids were used to introduce the chimeric CC83 light chain into Sp2/0 plasmacytoma cells, as discussed below.

All four of the chimeric light chain plasmid constructs (pRL105, pRL150, pRL203 and pRL230) can be linearized by digesting with the restriction enzyme Aat II. The Aat II site in the plasmids is in a region that is not essential for the expression of the chimeric light chain gene or the selectable marker gene, neo.

Chimeric Heavy Chains

Human Gamma Constant Gene Exons

Figure 22:
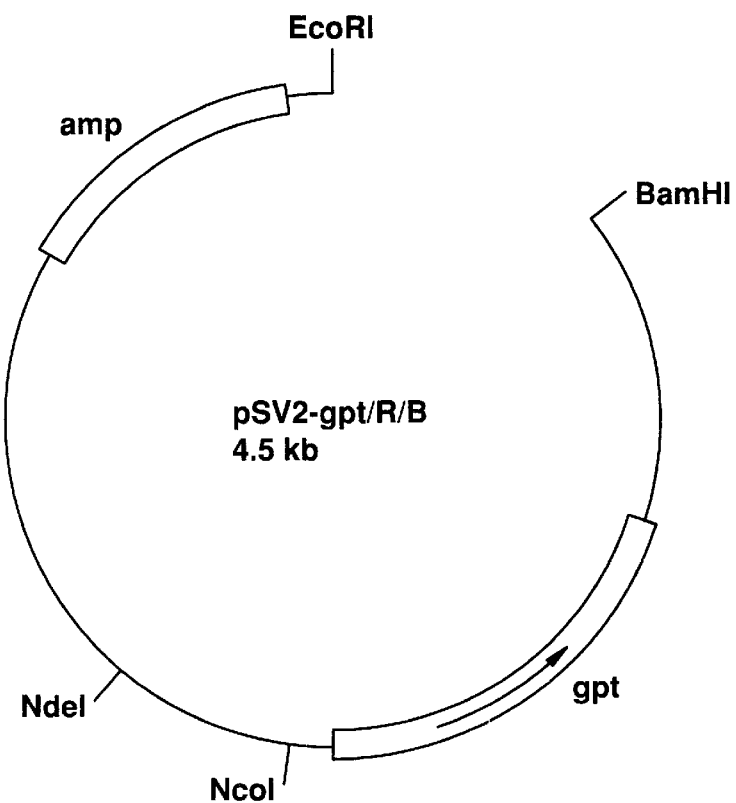
FIG. 22 illustrates the plasmid map of pSV2gpt/R/B.

The plasmid vector used to carry the chimeric heavy chain constructs is designated pSV2gpt, set forth in Mulligan and Berg, *Proc. Natl. Acad. Sci* (*USA*), 78(4): 2072–2076 (1982). pSV2gpt is a pBR322 derived plasmid containing the selectable marker gene, guanine phosphoribosyl transferase (gpt), which can be used for selective growth in media containing mycophenolic acid. To prepare pSVgpt as a recipient for the human Cγ1, Cγ2, Cγ3, Cγ4 exons, it was digested with Eco RI and Bam HI. The digested DNA was fractionated on a 4 percent polyacrylamide gel and the 4.5 kb vector fragment was recovered from the gel by electroelution as described in Maniatis. This linearized plasmid was designated pSV2gpt/R/B, a plasmid map is shown in FIG. 22. It is able to accept Eco RI-Bam HI ended fragments.

The 5' Hind III sites, present on the human $IgG_1$ constant region fragments, were converted to Eco RI sites for directed cloning into the Eco RI site of pSV2-gpt. For γ1, γ2, γ3, and γ4, the Eco RI site in vector, pBR322 was employed.

Cγ1

The fragment containing the human Cγ1 exons was obtained by digesting and linearizing pγ1 with Hind III followed by filling in the Hind III sticky ends using all four dNTP's and the Klenow fragment of DNA Polymerase to make the Hind III ends blunt. An Eco RI linker was ligated to the blunt ends to replace the Hind III site with an Eco RI site. This construct was then digested with Eco RI and Bam HI to release a 7.8 kb fragment containing the Cγ1 exons. This fragment was called Cγ1-7.8 kb.

Figure 23:
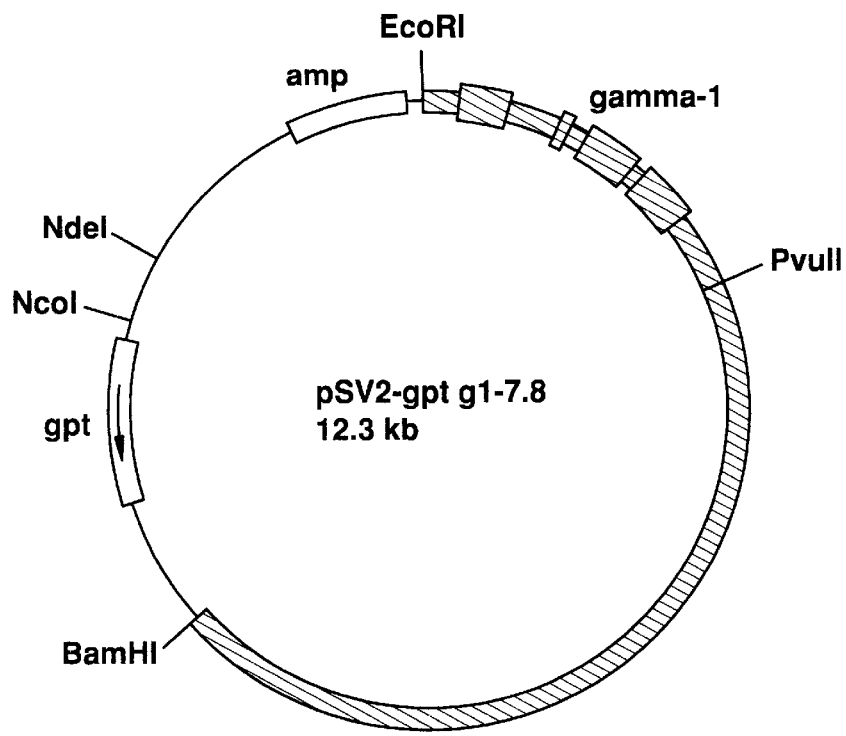
FIG. 23 illustrates the plasmid map of pSV2gpt-γ1-7.8.

The fragments were each ligated into the Eco RI-Bam HI sites of pSV2-gpt/R/B. This vector (pSV2-gpt-γ1-7.2) design allows us to insert any murine heavy chain variable region gene (with Eco RI ends) into the Eco RI site of the human IgG heavy chain vectors. More specifically, 125 ng of the human Cγ1-7.8 kb fragment was ligated to 100 ng of the linearized pSV2gpt/R/B vector in a volume of 10 μl using 400 units of T4 DNA ligase (obtained from New England Biolabs). Frozen competent *E. coli* DH1 cells from Invitrogen (San Diego, Calif., USA) were transformed with a ligation reaction according to the Invitrogen's protocol. The resulting plasmid was designated pSV2gptγ1-7.8. A plasmid map of pSV2gptγ1-7.8 is shown in FIG. 23.

In addition, another shorter fragment containing the Cγ1 exons was generated. Concerns about the total size of the chimeric heavy chain vector, with a 7.8 kb Cγ1 fragment, a 4.5kb pSV2-gpt/R/B vector, and a CC49 variable region of 1.9kb (total=14.2 kb) prompted the need to reduce the large size of the 7.8 kb Cγ1 Eco RI-Bam HI fragment. The coding region of 7.8 kb Cγ1 occupies only the first ⅓ of the 5' end of the fragment.

Size reduction was accomplished by converting a downstream Pvu II site to a Bam HI site by blunt-end addition of a Bam HI linker. The Hind III site of pγ-1 was converted to an Eco RI site by digestion of pγ-1 with Hind III, filling in the 3' end to create a blunt end, and addition of Eco RI linkers as above. The Pvu II site 2.3 kb downstream was converted to a Bam HI site by subsequent digestion with Pvu II and ligation of Bam HI linkers directly to the blunt Pvu II ends. This construct was then digested with Eco RI and Bam HI to release a 2.3 kb fragment containing the Cγ1 exons. The shortened Eco RI-Bam HI fragment (2.3 kb) still contains the γ1 exons and the 3' polyadenylation sequence. This reduces the total vector size by 5.5 kb, making the overall construct more manageable (total=8.7 kb).

Figure 24:
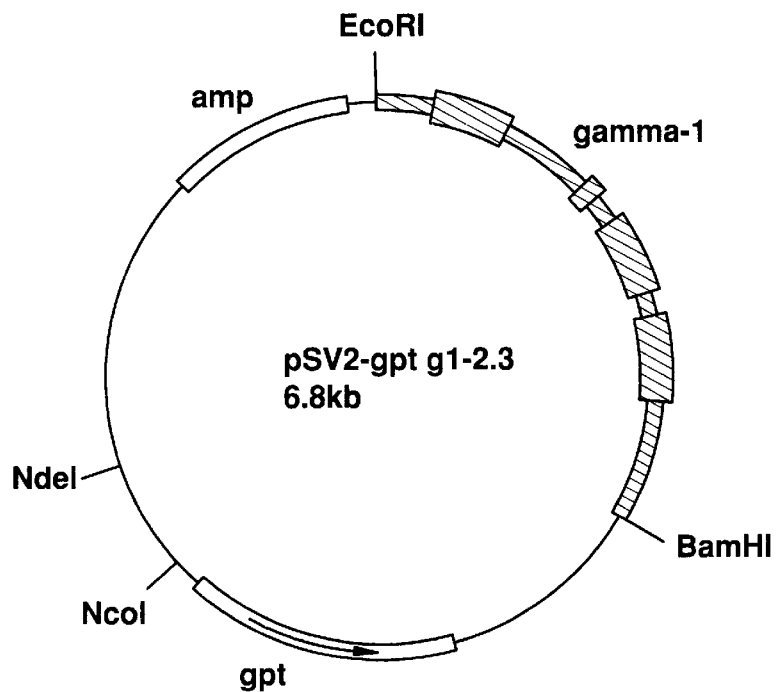
FIG. 24 illustrates the plasmid map of pSV2gpt-γ1-2.3.

Approximately 200 ng of the human Cγ1 2.3 kb fragment was ligated to 100 ng of the linearized plasmid pSV2gpt/R/B vector in a volume of 10 μl using 400 units of T4 DNA ligase (New England Biolabs). Frozen competent E. coli cells, obtained from Invitrogen, were transformed with the ligation reaction according to Invitrogen's protocol. The resulting plasmid was designated pSV2gptγ1-2.3. A plasmid map of pSV2gptγ1-2.3 is shown in FIG. 24.

Figure 25:
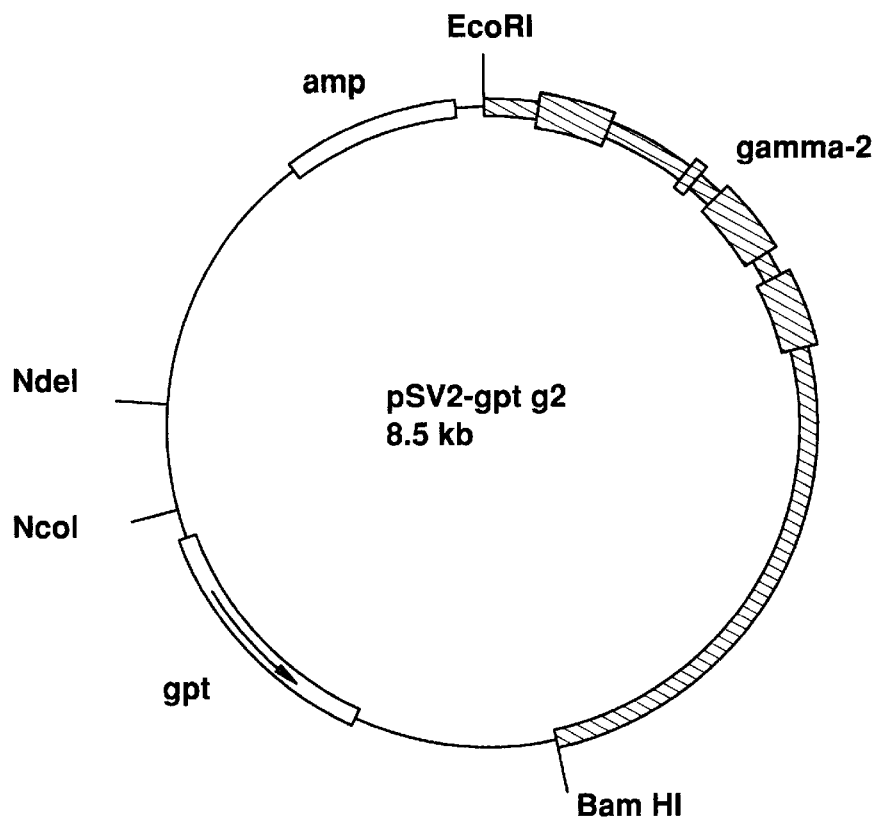
FIG. 25 illustrates the plasmid map of pSV2gpt-γ2.
Figure 26:
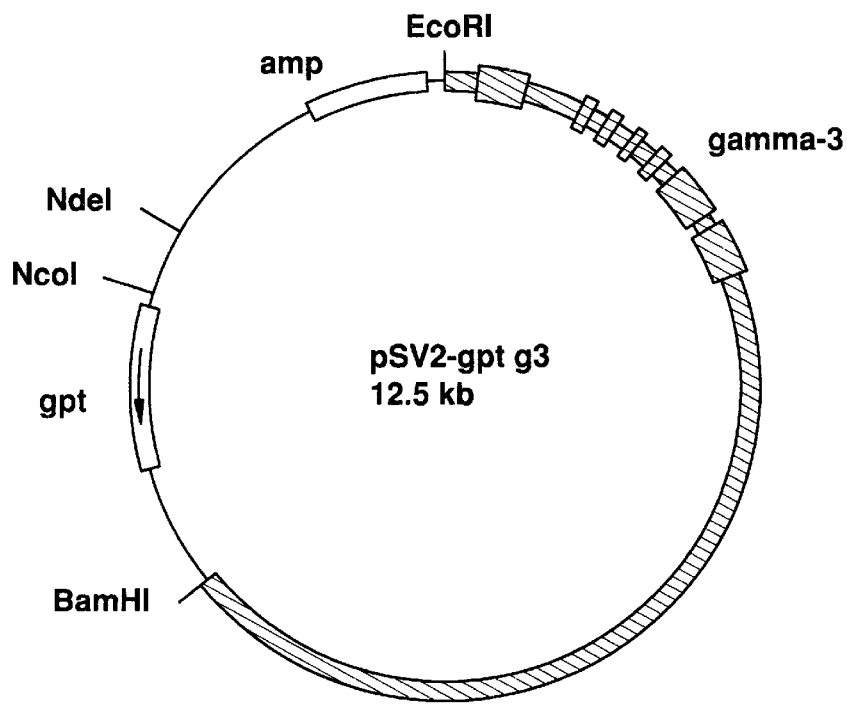
FIG. 26 illustrates the plasmid map of pSV2gpt-γ3.
Figure 27:
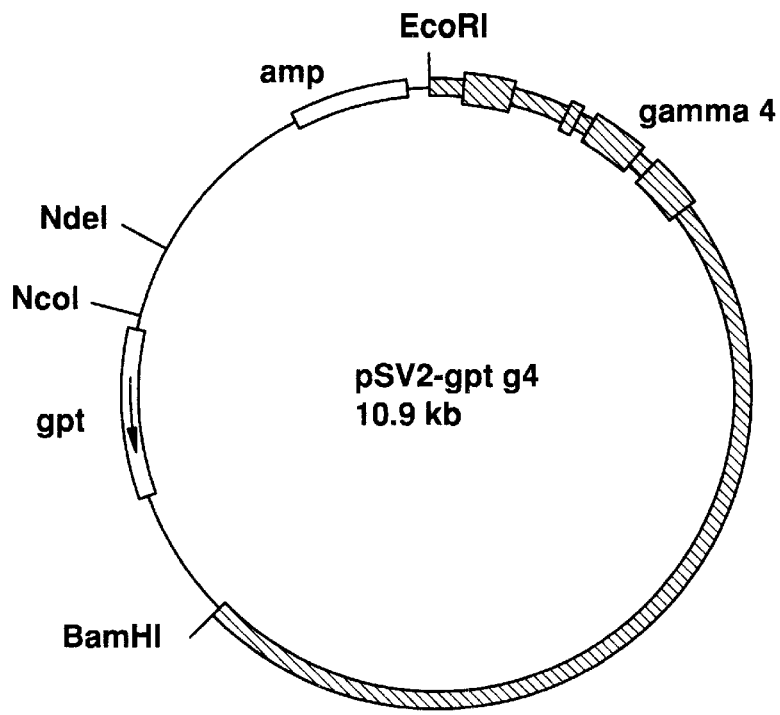
FIG. 27 illustrates the plasmid map of pSV2gpt-γ4.

DNA fragments containing the other three human IgG constant region exons were also isolated. The Cγ2 exons were recovered from the plasmid pγ2 as a 4.0 kb Eco RI-Bam HI fragment. The Cγ3 exons were recovered from the plasmid pγ3 as an 8.0 kb Eco RI-Bam HI fragment. The Cγ4 exons were recovered from the plasmid pγ4 as a 7.6 kb Eco RI-Bam HI fragment. The fragments were separately ligated into pSV2gpt/R/B as described for Cγ1-7.8 and Cγ1-2.3. Plasmid maps of the resultant plasmids are shown in FIG. 25, pSV2gpt-γ2; FIG. 26, pSV2gpt-γ3; and FIG. 27, pSV2gpt-γ4.

Heavy Chain Chimeric Constructs:

The complete heavy chain variable region human γ1 constant region chimeric constructs were generated by inserting a fragment containing the murine heavy chain variable region exons into the plasmids containing the human γ1 constant region exons described as follows.

Eco RI fragments containing the murine heavy chain variable region genes from CC49 and CC83 hybridoma cells were then ligated into each of the γ1-γ4-containing pSV2-gpt vectors (pSV2gpt-γ1; pSV2gpt-γ2; pSV2gpt-γ3; pSV2gpt-γ4) as follows:

CC49

A fragment containing the heavy chain variable region exons coding for the CC49 heavy chain variable region was prepared by digesting 14 μg of pHH49 with 50 units of Eco HI (obtained from BRL) at 37° C. for 2 hours. The digest was fractionated on a 4 percent polyacrylamide gel and the 1.9 kb Eco RI fragment containing the heavy chain variable region exons of CC49 was recovered by electroelution as described by Maniatis. This fragment was designated f49R.

A fragment containing the 7.8 kb sequence encoding for γ1 was prepared as follows:

Approximately 50 μg of the vector pSV2gpt γ1-7.8 was digested with Eco RI. The resultant fragment was dephosphorylated (to prevent self ligation) using calf intestinal alkaline phosphatase as described by Maniatis. The fragment was purified from the 0.8 percent agarose gel by electroelution. This vector was designated pSV2gptγ1-7.8/R.

The Eco RI site is located 245 bp upstream of the transcription initiation sites, and contains the promoter and the necessary tissue-specific sequences for efficient expression. The intron regions 3' of the variable region genes contain the murine heavy chain enhancer sequences which are absent on the human IgG heavy chain vectors. Therefore, the heavy chain chimeric vectors use both murine promoter and enhancer sequences.

Figure 28:
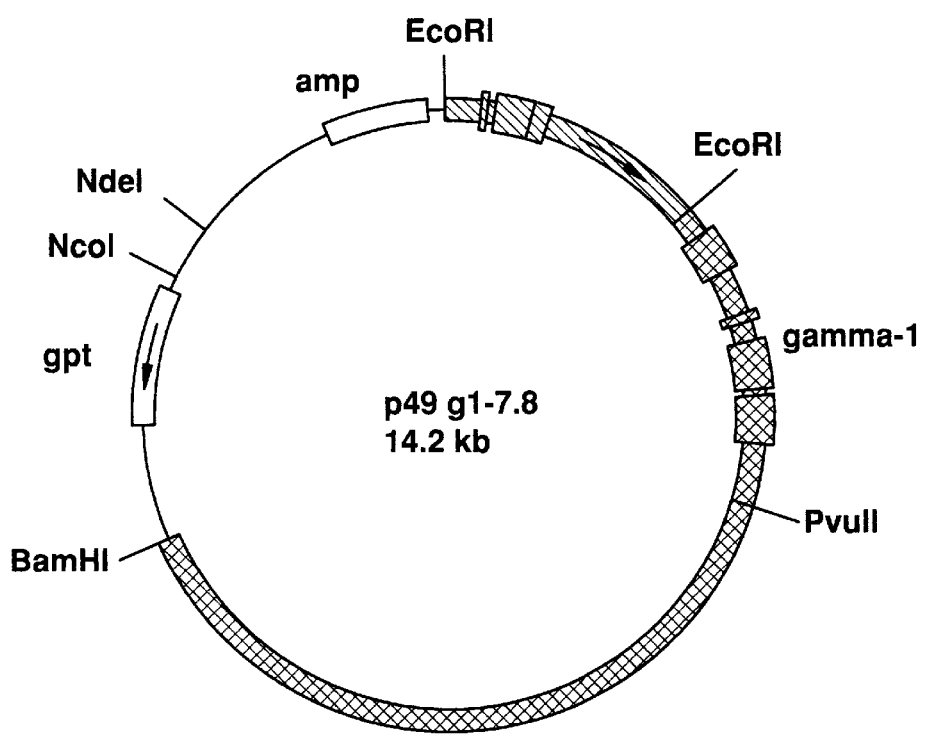
FIG. 28 illustrates the plasmid map of p49γ1-7.8.

Approximately 325 ng of linearized pSV2gptγ1-7.8/R was ligated with 188 ng of f49R in a volume of 10 μL with 1 unit of T4 DNA ligase (BRL). Frozen competent E. coli AG-1 cells from Stratagene were transformed with the ligation reaction according to their protocol. The resulting plasmid was designated p49γ1-7.8. FIG. 28 illustrates a plasmid map for p49γ1-7.8.

Approximately 50 μg of the vector pSV2gptγ1-2.3 was digested as for SV2gptγ1-7.8 with Eco RI. The resultant fragment was dephosphorylated using calf intestinal alkaline phosphatase as described by Maniatis. The fragment was purified from an 0.8 percent agarose gel by electroelution. This linearized plasmid was designated pSV2gptγ1-2.3/R.

Figure 29:
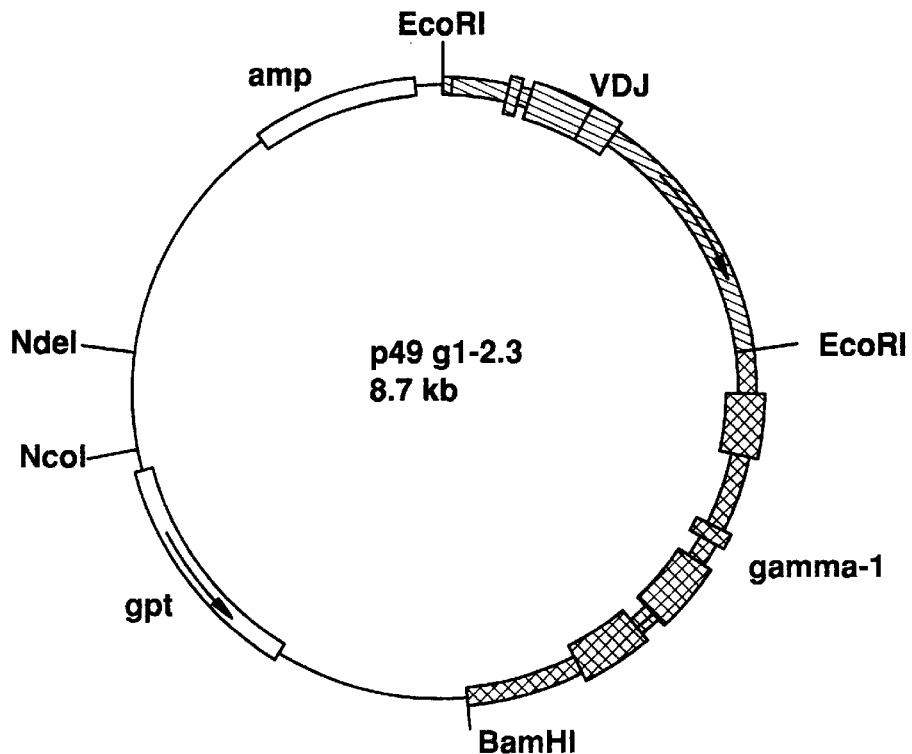
FIG. 29 illustrates the plasmid map of p49γ1-2.3.

Approximately 300 ng of the linearized plasmid pSV2gpt γ1-2.3/R was ligated with 188 ng of f49R in a volume of 10 μl with 1 unit of T4 DNA ligase (BRL). Frozen competent E. coli AG-1 cells from Stratagene (La Jolla, Calif., USA) were transformed with the ligation reaction according to their protocol. The resulting plasmid was designated p49γ1-2.3. FIG. 29 illustrates a plasmid map for p49γ1-2.3.

Figure 30:
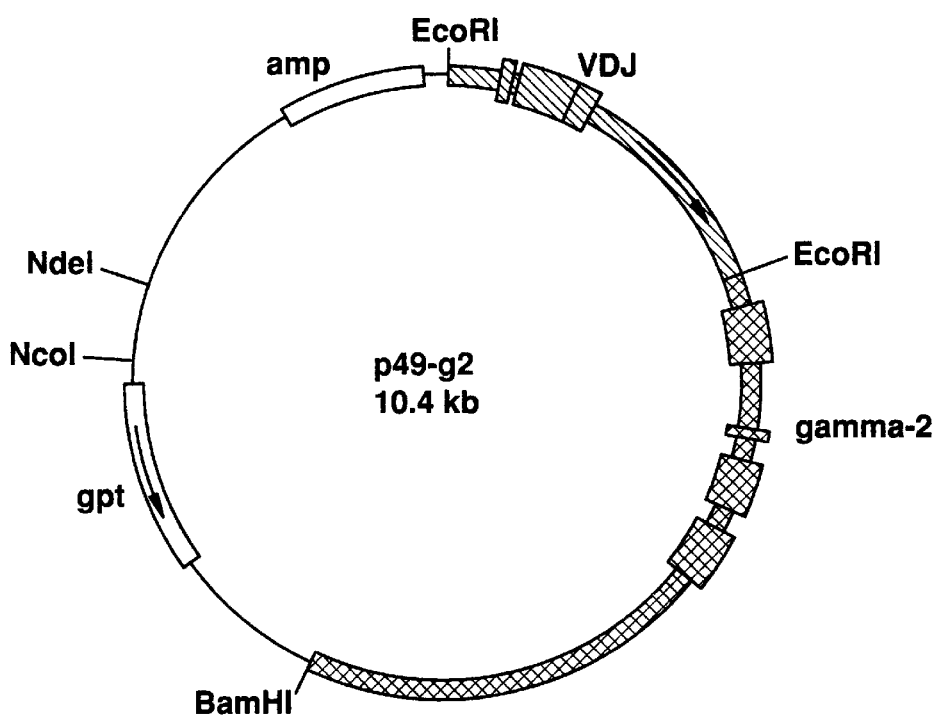
FIG. 30 illustrates the plasmid map of p49-γ2.
Figure 31:
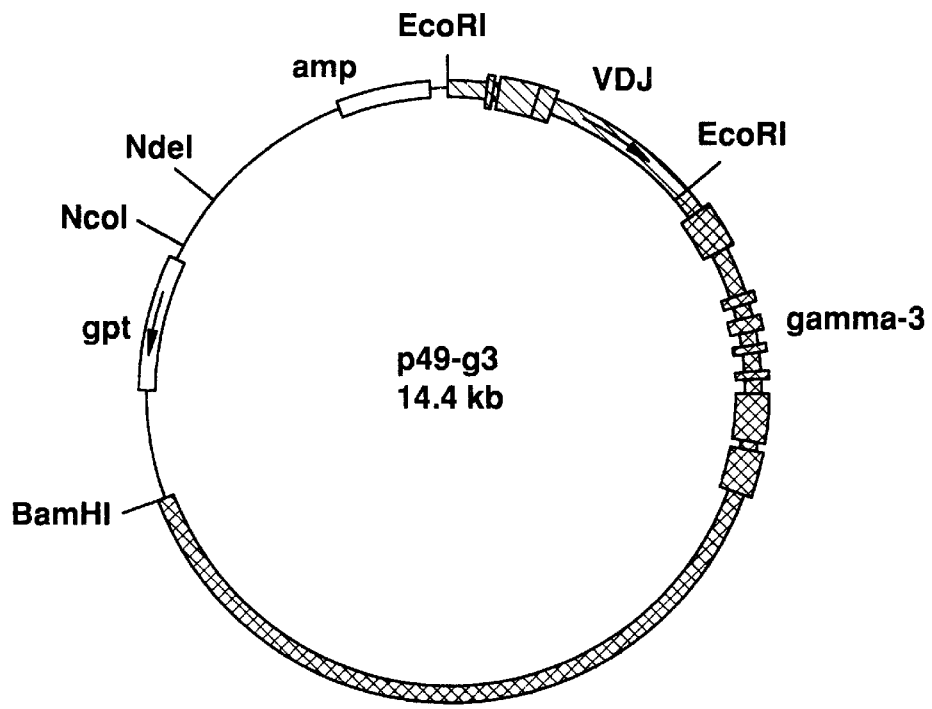
FIG. 31 illustrates the plasmid map of p49-γ3.
Figure 32:
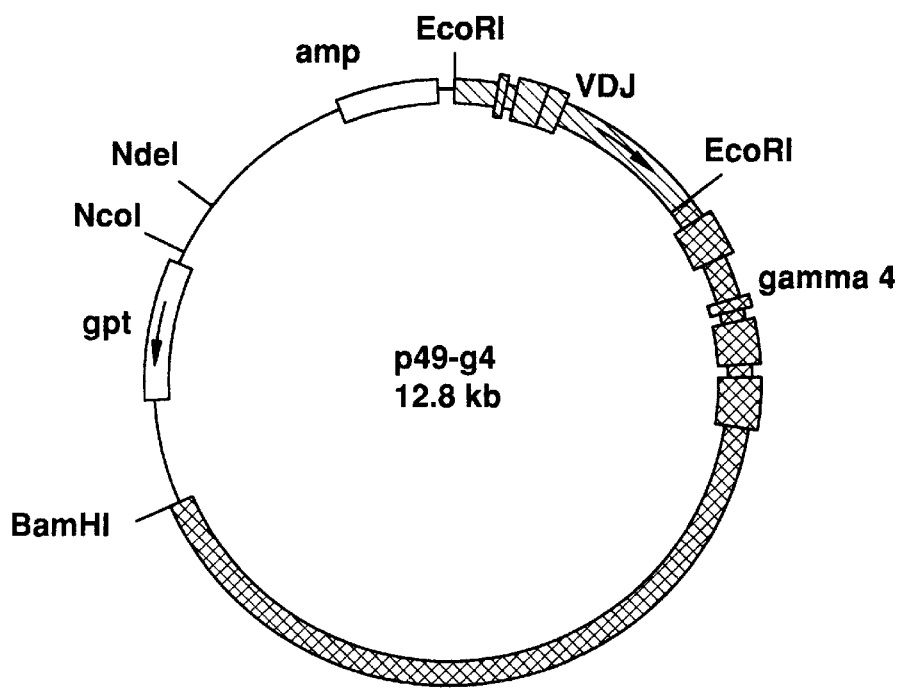
FIG. 32 illustrates the plasmid map of p49-γ4.

Plasmids pSV2gpt-γ2, pSV2gpt-γ3 and pSV2gpt-γ4 were separately digested with Eco RI to produce the linear plasmid vectors pSV2gpt-γ2/R, pSV2gpt-γ3/R and pSV2gpt-γ4/R respectively. Each of these 3 linear plasmid vectors were separately ligated with f49R. Plasmid maps of the resulting plasmids are shown in FIG. 30, p49-γ2; FIG. 31, p49-γ3; and FIG. 32, p49-γ4.

CC83

Chimeric constructs containing the heavy chain variable region of CC83 were generated in a similar manner as the chimeric constructs of CC49. A fragment containing the heavy chain variable region exons coding for the CC83 heavy chain region was prepared by digesting 19 μg of pHS83 with 50 units of Eco RI (obtained from BRL) at 37° C. for 2 hours. The digest was fractionated on a 4 percent polyacrylamide gel and the 2.9 kb Eco RI fragment containing the heavy chain variable region exons of CC83 were recovered by electroelution as described in Maniatis. This fragment was designated f83R.

Figure 33:
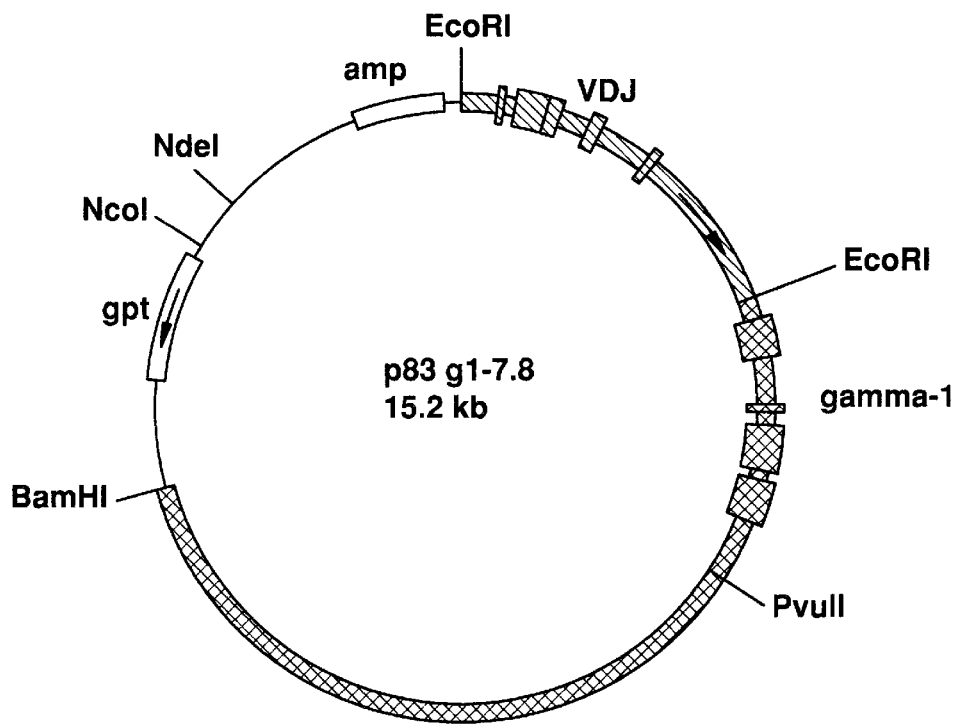
FIG. 33 illustrates the plasmid map of p83γ1-7.8.

Approximately 300 ng of the linearized plasmid pSV2gptγ1-7.8/R, obtained as above, was ligated with 270 ng of f83R in a volume of 10 μl with 1 unit of T4 DNA ligase (obtained from BRL). Frozen competent E. coli AG-1 cells, obtained from Stratagene, were transformed with the ligation reaction according to Stratagene's protocol. The resulting plasmid was designated p83γ1-7.8. FIG. 33 illustrates the plasmid map of p83γ1-7.8.

Figure 34:
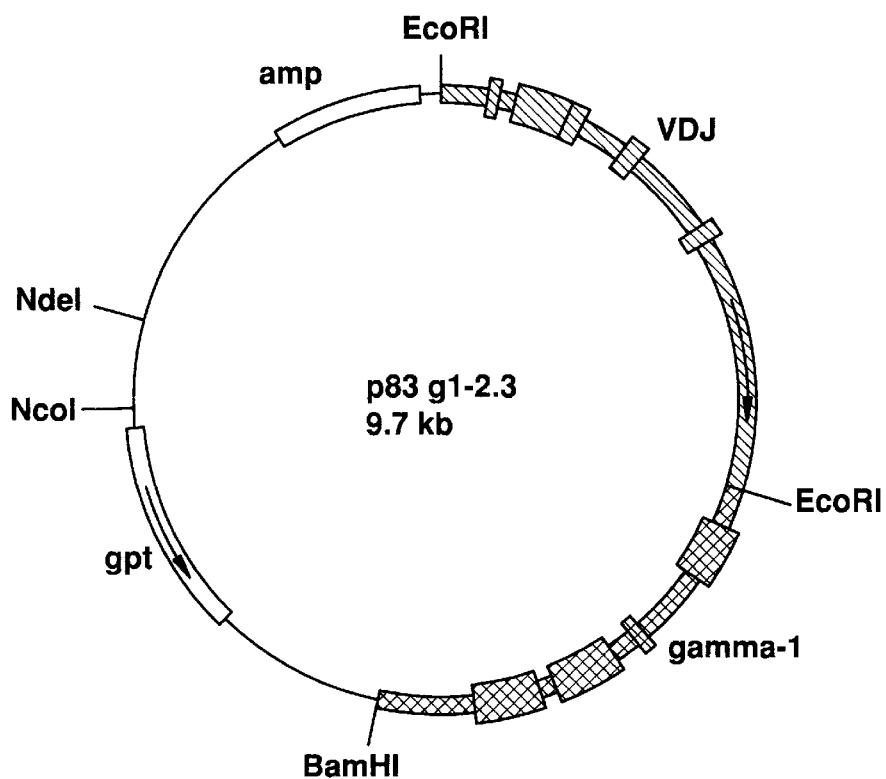
FIG. 34 illustrates the plasmid map of p83γ1-2.3.

Approximately 90 ng of linearized plasmid pSV2gpt γ1-2.3/R, obtained as above, was ligated with 270 ng of f83R in a volume of 10 μl with 1 unit of T4 DNA ligase (BRL). Frozen competent E. coli AG-1 cells from Stratagene were transformed with the ligation reaction according to their protocol. The resulting plasmid was designated p83γ1-2.3. FIG. 34 illustrates the plasmid map of p83γ1-2.3.

Figure 35:
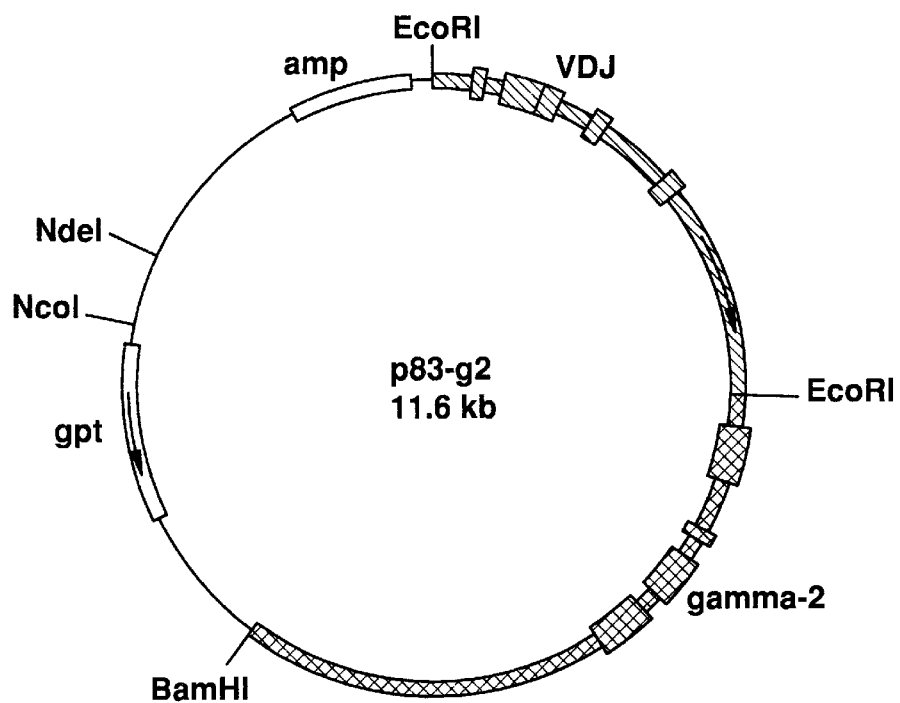
FIG. 35 illustrates the plasmid map of p83-γ2.
Figure 36:
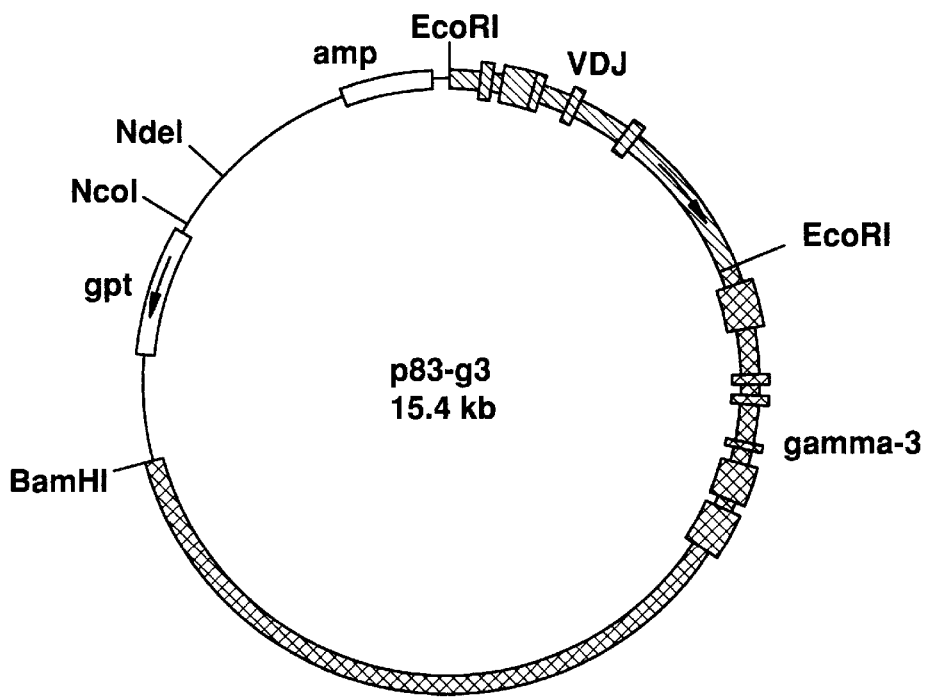
FIG. 36 illustrates the plasmid map of p83-γ3.
Figure 37:
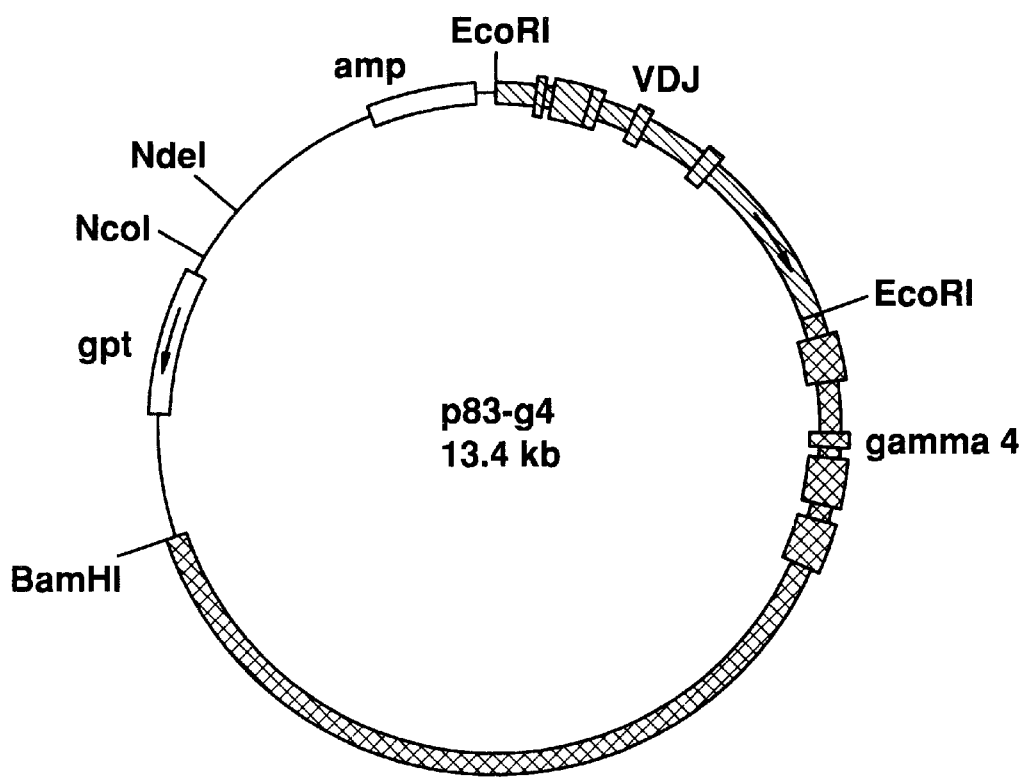
FIG. 37 illustrates the plasmid map of p83-γ4.

Plasmids pSV2gpt-γ2, pSV2gpt-γ3 and pSV2gpt-γ4 were separately digested as above for pSV2gpt-γ2/R, pSV2gpt-γ3/R and pSV2gpt-γ4/R, respectively, with Eco RI to produce the linear plasmid vectors pSV2gpt-γ2/R, pSV2gpt-γ3/R and pSV2gpt-γ4/R respectively. Each of these 3 linear plasmid vectors were separately ligated with f83R. Plasmid maps for the resulting plasmids are shown in FIG. 35, p83-γ2; FIG. 36, p83-γ3; and FIG. 37, p83-γ4.

All ten of the circular plasmid constructs (p49γ1-7.8; p49γ1-2.3; p83γ1-7.8; p83γ1-2.3, p49-γ2; p83-γ2; p49-γ3; p83-γ3; p49-γ4; and p83-γ4) were then linearized for transformation by digesting with the restriction enzyme Nde I. The Nde I site in the plasmids is in a region that is not essential for the expression of the chimeric immunoglobulin gene or the selectable marker gene, gpt. The plasmids need to be in a linear form prior to transformation into a recipient cell to enhance selected integration of the DNA into the host cell genomic DNA.

Verification of Construction

Since the Eco RI fragments can be ligated in either orientation, the correct orientation was determined by digestion with Nco I. In the constructions set forth above, correct ligations for plasmid construction are confirmed by performing restriction enzyme site mapping on the plasmid. The restriction enzyme map generated from restriction enzyme digestion and gel electrophoresis is compared to that which can be theoretically generated from the individual starting fragments. Because of the experience with the transcriptional orientation in the light chain vectors, the heavy chain vectors were constructed only in the opposite transcriptional orientation to the gpt gene.

Transformation of Plasmids into Mouse Plasmacytoma Cells

When both light chain and heavy chain chimeric genes were transformed into the same cell, tetrameric ($H_2L_2$) immunoglobulins are obtained. Synthesis and secretion of these "chimeric" antibody proteins was accomplished by introducing the chimeric (mouse V:human C region) genes into mouse plasmacytoma cells (Sp2/0). Transformation was achieved by electroporation (Sahagan et al., *J. Immunology*, 137:1066 (1986)).

Expression of chimeric (mouse V:human C region) genes in transformed Sp2/0 is achieved using two different techniques. In one mode, different ratios of light chain genes to heavy chain genes can be introduced together. This is referred to as cotransformation. Alternatively, stable clones carrying the chimeric light chain gene can be obtained and subsequently used in a second mode referred to as targeted transformation. In each method, the goal is to obtain clones containing genes for both the H chain and L chain which produce intact $H_2L_2$ immunoglobulin mentioned above.

A. Cotransformations

Co-transformation involves the transformation of cells with both drug resistance markers at the same time and subsequent selection with one or both drugs. Co-transformation of heavy chain and light chain vectors (at ratios of 1:1 and 1:10, respectively) was originally performed using only neo selection. Neo-resistant cell lines were obtained which expressed the first chimeric IgG1 antibodies with demonstrable TAG-72 binding activity. Cotransformation was conducted pursuant to the protocols set forth in Gorman, "High Efficiency Gene Transfer into Mammalian Cells", *DNA Cloning*, Vol II, D. M. Glover ed, IRL Press, Oxford, England (1985).

B. Targeted Transformations

Constructs containing light and heavy chimeric immunoglobulin genes were sequentially transformed into Sp2/0 mouse plasmacytoma cells. Targeted transformation involves transformation and selection with a vector containing a first drug-resistance gene (i.e., GENETICIN aminoglycoside for the chimeric light chain gene vector), followed by transformation and selection with a vector containing a second drug resistance gene (i.e., mycophenolic acid for the chimeric heavy chain gene vector).

Neo Selection

Prior to transformation with pSV2-neo vectors, which contain chimeric light chain constructions, drug selection conditions for inhibition of growth of untransformed Sp2/0 plasmacytoma cells [obtained from the American Type Culture Collection (ATCC)] were established by titration of GENETICIN aminoglycoside (GIBCO). Published values for concentrations of GENETICIN aminoglycoside used for drug selection ranged from 100–1000 µg/mL. Concentrations above 400 µg/mL were found to prevent growth of Sp2/0 cells in our tissue culture environment.

Construction of Light Chain Containing Cells

Sp2/0 mouse plasmacytoma cells were initially transformed with light chain-containing pSV2-neo vectors as follows. Cells were grown in RPMI 1640 medium with 5 percent fetal calf serum. Cells were washed in PBS and suspended to a concentration of $1\times10^7$ viable cells/mL PBS. 0.8 mL of cells were transferred to an electroporation curvette (on ice) containing 20 µg of light chain-containing pSV2neo vector (pRL105 and pRL150 for the CC49 chimeric L chain and pRL203 and pRL230 for the CC83 chimeric L chain) linearized with Aat II restriction endonuclease. Aat II was inactivated by heating the samples to 65° C. for 10 minutes. The linearized DNA was ethanol precipitated and subsequently dissolved in 10–20 µL of PBS. After 15 minutes on ice, electroporation was performed using a Gene Pulser™ electroporation apparatus with an added capacitance extender (BioRad) at 0.2 kvolts and 960 µF. The time constant (τ) was generally about 26 msec.

After transformation, cells were allowed to recover on ice for 15 minutes to allow relaxation of perturbed membranes. Afterwards, the cells were suspended in 24 mL of RPMI 1640 medium containing 5 percent fetal calf serum (RPMI+) and transferred to a 96 or 24 well plate. To decrease the probability of more than one drug resistant cell per well, the cells were also diluted 10-fold in medium (RPMI+) and plated into another 96-well (or 24-well) plate. The cell suspension was incubated at 37° C. and 5 percent $CO_2$ atmosphere.

After 48 hours (to allow for expression of drug resistance), the medium was removed and replaced with medium containing 1 mg/mL GENETICIN aminoglycoside. After 7–10 days, clones resistant to GENETICIN aminoglycoside were subcultured and the cells screened for chimeric light chains by cytostaining.

Cytostaining

Aliquots of cells were pelleted onto a glass slide using a CYTOSPIN-2™ centrifuge (Shandon, Inc.). After air drying, the cells were fixed in acetic acid/ethanol (5 parts acetic acid/95 parts ethanol). After rinsing 3 times with PBS (without $CA^{+2}$ and $Mg^{+2}$), the slides were placed in a humid chamber (100 percent RH), and stained for 20 minutes with 20 µl of goat anti-human Kappa-FITC, a fluorescent dye-conjugated antibody which is specific for human kappa light chains. The conjugated antibody was diluted 1:3 with 1 percent BSA in PBS. After washing overnight with PBS, the slides were mounted with fluoromount-G, histologic mounting medium (obtained from Southern Biotech) under a coverslip. The slides were observed with an Olympus model BH-2 microscope equipped with an epi-illumination U.V. attachment.

Based on the intensity of fluorescence, the constructions with the orientation of the light chain in opposite transcriptional orientation relative to the direction of transcription of the neo$^r$ gene in the vector, was found to give the highest L chain expression. Therefore, pRL105 was the preferred CC49 L chain construction and pRL230 was the favored CC83 L chain construction. As a result of these experiments the following chimeric light chain-containing cell lines (derived from Sp2/0) were used for the targeted transformations.

For the CC49 chimeric L chain one cell line (49K-13-13) was obtained which expressed the chimeric light chain derived from CC49. This cell line was used for all subsequent targeted transformations with chimeric heavy chain vectors for constructs using the chimeric CC49 light chain.

For the CC83 chimeric L chain three cell lines (83K-26-5, 83K-34-10, and 83K-42-2) were obtained which expressed the chimeric light chain derived from CC83. One cell line (83K-26-5) stained more intensely than the others and had localized regions of cytoplasmic immunofluorescence. All three cell lines were compared for their relative ability to produce high levels of chimeric antibody after transformation with the chimeric CC83 g1 heavy chain vector. More clones expressing chimeric antibodies were derived from electroporation of the 83K-34-10 target than either of the other two chimeric light chain target cell lines. Therefore, the 83K-34-10 light chain cell line was used as a target for subsequent electroporations with chimeric heavy chain vectors for constructs containing the CC83 light chain variable region.

Generation of gpt Resistant clones carrying CC49 and CC83 chimeric H chain constructions Prior to transformation with pSV2-gpt vectors, which contain chimeric heavy chain constructions, drug selection for inhibition of growth of untransformed Sp2/0 plasmacytoma cells [obtained from the American Type Culture Collection (ATCC)] were established. Conditions for drug selection of cells transformed with pSV2-gpt vectors were more difficult to establish. The *E. coli* gpt gene, which codes for the enzyme guanosine phosphoribosyl transferase, confers the ability to utilize xanthine and hypoxanthine as substrates for the biosynthesis of guanine when the mammalian guanine metabolic pathway is inhibited by mycophenolic acid (MPA).

Published values for the concentrations of MPA which allow for the growth of other lymphoid cell lines transformed with pSV2-gpt vectors were found to be almost two orders of magnitude too high to allow for the growth of Sp2/0 cells transformed with pSV2-gpt vectors in our tissue culture environment. Subsequently, a concentration of 0.1 µg/mL of MPA was found to be optimal for selection of gpt resistance. In addition, the use of aminopterin and thymidine (to further shut down the guanine pathway) was found to be unnecessary.

Generation of Clones Producing of Chimeric 44 Antibody
CH44-1

49K-13-13 cells were used as a target for chimeric heavy chain constructs. The cells were transformed with 20 µg chimeric heavy chain DNA vector (p49γ1-7.8 or p49γ1-2.3) linearized by Nde I digestion. Transformation by electroporation was performed as above for chimeric light chains.

Selection after 48 hours, however, was performed by replacing the medium containing GENETICIN aminoglycoside with medium containing GENETICIN aminoglycoside and 0.3 µg/mL mycophenolic acid, 250 µg/mL xanthine, and 10 µg/mL hypoxanthine.

Transformed cells grew to macroscopically visible colonies in 14 days. At that time, 50 µl of supernatant was removed and assayed by ELISA methods for binding to TAG and expression of human IgG constant region. Wells containing cells with positive TAG binding were expanded to 24-well plates with fresh drug selection medium and allowed to grow for 3–7 days.

Subcloning was performed as follows. Viable cell counts were determined and the cells were replated into two 96-well plates. One plate received 50 viable cells and the other received 250 viable cells. The unsubcloned cells were expanded to 6-well plates until the cell density was sufficient to allow for storage in liquid nitrogen in the event that re-subcloning would be necessary.

After subcloning, those clones exhibiting the highest chimeric antibody production were selected for chimeric antibody production in bioreactors.

CH44-2

The procedures used to sequentially transform the Sp2/0 plasmacytoma cells in the construction of CH44-1 were repeated with the exception that 20 µg of p49-γ2, was used as the chimeric heavy chain vector.

CH44-3

The procedures used to sequentially transform the Sp2/0 plasmacytoma cells in the construction of CH44-1 were repeated with the exception that 20 µg of p49-γ3, was used as the heavy chain vector.

CH44-4

The procedures used to sequentially transform the Sp2/0 plasmacytoma cells in the construction of CH44-1 were repeated with the exception that 20 µg of p49-γ4, was used as the heavy chain vector.

Generation of Clones Producing of Chimeric 88 Antibody
CH88-1

The procedures used to sequentially transform the Sp2/0 plasmacytoma cells in the construction of CH44-1 were repeated with the following exceptions:

83K-26-5, 83K-34-10, and 83K-42-2 cells demonstrating production Of chimeric CC83 light chain were transformed as described in the transformation of CH44-1, with the exception that 20 µg of p83γ1-7.8 or p83γ1-2.3, the pSV2gpt vector which contains the chimeric CC83 heavy chain gene was used as the heavy chain vector.

CH88-2

The procedures used to sequentially transform the Sp2/0 plasmacytoma cells in the construction of CH88-1 were repeated with the exception that 20 µg of p83-γ2, was used as the heavy chain vector.

CH88-3

The procedures used to sequentially transform the Sp2/0 plasmacytoma cells in the construction of CH88-1 were repeated with the exception that 20 µg of p83-γ3, was used as the heavy chain vector.

CH88-4

The procedures used to sequentially transform the Sp2/0 plasmacytoma cells in the construction of CH88-1 were repeated with the exception that 20 µg of p83-γ4, was used as the heavy chain vector.

Generation of Clones Producing of Chimeric 84 Antibody

Because of the high degree of sequence similarity between the heavy chain variable regions of CC49 and CC83, chimeric antibodies were generated whose light and heavy chains were derived from different parents by mixed targeted transformations. To generate both "mixed" combinations, the chimeric heavy chain γ1 isotype vectors of CC49 and CC83 were electroporated into the chimeric light chain targets 83K34-10 and 49K-13-13 respectively. The resulting cell lines were designated CH48-1 and CH84-1, where the first numerical designation represents the heavy chain and light chain parents, respectively. For example, CH48-1 represents the γ1 isotype with the heavy chain derived from CC49 and the light chain derived from CC83.

The CH48-1 composite antibody did not bind to TAG-72. This was not due to the inability to make chimeric antibody, since most drug-resistant cell lines produced chimeric IgG (as determined by ELISA analysis using Goat Anti-Human Ig trap with Goat Anti-Human IgG-Alkaline Phosphatase as a probe). If any binding affinity were present, it was significantly less than that observed for the first generation antibody B72.3, which was approximately an order of magnitude less affinity for TAG-72 than either CC49 or CC83. Surprisingly, CH84-1 bound to TAG-72 with affinity similar to both parents.

Competition studies were undertaken to determine the specificity of this new mixed-antibody, CH84-1. It should be noted that both CC49 and CC83 exhibit some competitive recognition for the TAG-72 antigen. It was found that CH84-1 competed more with CC49 for binding to TAG-72 than it did with CC83. This would indicate that the specificity for binding to TAG-72 lies in the light chain.

Human γ2, -3, and -4 isotypes were also generated with this mixed-antibody, producing CH84-2, CH84-3, CH84-4 clones.

CH84-1

The procedure used to sequentially transform the Sp2/0 plasmacytoma cells in the construction of CH44-1 were repeated with the following exception:

49K-13-13 cells demonstrating production of CH44 light chain by cytostaining were then transformed as described in the transformed of CH44-1, with the exception that 20 μg of p83γ1-2.3, the pSV2gpt vector which contains the CH83 heavy chain gene was substituted for p49γ1-2.3, the pSV2gpt vector which contains the CH44 heavy chain gene.

CH84-2

The procedures used to sequentially transform the Sp2/0 plasmacytoma cells in the construction of CH84-1 were repeated with the exception that 20 μg of p83-γ2, was substituted for p83γ1-2.3.

CH84-3

The procedures used to sequentially transform the Sp2/0 plasmacytoma cells in the construction of CH84-1 were repeated with the exception that 20 μg of p83-γ3, was substituted for p83γ1-2.3.

CH84-4

The procedures used to sequentially transform the Sp2/0 plasmacytoma cells in the construction of CH84-1 were repeated with the exception that 20 μg of p83-γ4, was substituted for p83γ1-2.3.

Purification of Recombinant Antibodies

Cells expressing the chimeric antibodies were removed by centrifugation from the culture medium and the medium was filtered through a 0.2 μm filter. Chimeric antibodies were purified in two steps from culture supernatants. In the first step of the purification, a protein A affinity cartridge (Nygene Corporation, Yonkers, N.Y., USA) was utilized according to the manufacturer's specifications. Up to 1.0 L of culture supernatant was passed through a 1 mg capacity cartridge, at 5 mL/min. The cartridge was washed with phosphate buffered saline (PBS) to remove traces of albumin. The chimeric antibody was recovered by elution with 0.1 M sodium nitrate buffer, pH 3.0. The pH of the fractions containing the chimeric antibody were immediately adjusted to neutrality with a 1 M solution of Trizma base. Final purification was achieved from this solution, after concentration on an Amicon centricon 30 unit, by gel filtration using a Pharmacia Superose 12 HR 16/50 column as specified by the manufacturer (Pharmacia, Piscataway, N.J., USA).

Figure 38:
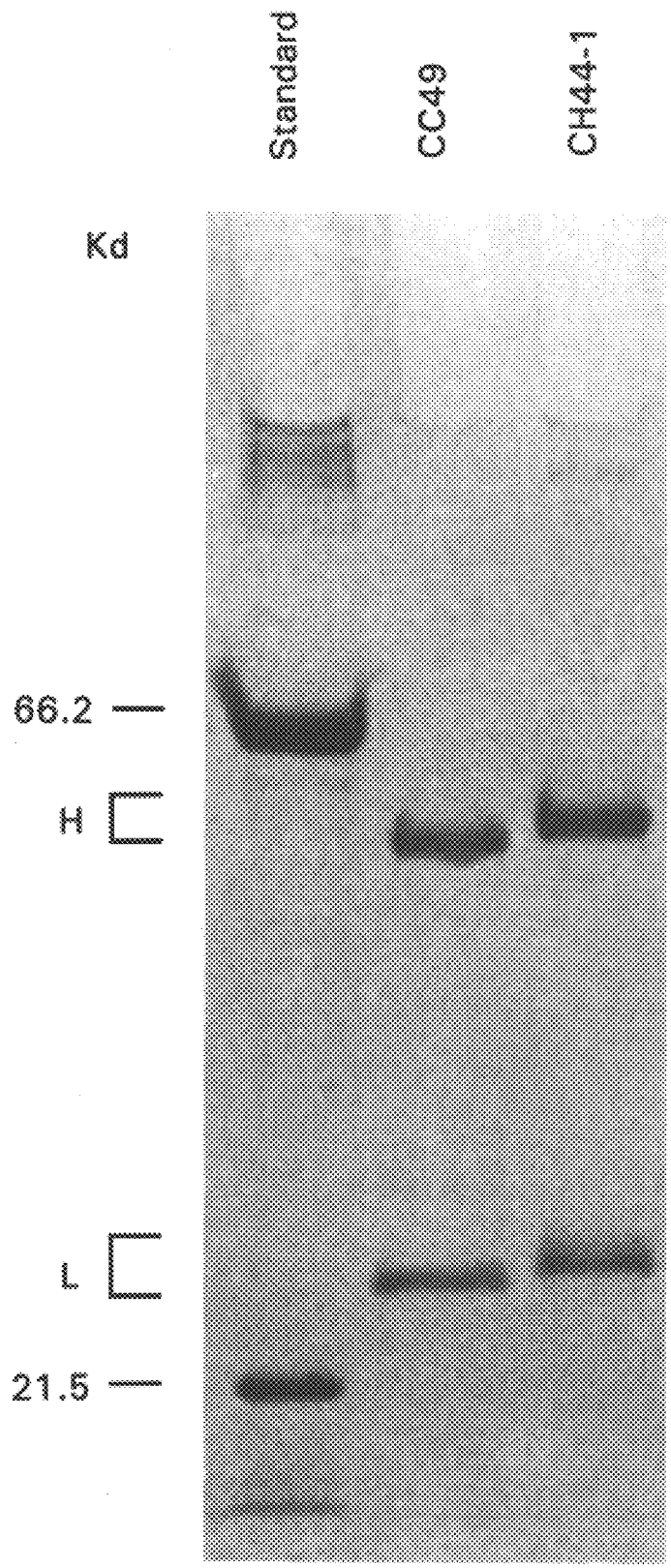
FIG. 38 illustrates an SDS polyacrylamide gel showing the variation in size among the CH44-1 heavy (H) and light (L) chains compared to the corresponding chains of CC49.

As seen in FIG. 38, three samples were run on an SDS polyacrylamide gel. The first sample was 2 μg of a mixture of molecular weight standards consisting of bovine serum albumin (66.2 kilodaltons (Kd)) and soybean trypsin inhibitor (21.5 Kd), commercially available from Biorad. The second sample consisted of 2 μg of purified CC49. The third sample was 2 μg of purified CH-44-1. The samples were loaded in 3 lanes of the gel, and electrophoresis was carried out at constant current (30 milliamperes (mA)) for a period of about 4 hours. The gel was stained with Coomassie Brilliant Blue R-250 for about 1 hour and subsequently destained. Note the variation in size among the CH-44-1 heavy (H) and light (L) chains compared to the corresponding chains of CC49.

Chimeric Antibody—Producing Cell Lines

Simultaneous detection of heavy and light chains was accomplished using two probe antibodies:

1) Goat anti-human kappa labeled with the fluorescing dye FITC and;
2) Goat anti-human IgG labeled with the fluorescing dye TRITC.

Cell lines having positive responses for both heavy and light chains were tested further for associated chimeric immunoglobulin production and biological activity viz. binding to TAG-72.

Enzyme-Linked Immunoassays (ELISA)

In order to select a transformed cell producing a chimeric monoclonal antibody, the ELISA technique was employed. Clones containing the heavy chain and light chain drug selection constructs were selected by their growth in selective culture medium. The following cell lines were tested (1) CH44-1: A cell line having CC49 $V_H$, CC49 $V_L$, and constant region of $IgG_1$; (2) CH44-2: A cell line having CC49 $V_H$, CC49 $V_L$, and constant region of $IgG_2$; (3) CH44-4: A cell line having CC49 $V_H$, CC49 $V_L$, and constant region of $IgG_4$; (4) CH88-1: A cell line having $V_H$, CC83 $V_L$, and constant region of $IgG_1$; (5) CH88-2: A cell line having CC83 $V_H$, CC83 $V_L$, and constant region of $IgG_2$; (6) CH88-3: A cell line having CC83 $V_H$, CC83 $V_L$, and constant region of $IgG_3$; (7) CH88-14: A cell line having CC83 $V_H$, CC83 $V_L$, and constant region of $IgG_4$; (8) CH84-1: A cell line having CC83 $V_H$, CC49 $V_L$, and constant region of $IgG_1$; (9) CH84-2: A cell line having CC83 $V_H$, CC49 $V_L$, and constant region of $IgG_2$; (10) CH84-3: A cell line having CC83 $V_H$, CC49 $V_L$, and constant region of $IgG_3$; and (11) CH84-4: A cell line having CC83 $V_H$, CC49 $V_L$, and constant region of $IgG_4$.

Supernatants of these cultures were subjected to ELISA. The presence of chimeric anti-TAG-72 antibody was measured directly by reaction of an excess of goat anti-human IgG antibody labeled with an enzyme such as alkaline phosphatase, after allowing the chimeric anti-TAG-72 antibody to bind to microtiter wells coated with antigen (TAG-72). Anti-TAG-72 activity was determined as a criterion for successful recombination.

After growth for 14 days, 50 μl of supernatant was removed from the wells of the subcloned cells and re-assayed for TAG binding by ELISA. Samples of supernatants (50 μl) from drug resistant cell lines were applied to wells of IMMULON™ 96-well plates (Nunc) which had previously been coated with TAG antigen (1/50 dilution). After washing to remove unbound material, the wells were incubated with Goat Anti-Human IgG antibodies conjugated with Alkaline Phosphatase (GAHIgG-AP) as a probe to detect the human constant regions of the chimeric antibodies which had bound to the TAG antigen immobilized on the plate. Another washing to remove unbound probe (GAHIgG-AP), followed by addition of a chromogenic alkaline phosphatase substrate, allowed color to develop in those wells which possessed TAG binding associated with human constant regions (i.e., chimeric anti-TAG-72 antibodies). Absorbance readings at 405 nm indicate the relative amount of chimeric antibody produced by the drug-resistant cell lines.

CH44-1

Anti-TAG-72 activity was used as a criterion for successful recombination. Wells of microtiter plates were coated with TAG by incubating 50 μl of a 1:75 dilution of purified TAG-72 (Muraro et al., Cancer Research, 48:4588–4596 (1988)) for 18 hours at room temperature. The wells were then washed 4 times with phosphate buffered saline (PBS), and then blocked with BSA, by incubating 50 μl of 0.5 percent BSA in PBS for 2 hours at 37° C., followed by washing 4 times with PBS. These plates are stable if kept moist at 4° C. 50 μl of a sample are then applied to each well. A blank containing fresh medium is used as a control. All of the samples were incubated either in the plate for 90 minutes at 37° C. or overnight at 4° C. in a closed container.

The plates were then washed 4 times with PBS, and goat anti-human IgG-alkaline phosphate (Southern Biotech Assoc.) was applied to each well by adding 50 μl of a 1:250 dilution. The solution was incubated at 37° C. for 90 minutes. Color development was monitored after washing the plates 4 times with PBS to remove the probe.

The substrate was incubated in 200 μl solution of substrate p-nitrophenyl phosphate (Kirkegaard & Perry) in ethanolamine buffered saline for 6 minutes at room temperature for color development. The optical density at 450 nm of each well was read by a Dynatech microplate reader (Dynatech Inc.).

The Sp2/0 colonies in wells with supernatants having TAG-72-binding chimeric antibody activity were subcloned by limited dilution. Individual subclones were chosen on the basis of relatively high production of chimeric antibody.

CH44-2

The TAG-ELISA procedure used with CH44-1 was repeated with the exception that the antibody was CH44-2.

CH44-3

The TAG-ELISA procedure used with CH44-1 was repeated with the exception that the antibody was CH44-3.

CH44-4

The TAG-ELISA procedure used with CH44-1 was repeated with the exception that the antibody was CH44-4.

CH88-1

The TAG-ELISA procedure used with CH44-1 was repeated with the exception that the antibody was CH88-1.

CH88-2

The TAG-ELISA procedure used with CH44-1 was repeated with the exception that the antibody was CH88-2.

CH88-3

The TAG-ELISA procedure used with CH44-1 was repeated with the exception that the antibody was CH88-3.

CH88-4

The TAG-ELISA procedure used with CH44-1 was repeated with the exception that the antibody was CH88-4.

CH84-1

The TAG-ELISA procedure used with CH44-1 was repeated with the exception that the antibody was CH84-1.

CH84-2

The TAG-ELISA procedure used with CH44-1 was repeated with the exception that the antibody was CH84-2.

CH84-3

The TAG-ELISA procedure used with CH44-1 was repeated with the exception that the antibody was CH84-3.

CH84-4

The TAG-ELISA procedure used with CH44-1 was repeated with the exception that the antibody was CH84-4.

CH48-1

The TAG-ELISA procedure used with CH44-1 was repeated with the exception that the antibody was CH84-4.

Generation of an Immunoglobulin Containing the Murine $V_H\alpha$TAG Germline Variable Region The following examples are set forth to provide a skilled artisan with a reproducible technique for preparing an antibody having a $V_H$ region encoded by a DNA sequence derived from $V_H\alpha$TAG.

Isolation of $V_H\alpha$TAG, Germline Gene

The procedures used to isolate the germline precursor gene to the heavy chain variable regions of CC46, CC49, CC83, and CC92 were essentially as outlined in Sambrook et al, supra. The DNA used to generate the LAMBDA-ZAP™ genomic DNA library (Stratagene, La Jolla, Calif., USA) came from an irrelevant hybridoma cell line, i.e., a cell line which produces antibodies that do not appreciably bind to TAG-72.

Total hybridoma cell, BALB/c mouse kidney cells and NS-1 plasmacytoma cell genomic DNA was isolated according to the procedures set forth in Sambrook et al., supra.

Generally, about 10–20 μg of the extracted DNA from each cell line was digested to completion with 80 units of Bam HI, Eco RI, Hind III, Spe I, Xba I, Sac I, Bgl II, and Pst I in 50–100 μl of a reaction mixture containing the appropriate reaction buffer at 37° C. overnight.

The genomic DNA digests were subjected to the Southern hybridization technique, developed by Southern, *J. Mol. Biol.*, 98:503–517 (1975). The DNA fragments were fractionated on the basis of their size by means of electrophoresis on a 0.8 percent agarose gel. The double-stranded DNA fragments were modified into single-stranded DNA fragments in an alkali solution; a nitrocellulose filter was then placed into close contact with the gel to transfer the modified DNA segments onto the filter in the presence of a high salt concentration solution.

Hybridization was carried out using, as the probe a 250 base pair (bp) Eco RI-Nco I fragment containing 200 bp of 5' flanking sequence and 50' bp of 5' nontranslated sequence from the CC49 $V_H$ gene. The probe was designated f49RN.

The probe was radiolabeled using $^{32}P$ α dCTP obtained from Amersham, Arlington Heights, Ill., USA, and the Oligolabeling™ kit obtained from Pharmacia, Piscataway, N.J., USA.

The results of the Southern hybridization technique indicated that two Hind III fragments were common among all three cell lines. A Hind III genomic library was generated from the hybridoma cell line DNA.

Approximately 900,000 plaques was screened from which one positive clone was isolated. The positive clone was named $PV_H\alpha$TAG-1. $pV_H\alpha$TAG-1 was about 5.2 kb, and the size of the DNA insert was determined by restriction enzyme mapping to be about 2.2 kb.

DNA Sequence of $V_H\alpha$TAG

The following oligonucleotide primers were used for determining the DNA sequence of $V_H\alpha$TAG:

B72.3/CC92     HC-20     mer:
  5'-CCTTGAACTTCTCATTGTAC-3';

CC49/CC83     HC     5'     (+):
  5'-GCACTGCTCATGATATGCAAATC-3';

CC49/CC83     HC     5'     (−):
  5'-GATTTGCATATCATGAGCAGTGC-3';

$V_H\alpha$TAG-1     IVS     (+):
  5'-CTAAAGTGGAGTCAGGGCCTG-3';

$V_H\alpha$TAG-1     IVS     (−):
  5'-CAGGCCCTGACTCCACTTTAG-3';

$V_H\alpha$TAG-1     CDR2     (+):
  5'-GAATGGATTGGATATATTTCTC-3'.

The nucleotide sequences of $V_H\alpha$TAG and CC46 $V_H$, CC49 $V_H$, CC83 $V_H$ and CC92 $V_H$ are set forth in FIG. 2. The extent of sequence identity in the 5' nontranslated region proves that these CC antibodies are derived from a common germline gene. FIG. 2 shows where somatic mutations have been introduced into the productively rearranged subset members. The predicted amino acid substitutions ascribed to those somatic mutations are shown in FIG. 3.

Components for an Expressible V$_H$αTAG Heavy Chain Gene

A mouse-human chimeric antibody molecule can be generated which contains the murine V$_H$αTAG germline heavy chain variable region, a light chain variable region that is complementary to the V$_H$αTAG V$_H$, such as either the CC49 or CC83 murine light chain variable region, and human constant regions.

Figure 39:
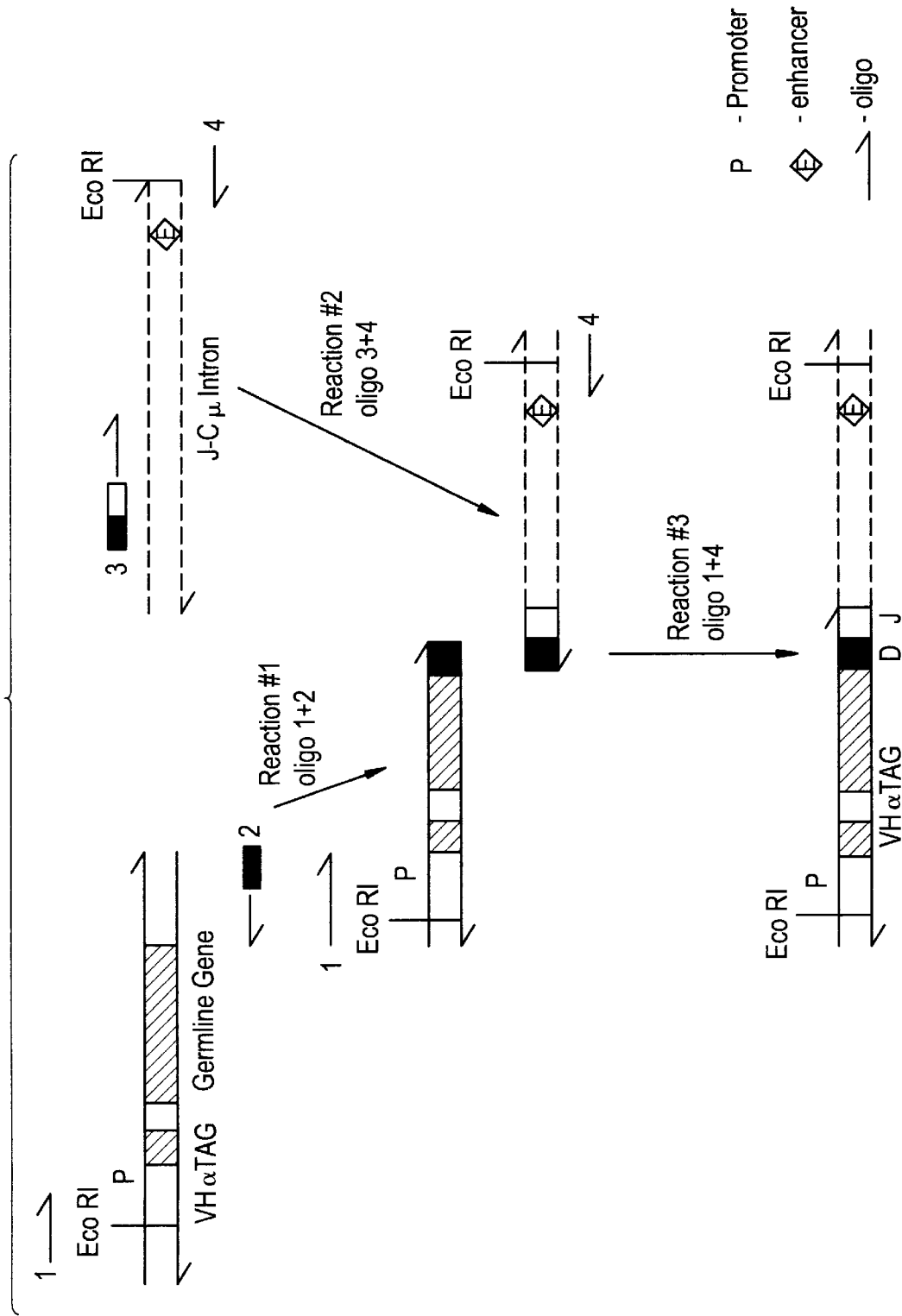
FIG. 39 illustrates the overall reaction for the engineering of hybrid genes based on the method of Horton et al., *Gene* 77:61 (1989).

The 2.2 kb Hind III germline DNA fragment containing the V$_H$αTAG V$_H$ exon sequence is used as a template to obtain a functionally rearranged V$_H$αTAG variable region. The murine genomic J-Cμ intron region is used as a source for the murine heavy chain enhancer sequences. This latter region is obtained from the plasmid pNP9 (see example "Isolation of CC49 Heavy Chain Variable Region", above). FIG. 39 shows the overall reaction for the engineering of hybrid genes based on the method of Horton et al., (1989), supra. Four oligonucleotides (oligos) are designed to be used in enzymatic amplification and modification of the target DNA. Oligo 1 anneals to the 5' end of V$_H$αTAG spanning the Eco RI site which is 249 bp 5' to the ATG initiation codon. Oligo 2 anneals to sequences complementary to the 3' end of the V$_H$αTAG exon and also contains sequences coding for a D segment. The D segment sequences in oligo 2 do not anneal with any V$_H$αTAG sequences. Oligo 3 contains sequences complementary to the 5' end of the murine genomic J-Cμ region and incorporates sequences encoding the D segment (same as in oligo 2) and the J segment. Oligo 4 anneals to the 3' end of the J-Cμ region and contains sequences complementary to the Eco RI site located 1219 bp 3' to J$_H$4. The sequence of these oligos follow:

within oligo 3. The amplified products from reaction 1 and 2 are gel purified, combined and oligos 1 and 4 are added to initiate reaction #3. In reaction 3, the products of reactions 1 and 2 anneal across their common D sequences. Subsequent DNA amplification from oligos 1 and 4 yields the product shown at the bottom of FIG. 39. This fragment is digested with Eco RI and gel purified. The modified V$_H$αTAG fragment is ligated into the Eco RI site of pSV2gptγ1 (2.3) as described in the example "Heavy Chain Chimeric Constructs", above. The entire V$_H$αTAG-D-J-enhancer containing fragment is sequenced completely to ensure that no mutations have been introduced during the DNA amplification reactions. The other three heavy chain γ isotypes can be generated by ligating the same modified V$_H$αTAG fragment into the other three γ containing pSV2gpt vectors (pSV2gpt-γ2; pSV2gpt-γ3; pSV2gpt-γ4).

Expression of the Modified V$_H$αTAG Gene

The modified V$_H$αTAG gene containing plasmids can be linearized with NdeI and introduced via electroporation into the chimeric CC49 or CC83 light chain expressing cell lines (see example "C. Targeted Transformations", above). The transformed cells are selected for growth in the presence of GENETICIN aminoglycoside and mycophenolic acid as outlined above in "C. Targeted Transformations". The presence of expressed antibody is monitored by TAG-72 ELISA (see section in RESULTS, Enzyme-Linked Immunoassays (ELISA)). The expressed antibody from these cells will contain human Ig γ1, κ constant regions with the CC49 or CC83 light chain variable region and a heavy chain variable region from the modified V$_H$αTAG germline V$_H$ exons.

Four examples of modified V$_H$αTAG heavy chain variable region constructs having a variety of D and J segments are shown below:

```
Oligo 1 (SEQ ID NO:50)   5'GTCTAGAATTCATAAAAACTTTATG                  (25 mer)

Oligo 2 (SEQ ID NO:51)   CAGTGTATTTCTGTAAAAGATCTACTATGGTTACG          (35 mer)

Oligo 3 (SEQ ID NO:52)   5'TCTACTATGGTTACGTGGGGTCAAGGAACCTCAGTCACC    (72 mer)
                         GTCTCCTCAGGTAAGAATGGCCTCTCCAGGTCT 3'

Oligo 4 (SEQ ID NO:53)   5'ACTTCTAAAATGTATTTAGAATTCATTTTC 3'
```

In this example, the D sequence is SP2.3 taken from the published sequence of Kurosawa and Tonegawa, *J. Exp. Med.*, 155:201 (1982). The D sequence is shown in bold face type in oligos 2 and 3. Any other characterized murine or human D segment can be used by substituting their sequence in these positions of oligo 2 and 3.

The J segment in oligo 3 is underlined. It is the murine J$_H$4 taken from the published sequence of Gough and Bernard, *Proc. Natl. Acad. Sci. (USA)*, 78:509 (1981). The inclusion of any other murine of human J segment can be made by substituting their sequences for the sequence of J$_H$4 in oligo 3.

In oligo 1 and 4 the Eco RI sites (GAATTC) are shown in italics.

Assembly of Intact V$_H$αTAG Genes

Two separate DNA amplification reactions are performed using the components described above. DNA amplification reaction #1 copies the V$_H$αTAG sequence and adds a D segment to its 3' end. DNA amplification reaction #2 copies the murine intron sequences containing the heavy chain enhancer sequences and adds the D and J segments encoded

| V$_H$ Segment | D Segment | J Segment |
| --- | --- | --- |
| V$_H$αTAG #i | mouse D (SP2.3) | mouse J |
| V$_H$αTAG #ii | human D (D1) | mouse J |
| V$_H$αTAG #iii | mouse D (SP2.3) | human J |
| V$_H$αTAG #iv | human D (D1) | human J |

The sequence of the human D sequence D1 is obtained from Siebenlist et al., *Nature*, 294:631 (1981). The sequence of the human J$_H$1 is obtained from Ravetch et al., *Cell*, 27:583 (1981).

The generation of V$_H$αTAG #i is described with the above diagramed oligos 1 through 4. To generate V$_H$αTAG #ii through -iv the corresponding D and J segments need to be changed in oligos 2 and 3. The following oligos delineate these changes. Substitution of these oligos in reaction #1 and reaction #2 will result in the generation of the V$_H$αTAG #ii through -iv.

$V_H\alpha TAG$ #ii

| | | |
|---|---|---|
| Oligo 2 (SEQ ID NO:54) | 5' CAGTGTATTTCTGTAAAAGAGTACTGGTGGT GTAT | (35 mer) |
| Oligo 3 (SEQ ID NO:55) | 5' GTACTGGTGGTGTAT<u>TGGGGTCAAGGAACC TCAGTCACCGTCTCCTCAGGTAAGAATGGCCT CTCCAGGTCT</u> 3' | (72 mer) |

$V_H\alpha TAG$ #iii

| | | |
|---|---|---|
| Oligo 2 | 5' CAGTGTATTTCTGTAAAAGATCTACTATGG TTACG | (35 mer) |
| Oligo 3 (SEQ ID NO:56) | 5' TCTACTATGGTTACG<u>TGGGGCCAGGGCAC CCTGGTCACCGTCTCCTCAGGTAAGAATGGCCTCTCCAGGTCT</u> 3' | (72 mer) |

$V_H\alpha TAG$ #iv

| | | |
|---|---|---|
| Oligo 2 | 5' CAGTGTATTTCTGTAAAAGAGTACTGGTG GTGTAT | (35 mer) |
| Oligo 3 (SEQ ID NO:57) | 5' GTACTGGTGGTGTAT<u>TGGGGCCAGGGCAC CCTGGTCACCGTCTCCTCAGGTAAGAATGGC CTCTCCAGGTCT</u> 3' | (72 mer) |

Probing for Additional Subset Members of $V_H\alpha TAG$

Based on the sequence information deduced from FIG. 2, a nucleic acid probe was designed to hybridize with the 5' nontranslated region of all heavy chain variable region mRNAs derived from $V_H\alpha TAG$. The hybridization probe was isolated from the heavy chain variable region gene of CC49 as an Eco RI-Nco I restriction enzyme digested fragment.

Fifty micrograms of a plasmid containing the gene encoding the heavy chain variable region of CC49 were digested with 40 units of Eco RI [Bethesda Research Laboratories, Gaithersburg, Md., USA, (BRL)] and 21 units of Nco I [BRL]. The digested DNA was fractionated on a 4 percent polyacrylamide gel and the 250 base pair fragment containing the 5' nontranslated sequence was purified by electroelution [Sambrook et al., supra]. The 248 bp fragment was designated f49RN and it contained 52 base pairs of 5' nontranslated sequence and 196 base pairs of 5' gene flanking sequence. The sequence of f49RN follows:

5'-AATTCATAAAAACTTTATGGGATACATTTCCTCAGAGAGGAATAGGATTTGGA

CCTGACGATCCTGCTGCCCGAGCCATGTGATGACAGTTCTTCTCCAGTTGAACTAG

GTCCTTATCTAAGAAATGCACTGCTCATGAATATGCAAATCACCCGAGTCTATGGC

AGTAAATACAGAGATGTTCATACCATAAAAA<u>CAATATGTGATCAGTGTCTTCTCCG

CTATCCCTGGACACACTGACTCTAACC</u>-3'

The underlined sequence corresponds to the 5' nontranslated sequence.

f49RN was recloned into pBluescript SK(−) (Stratagene, La Jolla, Calif., USA). The cloned insert was sequenced and shown to be a 496 base pair doublet of f49RN. This insert fragment was designated f49-5'.

Fragment f49-5' was radiolabeled using a Pharmacia Oligolabelling™ Kit (Pharmacia LKB Biotechnology, Piscataway, N.J., USA). One hundred nanograms of DNA in 20 μl sterile deionized water (dH20) was denatured at 90° C. for 15 minutes, then incubated at 37° C. for 5 minutes before being placed on ice. Twelve microliters of the Pharmacia reagent mix, 2 μl BSA (3 mg/ml) about 70–80 μCi $^{32}$P α-dCTP and 2.5 μl of Klenow fragment were added and the reaction incubated for about 6 hours at room temperature. The reaction was terminated by addition of 20 μl Stop™ reagent. The $p^{32}$-labeled f49-5' was separated from free isotope on a G50 Nick™ Column (Pharmacia LKB Biotechnology) equilibrated in 10 mM Tris-HCl, 1 mM EDTA, pH 8.0 (TE buffer). Radiolabeled probe was used within 5 days of preparation.

Test medium:

A novel library of antibodies was prepared by immunizing mice against immunoaffinity purified TAG-72. Members of this library, designated as the AHC series, were examined for the presence of $V_H$ encoded by DNA derived from $V_H\alpha TAG$.

Three to four week old BALB/c female mice were immunized with immunoaffinity purified TAG-72. Emulsions of Freund's complete or incomplete adjuvants (Sigma Chemical Company, St. Louis, Miss., USA) were prepared using equal volumes of the adjuvant and immunogen.

The mice were sacrificed by cervical dislocation and the spleens of popliteal lymph nodes removed aseptically. Single cell suspensions of the spleens or nodes were prepared by expelling the cell mass from the sac with syringe needles. The lymphocytes were washed with sterile PBS twice. The lymphocytes were mixed in a ratio of 4:1 (1:1 in the case of the lymph nodes) with plasmacytoma cells from the line P3X63-Ag8.653 (ATCC CRL158) in PBS and fused with 45 percent (v/v) polyethylene glycol (molecular weight 3700). After fusion the cells were plated out at between $5\times10^5$ to $5\times10^6$ nucleated cells per ml in 96 well plates using RPMI-1640 medium containing L-glutamine (2 mM), sodium pyruvate (1 mM), penicillin (50 units/ml) and streptomycin (50 μg/ml). The medium was supplemented with 8.8 percent (v/v) fetal bovine serum (Hyclone Laboratories, Logan, Utah, USA) and at least 1×10$^4$ murine peritoneal exudate cells/ml). For the selection of hybrids, the medium was further supplemented with hypoxanthine-aminopterin-thymidine (Sigma Chemical Company) according to the manufacturer's instructions. The cells were incubated at 37° C. in 7 percent $CO_2$.

Cells at mid to high densities (at least 2×10$^5$/ml) were suspended in 200 μl medium RPMI-1640 medium and plated in 96 well tissue culture plates. After settling, half the medium was removed and replaced with 100 μl of a lysis buffer containing 5.0 M KSCN and 50 percent v/v DMSO (both obtained from the Sigma Chemical Company). RNA from the lysates was adsorbed onto Optibind™ nitrocellulose paper (Schleicher and Schuell, Keene, N.H., USA) pre-wetted with 20× SSC (Sigma Chemical Co.) using a 96 well Minifold™ dot blot apparatus (Schleicher and Schuell, Keene, N.H.). The Minifold™ dot blot apparatus was rinsed with 200 μl of 20× SSC and the membrane washed twice in the same buffer. The blot was dried under vacuum at 80° C. for about 2 hours. Blots could also be stored wet at −20° C. or after drying at room temperature before probing.

Blots were prehybridized in buffer containing 5× Denhardt's solution, 5× SSPE, 100 μg/ml boiled salmon sperm (all Sigma Chemical, St Louis, Miss., USA), 50 percent (v/v) deionized formamide (Bethesda Research Labs, Bethesda, Md., USA) and 20 percent (w/v) SDS at 42° C. for 60 minutes. For hybridization, dextran sulfate (Oncor, Gaithersburg, Md., USA) was added to 5 percent (v/v) solution. Twenty microcuries of radiolabeled probe was boiled for 5 minutes to denature the probe and then added to 20 ml hybridization buffer. The probe was allowed to hybridize overnight at 42° C. Blots were washed in 2× SSPE containing 0.1 percent SDS for 10 minutes at room temperature and 0.1× SSPE containing 0.1 percent SDS for 10 minutes at room temperature and 0.1× SSPE containing 0.1 percent SDS for 60 minutes at 42° C., wrapped in Saran Wrap™ and exposed to X ray film with two enhancer screens overnight at −70° C.

The cell lysates were plated out as described above and probed with f49-5' for the presence of RNA containing sequences from the 5' nontranslated region of the $V_H\alpha TAG$ germline gene. In each case, samples of an anti-TAG-72 antibody and P3X63-Ag8.653 were used as positive and negative controls, respectively. Of the 94 TAG-72 specific hybridoma lines tested, 20 demonstrated binding with the f49-5' probe.

In order to confirm the relationship of probe binding with the $V_H$ sequence of the antibodies, Poly A$^+$ RNA was prepared from several of these lines and sequenced.

Poly A$^+$ RNA was prepared using the Invitrogen Fast-Track™ kit (Invitrogen, San Diego, Calif., USA) according to the manufacturer's instructions. Alternatively, total RNA was prepared by guanidinium isothiocyanate lysis of a washed cell pellet followed by CsCl density gradient centrifugation. The poly A$^+$ RNA was purified using an oligo dT cellulose column (Invitrogen, San Diego Calif., USA).

Poly A$^+$ RNA was sequenced using AMV reverse transcriptase and dideoxy nucleotides in a protocol derived from Geleibter (1987), supra. Briefly, the priming oligonucleotides (see below) were end-labeled using T4 kinase (BRL) and $^{32}$P γ ATP. Between 7 and 11 μg poly A$^+$ RNA was precipitated with ethanol and rehydrated with 10 μl annealing buffer. Five ng labeled oligonucleotide (in 1 μl) were added to the RNA and incubated at 80° C. for about 3 minutes. The temperature was then ramped back to about 50° C. and held for 15 minutes. Annealed RNA and oligonucleotides were added to enzyme and dideoxy and deoxynucleotides and incubated at 50° C. for about 50 minutes. The reaction was stopped with formamide and the samples analyzed on a 6 percent polyacrylamide/7 M urea gel at 35 mAmps.

Two oligonucleotides were used for priming of the sequencing. Cγ1 is a 24 base oligonucleotide (SEQ ID NO: 60) complementary to the CH1 domain of IgG1 heavy chain. Its sequence is shown below:
5'-ATGGAGTTAGTTTGGGCAGCAGAT-3'

A second oligonucleotide, DC113 (SEQ ID NO: 60), complementary to the Framework 2 region of the germline gene $V_H\alpha TAG$, was prepared and has the following sequence:
5'-TCCAATCCATTCCAGGCCCTGTTCAGG-3'

Figure 42A:
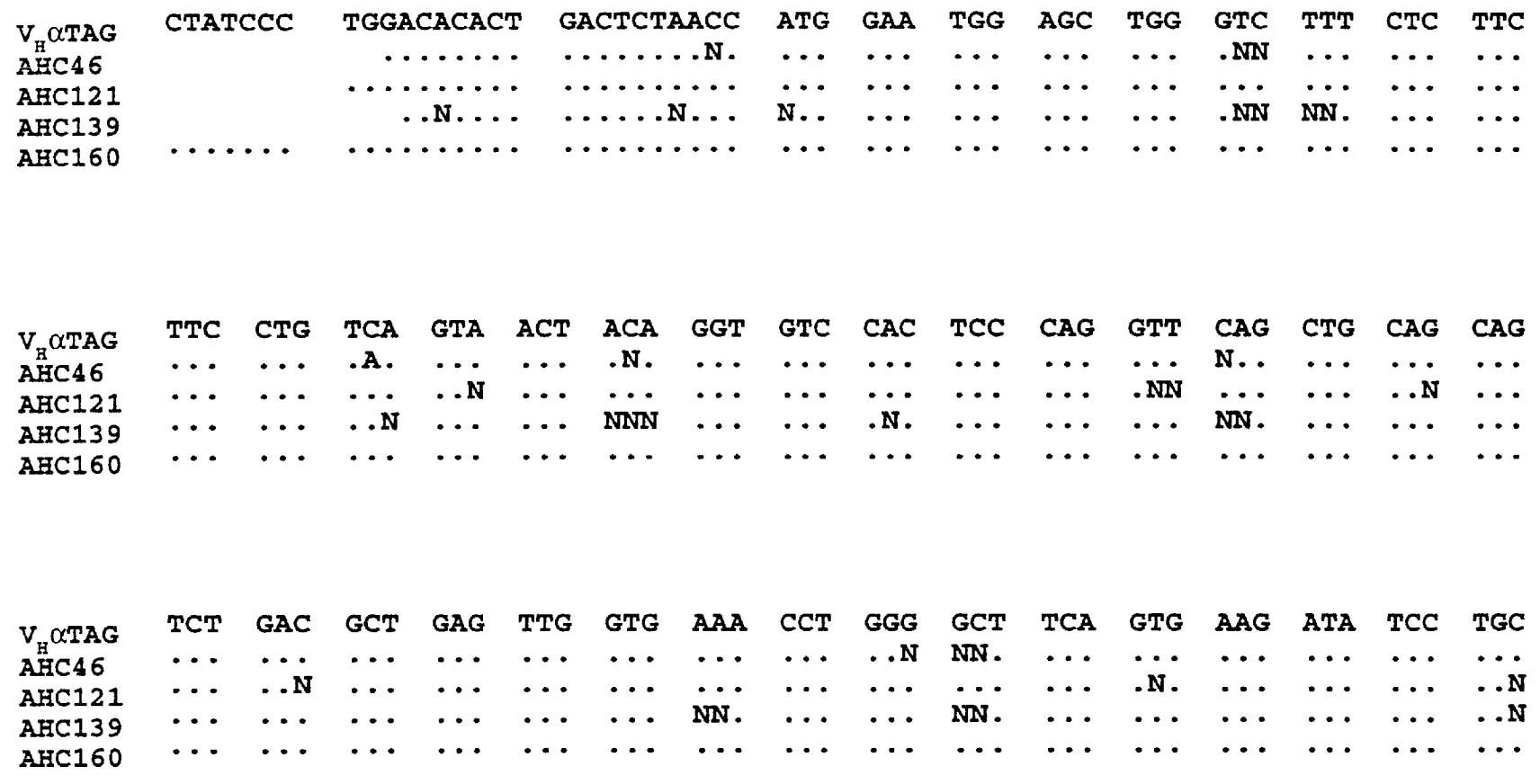

All oligonucleotides were prepared on Model 380A DNA Synthesizer (Applied Biosystems Inc., Foster City, Calif., USA) and gel purified before use. The partial sequences obtained from four AHC hybridomas which bound the probe are shown in FIG. 42. SEQ ID NO:61 for UHaTAG; SEQ ID NO:62 for AHC46; SEQ ID NO:63 for AHC121; SEQ ID NO:64 for ACH139; and SEQ ID NO:65 for AHC160.

The procedures set forth above in screening the AHC library with a DNA probe are repeated with the exception that the probe is RNA generated by in vitro transcription of the mRNA in the f49-5' insert. Screening of the AHC library confirms the results obtained above with screening the AHC library with a DNA probe.

Constant Region-Modified Antibodies

The following examples are provided to show that the variable regions of subset members can be expressed with modified constant regions. The smaller of these molecules resemble enzymatically derived Fab and F(ab')2. The larger molecule (CH3-minus) is intermediate in size between a F(ab')2 and a full-sized antibody. The respective molecular weights are ⅓, ⅔ and ⅚ of a full-sized antibody (150,000 daltons).

The heavy chains were modified by successively removing the CH3, CH2, and hinge domains of the human γ1 and γ3 constant region genes used in the expression of chimeric antibodies. For a discussion of the human γ1, see Ellison et al. (1982), supra; Takahashi et al. (1982), supra. For a discussion of human γ3, see Krawinkel et al. (1982), supra, and Takahashi et al., supra. Because the sequences for γ1 and γ3 have been provided, it is possible to prepare oligonucleotides for PCR and obtain the genes from human DNA.

Figure 43:
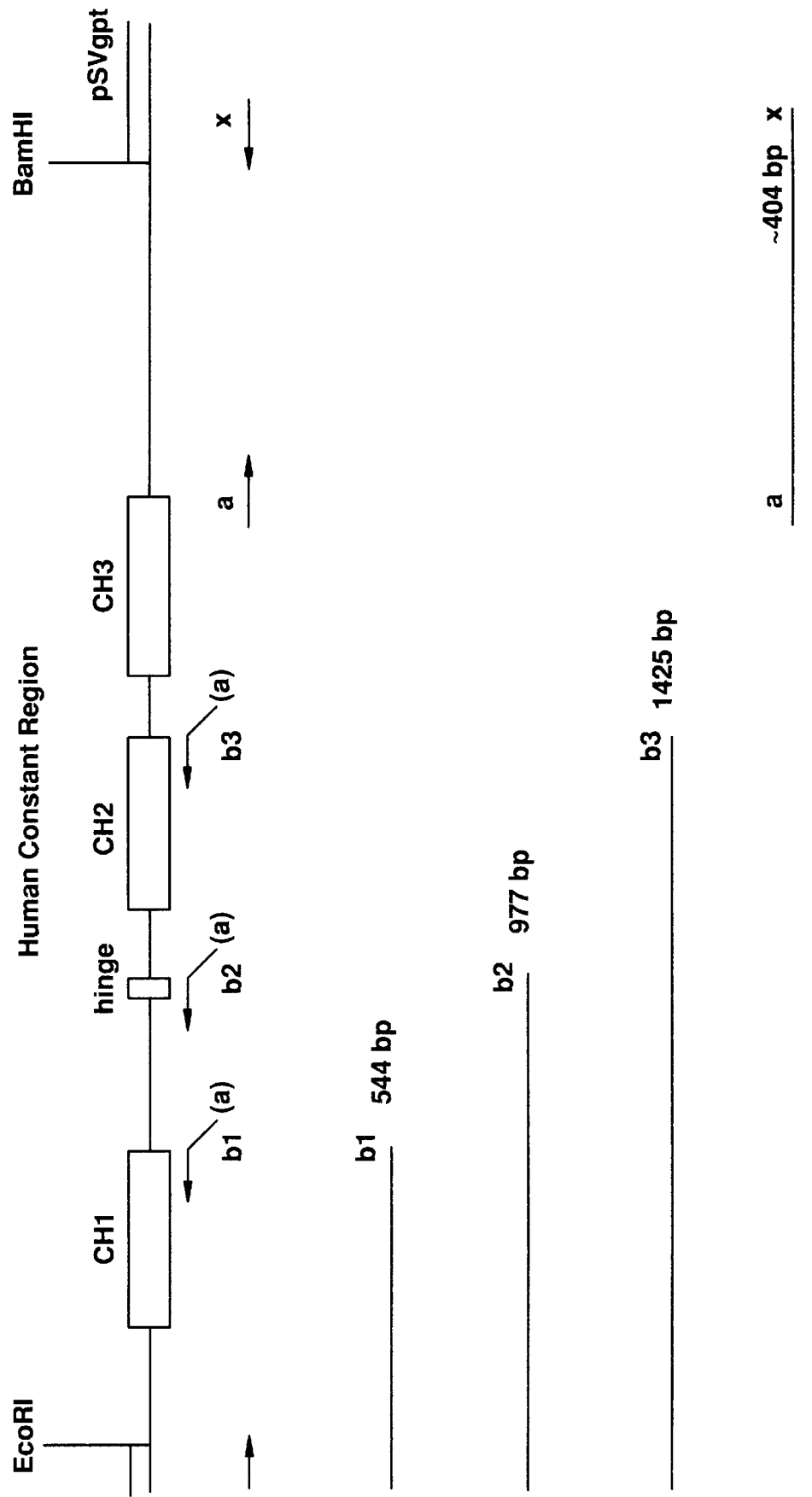
FIG. 43 illustrates a technique for removing heavy chain constant region domains by use splicing by overlap extension.

Each of the domains was removed by use of the techniques of PCR (Mullis et al. (1988), supra) and splicing by overlap extension (SOE) (Horton et al. (1989), supra). FIG. 43 illustrates the process: Two DNA fragments designated y-b1 and a-x (which eliminate the desired exons between them) were generated separately by PCR. This was accomplished by the use of short oligonucleotide primers, corresponding to each of the 5' end (primers y and a) and 3' end (primers bi and x) of the fragments of interest. The unique advantage of the SOE technique is accomplished by the inclusion of a "wagging tail" on at least one side of the intended junction. This "wagging" region (designated "(a)" on each of primers b1, b2, and b3) must be complementary to the opposite strand of the intended junction. After purification, the two PCR-derived DNA (y-b1 and a-x) were mixed, denatured and reannealed over the regions of overlap derived from the "wagging tail". By subjecting this reannealed mixture of fragments to PCR using the outermost oligonucleotide primers (primers y and x), the overlap is extended and amplified.

Each shortened construction was terminated by the last two amino acids of the C-terminus of the γ1 heavy chain. Thus, the 524 base pair DNA fragment, a-x, starts with the Gly-Lys and termination codons, and includes the polyadenylation signal plus any other sequences from the 3' end of the fragment which may be of importance. This fragment was used as the 3' joining fragment for all of the above constructs. Although the DNA sequence of the approximately 300 bp at the 3' end of the fragment is not known, the PCR was performed from a 3' primer derived from the adjacent vector sequence and included the Bam HI restriction site of the fragment.

The human γ1 heavy chain is unique in that it is covalently attached to the light chain via a disulfide bond with Cys-H233, which is located in the hinge domain, rather than via Cys-H127, found in the CH1 domains of the other heavy chains, with the exception of α1 (set forth in Kabat et al. (1987), supra). The CH1 domain of the γ3 heavy chain was chosen for the Fab construct because it contains the appropriate Cys-H127 and only three other amino acid differences, two of which are conservative changes (Lys to Arg) for an overall amino acid similarity of 96 percent.

The initial PCR resulted in an a-x fragment of 524 bp, a y-b1 fragment of 544 bp, a y-b2 fragment of 977 bp, and a y-b3 fragment of 1425 bp. The results from the SOE reaction using the 5' and 3' oligos (y and x, respectively) of y-b1 and a-x yields a fragment y-b1-x of 1068 bp. The results from the SOE reaction using the 5' and 3' oligos (y and x, respectively) of y-b2 and a-x yields a fragment y-b2-x of 1501 bp. The results from the SOE reaction using the 5' and 3' oligos (y and x, respectively) of y-b3 and a-x yields fragment y-b3-x of 1949 bp. Each final fragment was digested with Eco RI and Bam HI to generate compatible ends for subsequent ligation into the pSV2-gpt vector (see Gorman, DNA Cloning, Vol. II, Glover (ed.), (1985)).

The oligonucleotide primers described above have the following sequences:

```
x  (SEQ ID NO:66): 5'-TATCTTATCATGTCTGGATCC-3';

y  (SEQ ID NO:67): 5'-GGCCCTTTCGTCTTCAAGAATTC-3';

a  (SEQ ID NO:68): 5'-GGTAAATGAGTGCGACGG-3';

b1 (SEQ ID NO:69): 5'-CCGTCGCACTCATTTACCAACTCTCTTGTCCACCTT-3';

b2 (SEQ ID NO:70): 5'-CCGTCGCACTCATTTACCTGGGCACGGTGGGCATGT-3';

b3 (SEQ ID NO:71): 5'-CCGTCGCACTCATTTACCTTTGGCTTTGGAGATGGT-3'.
```

Thermal cycling was performed. Template and primer concentrations were 0.1–1.0 ng/ml and 1 nmole/ml, respectively, in 0.1 ml (Saiki et al., (1988), Science, 239:487–491). PCR and SOE conditions were: Denaturation-2 minutes at 92–96° C.; annealing-3 minutes at 37° C. to 50° C.; extension for 10 minutes at 71–74° C. (30 cycles).

After phenol/chloroform extraction and ethanol precipitation of the SOE reactions, the fragments were digested with Eco RI and Bam HI and gel purified (Maniatis, et al. (1982), supra). Each fragment was ligated with the Eco RI/Bam HI fragment of the SV2-gpt vector. These vectors are able to accept any $V_H$ fragment with Eco RI ends. The 1.9 kb Eco RI fragment containing the CC49 $V_H$ was ligated into the Eco RI site of each of the shortened heavy chain vectors and clones analyzed by Nco I digestion for correct orientation of the $V_H$ fragment.

Electroporation Selection and Expression

Each of the chimeric CC49 shortened heavy chain vectors was linearized with Nde I and electroporated into target cells which express the chimeric CC49 light chain. TAG-72 binding activity in the medium of mycophenolic acid (MPA)-resistant colonies was detected by ELISA with alkaline phosphatase-conjugated goat anti-human kappa antibody (Southern Biotechnology Associates, Inc., Birmingham, Ala., USA). The vector containing the 49Hv fragment alone (p49Vh-gpt) was also electroporated into target cells (SP2/0) which do not express light chain or heavy chain (Shulman et al., Nature, 276:269–270 (1978)). The possible TAG-72 binding activity produced by these MPA-resistant colonies was measured by competition ELISA. Colonies with positive TAG-72 ELISA activity were expanded to 24-well plates, subcloned, and selected.

Three of the cell lines were designated Ch44-CH3⁻: a constant region of the human γ1 heavy chain with a removed CH3 domain (the sequence of which is set forth in FIG. 44 (SEQ ID NO: 72)); Ch44-F(ab')₂: a constant region of the human γ1 heavy chain with removed CH2 and CH3 domains (the sequence of which is set forth in FIG. 45 (SEQ ID NO: 73)) and Ch44-Fab: a constant region of the human γ3 heavy chain with a removed hinge region and CH2 and CH3 domains (the sequence of which is set forth in FIG. 46 (SEQ ID NO: 75)).

Results

In Vivo Carcinoma Targeting

The chimeric monoclonal antibodies used in animal studies and shown in Tables 1–4 below were labeled with Na$^{125}$I using IODOGEN® iodination reagent (Pierce Chemical, Rockford, Ill., USA). More specifically, from about 0.5–2 mg of purified chimeric monoclonal antibodies were adjusted to about 0.5 mL 0.1 M sodium phosphate buffer (pH 7.2) and then added to a 12 cm×75 cm glass tube coated with 50 μg of IODOGEN® iodination reagent followed by addition of from 0.1–0.5 mCi of Na$^{125}$I (New England Nuclear, Boston, Mass., USA). After a 2 minute incubation at room temperature, the protein was removed from the insoluble IODOGEN® iodination reagent, and the unincorporated $^{125}$I was separated from the antibody by gel filtration through a 10 mL column Sephadex G-25 using PBS as the buffer. The iodination protocol yielded labeled IgG chimeric antibody with a specific activity of 0.05 to 0.2 μCi/μg.

Female athymic mice (nu/nu) on a CD1 background were obtained from Charles River at approximately 4 weeks of age. Nine days later, mice were inoculated subcutaneously (0.1 mL/mouse) with LS174T cells (1×10⁶ cells/animal).

Athymic mice bearing carcinomas 70 to 400 mg in weight, approximately 12 to 13 days after inoculation of the cells were given injections intravenously of from 0.5 to 2.0 μCi (10–50 μg protein) in PBS of the chimeric monoclonal antibodies, which had been iodinated as described above. Groups of five mice were sacrificed at varying times by exsanguination, the carcinoma and normal tissues were excised and weighed, and the cpm were measured in a gamma counter. The cpm/mg of each tissue was then determined and compared to that found in the carcinoma.

Figure 40A:
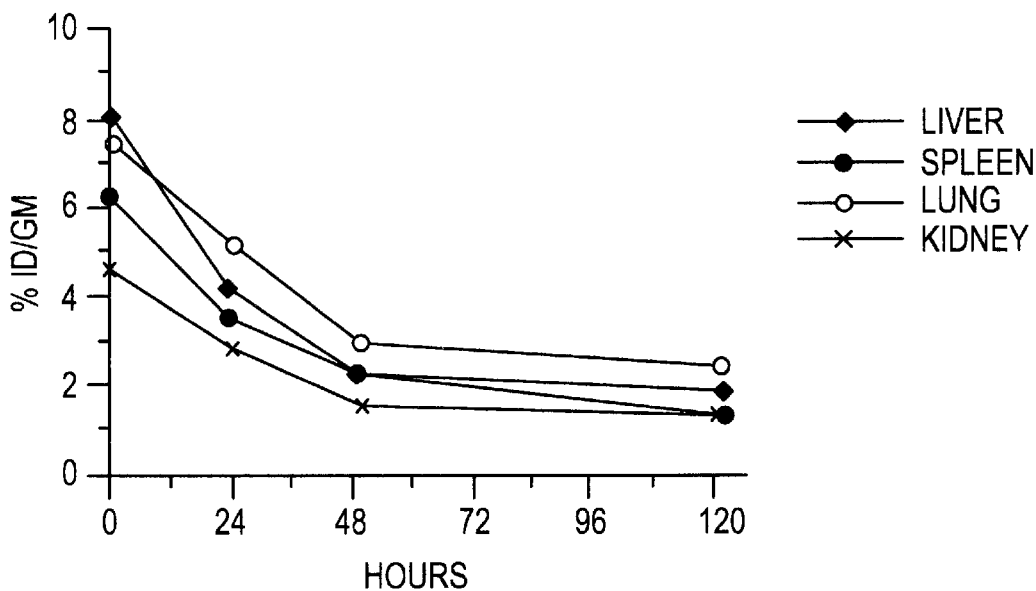
FIGS. 40A, 40B, and 40C show the biodistribution and whole body retention of CH44-1.
Figure 40B:
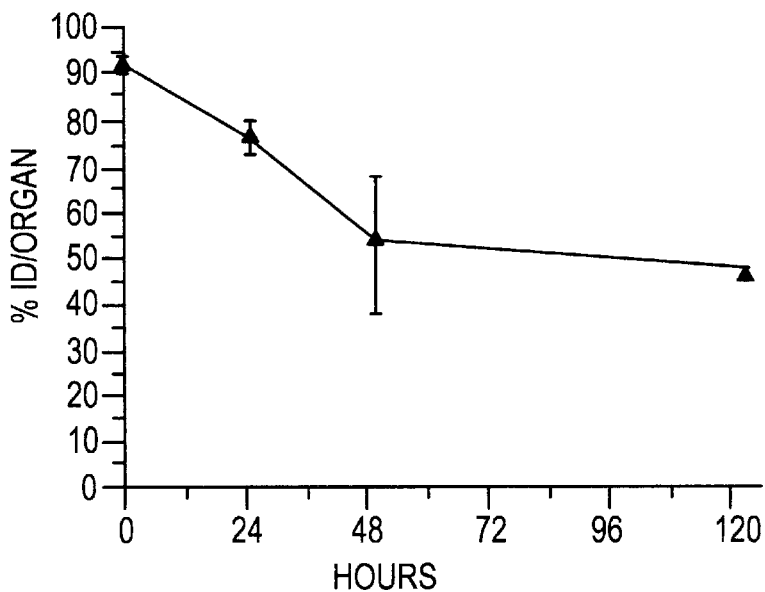
Figure 40C:
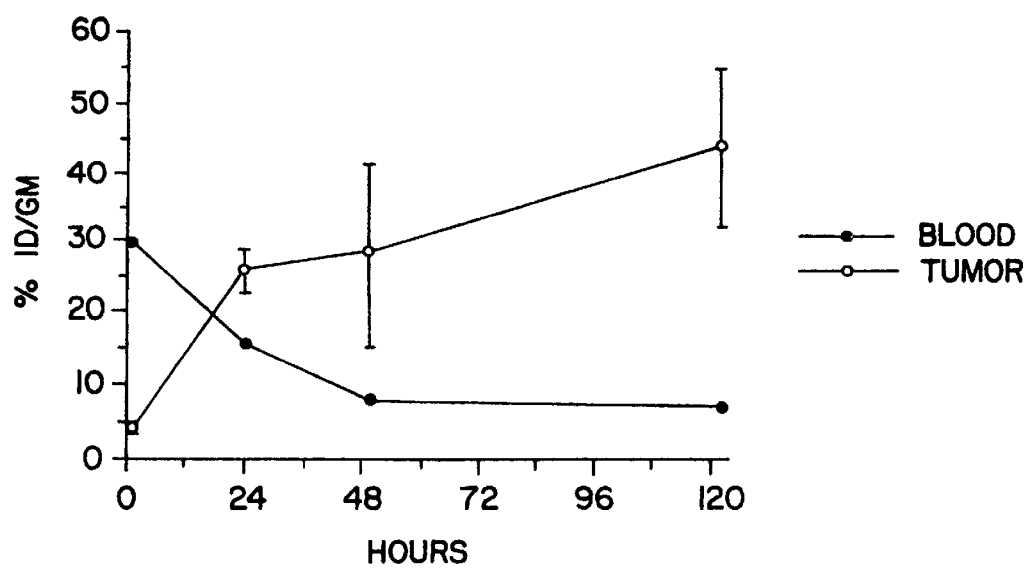
Figure 41A:
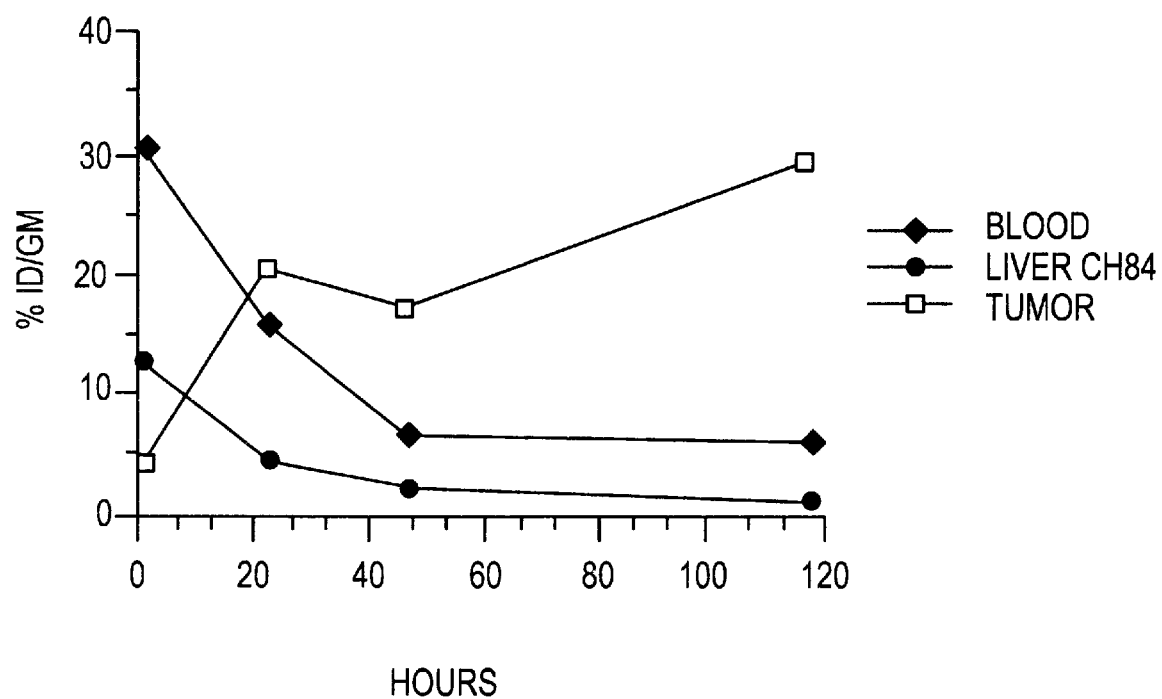
FIGS. 41A and 41B show the biodistribution and whole body retention of CH84-1.
Figure 41B:
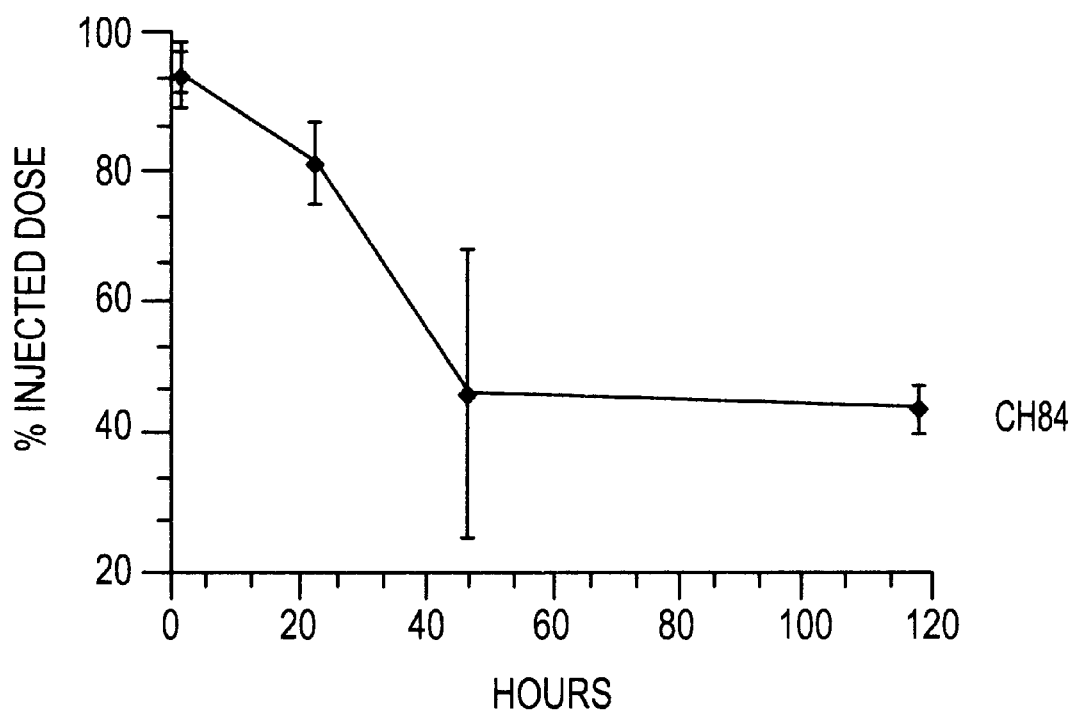

The results for CH44-1 are shown in Tables 1–2, and FIGS. 40A, 40B, and 40C. The results for CH84-1 are shown in Tables 3–4, and FIGS. 41A and 41B.

TABLE 1

Percent Injected Dose Per Gram of $^{125}$I-Labeled Antibody

| | CH44-1 | | | |
|---|---|---|---|---|
| Tissue | 0.75 Hour | 23.5 Hours | 49.5 Hours | 122 Hours |
| blood, total | 29.70 | 15.84 | 8.09 | 7.31 |
| Liver | 8.13 | 4.13 | 2.19 | 1.96 |
| Spleen | 6.19 | 3.39 | 2.12 | 1.36 |
| Kidney | 4.35 | 2.80 | 1.52 | 1.33 |
| tumor | 3.31 | 25.95 | 28.83 | 44.16 |
| lung | 7.34 | 5.39 | 2.90 | 2.36 |
| tumor, wt | 0.18 | 0.12 | 0.09 | 0.11 |

As shown in Table 1, at approximately 122 hours post-injection, the percent injected dose to tumor for CH44-1 was 44.16 percent. CH44-1 was, therefore, efficient in targeting the human tumor in situ. This demonstrates that the chimeric monoclonal antibodies of the present invention were efficient for in vivo carcinoma targeting and thus are useful for in vivo treatment of cancer.

TABLE 2

Percent Injected Dose Per Organ of $^{125}$I-Labeled Antibody

| | CH44-1 | | | |
|---|---|---|---|---|
| Tissue | 0.75 Hour | 23.5 Hours | 49.5 Hours | 122 Hours |
| blood, total | 47.72 | 23.03 | 13.29 | 12.01 |
| Liver | 10.97 | 5.20 | 3.20 | 2.69 |
| Spleen | 1.09 | 0.48 | 0.25 | 0.22 |
| Kidney | 1.25 | 0.72 | 0.42 | 0.40 |
| tumor | 0.57 | 3.08 | 2.82 | 4.55 |
| lung | 1.20 | 0.87 | 0.57 | 0.37 |
| GI tract | 6.64 | 4.78 | 3.96 | 2.83 |
| carcass | 43.17 | 49.68 | 35.35 | 29.95 |
| whole body retention | 91.30 | 76.34 | 53.28 | 46.20 |

As shown in Table 2, at 122 hours post-injection, the percent of injected dose tumor for CH44-1 was 4.55 percent. CH84-1 was, therefore, efficient in targeting the human tumor in situ. This demonstrates that the chimeric monoclonal antibodies of the present invention were efficient for in vivo carcinoma targeting and thus were useful in in vivo treatment of cancer.

TABLE 3

Percent Injected Dose Per Gram of $^{125}$I-Labeled Antibody

| | CH84-1 | | | |
|---|---|---|---|---|
| Tissue | 1 Hour | 23 Hours | 47 Hours | 118–119 Hours |
| blood | 30.68 | 15.65 | 6.74 | 6.49 |
| Liver | 12.55 | 4.26 | 2.35 | 1.57 |
| Spleen | 10.93 | 3.35 | 2.56 | 1.70 |
| Kidney | 5.59 | 2.51 | 1.53 | 1.55 |
| tumor | 4.06 | 20.52 | 17.58 | 30.27 |
| lung | 10.77 | 4.80 | 2.58 | 2.24 |
| tumor, wt. | 0.15 | 0.22 | 0.20 | 0.24 |

As shown in Table 3, at approximately 118 hours post-injection, the percent of injected dose to tumor for CH84-1 was 30.27 percent. CH84-1 was, therefore, efficient in targeting the human tumor in situ. This demonstrates that the chimeric monoclonal antibodies of the present invention were efficient for in vivo carcinoma targeting and thus were useful in in vivo treatment of cancer.

TABLE 4

Percent Injected Dose Per Organ of $^{125}$I-Labeled Antibody

| | CH84-1 | | | |
|---|---|---|---|---|
| Tissue | 1 Hour | 23 Hours | 47 Hours | 118–119 Hours |
| blood, total | 45.98 | 22.11 | 10.08 | 9.37 |
| Liver | 13.64 | 5.34 | 3.13 | 1.94 |
| Spleen | 1.35 | 0.49 | 0.32 | 0.16 |
| Kidney | 1.39 | 0.62 | 0.38 | 0.38 |
| tumor | 0.59 | 4.33 | 3.63 | 7.02 |
| lung | 1.77 | 0.69 | 0.42 | 0.31 |
| GI tract | 7.38 | 4.92 | 3.41 | 2.32 |
| carcass | 44.83 | 52.19 | 30.32 | 24.06 |
| whole body retention | 93.58 | 81.00 | 47.14 | 45.48 |

As shown in Table 4, at approximately 118 post-injection, the percent of injected dose to tumor for CH84-1 was 7.02 percent. CH84-1 was, therefore, efficient in targeting the human tumor in situ. This demonstrates that the chimeric monoclonal antibodies of the present invention were efficient for in vivo carcinoma targeting and thus were useful in in vivo treatment of cancer.

Deposit of Cell Lines Producing Chimeric Antibodies

Eleven illustrative cell lines secreting chimeric antibodies, all having a kappa light chains, made by the above examples were deposited at the American Type Culture Collection (ATCC) on Oct. 19, 1988. Specifically, the following cell lines have been deposited: (1) CH44-1 (ATCC No. HB 9884); (2) CH88-2 (ATCC No. HB 9880); (3) CH44-4 (ATCC No. 9877); (4) CH88-1 (ATCC No. 9882); (5) CH44-2 (ATCC No. 9881); (6) CH88-3 (ATCC No. 9876); (7) CH88-4 (ATCC No. 9874); (8) CH84-1 (ATCC No. 9883); (9) CH84-2 (ATCC No. 9879); (10) CH84-3 (ATCC No. 9878); (11) CH84-4 (ATCC No. 9875); (12) CH44-Fab (ATCC HB 10428); (13) Ch44-F(ab')$_2$ (ATCC No. 10429); and (14) Ch44-CH3- (ATCC No. 10430).

The present invention is not to be limited in scope by the cell lines deposited since the deposited embodiment is intended as a single illustration of one aspect of the invention and all cell lines which are functionally equivalent are within the scope of the invention. Indeed, while this invention has been described in detail and with reference to specific embodiments thereof, it will be apparent to one skilled in the art that various changes and modifications could be made therein without departing from the spirit and scope of the appended claims.

What is claimed is:

1. A method for in vivo carcinoma targeting which comprises administering to an animal a pharmaceutically acceptable amount of a composition comprising an anti-TAG-72 mouse-human chimeric antibody produced by one of the cell lines CH44-1 (ATCC HB9884), CH44-2 (ATCC HB9880), CH44-4 (ATCC HB9877), CH88-1 (ATCC HB9882), CH88-2 (ATCC HB9881), CH88-3 (ATCC HB9876), CH88-4 (ATCC HB9874), CH84-1 (ATCC HB9883), CH84-2 (ATCC HB9879), CH84-3 (ATCC HB9878), or CH84-4 (ATCC HB9875), or an antibody fragment thereof, said antibody or fragment being conjugated to an imaging marker or therapeutic agent, in a pharmaceutically acceptable, non-toxic, sterile carrier, wherein said antibody is capable of binding to TAG-72 with an affinity at least 25% greater than that of B72.3, with the binding affinities of B72.3 and said antibody being measured by the same technique.

2. The method according to claim 1, wherein the imaging marker is selected from the group consisting of $^{125}I$, $^{131}I$, $^{123}$I, $^{111}$In, $^{105}$Rh, $^{153}$Sm, $^{67}$Cu, $^{67}$Ga, $^{166}$Ho, $^{177}$Lu, $^{186}$Re, $^{188}$Re, and $^{99m}$Tc.

3. The method according to claim 1, wherein the therapeutic agent is selected from the group consisting of radionuclides, drugs, biological response modifiers, toxins, and other antibodies.

4. The method according to claim 3, wherein the radionuclide is selected from the group consisting of $^{131}$I, $^{90}$Y, $^{105}$Rh, $^{47}$Sc, $^{67}$Cu, $^{212}$Bi, $^{211}$At, $^{67}$Ga, 125I, $^{186}$Re, $^{188}$Re, $^{177}$Lu, $^{99m}$Tc, $^{153}$Sm, $^{123}$I and $^{111}$In.

5. The method according to claim 3, wherein the drug or biological response modifier is selected from the group consisting of methotrexate, adriamycin, and interferon.

6. The method according to claim 1 wherein said method further comprises a step of localizing said antibody or fragment upon one or more tumors, by detecting the imaging marker or therapeutic agent to which such antibody or fragment is conjugated, said step being performed after the step of administering the composition to an animal.

7. The method according to claim 6 wherein said method further comprises a step of excising the tumor(s) upon which said antibody or fragment has been localized, whereby said method is utilized for intraoperative therapy.

8. The method according to claim 6, wherein the imaging marker is selected from the group consisting of $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re, $^{188}$Re, and $^{99m}$Tc.

9. The method according to claim 6 wherein the therapeutic agent is a radionuclide.

10. The method according to claim 9 wherein said radionuclide is selected from the group consisting of $^{131}$I, $^{90}$Y, $^{105}$Rh, $^{47}$Sc, $^{67}$Cu, $^{212}$Bi, $^{211}$At, $^{67}$Ga, 125I, $^{186}$Re, $^{188}$Re, $^{177}$Lu, $^{99m}$Tc, $^{153}$Sm, $^{123}$I, and $^{111}$In.

11. The method according to claim 7, wherein the imaging marker is selected from the group consisting of $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re, $^{188}$Re, and $^{99m}$Tc.

12. The method according to claim 7 wherein the therapeutic agent is a radionuclide.

13. The method according to claim 12 wherein said radionuclide is selected from the group consisting of $^{131}$I, $^{90}$Y, $^{105}$Rh, $^{47}$Sc, $^{67}$Cu, $^{212}$Bi, $^{211}$At, $^{67}$Ga, 125I, $^{186}$Re, $^{188}$Re, $^{177}$Lu, $^{99m}$Tc, $^{153}$Sm, $^{123}$I, and $^{111}$In.

\* \* \* \* \*

SEQUENCE LISTING (1) GENERAL INFORMATION:

(iii) NUMBER OF SEQUENCES: 74

(2) INFORMATION FOR SEQ ID NO:1:

(i) SEQUENCE CHARACTERISTICS:
       (A) LENGTH: 982 base pairs
       (B) TYPE: nucleic acid
       (C) STRANDEDNESS: double
       (D) TOPOLOGY: linear (ii) MOLECULE TYPE: DNA (genomic)

(ix) FEATURE:
       (A) NAME/KEY: CDS
       (B) LOCATION: join(384..429, 509..813)

(ix) FEATURE:
       (A) NAME/KEY: sig_peptide
       (B) LOCATION: join(384..429, 509..519)

(ix) FEATURE:
       (A) NAME/KEY: mat_peptide
       (B) LOCATION: 520..813

(xi) SEQUENCE DESCRIPTION: SEQ ID NO:1:

```
CCTTCTCTTC CTCCACCACC AAATCCACCA TTTGTAAATC AACATGTTAA CATATCACAG      60

AGTGGAGCAA CAGAATCAGG GCAAAAATAT GCTGAGAGAT TTATCCCTGT CGTTACAACC     120

AAAGCATCTG TCTAGAATTC ATAAAAACTT TATGGGATAC ATTTCCTCAG AGAGGAATAG     180

GATTTGGACC TGACGATCCT GCTGCCCGAG CCATGTGATG ACAGTTCTTC TCCAGTTGAA     240

CTAGGTCCTT ATCTAAGAAA TGCACTGCTC ATGAATATGC AAATCACCCG AGTCTATGGC     300

AGTAAATACA GAGATGTTCA TACCATAAAA ACAATATATG ATCAGTGTCT TCTCCGCTAT     360

CCCTGGACAC ACTGACTCTA ACC ATG GAA TGG AGC TGG GTC TTT CTC TTC        410
                          Met Glu Trp Ser Trp Val Phe Leu Phe
                          -19                 -15

TTC CTG TCA GTA ACT ACA  G GTAAGGGGCT CACCATTTCC AAATCTAAAG            459
Phe Leu Ser Val Thr Thr
-10              -5

TGGAGTCAGG GCCTGAGGTG ACAAAGATAT CCACTTTGGC TTTCCACAG GT GTC           513
                                                      Gly Val
                                                          -3

CAC TCC CAG GTT CAG CTG CAG CAG TCT GAC GCT GAG TTG GTG AAA CCT        561
His Ser Gln Val Gln Leu Gln Gln Ser Asp Ala Glu Leu Val Lys Pro
        1               5              10

GGG GCT TCA GTG AAG ATA TCC TGC AAG GCT TCT GGC TAC ACC TTC ACT        609
Gly Ala Ser Val Lys Ile Ser Cys Lys Ala Ser Gly Tyr Thr Phe Thr
 15              20              25              30

GAC CAT GCT ATT CAC TGG GTG AAG CAG AAG CCT GAA CAG GGC CTG GAA        657
Asp His Ala Ile His Trp Val Lys Gln Lys Pro Glu Gln Gly Leu Glu
             35              40              45

TGG ATT GGA TAT ATT TCT CCC GGA AAT GGT GAT ATT AAG TAC AAT GAG        705
Trp Ile Gly Tyr Ile Ser Pro Gly Asn Gly Asp Ile Lys Tyr Asn Glu
         50              55              60

AAG TTC AAG GGC AAG GCC ACA CTG ACT GCA GAC AAA TCC TCC AGC ACT        753
Lys Phe Lys Gly Lys Ala Thr Leu Thr Ala Asp Lys Ser Ser Ser Thr
             65              70              75

GCC TAC ATG CAG CTC AAC AGC CTG ACA TCT GAG GAT TCT GCA GTG TAT        801
Ala Tyr Met Gln Leu Asn Ser Leu Thr Ser Glu Asp Ser Ala Val Tyr
 80              85              90
```

```
TTC TGT AAA AGA CACAGTGTTG TAACCACATC CTGAGTGTGT CAGAAATCCT        853
Phe Cys Lys Arg
 95

GGGGGAGCAG AAAGATACAC TGGGACTGAG AAGACAGAAA AATTAATCCT TAGACTTGCT  913

CAGAAATCGT AATTTTGAAT GCCTATTTAT TTCATCTTGC TCACACACCT ATATTGCTTT  973

TGTAAGCTT                                                         982
```

(2) INFORMATION FOR SEQ ID NO:2:

(i) SEQUENCE CHARACTERISTICS:
        (A) LENGTH: 117 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Trp Ser Trp Val Phe Leu Phe Phe Leu Ser Val Thr Thr Gly
-19             -15                 -10                 -5

Val His Ser Gln Val Gln Leu Gln Gln Ser Asp Ala Glu Leu Val Lys
          1                 5                  10

Pro Gly Ala Ser Val Lys Ile Ser Cys Lys Ala Ser Gly Tyr Thr Phe
         15                 20                 25

Thr Asp His Ala Ile His Trp Val Lys Gln Lys Pro Glu Gln Gly Leu
 30              35                 40                     45

Glu Trp Ile Gly Tyr Ile Ser Pro Gly Asn Gly Asp Ile Lys Tyr Asn
             50                 55                 60

Glu Lys Phe Lys Gly Lys Ala Thr Leu Thr Ala Asp Lys Ser Ser Ser
             65                 70                 75

Thr Ala Tyr Met Gln Leu Asn Ser Leu Thr Ser Glu Asp Ser Ala Val
         80                 85                 90

Tyr Phe Cys Lys Arg
         95
```

(2) INFORMATION FOR SEQ ID NO:3:

(i) SEQUENCE CHARACTERISTICS:
        (A) LENGTH: 865 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(384..429, 509..865)

(ix) FEATURE:
        (A) NAME/KEY: sig_peptide
        (B) LOCATION: join(384..429, 509..519)

(ix) FEATURE:
        (A) NAME/KEY: mat_peptide
        (B) LOCATION: 520..865

(xi) SEQUENCE DESCRIPTION: SEQ ID NO:3:

```
CCTTCTCTTC CTCCACCACC AAATCCACCA TTTGTAAATC AACATGTTAA CATATCACAG   60

AGTGGAGCAA CAGAATCAGG GCAAAAATAT GCTGAGAGAT TTTTCCCTGT CGTTACAACC  120

AAAGCATCTG TCTAGAATTC ATAAAAACTT TATGGGATAC ATTTCCTCAG AGAGGAATAG  180

GATTTGGACC TGACGATCCT GCTGCCCGAG CCATGTGATG ACAGTTCTTC TCCAGTTGAA  240
```

```
CTAGGTCCTT ATCTAAGAAA TGCACTGCTC ATGAATATGC AAATCACCCG AGTCTATGGC        300

AGTAAATACA GAGATGTTCA TACCATAAAA ACAATATGTG ATCAGTGTCT TCTCCGCTAT        360

CCCTGGACAC ACTGACTCTA ACC ATG GAA TGG AGC TGG GTC TTT CTC TTC           410
                          Met Glu Trp Ser Trp Val Phe Leu Phe
                          -19             -15

TTC CTG TCA GTA ACT ACA  G GTAAGGGGCT CACCATTTCC AAATCTAAAG              459
Phe Leu Ser Val Thr Thr
-10              -5

TGGAGTCAGG GCCTGAGGTG ACAAAGATGT CCACTTTGGC TGTCCACAG  GT GTC            513
                                                         Gly Val
                                                          -3

CAC TCC CAG GTT CAG TTG CAG CAG TCT GAC GCT GAG TTG GTG AAA CCT         561
His Ser Gln Val Gln Leu Gln Gln Ser Asp Ala Glu Leu Val Lys Pro
         1           5                  10

GGG GCT TCA GTG AAG ATT TCC TGC AAG GCT TCT GGC TAC ACC TTC ACT         609
Gly Ala Ser Val Lys Ile Ser Cys Lys Ala Ser Gly Tyr Thr Phe Thr
15                  20                  25                  30

GAC CAT GCA ATT CAC TGG GTG AAA CAG AAC CCT GAA CAG GGC CTG GAA         657
Asp His Ala Ile His Trp Val Lys Gln Asn Pro Glu Gln Gly Leu Glu
                35                  40                  45

TGG ATT GGA TAT TTT TCT CCC GGA AAT GAT GAT TTT AAA TAC AAT GAG         705
Trp Ile Gly Tyr Phe Ser Pro Gly Asn Asp Asp Phe Lys Tyr Asn Glu
            50                  55                  60

AGG TTC AAG GGC AAG GCC ACA CTG ACT GCA GAC AAA TCC TCC AGC ACT         753
Arg Phe Lys Gly Lys Ala Thr Leu Thr Ala Asp Lys Ser Ser Ser Thr
        65                  70                  75

GCC TAC GTG CAG CTC AAC AGC CTG ACA TCT GAG GAT TCT GCA GTG TAT         801
Ala Tyr Val Gln Leu Asn Ser Leu Thr Ser Glu Asp Ser Ala Val Tyr
    80                  85                  90

TTC TGT ACA AGA TCC CTG AAT ATG GCC TAC TGG GGT CAA GGA ACC TCA         849
Phe Cys Thr Arg Ser Leu Asn Met Ala Tyr Trp Gly Gln Gly Thr Ser
95                  100                 105                 110

GTC ACC GTC TCC TCAG                                                    865
Val Thr Val Ser Ser
            115

(2) INFORMATION FOR SEQ ID NO:4:

(i) SEQUENCE CHARACTERISTICS:
        (A) LENGTH: 134 amino acids
        (B) TYPE: amino acid
        (D) TOPOLOGY: linear (ii) MOLECULE TYPE: protein (xi) SEQUENCE DESCRIPTION: SEQ ID NO:4:

Met Glu Trp Ser Trp Val Phe Leu Phe Phe Leu Ser Val Thr Thr Gly
-19             -15                 -10                 -5

Val His Ser Gln Val Gln Leu Gln Gln Ser Asp Ala Glu Leu Val Lys
        1           5                   10

Pro Gly Ala Ser Val Lys Ile Ser Cys Lys Ala Ser Gly Tyr Thr Phe
            15                  20                  25

Thr Asp His Ala Ile His Trp Val Lys Gln Asn Pro Glu Gln Gly Leu
30                  35                  40                  45

Glu Trp Ile Gly Tyr Phe Ser Pro Gly Asn Asp Asp Phe Lys Tyr Asn
                50                  55                  60

Glu Arg Phe Lys Gly Lys Ala Thr Leu Thr Ala Asp Lys Ser Ser Ser
                    65                  70                  75

Thr Ala Tyr Val Gln Leu Asn Ser Leu Thr Ser Glu Asp Ser Ala Val
            80                  85                  90
```

```
Tyr Phe Cys Thr Arg Ser Leu Asn Met Ala Tyr Trp Gly Gln Gly Thr
         95                 100                 105

Ser Val Thr Val Ser Ser
110                 115

(2) INFORMATION FOR SEQ ID NO:5:

(i) SEQUENCE CHARACTERISTICS:
        (A) LENGTH: 862 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(384..429, 509..862)

(ix) FEATURE:
        (A) NAME/KEY: sig_peptide
        (B) LOCATION: join(384..429, 509..519)

(ix) FEATURE:
        (A) NAME/KEY: mat_peptide
        (B) LOCATION: 520..862

(xi) SEQUENCE DESCRIPTION: SEQ ID NO:5:
```

```
CCTTCTCTTC CTCCACCACC AAATCCACCA TTTGTAAATC AACATGTTAA CATATCACAG      60

AGTGGAGCAA CAGAATCAGG GCAAAAATAT GCTGAGAGAT TTATCCCTGT CGTTACAACC     120

AAAGCATCTG TCTAGAATTC ATAAAAACTT TATGGGATAC ATTTCCTCAG AGAGGAATAG     180

GATTTGGACC TGACGATCCT GCTGCCCGAG CCATGTGATG ACAGTTCTTC TCCAGTTGAA     240

CTAGGTCCTT ATCTAAGAAA TGCACTGCTC ATGAATATGC AAATCACCCG AGTCTATGGC     300

AGTAAATACA GAGATGTTCA TACCATAAAA ACAATATATG ATCAGTGTCT TCTCCGCTAT     360

CCCTGGACAC ACTGACTCTA ACC ATG GAA TGG AGC TGG GTC TTT CTC TTC        410
                           Met Glu Trp Ser Trp Val Phe Leu Phe
                           -19             -15

TTC CTG TCA GTA ACT ACA  G GTAAGGGGCT CACCATTTCC AAATCTAAAG           459
Phe Leu Ser Val Thr Thr
-10             -5

TGGAGTCAGG GCCTGAGGTG ACAAAGATAT CCACTTTGGC TTTCCACAG  GT GTC         513
                                                          Gly Val
                                                                -3

CAC TCC CAG GTT CAG TTG CAG CAG TCT GAC GCT GAG TTG GTG AAA CCT      561
His Ser Gln Val Gln Leu Gln Gln Ser Asp Ala Glu Leu Val Lys Pro
            1               5                  10

GGG GCT TCA GTG AAG ATT TCC TGC AAG GCT TCT GGC TAC ACC TTC ACT      609
Gly Ala Ser Val Lys Ile Ser Cys Lys Ala Ser Gly Tyr Thr Phe Thr
 15              20                  25                  30

GAC CAT GCT ATT CAC TGG GTG AAG CAG AAG CCT GAA CAG GGC CTG GAA      657
Asp His Ala Ile His Trp Val Lys Gln Lys Pro Glu Gln Gly Leu Glu
             35                  40                  45

TGG ATT GGA TAT ATT TCT CCC GGA AAT GAT GAT ATT AAG TAC AAT GAG      705
Trp Ile Gly Tyr Ile Ser Pro Gly Asn Asp Asp Ile Lys Tyr Asn Glu
         50                  55                  60

AAG TTC AAG GGC AAG GCC ACA CTG ACT GCA GAC AAA TCC TCC AGT ACT      753
Lys Phe Lys Gly Lys Ala Thr Leu Thr Ala Asp Lys Ser Ser Ser Thr
     65                  70                  75

GCC TAC ATG CAA CTC AAC AGC CTG ACA TCT GAG GAT TCT GCA GTG TAT      801
Ala Tyr Met Gln Leu Asn Ser Leu Thr Ser Glu Asp Ser Ala Val Tyr
 80                  85                  90
```

```
TTC TGT AGA AGA TCC TTC TAC GGC AAC TGG GGC CAA GGC ACC ACC CTC        849
Phe Cys Arg Arg Ser Phe Tyr Gly Asn Trp Gly Gln Gly Thr Thr Leu
 95              100                 105                 110

ACA GTC TCC TCAG                                                       862
Thr Val Ser Ser
```

(2) INFORMATION FOR SEQ ID NO:6:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO:6:

```
Met Glu Trp Ser Trp Val Phe Leu Phe Phe Leu Ser Val Thr Thr Gly
-19             -15                 -10                 -5

Val His Ser Gln Val Gln Leu Gln Gln Ser Asp Ala Glu Leu Val Lys
                 1               5                  10

Pro Gly Ala Ser Val Lys Ile Ser Cys Lys Ala Ser Gly Tyr Thr Phe
             15                  20                  25

Thr Asp His Ala Ile His Trp Val Lys Gln Lys Pro Glu Gln Gly Leu
 30                  35                  40                  45

Glu Trp Ile Gly Tyr Ile Ser Pro Gly Asn Asp Asp Ile Lys Tyr Asn
                 50                  55                  60

Glu Lys Phe Lys Gly Lys Ala Thr Leu Thr Ala Asp Lys Ser Ser Ser
             65                  70                  75

Thr Ala Tyr Met Gln Leu Asn Ser Leu Thr Ser Glu Asp Ser Ala Val
             80                  85                  90

Tyr Phe Cys Arg Arg Ser Phe Tyr Gly Asn Trp Gly Gln Gly Thr Thr
             95                 100                 105

Leu Thr Val Ser Ser
110
```

(2) INFORMATION FOR SEQ ID NO:7:

(i) SEQUENCE CHARACTERISTICS:
        (A) LENGTH: 451 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 49..451

(ix) FEATURE:
        (A) NAME/KEY: sig_peptide
        (B) LOCATION: 49..105

(ix) FEATURE:
        (A) NAME/KEY: mat_peptide
        (B) LOCATION: 106..451

(xi) SEQUENCE DESCRIPTION: SEQ ID NO:7:

```
ATATGATCAG TGTCTTCTCC GCTATCCCTG GACACACTGA CTCTAACC ATG GAA TGG        57
                                                    Met Glu Trp
                                                    -19

AGC TGG GTC TTT CTC TTC TTC CTG TCA GTA ACT ACA GGT GTC CAC TCC       105
Ser Trp Val Phe Leu Phe Phe Leu Ser Val Thr Thr Gly Val His Ser
    -15                 -10                 -5
```

```
CAA TTT CAG CTA CAG CAG TCT GAC GCT GAG TTG GTG AGA CCT GGG GCT        153
Gln Phe Gln Leu Gln Gln Ser Asp Ala Glu Leu Val Arg Pro Gly Ala
  1               5                  10                  15

TCA GTG AAG ATT TCC TGC AAG GCT TCT GGC TAC ACC TTC ACT GAC CAT        201
Ser Val Lys Ile Ser Cys Lys Ala Ser Gly Tyr Thr Phe Thr Asp His
             20                  25                  30

GCT ATT CAC TGG GTG AAG CAG AAG CCT GAA CAG GGC CTG GAA TGG ATT        249
Ala Ile His Trp Val Lys Gln Lys Pro Glu Gln Gly Leu Glu Trp Ile
         35                  40                  45

GGA TAT TTT TCT CCC GGA AAT GGT GAT ATT AAG TAC AAT GAG AAG TTC        297
Gly Tyr Phe Ser Pro Gly Asn Gly Asp Ile Lys Tyr Asn Glu Lys Phe
     50                  55                  60

AAG GGC AAG GCC ACA CTG ACT GCA GAC AAA TCC TCC AGC ACT GCC TAC        345
Lys Gly Lys Ala Thr Leu Thr Ala Asp Lys Ser Ser Ser Thr Ala Tyr
 65              70                  75                  80

ATG CAG TTC AAC AGC CTG ACA TCT GAG GAC TCT GCA GTG TAT TTC TGT        393
Met Gln Phe Asn Ser Leu Thr Ser Glu Asp Ser Ala Val Tyr Phe Cys
             85                  90                  95

ACG GGC GGC TAC GGG TTT GCT TTC TGG GGC CAA GGG ACT CTG GTC ACT        441
Thr Gly Gly Tyr Gly Phe Ala Phe Trp Gly Gln Gly Thr Leu Val Thr
        100                 105                 110

GTC TCT GCA G                                                          451
Val Ser Ala
        115

(2) INFORMATION FOR SEQ ID NO:8:

(i) SEQUENCE CHARACTERISTICS:
        (A) LENGTH: 134 amino acids
        (B) TYPE: amino acid
        (D) TOPOLOGY: linear (ii) MOLECULE TYPE: protein (xi) SEQUENCE DESCRIPTION: SEQ ID NO:8:

Met Glu Trp Ser Trp Val Phe Leu Phe Phe Leu Ser Val Thr Thr Gly
-19             -15                 -10                  -5

Val His Ser Gln Phe Gln Leu Gln Gln Ser Asp Ala Glu Leu Val Arg
             1                   5                  10

Pro Gly Ala Ser Val Lys Ile Ser Cys Lys Ala Ser Gly Tyr Thr Phe
        15                  20                  25

Thr Asp His Ala Ile His Trp Val Lys Gln Lys Pro Glu Gln Gly Leu
 30                  35                  40                  45

Glu Trp Ile Gly Tyr Phe Ser Pro Gly Asn Gly Asp Ile Lys Tyr Asn
                 50                  55                  60

Glu Lys Phe Lys Gly Lys Ala Thr Leu Thr Ala Asp Lys Ser Ser Ser
             65                  70                  75

Thr Ala Tyr Met Gln Phe Asn Ser Leu Thr Ser Glu Asp Ser Ala Val
         80                  85                  90

Tyr Phe Cys Thr Gly Gly Tyr Gly Phe Ala Phe Trp Gly Gln Gly Thr
     95                 100                 105

Leu Val Thr Val Ser Ala
110                 115

(2) INFORMATION FOR SEQ ID NO:9:

(i) SEQUENCE CHARACTERISTICS:
        (A) LENGTH: 430 base pairs
        (B) TYPE: nucleic acid
        (C) STRANDEDNESS: double
        (D) TOPOLOGY: linear
```

(ii) MOLECULE TYPE: cDNA to mRNA (ix) FEATURE:
    (A) NAME/KEY: CDS
    (B) LOCATION: 28..430

(ix) FEATURE:
    (A) NAME/KEY: sig_peptide
    (B) LOCATION: 28..84

(ix) FEATURE:
    (A) NAME/KEY: mat_peptide
    (B) LOCATION: 85..430

(xi) SEQUENCE DESCRIPTION: SEQ ID NO:9:

```
CTATCCCTGG ACACACTGAC TCTAACC ATG GAA TGG AGC TGG GTC TTT CTC         51
                                Met Glu Trp Ser Trp Val Phe Leu
                                -19                 -15

TTC TTC CTG TCA GTA ACT ACA GGT GTC CAC TCC CAG GTT CAA CTG CAG        99
Phe Phe Leu Ser Val Thr Thr Gly Val His Ser Gln Val Gln Leu Gln
        -10                 -5                   1               5

CAG TCT GAC GCT GAG TTG GTG AAA CCT GGG GCT TCA GTG AAG ATA TCC       147
Gln Ser Asp Ala Glu Leu Val Lys Pro Gly Ala Ser Val Lys Ile Ser
                10                  15                  20

TGC AAG GCT TCT GGC TAC ACC TTC ACT GAC CAT GCT ATT CAC TGG GTG       195
Cys Lys Ala Ser Gly Tyr Thr Phe Thr Asp His Ala Ile His Trp Val
            25                  30                  35

AAG CAG AAA CCT GAA CAG GGC CTG GAA TGG ATT GGA TAT ATT TCT CCC       243
Lys Gln Lys Pro Glu Gln Gly Leu Glu Trp Ile Gly Tyr Ile Ser Pro
        40                  45                  50

GGA AAT GAT GAT ATT AAG TAC AAT GAG AAG TTC AAG GGT AAG GCC ACA       291
Gly Asn Asp Asp Ile Lys Tyr Asn Glu Lys Phe Lys Gly Lys Ala Thr
    55                  60                  65

CTG ACT GCA GAC AAA CCC TCC AAC ACT GTC TAC ATG CAG CTC AAC AGC       339
Leu Thr Ala Asp Lys Pro Ser Asn Thr Val Tyr Met Gln Leu Asn Ser
70                  75                  80                  85

CTG ACC TCT GAG GAT TCT GCA GTG TAT TTC TGT ACA AGA TCT CTA TCC       387
Leu Thr Ser Glu Asp Ser Ala Val Tyr Phe Cys Thr Arg Ser Leu Ser
                90                  95                 100

GGG AAC TCC TGG GGC CAG GGC ACC ACT CTC ACA GTC TCC TCA G             430
Gly Asn Ser Trp Gly Gln Gly Thr Thr Leu Thr Val Ser Ser
            105                 110                 115
```

(2) INFORMATION FOR SEQ ID NO:10:

(i) SEQUENCE CHARACTERISTICS:
        (A) LENGTH: 134 amino acids
        (B) TYPE: amino acid
        (D) TOPOLOGY: linear (ii) MOLECULE TYPE: protein (xi) SEQUENCE DESCRIPTION: SEQ ID NO:10:

```
Met Glu Trp Ser Trp Val Phe Leu Phe Leu Ser Val Thr Thr Gly
-19                 -15                 -10                 -5

Val His Ser Gln Val Gln Leu Gln Gln Ser Asp Ala Glu Leu Val Lys
                 1               5                  10

Pro Gly Ala Ser Val Lys Ile Ser Cys Lys Ala Ser Gly Tyr Thr Phe
        15                  20                  25

Thr Asp His Ala Ile His Trp Val Lys Gln Lys Pro Glu Gln Gly Leu
    30                  35                  40                  45

Glu Trp Ile Gly Tyr Ile Ser Pro Gly Asn Asp Asp Ile Lys Tyr Asn
                50                  55                  60
```

-continued

```
Glu Lys Phe Lys Gly Lys Ala Thr Leu Thr Ala Asp Lys Pro Ser Asn
             65                  70                  75

Thr Val Tyr Met Gln Leu Asn Ser Leu Thr Ser Glu Asp Ser Ala Val
         80                  85                  90

Tyr Phe Cys Thr Arg Ser Leu Ser Gly Asn Ser Trp Gly Gln Gly Thr
     95                 100                 105

Thr Leu Thr Val Ser Ser
110             115
```

(2) INFORMATION FOR SEQ ID NO:11:

(i) SEQUENCE CHARACTERISTICS:
        (A) LENGTH: 795 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(144..192, 385..735)

(ix) FEATURE:
        (A) NAME/KEY: sig_peptide
        (B) LOCATION: join(144..192, 385..395)

(ix) FEATURE:
        (A) NAME/KEY: mat_peptide
        (B) LOCATION: 396..735

(xi) SEQUENCE DESCRIPTION: SEQ ID NO:11:

```
CCATCCACTC TCACACACAC TGCCCAGGCA TTTGCTTTTG TATTTGCTGG CTGCTTTGCA      60

TAGACCCCTC CAGCCTAACC CAGCTGCTCA GAATTTATAA ACCAGTATGA ACTGAGCAGC     120

ATCAGACAGG CAGGGGAAGC AAG ATG GAT TCA CAG GCC CAG GTT CTT ATG         170
                        Met Asp Ser Gln Ala Gln Val Leu Met
                        -20                 -15

TTA CTG CTG CTA TGG GTA TCT  G GTGAGAAATT TAAAAGTATT ATCATTTCAG        222
Leu Leu Leu Leu Trp Val Ser
    -10                 -5

AGTTACACCT TTTTATATAA GAAATTTATA CTTTGTGCAA GTGTGTAATA TTACTTCCAT     282

AATAACTCTG ACAATATGAC ATTACAAAGA CCTTTGACAA ATTTCAACTG TTATAATAAT     342

CTATTTGTGT ATGTATTCAT GTTCACTTTC TACTTATTTC AG  GT ACC TGT GGG        395
                                                Gly Thr Cys Gly
                                                        -3

GAC ATT GTG ATG TCA CAG TCT CCA TCC TCC CTA CCT GTG TCA GTT GGC       443
Asp Ile Val Met Ser Gln Ser Pro Ser Ser Leu Pro Val Ser Val Gly
  1               5                  10                  15

GAG AAG GTT ACT TTG AGC TGC AAG TCC AGT CAG AGC CTT TTA TAT AGT       491
Glu Lys Val Thr Leu Ser Cys Lys Ser Ser Gln Ser Leu Leu Tyr Ser
                 20                  25                  30

GGT AAT CAA AAG AAC TAC TTG GCC TGG TAC CAG CAG AAA CCA GGG CAG       539
Gly Asn Gln Lys Asn Tyr Leu Ala Trp Tyr Gln Gln Lys Pro Gly Gln
         35                  40                  45

TCT CCT AAA CTG CTG ATT TAC TGG GCA TCC GCT AGG GAA TCT GGG GTC       587
Ser Pro Lys Leu Leu Ile Tyr Trp Ala Ser Ala Arg Glu Ser Gly Val
 50                  55                  60

CCT GAT CGC TTC ACA GGC AGT GGA TCT GGG ACA GAT TTC ACT CTC TCC       635
Pro Asp Arg Phe Thr Gly Ser Gly Ser Gly Thr Asp Phe Thr Leu Ser
 65                  70                  75                  80

ATC AGC AGT GTG AAG ACT GAA GAC CTG GCA GTT TAT TAC TGT CAG CAG       683
Ile Ser Ser Val Lys Thr Glu Asp Leu Ala Val Tyr Tyr Cys Gln Gln
             85                  90                  95
```

```
TAT TAT AGC TAT CCC CTC ACG TTC GGT GCT GGG ACC AAG CTG GTG CTG     731
Tyr Tyr Ser Tyr Pro Leu Thr Phe Gly Ala Gly Thr Lys Leu Val Leu
            100                 105                 110

AAACGTAAGT ACACTTTTCT CATCTTTTTT TATGTGTAAG ACACAGGTTT TCATGTTAGG    791
Lys

AGTT                                                                 795
```

(2) INFORMATION FOR SEQ ID NO:12:

(i) SEQUENCE CHARACTERISTICS:
        (A) LENGTH: 133 amino acids
        (B) TYPE: amino acid
        (D) TOPOLOGY: linear (ii) MOLECULE TYPE: protein (xi) SEQUENCE DESCRIPTION: SEQ ID NO:12:

```
Met Asp Ser Gln Ala Gln Val Leu Met Leu Leu Leu Trp Val Ser
-20             -15                 -10                 -5

Gly Thr Cys Gly Asp Ile Val Met Ser Gln Ser Pro Ser Ser Leu Pro
                 1               5                  10

Val Ser Val Gly Glu Lys Val Thr Leu Ser Cys Lys Ser Ser Gln Ser
            15                  20                  25

Leu Leu Tyr Ser Gly Asn Gln Lys Asn Tyr Leu Ala Trp Tyr Gln Gln
        30                  35                  40

Lys Pro Gly Gln Ser Pro Lys Leu Leu Ile Tyr Trp Ala Ser Ala Arg
45                  50                  55                  60

Glu Ser Gly Val Pro Asp Arg Phe Thr Gly Ser Gly Ser Gly Thr Asp
                65                  70                  75

Phe Thr Leu Ser Ile Ser Ser Val Lys Thr Glu Asp Leu Ala Val Tyr
            80                  85                  90

Tyr Cys Gln Gln Tyr Tyr Ser Tyr Pro Leu Thr Phe Gly Ala Gly Thr
        95                  100                 105

Lys Leu Val Leu Lys
    110
```

(2) INFORMATION FOR SEQ ID NO:13:

(i) SEQUENCE CHARACTERISTICS:
        (A) LENGTH: 685 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: double (ix) FEATURE:
        (A) NAME/KEY: CDS
        (B) LOCATION: join(76..136, 315..647)

(ix) FEATURE:
        (A) NAME/KEY: sig_peptide
        (B) LOCATION: join(76..136, 315..325)

(ix) FEATURE:
        (A) NAME/KEY: mat_peptide
        (B) LOCATION: 326..647

(xi) SEQUENCE DESCRIPTION: SEQ ID NO:13:

```
CCTAGAGGCC AGCACAGCTG CCCATGATTT ATAAACCAGG TCTTTGCAGT GAGATCTCAA        60

ATACATCAGA CCAGC ATG GGC ATC AAG ATG GAG ACA CAT TCT CAG GTC TTT        111
               Met Gly Ile Lys Met Glu Thr His Ser Gln Val Phe
               -24             -20                 -15

GTA TAC ATG TTG CTG TGG TTG TCT  G GTGAGACATT TAAAAGTATT                 156
Val Tyr Met Leu Leu Trp Leu Ser
        -10             -5

ATAAAATCTT AAAAGTAATC TATTTAAATA GCTTTTTCCT ATAGGAAGCC AATATTAGGC        216

AGACAATGCC ATTAGATAAG ACATTTTGGA TTCTAACATT TGTATCTTGA AGTCTTTATA        276

TGTGTGAGTT TATACACATT ATCTGTTTCT GTTTGCAG  GT GTT GAA GGA GAC           328
                                             Gly Val Glu Gly Asp
                                                 -3              1

ATT GTG ATG ACC CAG TCT CAC AAA TTC ATG TCC GCA TCA GTG GGA GAC          376
Ile Val Met Thr Gln Ser His Lys Phe Met Ser Ala Ser Val Gly Asp
            5                  10                 15

AGG GTC AAC ATC ACC TGC AAG GCC AGT CAG TAT GTG GCT ACT GCT GTA          424
Arg Val Asn Ile Thr Cys Lys Ala Ser Gln Tyr Val Ala Thr Ala Val
            20                 25                 30

GCC TGG TTT CAG CAT AAA CCA GGT CAG TCT CCT AAA CTA CTG ATT TAC          472
Ala Trp Phe Gln His Lys Pro Gly Gln Ser Pro Lys Leu Leu Ile Tyr
        35                  40                 45

GGG GCA TCC ACC CGG CAC ACT GGA GTC CCT GAT CGC TTC ACA GGC AGT          520
Gly Ala Ser Thr Arg His Thr Gly Val Pro Asp Arg Phe Thr Gly Ser
50              55                  60                 65

GGA TCT GGG ACA GAT TTC ACT CTC ATC ATT AGC AAT GTG CAG TCT GAG          568
Gly Ser Gly Thr Asp Phe Thr Leu Ile Ile Ser Asn Val Gln Ser Glu
            70                 75                  80

GAC TTG GCA GAT TAT TTG TGT CAG CAT TAT AGC GGC TAT CCA TTC ACG          616
Asp Leu Ala Asp Tyr Leu Cys Gln His Tyr Ser Gly Tyr Pro Phe Thr
            85                 90                  95

TTC GGC TCG GGG ACA AAG TTG GAA ATA AAACGTAAGT AGACTTTTGC                663
Phe Gly Ser Gly Thr Lys Leu Glu Ile Lys
        100                 105

TCATTTACTT GTGACGTTTT GG                                                 685
```

(2) INFORMATION FOR SEQ ID NO:14:

(i) SEQUENCE CHARACTERISTICS:
        (A) LENGTH: 131 amino acids
        (B) TYPE: amino acid
        (D) TOPOLOGY: linear (ii) MOLECULE TYPE: protein (xi) SEQUENCE DESCRIPTION: SEQ ID NO:14:

```
Met Gly Ile Lys Met Glu Thr His Ser Gln Val Phe Val Tyr Met Leu
-24             -20                 -15                 -10

Leu Trp Leu Ser Gly Val Glu Gly Asp Ile Val Met Thr Gln Ser His
            -5              1                   5

Lys Phe Met Ser Ala Ser Val Gly Asp Arg Val Asn Ile Thr Cys Lys
        10                  15                  20

Ala Ser Gln Tyr Val Ala Thr Ala Val Ala Trp Phe Gln His Lys Pro
25                  30                  35                  40

Gly Gln Ser Pro Lys Leu Leu Ile Tyr Gly Ala Ser Thr Arg His Thr
            45                  50                  55

Gly Val Pro Asp Arg Phe Thr Gly Ser Gly Ser Gly Thr Asp Phe Thr
            60                  65                  70
```

```
Leu Ile Ile Ser Asn Val Gln Ser Glu Asp Leu Ala Asp Tyr Leu Cys
        75                  80                  85

Gln His Tyr Ser Gly Tyr Pro Phe Thr Phe Gly Ser Gly Thr Lys Leu
        90                  95                 100

Glu Ile Lys
105
```

(2) INFORMATION FOR SEQ ID NO:15:

(i) SEQUENCE CHARACTERISTICS:
        (A) LENGTH: 1716 base pairs
        (B) TYPE: nucleic acid
        (C) STRANDEDNESS: double
        (D) TOPOLOGY: linear (xi) SEQUENCE DESCRIPTION: SEQ ID NO:15:

```
AAGCTTTCGC CTACCCACTG CTCTGTTCCT CTTCAGTGAG GAGGGTTTTT GTACAGCCAG      60

ACAGTGGAGT ACTACCACTG TGGTGGACGT TCGGTGGAGG CACCAAGCTG GAAATCAAAC     120

GTAAGTAGAA TCCAAAGTCT CTTTCTTCCG TTGTCTATGT CTGTGGCTTC TATGTCTAAA     180

AATGATGTAT AAAATCTTAC TCTGAAACCA GATTCTGGCA CTCTCCAAGG CAAAGATACA     240

GAGTAACTCC GTAAGCAAAG CTGGGAATAG GCTAGACATG TTCTCTGGAG AATGAATGCC     300

AGTGTAATAA TTAACACAAG TGATAGTTTC AGAAATGCTC AAAGAAGCAG GGTAGCCTGC     360

CCTAGACAAA CCTTTACTCG GTGCTCAGAC CATGCTCAGT TTTTGTATGG GGGTTGAGTG     420

AAGGGACACC AGTGTGTGTA CACGTTCGGA GGGGGGACCA AGCTGGAAAT AAAACGTAAG     480

TAGTCTTCTC AACTCTTGTT CACTAAGTCT AACCTTGTTA AGTTGTTCTT TGTTGTGTGT     540

TTTTCTTAAG GAGATTTCAG GGATTTAGCA AATTCCATTC TCAGATCAGG TGTTAAGGAG     600

GGAAAACTGT CCCACAAGAG GTTGGAATGA TTTTCAGGCT AAATTTTAGG CTTTCTAAAC     660

CAAAGTAACT AAACTAGGGG AAGAGGGATA ATTGTCTACC TAGGGAGGGT TTTGTGGAGG     720

TAAAGTTAAA ATAAATCACT GTAAATCACA TTCAGTGATG GGACCAGACT GGAAATAAAA     780

CCTAAGTACA TTTTTGCTCA ACTGCTTGTG AAGTTTTGGT CCCATTGTGT CCTTTGTATG     840

AGTTTGTGGT GTACATTAGA TAAATGAACT ATTCCTTGTA ACCCAAAACT TAAATAGAAG     900

AGAACCAAAA ATCTAGCTAC TGTACAAGCT GAGCAAACAG ACTGACCTCA TGTCAGATTT     960

GTGGGAGAAA TGAGAAAGGA ACAGTTTTTC TCTGAACTTA GCCTATCTAA CTGGATCGCC    1020

TCAGGCAGGT TTTTGTAAAG GGGGGCGCAG TGATATGAAT CACTGTGATT CACGTTCGGC    1080

TCGGGGACAA AGTTGGAAAT AAAACGTAAG TAGACTTTTG CTCATTTACT TGTGACGTTT    1140

TGGTTCTGTT TGGGTAACTT GTGTGAATTT GTGACATTTT GGCTAAATGA GCCATTCCTG    1200

GCAACCTGTG CATCAATAGA AGATCCCCCA GAAAAGAGTC AGTGTGAAAG CTGAGCGAAA    1260

AACTCGTCTT AGGCTTCTGA GACCAGTTTT GTAAGGGGAA TGTAGAAGAA AGAGCTGGGC    1320

TTTTCCTCTG AATTTGGCCC ATCTAGTTGG ACTGGCTTCA CAGGCAGGTT TTTGTAGAGA    1380

GGGGCATGTC ATAGTCCTCA CTGTGGCTCA CGTTCGGTGC TGGGACCAAG CTGGAGCTGA    1440

AACGTAAGTA CACTTTTCTC ATCTTTTTTT ATGTGTAAGA CACAGGTTTT CATGTTAGGA    1500

GTTAAAGTCA GTTCAGAAAA TCTTGAGAAA ATGGAGAGGG CTCATTATCA GTTGACGTGG    1560

CATACAGTGT CAGATTTTCT GTTTATCAAG CTAGTGAGAT TAGGGGCAAA AAGAGGCTTT    1620

AGTTGAGAGG AAAGTAATTA ATACTATGGT CACCATCCAA GAGATTGGAT CGGAGAATAA    1680

GCATGAGTAG TTATTGAGAT CTGGGTCTGA CTGCAG                             1716
```

(2) INFORMATION FOR SEQ ID NO:16:

(i) SEQUENCE CHARACTERISTICS:
    (A) LENGTH: 1984 base pairs
    (B) TYPE: nucleic acid
    (C) STRANDEDNESS: double
    (D) TOPOLOGY: linear (xi) SEQUENCE DESCRIPTION: SEQ ID NO:16:

```
GGATCCTGGC CAGCATTGCC GCTAGGTCCC TCTCTTCTAT GCTTTCTTTG TCCCTCACTG      60
GCCTCCATCT GAGATAATCC TGGAGCCCTA GCCAAGGATC ATTTATTGTC AGGGGTCTAA     120
TCATTGTTGT CACAATGTGC CTGGTTTGCT TACTGGGGCC AAGGGACTCT GGTCACTGTC     180
TCTGCAGGTG AGTCCTAACT TCTCCCATTC TAAATGCATG TTGGGGGAT  TCTGAGCCTT     240
CAGGACCAAG ATTCTCTGCA AACGGGAATC AAGATTCAAC CCCTTTGTCC CAAAGTTGAG     300
ACATGGGTCT GGGTCAGGGA CTCTCTGCCT GCTGGTCTGT GGTGACATTA GAACTGAAGT     360
ATGATGAAGG ATCTGCCAGA ACTGAAGCTT GAAGTCTGAG GCAGAATCTT GTCCAGGGTC     420
TATCGGACTC TTGTGAGAAT TAGGGGCTGA CAGTTGATGG TGACAATTTC AGGGTCAGTG     480
ACTGTCAGGT TTCTCTGAGG TGAGGCTGGA ATATAGGTCA CCTTGAAGAC TAAAGAGGGG     540
TCCAGGGGCT TTTCTGCACA GGCAGGGAAC AGAATGTGGA ACAATGACTT GAATGGTTGA     600
TTCTTGTGTG ACACCAAGAA TTGGCATAAT GTCTGAGTTG CCCAAGGGTG ATCTTAGCTA     660
GACTCTGGGG TTTTTGTCGG GTACAGAGGA AAAACCCACT ATTGTGATTA CTATGCTATG     720
GACTACTGGG GTCAAGGAAC CTCAGTCACC GTCCTCAG  GTAAGAATGG CCTCTCCAGG     780
TCTTTATTTT TAACCTTTGT TATGGAGTTT TCTGAGCATT GCAGACTAAT CTTGGATATT     840
TGCCCTGAGG GAGCCGGCTG AGAGAAGTTG GGAAATAAAT CTGTCTAGGG ATCTCAGAGC     900
CTTTAGGACA GATTATCTCC ACATCTTTGA AAAACTAAGA ATCTGTGTGA TGGTGTTGGT     960
GGAGTCCCTG GATGATGGGA TAGGGACTTT GGAGGCTCAT TTGAGGGAGA TGCTAAAACA    1020
ATCCTATGGC TGGAGGGATA GTTGGGGCTG TAGTTGGAGA TTTTCAGTTT TTAGAATGAA    1080
GTATTAGCTG CAATACTTCA AGGACCACCT CTGTGACAAC CATTTTATAC AGTATCCAGG    1140
CATAGGGACA AAAAGTGGAG TGGGGCACTT TCTTTAGATT TGTGAGGAAT GTTCCACACT    1200
AGATTGTTTA AAACTTCATT TGTTGGAAGG AGCTGTCTTA GTGATTGAGT CAAGGGAGAA    1260
AGGCATCTAG CCTCGGTCTC AAAAGGGTAG TTGCTGTCTA GAGAGGTCTG GTGGAGCCTG    1320
CAAAAGTCCA GCTTTCAAAG GAACACAGAA GTATGTGTAT GGAATATTAG AAGATGTTGC    1380
TTTTACTCTT AAGTTGGTTC CTAGGAAAAA TAGTTAAATA CTGTGACTTT AAAATGTGAG    1440
AGGGTTTTCA AGTACTCATT TTTTTAAATG TCCAAAATTT TTGTCAATCA ATTTGAGGTC    1500
TTGTTTGTGT AGAACTGACA TTACTTAAAG TTTAACCGAG GAATGGGAGT GAGGCTCTCT    1560
CATACCCTAT TCAGAACTGA CTTTTAACAA TAATAAATTA AGTTTAAAAT ATTTTTAAAT    1620
GAATTGAGCA ATGTTGAGTT GAGTCAAGAT GGCCGATCAG AACCGGAACA CCTGCAGCAG    1680
CTGGCAGGAA GCAGGTCATG TGGCAAGGCT ATTTGGGGAA GGGAAAATAA AACCACTAGG    1740
TAAACTTGTA GCTGTGGTTT GAAGAAGTGG TTTTGAAACA CTCTGTCCAG CCCCACCAAA    1800
CCGAAAGTCC AGGCTGAGCA AAACACCACC TGGGTAATTT GCATTTCTAA AATAAGTTGA    1860
GGATTCAGCC GAAACTGGAG AGGTCCTCTT TTAACTTATT GAGTTCAACC TTTTAATTTT    1920
AGCTTGAGTA GTTCTAGTTT CCCCAAACTT AAGTTTATCG ACTTCTAAAA TGTATTTAGA    1980
ATTC                                                                 1984
```

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (xi) SEQUENCE DESCRIPTION: SEQ ID NO:17:

GGAAGATGGA TACAGTTGGT GC                    22

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (xi) SEQUENCE DESCRIPTION: SEQ ID NO:18:

GGAAGATGGA TACAGTTGGT GC                    22

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (xi) SEQUENCE DESCRIPTION: SEQ ID NO:19:

CCAACTTTGT CCCCGAGCCG AACG                  24

(2) INFORMATION FOR SEQ ID NO:20:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (xi) SEQUENCE DESCRIPTION: SEQ ID NO:20:

CGTTTCAGCT CCAGCTTGGT CCC                   23

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (xi) SEQUENCE DESCRIPTION: SEQ ID NO:21:

ATGGAGTTAG TTTGGGCAGC AGAT                  24

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO:22:

GGTGACTGAG GTTCCTTGAC                       20

(2) INFORMATION FOR SEQ ID NO:23:

(i) SEQUENCE CHARACTERISTICS:
        (A) LENGTH: 16 base pairs (B) TYPE: nucleic acid
        (C) STRANDEDNESS: double
        (D) TOPOLOGY: linear (xi) SEQUENCE DESCRIPTION: SEQ ID NO:23:

CTGAGGAGAC TGTGAG                                                           16

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO:24:

CCTTGAACTT CTCATTGTAC                                                       20

(2) INFORMATION FOR SEQ ID NO:25:

(i) SEQUENCE CHARACTERISTICS:
        (A) LENGTH: 819 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:25:

TTAACATATC ACAGAGTGGA GCAACAGAAT CAGGGCAAAA ATATGCTGAG AGATTTTTCC            60

CTGTCGTTAC AACCAAAGCA TCTGTCTAGA ATTCATAAAA ACTTTATGGG ATACATTTCC           120

TCAGAGAGGA ATAGGATTTG GACCTGACGA TCCTGCTGCC CGAGCCATGT GATGACAGTT          180

CTTCTCCAGT TGAACTAGGT CCTTATCTAA GAAATGCACT GCTCATGAAT ATGCAAATCA          240

CCCGAGTCTA TGGCAGTAAA TACAGAGATG TTCATACCAT AAAAACAATA TGTGATCAGT          300

GTCTTCTCCG CTATCCCTGG ACACACTGAC TCTAACCATG GAATGGAGCT GGGTCTTTCT          360

CTTCTTCCTG TCAGTAACTA CAGGTAAGGG GCTCACCATT TCCAAATCTA AAGTGGAGTC          420

AGGGCCTGAG GTGACAAAGA TGTCCACTTT GGCTGTCCAC AGGTGTCCAC TCCCAGGTTC          480

AGTTGCAGCA GTCTGACGCT GAGTTGGTGA AACCTGGGGC TTCAGTGAAG ATTTCCTGCA          540

AGGCTTCTGG CTACACCTTC ACTGACCATG CAATTCACTG GGTGAAACAG AACCCTGAAC          600

AGGGCCTGGA ATGGATTGGA TATTTTTCTC CCGGAAATGA TGATTTTAAA TACAATGAGA          660

GGTTCAAGGG CAAGGCCACA CTGACTGCAG ACAAATCCTC CAGCACTGCC TACGTGCAGC          720

TCAACAGCCT GACATCTGAG GATTCTGCAG TGTATTTCTG TACAAGATCC CTGAATATGG          780

CCTACTGGGG TCAAGGAACC TCAGTCACCG TCTCCTCAG                                 819

(2) INFORMATION FOR SEQ ID NO:26:

(i) SEQUENCE CHARACTERISTICS:
        (A) LENGTH: 816 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:26:

TTAACATATC ACAGAGTGGA GCAACAGAAT CAGGGCAAAA ATATGCTGAG AGATTTATCC           60

CTGTCGTTAC AACCAAAGCA TCTGTCTAGA ATTCATAAAA ACTTTATGGG ATACATTTCC          120

TCAGAGAGGA ATAGGATTTG GACCTGACGA TCCTGCTGCC CGAGCCATGT GATGACAGTT          180

```
CTTCTCCAGT TGAACTAGGT CCTTATCTAA GAAATGCACT GCTCATGAAT ATGCAAATCA    240

CCCGAGTCTA TGGCAGTAAA TACAGAGATG TTCATACCAT AAAAACAATA TATGATCAGT    300

GTCTTCTCCG CTATCCCTGG ACACACTGAC TCTAACCATG GAATGGAGCT GGGTCTTTCT    360

CTTCTTCCTG TCAGTAACTA CAGGTAAGGG GCTCACCATT TCCAAATCTA AAGTGGAGTC    420

AGGGCCTGAG GTGACAAAGA TATCCACTTT GGCTTTCCAC AGGTGTCCAC TCCCAGGTTC    480

AGTTGCAGCA GTCTGACGCT GAGTTGGTGA AACCTGGGGC TTCAGTGAAG ATTTCCTGCA    540

AGGCTTCTGG CTACACCTTC ACTGACCATG CTATTCACTG GGTGAAGCAG AAGCCTGAAC    600

AGGGCCTGGA ATGGATTGGA TATATTTCTC CCGGAAATGA TGATATTAAG TACAATGAGA    660

AGTTCAAGGG CAAGGCCACA CTGACTGCAG ACAAATCCTC CAGTACTGCC TACATGCAAC    720

TCAACAGCCT GACATCTGAG GATTCTGCAG TGTATTTCTG TAGAAGATCC TTCTACGGCA    780

ACTGGGGCCA AGGCACCACC CTCACAGTCT CCTCAG                              816

(2) INFORMATION FOR SEQ ID NO:27:

(i) SEQUENCE CHARACTERISTICS:
        (A) LENGTH: 380 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 2..380

(ix) FEATURE:
        (A) NAME/KEY: sig_peptide
        (B) LOCATION: 2..58
        (D) OTHER INFORMATION: /partial (ix) FEATURE:
        (A) NAME/KEY: mat_peptide
        (B) LOCATION: 59..380

(xi) SEQUENCE DESCRIPTION: SEQ ID NO:27:

G AGT CAC AGA TCC AGG TCC TTT GTA TTC GTG TTT CTC TGG TTG TCT            46
  Ser His Arg Ser Arg Ser Phe Val Phe Val Phe Leu Trp Leu Ser
  -19             -15                 -10                 -5

GGT GTT GAC GGA GAC ATT GTG ATG ACC CAG TCT CAC AAA TTC ATG TCC         94
Gly Val Asp Gly Asp Ile Val Met Thr Gln Ser His Lys Phe Met Ser
                 1               5                  10

ACA TCA GTA GGA GAC AGG GTC AGC ATC ACC TGC AAG GCC AGT CAG GAT        142
Thr Ser Val Gly Asp Arg Val Ser Ile Thr Cys Lys Ala Ser Gln Asp
         15                  20                  25

GTG AGT AGT GCT GTA GGG TGG TTT CAA CAG AAA CCA GGA CAA TCT CCT        190
Val Ser Ser Ala Val Gly Trp Phe Gln Gln Lys Pro Gly Gln Ser Pro
     30                  35                  40

AAA TTA CTG ATT TAT TCG GCA TCC TAC CGG TAT ACT GGA GTC CCT GAT        238
Lys Leu Leu Ile Tyr Ser Ala Ser Tyr Arg Tyr Thr Gly Val Pro Asp
 45                  50                  55                  60

CGC TTC ACT GGC AGT GGA TCT CGG ACG GAT TTC ACT TTC ACC ATC ACC        286
Arg Phe Thr Gly Ser Gly Ser Arg Thr Asp Phe Thr Phe Thr Ile Thr
                 65                  70                  75

AGT GTG CAG GCT GAA GAC CTG GCA GTT TAT TAC TGT CAG CAA CAT TAT        334
Ser Val Gln Ala Glu Asp Leu Ala Val Tyr Tyr Cys Gln Gln His Tyr
         80                  85                  90

AGT AGT CCG CTC ACG TTC GGT GCT GGG ACC AAG CTG GAG CTG AAA C          380
Ser Ser Pro Leu Thr Phe Gly Ala Gly Thr Lys Leu Glu Leu Lys
             95                  100                 105
```

(2) INFORMATION FOR SEQ ID NO:28:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:28:

```
Ser His Arg Ser Arg Ser Phe Val Phe Val Phe Leu Trp Leu Ser Gly
-19         -15                 -10                 -5

Val Asp Gly Asp Ile Val Met Thr Gln Ser His Lys Phe Met Ser Thr
             1               5                  10

Ser Val Gly Asp Arg Val Ser Ile Thr Cys Lys Ala Ser Gln Asp Val
        15              20              25

Ser Ser Ala Val Gly Trp Phe Gln Gln Lys Pro Gly Gln Ser Pro Lys
 30              35              40                  45

Leu Leu Ile Tyr Ser Ala Ser Tyr Arg Tyr Thr Gly Val Pro Asp Arg
             50              55                  60

Phe Thr Gly Ser Gly Ser Arg Thr Asp Phe Thr Phe Thr Ile Thr Ser
             65              70              75

Val Gln Ala Glu Asp Leu Ala Val Tyr Tyr Cys Gln Gln His Tyr Ser
         80              85              90

Ser Pro Leu Thr Phe Gly Ala Gly Thr Lys Leu Glu Leu Lys
     95              100             105
```

(2) INFORMATION FOR SEQ ID NO:29:

(i) SEQUENCE CHARACTERISTICS:
        (A) LENGTH: 134 amino acids
        (B) TYPE: amino acid
        (C) STRANDEDNESS: double
        (D) TOPOLOGY: linear (ii) MOLECULE TYPE: protein (xi) SEQUENCE DESCRIPTION: SEQ ID NO:29:

```
Met Glu Trp Ser Trp Val Phe Leu Phe Phe Leu Ser Val Thr Thr Gly
 1               5                  10                  15

Val His Ser Gln Val Gln Leu Gln Gln Ser Asp Ala Glu Leu Val Lys
             20              25              30

Pro Gly Ala Ser Val Lys Ile Ser Cys Lys Ala Ser Gly Tyr Thr Phe
         35              40              45

Thr Asp His Ala Ile His Trp Val Lys Gln Asn Pro Glu Gln Gly Leu
 50              55              60

Glu Trp Ile Gly Tyr Phe Ser Pro Gly Asn Asp Asp Phe Lys Tyr Asn
65              70              75              80

Glu Arg Phe Lys Gly Lys Ala Thr Leu Thr Ala Asp Lys Ser Ser Ser
             85              90              95

Thr Ala Tyr Val Gln Leu Asn Ser Leu Thr Ser Glu Asp Ser Ala Val
             100             105             110

Tyr Phe Cys Thr Arg Ser Leu Asn Met Ala Tyr Trp Gly Gln Gly Thr
         115             120             125

Ser Val Thr Val Ser Ser
     130
```

(2) INFORMATION FOR SEQ ID NO:30:

(i) SEQUENCE CHARACTERISTICS:
        (A) LENGTH: 133 amino acids
        (B) TYPE: amino acid
        (C) STRANDEDNESS: double
        (D) TOPOLOGY: linear (ii) MOLECULE TYPE: protein (xi) SEQUENCE DESCRIPTION: SEQ ID NO:30:

Met Glu Trp Ser Trp Val Phe Leu Phe Phe Leu Ser Val Thr Thr Gly
1               5                   10                  15

Val His Ser Gln Val Gln Leu Gln Gln Ser Asp Ala Glu Leu Val Lys
            20                  25                  30

Pro Gly Ala Ser Val Lys Ile Ser Cys Lys Ala Ser Gly Tyr Thr Phe
            35                  40                  45

Thr Asp His Ala Ile His Trp Val Lys Gln Lys Pro Glu Gln Gly Leu
        50                  55                  60

Glu Trp Ile Gly Tyr Ile Ser Pro Gly Asn Asp Asp Ile Lys Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Asn Ser Leu Thr Ser Glu Asp Ser Ala Val
            100                 105                 110

Tyr Phe Cys Arg Arg Ser Phe Tyr Gly Asn Trp Gly Gln Gly Thr Thr
            115                 120                 125

Leu Thr Val Ser Ser
    130

(2) INFORMATION FOR SEQ ID NO:31:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (xi) SEQUENCE DESCRIPTION: SEQ ID NO:31:

GAAAACCTGT GTCTTACAC                                                    19

(2) INFORMATION FOR SEQ ID NO:32:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (xi) SEQUENCE DESCRIPTION: SEQ ID NO:32:

GTACCTGTGG GGACATTG                                                     18

(2) INFORMATION FOR SEQ ID NO:33:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (xi) SEQUENCE DESCRIPTION: SEQ ID NO:33:

CGTTTCAGCT CCAGCTTGGT CCC                                               23

(2) INFORMATION FOR SEQ ID NO:34:

(i) SEQUENCE CHARACTERISTICS:

(A) LENGTH: 17 base pairs
        (B) TYPE: nucleic acid
        (C) STRANDEDNESS: double
        (D) TOPOLOGY: linear (xi) SEQUENCE DESCRIPTION: SEQ ID NO:34:

CAGGGACTCC AGTGTGC                                                              17

(2) INFORMATION FOR SEQ ID NO:35:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (xi) SEQUENCE DESCRIPTION: SEQ ID NO:35:

GACTTCAAGA TACAAATGTT AG                                                        22

(2) INFORMATION FOR SEQ ID NO:36:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (xi) SEQUENCE DESCRIPTION: SEQ ID NO:36:

CCAACTTTGT CCCCGAGCCG AACG                                                      24

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO:37:

GGTGACTGAG GTTCCTTGAC                                                           20

(2) INFORMATION FOR SEQ ID NO:38:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (xi) SEQUENCE DESCRIPTION: SEQ ID NO:38:

GCAATGCTCA GAAAACTCC                                                            19

(2) INFORMATION FOR SEQ ID NO:39:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (xi) SEQUENCE DESCRIPTION: SEQ ID NO:39:

CTGAGGAGAC TGTGAG                                                               16

(2) INFORMATION FOR SEQ ID NO:40:

(i) SEQUENCE CHARACTERISTICS:
        (A) LENGTH: 22 base pairs
        (B) TYPE: nucleic acid

```
        (C) STRANDEDNESS: double
        (D) TOPOLOGY: linear (xi) SEQUENCE DESCRIPTION: SEQ ID NO:40:

GCAGTAAAAT CTATCTAAGC TG                                            22

(2) INFORMATION FOR SEQ ID NO:41:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (xi) SEQUENCE DESCRIPTION: SEQ ID NO:41:

GCACTGCTCA TGATATGCAA ATC                                           23

(2) INFORMATION FOR SEQ ID NO:42:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (xi) SEQUENCE DESCRIPTION: SEQ ID NO:42:

GATTTGCATA TCATGAGCAG TGC                                           23

(2) INFORMATION FOR SEQ ID NO:43:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (xi) SEQUENCE DESCRIPTION: SEQ ID NO:43:

CTCAGCGTCA GACTGCTG                                                 18

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (xi) SEQUENCE DESCRIPTION: SEQ ID NO:44:

CTTGAACTT CTCATTGTAC                                                20

(2) INFORMATION FOR SEQ ID NO:45:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (xi) SEQUENCE DESCRIPTION: SEQ ID NO:45:

GCACTGCTCA TGATATGCAA ATC                                           23

(2) INFORMATION FOR SEQ ID NO:46:

(i) SEQUENCE CHARACTERISTICS:
        (A) LENGTH: 23 base pairs
        (B) TYPE: nucleic acid
        (C) STRANDEDNESS: double
        (D) TOPOLOGY: linear
```

(xi) SEQUENCE DESCRIPTION: SEQ ID NO:46:

GATTTGCATA TCATGAGCAG TGC                                          23

(2) INFORMATION FOR SEQ ID NO:47:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (xi) SEQUENCE DESCRIPTION: SEQ ID NO:47:

CTAAAGTGGA GTCAGGGCCT G                                            21

(2) INFORMATION FOR SEQ ID NO:48:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (xi) SEQUENCE DESCRIPTION: SEQ ID NO:48:

CAGGCCCTGA CTCCACTTTA G                                            21

(2) INFORMATION FOR SEQ ID NO:49:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (xi) SEQUENCE DESCRIPTION: SEQ ID NO:49:

GAATGGATTG GATATATTTC TC                                           22

(2) INFORMATION FOR SEQ ID NO:50:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (xi) SEQUENCE DESCRIPTION: SEQ ID NO:50:

GTCTAGAATT CATAAAAACT TTATG                                        25

(2) INFORMATION FOR SEQ ID NO:51:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (xi) SEQUENCE DESCRIPTION: SEQ ID NO:51:

CAGTGTATTT CTGTAAAAGA TCTACTATGG TTACG                             35

(2) INFORMATION FOR SEQ ID NO:52:

(i) SEQUENCE CHARACTERISTICS:
        (A) LENGTH: 72 base pairs
        (B) TYPE: nucleic acid
        (C) STRANDEDNESS: double
        (D) TOPOLOGY: linear (xi) SEQUENCE DESCRIPTION: SEQ ID NO:52:

```
TCTACTATGG TTACGTGGGG TCAAGGAACC TCAGTCACCG TCTCCTCAGG TAAGAATGGC      60

CTCTCCAGGT CT                                                          72

(2) INFORMATION FOR SEQ ID NO:53:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (xi) SEQUENCE DESCRIPTION: SEQ ID NO:53:

ACTTCTAAAA TGTATTTAGA ATTCATTTTC                                       30

(2) INFORMATION FOR SEQ ID NO:54:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (xi) SEQUENCE DESCRIPTION: SEQ ID NO:54:

CAGTGTATTT CTGTAAAAGA GTACTGGTGG TGTAT                                 35

(2) INFORMATION FOR SEQ ID NO:55:

(i) SEQUENCE CHARACTERISTICS:
        (A) LENGTH: 72 base pairs
        (B) TYPE: nucleic acid
        (C) STRANDEDNESS: double
        (D) TOPOLOGY: linear (xi) SEQUENCE DESCRIPTION: SEQ ID NO:55:

GTACTGGTGG TGTATTGGGG TCAAGGAACC TCAGTCACCG TCTCCTCAGG TAAGAATGGC      60

CTCTCCAGGT CT                                                          72

(2) INFORMATION FOR SEQ ID NO:56:

(i) SEQUENCE CHARACTERISTICS:
        (A) LENGTH: 72 base pairs
        (B) TYPE: nucleic acid
        (C) STRANDEDNESS: double
        (D) TOPOLOGY: linear (xi) SEQUENCE DESCRIPTION: SEQ ID NO:56:

TCTACTATGG TTACGTGGGG CCAGGGCACC CTGGTCACCG TCTCCTCAGG TAAGAATGGC      60

CTCTCCAGGT CT                                                          72

(2) INFORMATION FOR SEQ ID NO:57:

(i) SEQUENCE CHARACTERISTICS:
        (A) LENGTH: 72 base pairs
        (B) TYPE: nucleic acid
        (C) STRANDEDNESS: double
        (D) TOPOLOGY: linear (xi) SEQUENCE DESCRIPTION: SEQ ID NO:57:

GTACTGGTGG TGTATTGGGG CCAGGGCACC CTGGTCACCG TCTCCTCAGG TAAGAATGGC      60

CTCTCCAGGT CT                                                          72

(2) INFORMATION FOR SEQ ID NO:58:

(i) SEQUENCE CHARACTERISTICS:
```

(A) LENGTH: 248 base pairs
            (B) TYPE: nucleic acid
            (C) STRANDEDNESS: double
            (D) TOPOLOGY: linear (xi) SEQUENCE DESCRIPTION: SEQ ID NO:58:

AATTCATAAA AACTTTATGG GATACATTTC CTCAGAGAGG AATAGGATTT GGACCTGACG        60

ATCCTGCTGC CCGAGCCATG TGATGACAGT TCTTCTCCAG TTGAACTAGG TCCTTATCTA       120

AGAAATGCAC TGCTCATGAA TATGCAAATC ACCCGAGTCT ATGGCAGTAA ATACAGAGAT       180

GTTCATACCA TAAAAACAAT ATGTGATCAG TGTCTTCTCC GCTATCCCTG ACACACTGA        240

CTCTAACC                                                                248

(2) INFORMATION FOR SEQ ID NO:59:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (xi) SEQUENCE DESCRIPTION: SEQ ID NO:59:

ATGGAGTTAG TTTGGGCAGC AGAT                                               24

(2) INFORMATION FOR SEQ ID NO:60:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (xi) SEQUENCE DESCRIPTION: SEQ ID NO:60:

TCCAATCCAT TCCAGGCCCT GTTCAGG                                            27

(2) INFORMATION FOR SEQ ID NO:61:

(i) SEQUENCE CHARACTERISTICS:
            (A) LENGTH: 378 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:61:

CTATCCCTGG ACACACTGAC TCTAACCATG GAATGGAGCT GGGTCTTTCT CTTCTTCCTG        60

TCAGTAACTA CAGGTGTCCA CTCCCAGGTT CAGCTGCAGC AGTCTGACGC TGAGTTGGTG       120

AAACCTGGGG CTTCAGTGAA GATATCCTGC AAGGCTTCTG GCTACACCTT CACTGACCAT       180

GCTATTCACT GGGTGAAGCA GAAGCCTGAA CAGGGCCTGG AATGGATTGG ATATATTTCT       240

CCCGGAAATG GTGATATTAA GTACAATGAG AAGTTCAAGG GCAAGGCCAC ACTGACTGCA       300

GACAAATCCT CCAGCACTGC CTACATGCAG CTCAACAGCC TGACATCTGA GGATTCTGCA       360

GTGTATTTCT GTAAAAGA                                                     378

(2) INFORMATION FOR SEQ ID NO:62:

(i) SEQUENCE CHARACTERISTICS:
            (A) LENGTH: 423 base pairs
            (B) TYPE: nucleic acid
            (C) STRANDEDNESS: double
            (D) TOPOLOGY: linear (ii) MOLECULE TYPE: cDNA to mRNA (xi) SEQUENCE DESCRIPTION: SEQ ID NO:62:

```
GACACACTGA CTCTAANCAT GGAATGGAGC TGGGNNTTTC TCTTCTTCCT GTAAGTAACT      60

ANAGGTGTCC ACTCCCAGGT TNAGCTGCAG CAGTCTGACG CTGAGTTGGT GAAACCTGGN     120

NNTTCAGTGA AGATATCCTG CAAGGCTTCT GGCTACACCT TCACTGACCA TGCTATTNNN     180

NNNNNNNNNN NNNNNNNNNN NNNNNNNNNN NNNNNNNNNN NNNNNNNNNN NNNNNNNNNN     240

NNNNNNNNNN NNNNNNNNGT GAAGTTCTAG GGCNAGGCCA CACTGACTGC AGACAGATCC     300

TCCAGCACTG CCTNCNTGCA GCTCAACAGC CTGACATCTG AGGATTCTGC AGTGTATTTC     360

TGTAAAAGAT CGGTCAATGC TTTTGACTAC TGGGGCCAAG GCACCNCTCT CNNNGTCTCC     420

TCA                                                                   423
```

(2) INFORMATION FOR SEQ ID NO:63:

(i) SEQUENCE CHARACTERISTICS:
        (A) LENGTH: 192 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:63:

```
TGGACACACT GACTCTAACC ATGGAATGGA GCTGGGTCTT TCTCTTCTTC CTGTCAGTNA      60

CTACAGGTGT CCACTCCCAG GNNCAGCTGC ANCAGTCTGA NGCTGAGTTG GTGAAACCTG     120

GGGCTTCAGN GAAGATATCC TGNAAGGCTT CNGGCTACAC CTTCACTGAC CATGCTATTC     180

ACTGGGTGAA GC                                                         192
```

(2) INFORMATION FOR SEQ ID NO:64:

(i) SEQUENCE CHARACTERISTICS:
        (A) LENGTH: 422 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:64:

```
ACNCACTGAC TCTNACCNTG GAATGGAGCT GGGNNNNTCT CTTCTTCCTG TCNGTAACTN      60

NNGGTGTCCN CTCCCAGGTT NNGCTGCAGC AGTCTGACGC TGAGTTGGTG NNACCTGGGN     120

NTTCAGTGAA GATATCCTGN AAGGCTTNTG GCTNCACCTT CNCTGACTAT GCTATTCACT     180

GGGTGAAGCA GAAGCCTGAA CAGGGCCTGG AATGGATTGG ATATATTTCT CCCGGAAATG     240

GTGATATTAA GTACAATGAG AAGTTCAAGG GCAAGGCCAC ACTGACTGCA GACAAATCCT     300

CCAGCACTGC CTACATGCAG CTCAACAGCC TGACATCTGA GGATTCTGCA GTGTATTTCT     360

GTAAAAGATC CCTGGGACGT TTTGACTACT GGGGCCAAGG CACCACTCTC ACAGTCTCCT     420

CA                                                                    422
```

(2) INFORMATION FOR SEQ ID NO:65:

(i) SEQUENCE CHARACTERISTICS:
        (A) LENGTH: 426 base pairs
        (B) TYPE: nucleic acid
        (C) STRANDEDNESS: double
        (D) TOPOLOGY: linear (ii) MOLECULE TYPE: cDNA to mRNA (xi) SEQUENCE DESCRIPTION: SEQ ID NO:65:

```
CTATCCCTGG ACACACTGAC TCTAACCATG GAATGGAGCT GGGTCTTTCT CTTCTTCCTG      60
TCAGTAACTA CAGGTGTCCA CTCCCAGGTT CAGCTGCAGC AGTCTGACGC TGAGTTGGTG     120
AAACCTGGGG CTTCAGTGAA GATATCCTGC AAGGCTTCTG GCTACACCTT CACTGACCAT     180
GCTATTCACT GGGTGAAGCA GNNNNNNNNN NNNNNNNNNN NNNNNNNNNN NNNNNNNNNN     240
NNNNNNNNNN NNNNNNNNNN NNNNAATGAG AAGTTCAAGG GCAAGGCCAC ACTGACTGCA     300
GACAAATCCT CCAGCACTGC CTATATGCAA CTCGACAGCC TGACATCTGA GGATTCTGCA     360
GTGTATTTCT GTAAAGCCTC CTACTATGGT AACTGGGGCC AAGGCACNAC TCTCACAGTC     420
TCCTCA                                                                426
```

(2) INFORMATION FOR SEQ ID NO:66:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (xi) SEQUENCE DESCRIPTION: SEQ ID NO:66:

```
TATCTTATCA TGTCTGGATC C                                                21
```

(2) INFORMATION FOR SEQ ID NO:67:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (xi) SEQUENCE DESCRIPTION: SEQ ID NO:67:

```
GGCCCTTTCG TCTTCAAGAA TTC                                              23
```

(2) INFORMATION FOR SEQ ID NO:68:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (xi) SEQUENCE DESCRIPTION: SEQ ID NO:68:

```
GGTAAATGAG TGCGACGG                                                    18
```

(2) INFORMATION FOR SEQ ID NO:69:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (xi) SEQUENCE DESCRIPTION: SEQ ID NO:69:

```
CCGTCGCACT CATTTACCAA CTCTCTTGTC CACCTT                                36
```

(2) INFORMATION FOR SEQ ID NO:70:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (xi) SEQUENCE DESCRIPTION: SEQ ID NO:70:

CCGTCGCACT CATTTACCTG GGCACGGTGG GCATGT                                 36

(2) INFORMATION FOR SEQ ID NO:71:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (xi) SEQUENCE DESCRIPTION: SEQ ID NO:71:

CCGTCGCACT CATTTACCTT TGGCTTTGGA GATGGT                                 36

(2) INFORMATION FOR SEQ ID NO:72:

(i) SEQUENCE CHARACTERISTICS:
        (A) LENGTH: 1383 base pairs
        (B) TYPE: nucleic acid
        (C) STRANDEDNESS: double
        (D) TOPOLOGY: linear (xi) SEQUENCE DESCRIPTION: SEQ ID NO:72:

AGCTTTCTGG GGCAGGCCAG GCCTGACCTT GGCTTTGGGG CAGGGAGGGG GCTAAGGTGA       60

GGCAGGTGGC GCCAGCAGGT GCACACCCAA TGCCCATGAG CCCAGACACT GGACGCTGAA      120

CCTCGCGGAC AGTTAAGAAC CCAGGGGCCT CTGCGCCTGG GCCCAGCTCT GTCCCACACC      180

GCGGTCACAT GGCACCACCT CTCTTGCAGC CTCCACCAAG GGCCCATCGG TCTTCCCCCT      240

GGCACCCTCC TCCAAGAGCA CCTCTGGGGG CACAGCGGCC CTGGGCTGCC TGGTCAAGGA      300

CTACTTCCCC GAACCGGTGA CGGTGTCGTG GAACTCAGGC GCCCTGACCA GCGGCGTGCA      360

CACCTTCCCG GCTGTCCTAC AGTCCTCAGG ACTCTACTCC CTCAGCAGCG TGGTGACCGT      420

GCCCTCCAGC AGCTTGGGCA CCCAGACCTA CATCTGCAAC GTGAATCACA AGCCCAGCAA      480

CACCAAGGTG GACAAGAAAG TTGGTGAGAG GCCAGCACAG GGAGGGAGGG TGTCTGCTGG      540

AAGCAGGCTC AGCGCTCCTG CCTGGACGCA TCCCGGCTAT GCAGCCCCAG TCCAGGGCAG      600

CAAGGCAGGC CCCGTCTGCC TCTTCACCCG GAGCCTCTGC CCGCCCCACT CATGCTCAGG      660

GAGAGGGTCT TCTGGCTTTT TCCCAGGCTC TGGGCAGGCA CAGGCTAGGT GCCCCTAACC      720

CAGGCCCTGC ACACAAAGGG GCAGGTGCTG GGCTCAGACC TGCCAAGAGC CATATCCGGG      780

AGGACCCTGC CCCTGACCTA AGCCCACCCC AAAGGCCAAA CTCTCCACTC CCTCAGCTCG      840

GACACCTTCT CTCCTCCCAG ATTCCAGTAA CTCCCAATCT TCTCTCTGCA GAGCCCAAAT      900

CTTGTGACAA AACTCACACA TGCCCACCGT GCCCAGGTAA GCCAGCCCAG GCCTCGCCCT      960

CCAGCTCAAG GCGGGACAGG TGCCCTAGAG TAGCCTGCAT CCAGGGACAG GCCCCAGCCG     1020

GGTGCTGACA CGTCCACCTC CATCTCTTCC TCAGCACCTG AACTCCTGGG GGACCGTCA      1080

GTCTTCCTCT TCCCCCCAAA ACCCAAGGAC ACCCTCATGA TCTCCCGGAC CCCTGAGGTC     1140

ACATGCGTGG TGGTGGACGT GAGCCACGAA GACCCTGAGG TCAAGTTCAA CTGGTACGTG     1200

GACGGCGTGG AGGTGCATAA TGCCAAGACA AAGCCGCGGG AGGAGCAGTA CAACAGCACG     1260

TACCGGGTGG TCAGCGTCCT CACCGTCCTG CACCAGGACT GGCTGAATGG CAAGGAGTAC     1320

AAGTGCAAGG TCTCCAACAA AGCCCTCCCA GCCCCCATCG AGAAAACCAT CTCCAAAGCC     1380

AAA                                                                  1383

(2) INFORMATION FOR SEQ ID NO:73:

(i) SEQUENCE CHARACTERISTICS:
        (A) LENGTH: 935 base pairs (B) TYPE: nucleic acid
        (C) STRANDEDNESS: double
        (D) TOPOLOGY: linear (xi) SEQUENCE DESCRIPTION: SEQ ID NO:73:

```
AGCTTTCTGG GGCAGGCCAG GCCTGACCTT GGCTTTGGGG CAGGGAGGGG GCTAAGGTGA      60

GGCAGGTGGC GCCAGCAGGT GCACACCCAA TGCCCATGAG CCCAGACACT GGACGCTGAA     120

CCTCGCGGAC AGTTAAGAAC CCAGGGGCCT CTGCGCCTGG GCCCAGCTCT GTCCCACACC     180

GCGGTCACAT GGCACCACCT CTCTTGCAGC CTCCACCAAG GGCCCATCGG TCTTCCCCCT     240

GGCACCCTCC TCCAAGAGCA CCTCTGGGGG CACAGCGGCC CTGGGCTGCC TGGTCAAGGA     300

CTACTTCCCC GAACCGGTGA CGGTGTCGTG GAACTCAGGC GCCCTGACCA GCGGCGTGCA     360

CACCTTCCCG GCTGTCCTAC AGTCCTCAGG ACTCTACTCC CTCAGCAGCG TGGTGACCGT     420

GCCCTCCAGC AGCTTGGGCA CCCAGACCTA CATCTGCAAC GTGAATCACA AGCCCAGCAA     480

CACCAAGGTG GACAAGAAAG TTGGTGAGAG GCCAGCACAG GGAGGGAGGG TGTCTGCTGG     540

AAGCAGGCTC AGCGCTCCTG CCTGGACGCA TCCCGGCTAT GCAGCCCCAG TCCAGGGCAG     600

CAAGGCAGGC CCCGTCTGCC TCTTCACCCG GAGCCTCTGC CCGCCCCACT CATGCTCAGG     660

GAGAGGGTCT TCTGGCTTTT TCCCAGGCTC TGGGCAGGCA CAGGCTAGGT GCCCCTAACC     720

CAGGCCCTGC ACACAAAGGG GCAGGTGCTG GGCTCAGACC TGCCAAGAGC CATATCCGGG     780

AGGACCCTGC CCCTGACCTA AGCCCACCCC AAAGGCCAAA CTCTCCACTC CCTCAGCTCG     840

GACACCTTCT CTCCTCCCAG ATTCCAGTAA CTCCCAATCT TCTCTCTGCA GAGCCCAAAT     900

CTTGTGACAA AACTCACACA TGCCCACCGT GCCCA                                935
```

(2) INFORMATION FOR SEQ ID NO:74:

(i) SEQUENCE CHARACTERISTICS:
        (A) LENGTH: 508 base pairs
        (B) TYPE: nucleic acid
        (C) STRANDEDNESS: double
        (D) TOPOLOGY: linear (xi) SEQUENCE DESCRIPTION: SEQ ID NO:74:

```
AGCTTTCTGG GGCAGGCCAG GCCTGACTTT GGCTGGGGGC AGGGAGGGGG CTAAGGTGAC      60

GCAGGTGGCG CCAGCCAGGC GCACACCCAA TGCCCGTGAG CCCAGACACT GGACCCTGCC     120

TGGACCCTCG TGGATAGACA AGAACCGAGG GGCCTCTGCG CCCTGGGCCC AGCTCTGTCC     180

CACACCGCAG TCACATGGCG CCATCTCTCT TGCAGCTTCC ACCAAGGGCC CATCGGTCTT     240

CCCCCTGGCG CCCTGCTCCA GGAGCACCTC TGGGGGCACA GCGGCCCTGG GCTGCCTGGT     300

CAAGGACTAC TTCCCCGAAC CGGTGACGGT GTCGTGGAAC TCAGGCGCCC TGACCAGCGG     360

CGTGCACACC TTCCCGGCTG TCCTACAGTC CTCAGGACTC TACTCCCTCA GCAGCGTGGT     420

GACCGTGCCC TCCAGCAGCT TGGGCACCCA GACCTACACC TGCAACGTGA ATCACAAGCC     480

CAGCAACACC AAGGTGGACA AGAGAGTT                                       508
```